United States Patent
Lira et al.

(10) Patent No.: US 10,577,619 B2
(45) Date of Patent: *Mar. 3, 2020

(54) GLYPHOSATE RESISTANT PLANTS AND ASSOCIATED METHODS

(71) Applicant: Dow AgroSciences LLC, Indianapolis, IN (US)

(72) Inventors: Justin M. Lira, Zionsville, IN (US); Robert Cicchillo, Zionsville, IN (US); Carla N Yerkes, Crawfordsville, IN (US); Andrew E Robinson, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 101 days.

This patent is subject to a terminal disclaimer.

(21) Appl. No.: 15/198,740

(22) Filed: Jun. 30, 2016

(65) Prior Publication Data

US 2016/0304897 A1    Oct. 20, 2016

Related U.S. Application Data

(63) Continuation of application No. 13/757,536, filed on Feb. 1, 2013, now Pat. No. 9,382,549.

(60) Provisional application No. 61/593,555, filed on Feb. 1, 2012, provisional application No. 61/625,222, filed on Apr. 17, 2012.

(51) Int. Cl.
| | | |
|---|---|---|
| C12N 15/82 | (2006.01) | |
| C07K 14/415 | (2006.01) | |
| A01N 57/20 | (2006.01) | |
| C12N 9/02 | (2006.01) | |
| C12N 9/10 | (2006.01) | |
| C12N 9/96 | (2006.01) | |
| C12N 15/62 | (2006.01) | |

(52) U.S. Cl.
CPC ......... *C12N 15/8221* (2013.01); *A01N 57/20* (2013.01); *C07K 14/415* (2013.01); *C12N 9/0069* (2013.01); *C12N 9/0071* (2013.01); *C12N 9/1085* (2013.01); *C12N 9/96* (2013.01); *C12N 15/62* (2013.01); *C12N 15/8205* (2013.01); *C12N 15/8209* (2013.01); *C12N 15/8214* (2013.01); *C12N 15/8241* (2013.01); *C12N 15/8245* (2013.01); *C12N 15/8247* (2013.01); *C12N 15/8274* (2013.01); *C12N 15/8275* (2013.01); *C12N 15/8281* (2013.01); *C12N 15/8283* (2013.01); *C12N 15/8286* (2013.01); *C12Y 113/00* (2013.01); *C12Y 114/11* (2013.01); *C12Y 205/01019* (2013.01); *C07K 2319/08* (2013.01); *C12N 9/1092* (2013.01); *Y02A 40/162* (2018.01)

(58) Field of Classification Search
CPC ............................. C12N 15/8281; A01H 5/10
See application file for complete search history.

(56) References Cited

U.S. PATENT DOCUMENTS

| | | | |
|---|---|---|---|
| 5,886,775 A | 3/1999 | Houser et al. | |
| 7,674,958 B2* | 3/2010 | Peters | C07K 14/195 435/252.3 |
| 7,834,249 B2* | 11/2010 | Schouten | C12N 9/1092 435/252.3 |
| 7,906,709 B2 | 3/2011 | Penner et al. | |
| 8,071,305 B2* | 12/2011 | Brandon | C12Q 1/705 435/6.11 |
| 9,359,614 B2* | 6/2016 | Lira | C12N 15/8209 |
| 9,382,549 B2* | 7/2016 | Lira | C12N 15/8209 |
| 2007/0289037 P1 | 12/2007 | Koziel et al. | |
| 2008/0127372 A1 | 5/2008 | Schouten et al. | |
| 2009/0093366 A1* | 4/2009 | Wright | C12N 9/0069 504/142 |
| 2011/0124503 A1 | 5/2011 | Wright et al. | |
| 2011/0195845 A1 | 8/2011 | Lira et al. | |
| 2011/0289620 A1 | 11/2011 | Cui et al. | |
| 2013/0217577 A1 | 8/2013 | Lira et al. | |

FOREIGN PATENT DOCUMENTS

| | | |
|---|---|---|
| WO | 2006102080 | 9/2006 |
| WO | 2007053482 | 5/2007 |
| WO | 2007082269 | 7/2007 |
| WO | 2010078156 | 7/2010 |

OTHER PUBLICATIONS

Yi, Shu-yuan, et al. "A novel naturally occurring Class I 5-Enolpyruvylshikimate-3-Phosphate synthase from *Janibacter* sp. confers high glyphosate tolerance to rice." Scientific reports 6 (2016): 19104.*
Zhang, Yi, et al. "Characterization and site-directed mutagenesis of a novel class II 5-enopyruvylshikimate-3-phosphate (EPSP) synthase from the deep-sea bacterium *Alcanivorax* sp. L27." Enzyme and microbial technology 63 (2014): 64-70.*
Genbank nucleotide sequence Accession No. EDY54343.1; retrieed from http www.ncbi.nlm.nih.gov/protein/EDY54343.1.*
Gamborg, O. L., B. P. Davis, and R. W. Stahlhut. "Cell division and differentiation in protoplasts from cell cultures of Glycine species and leaf tissue of soybean." Plant cell reports 2.4 (1983): 213-215.*
Funke, Todd, et al. "Molecular basis for the herbicide resistance of Roundup Ready crops." Proceedings of the National Academy of Sciences 103.35 (2006): 13010-13015.*
Gaines, Todd A., et al. "Gene amplification confers glyphosate resistance in Amaranthus palmeri." Proceedings of the National Academy of Sciences 107.3 (2010): 1029-1034.*

(Continued)

*Primary Examiner* — Weihua Fan

(74) *Attorney, Agent, or Firm* — Magleby Cataxinos & Greenwood

(57) ABSTRACT

The present disclosure relates to certain polypeptides derived from prokaryotic DGT enzymes, and nucleic acids useful in encoding the same.

23 Claims, 54 Drawing Sheets

Specification includes a Sequence Listing.

(56) References Cited

OTHER PUBLICATIONS

Zhang, Yi, et al. "Characterization and site-directed mutagenesis of a novel class II 5-enopyruvylshikimate-3-phosphate (EPSP) synthase from the deep-sea bacterium *Alcanivorax* sp. L27." Enzyme and microbial technology 63 (2014): 64-70. (Year: 2014).*
Dilella, Anthony G., and Savio LC Woo. "[49] Hybridization of genomic DNA to oligonucleotide probes in the presence of tetramethylammonium chloride." Methods in enzymology. vol. 152. Academic Press, 1987. 447-451. (Year: 1987).*
Mastali, Mitra, et al. "Optimal probe length and target location for electrochemical detection of selected uropathogens at ambient temperature." Journal of clinical microbiology 46.8 (2008): 2707-2716. (Year: 2008).*
Gotoh, Masanori, et al. "A new approach to determine the effect of mismatches on kinetic parameters in DNA hybridization using an optical biosensor." DNA Research 2.6 (1995): 285-293. (Year: 1995).*
Yi, Shu-yuan, et al. "A novel naturally occurring Class I 5-Enolpyruvylshikinnate-3-Phosphate synthase from *Janibacter* sp. confers high glyphosate tolerance to rice." Scientific reports6 (2016): 19104. (Year: 2016).*
Zhang, Yi, et al. "Characterization and site-directed mutagenesis of a novel class II 5-enolpyruvylshikimate-3-phosphate (EPSP) synthase from the deep-sea bacterium *Alcanivorax* sp. L27." Enzynne and microbial technology63 (2014): 64-70. (Year : 2014).*
Bartley, Glenn E., et al. "Molecular cloning and expression in photosynthetic bacteria of a soybean cDNA coding for phytoene desaturase, an enzyme of the carotenoid biosynthesis pathway." Proceedings of the National Academy of Sciences 88.15 (1991): 6532-6536. (Year: 1991).*
Berlyn, Mary B., Robert L. Last, and Gerald R. Fink. "A gene encoding the tryptophan synthase beta subunit of *Arabidopsis thaliana*." Proceedings of the National Academy of Sciences86.12 (1989): 4604-4608. (Year: 1989).*
Dilella, Anthony G., and Savio LC Woo. "[49] Hybridization of genomic DNA to oligonucleotide probes in the presence of tetramethylammonium chloride." Methods in enzymology. vol. 152. Academic Press, 1987. 447-451. (Year: 1987).*
Mastali, Mitra, et al. "Optimal probe length and target location for electrochemical detection of selected uropathogens at ambient ten-nperature."Journal of clinical microbiology 46.8 (2008): 2707-2716. (Year: 2008).*
Wallace, R. Bruce, et al. "Hybridization of synthetic oligodeoxyribonucleotides to φ x 174 DNA: the effect of single base pair mismatch." Nucleic acids research 6.11 (1979): 3543-3558 (Year: 1979).*
Gotoh, Masanori, et al. "A new approach to determine the effect of mismatches on kinetic parameters in DNA hybridization using an optical biosensor." DNA Research;2.6 (1995): 285-293. (Year: 1995).*
Ullrich, Axel, et al. "Isolation of the human insulin-like growth factor I gene using a single synthetic DNA probe." The EMBO journal 3.2 (1984): 361-364. (Year: 1984).*

DATABASE UniProt [Online]Oct. 14, 2008 (Oct. 14, 2008), "RecName: Full=3-phosphoshikimate 1-carboxyvinyltransferase {ECO: 0000256IHAMAP-Rule:MF_00210, EC0:00002561 RuleBasesRU000531}; EC=2.5.1.19;",retrieved from EBI accession No. UNIPROT:BSHND8; Database accession No. BSHNDB (Year: 2008).*
Eschenburg, S., et al., "How the mutation glycine96 to alanine confers glyphosate insensitivity to 5-enolpyruvyl shikimate-3-phosphate synthase from *Escherichia coli*," Planta (2002) vol. 216, pp. 129-135.
Fischbach, M. et al., "3-phosphoshikimate 1-carboxyvinyltransferase [*Streptomyces sviceus* ATCC 29083] (GI: 197710309):" The broad Institute Genome Sequencing Platform. Annotation of *Streptomyces sviceus* ATCC, Sep. 2, 2008.
Funke et al. "Molecular basis for the herbicide resistance of Roundup Ready crops," PNAS, vol. 103, No. 35 (Aug. 29, 2006) pp. 13010-13015.
Gaines, et al.; Gene amplification confers glyphosate resistance in Amaranthus palmeri; Proceeding of the National Academy of Sciences 107.3 (2010): 1029-1034.
GenBank Accession No. AATS01000008, dated Sep. 15, 2006.
GenBank Accession No. EDY54343, dated Mar. 15, 2015.
Guo et al., 2004, Proc. Natl. Acad. Sci. USA 101: 9205-9210.
Haghani K et al: "Comparative studies of wild type *Escherichia coli* 5-enolpyruvylshikimate 3-phosphate synthase with three glyphosate-insensitive mutated forms: Activity, stability and structural characterization", Biochimica Et Biophysica Acta (BBA)—Proteins & Proteomics, Elsevier, Netherlands, vol. 1784, No. 9, Sep. 1, 2008, pp. 1167-1175.
He, Y., et al., Cloning and characterization of two novel chloroplastic glycerol-3-phosphate dehydrogenases from Dunaliella viridis, Plant Mol Biol (2009) 71: 193-205.
International Search Report and Written Opinion of International Application No. PCT/US2013/024410, dated Jun. 2, 2013, 13 pages.
Liang, L. et al., "A Novel RPMXR motif among class II 5-enolpyruvylshikimate-3phosphate synthases is required for enzymatic activity and glyphosate resistance." Journal of Biotech (2009).
NCBI Gene ID: 6853537, (Oct. 14, 2008).
NCBI GeneBank Accession No. ZP_06917240.1, Sep. 22, 2011.
Pollegioni Loredano et al: "Molecular basis of glyphosate resistance- different approaches through protein engineering", FEBS Journal, val. 278, No. 16, Aug. 2011 (Aug. 2011), pp. 2753-2766.
Priestman, M., et al., "Molecular basis for the glyphosate-insensitivity of the reaction of 5-enolpyruvylshikimate 3-phosphate synthase with shikimate," FEBS Letters 579 (2005) pp. 5773-5780.
Wright, T. et al., "Robust crop resistance to broadleaf and grass herbicides provided by aryloxyalkanoate dioxygenase transgenes," PNAS, vol. 107, No. 47, Sep. 23, 2010, pp. 20240-20245.
Zhong, H., et al., The pea (*Pisum stavium* L.) rbcS transit peptide directs the Alcaligenes eutrophus polyhydroxybutyrate enzymes into the maize (*Zea mays* L.) Chloroplasts, Plant Science 165 (2003) pp. 455-462.

* cited by examiner

GLYPHOSATE RESISTANT PLANTS AND ASSOCIATED METHODS

CROSS-REFERENCE TO RELATED APPLICATIONS

This application is a continuation of U.S. patent application Ser. No. 13/757,536 filed Feb. 1, 2013, which claims the benefit of U.S. Provisional Patent Application Ser. No. 61/593,555 filed Feb. 1, 2012, and also to U.S. Provisional Patent Application Ser. No. 61/625,222, filed Apr. 17, 2012, the disclosure of each of which is hereby incorporated herein in its entirety by this reference.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The present disclosure relates to plant biotechnology. Particular embodiments relate to novel polypeptides involved in metabolism of N-(phosphonomethyl) glycine, and nucleic acids encoding such polypeptides. Particular embodiments relate to plants, plant plant parts, and plant cells that comprise a foregoing polypeptides and/or nucleic acids.

BACKGROUND

Weed species have long been a problem in cultivated fields. Although weed control can be a labor intensive operation, it has been made easier by the availability of efficient weed killing chemical herbicides. The widespread use of herbicides, along with improved crop varieties and fertilizers, has made a significant contribution to the "green revolution" in agriculture. Particularly useful herbicides are those that have a broad spectrum of herbicidal activity. Unfortunately, broad spectrum herbicides typically have a deleterious effect on crop plants exposed to the herbicide. One way to overcome this problem is to produce crop plants that are tolerant to the broad spectrum herbicide.

One example of a broad spectrum herbicide is N-phosphonomethyl-glycine, also known as glyphosate. Glyphosate has been used extensively by farmers worldwide for controlling weeds prior to crop planting, for example, in no-till farming. In addition, glyphosate is an efficient means to control weeds and volunteer plants between production cycles or crop rotations. Glyphosate does not carry-over in soils after use, and it is widely considered to be one of the most environmentally safe and broadly effective chemical herbicides available for use in agriculture.

Glyphosate kills plants by inhibiting the shikimic acid pathway. This pathway leads to the biosynthesis of aromatic compounds, including amino acids, vitamins, and plant hormones. Glyphosate blocks the condensation of phosphoenolpyruvic acid (PEP) and 3-phosphoshikimic acid to 5-enolpyruvyl-3-phosphoshikimic acid by binding to and inhibiting activity of the enzyme 5-enolpyruvylshikimate-3-phosphate synthase, commonly referred to as "EPSP synthase," and "EPSPS."

Unfortunately, no crop plants are known that are naturally tolerant to glyphosate, and, therefore, the utility of this herbicide for weed control in cultivated crops has been limited. One method to produce glyphosate-tolerant crop plants is to introduce a gene encoding a heterologous glyphosate-tolerant form of an EPSPS gene into the crop plant using the techniques of genetic engineering. Using chemical mutagenesis, glyphosate tolerant forms of EPSPS have been produced in bacteria, and the heterologous genes were introduced into plants to produce glyphosate-tolerant plants. See, e.g., Comai et al. (1983) Science 221:370-71. The heterologous EPSPS genes may be overexpressed in the crop plants to obtain a desired level of tolerance.

The foregoing examples of the related art and limitations related therewith are intended to be illustrative and not exclusive. Other limitations of the related art will become apparent to those of skill in the art upon a reading of the specification.

BRIEF SUMMARY OF THE DISCLOSURE

Described herein are isolated polypeptides having at least 90% identity to SEQ ID NO:1, and nucleic acids encoding a polypeptide having at least 90% identity to SEQ ID NO:1 (e.g., SEQ ID NOs:2-4). Also described are plants, plant parts, plant organs, plant seed, and plant cells comprising a heterologous polypeptide having at least 90% identity to SEQ ID NO:1.

Some embodiments include a plant, plant part, plant organ, plant seed, and/or plant cell comprising a heterologous nucleic acid encoding a polypeptide having at least 90% identity to SEQ ID NO:1. In particular examples, the heterologous nucleic acid comprises a nucleotide sequence having at least 80% sequence identity to SEQ ID NO:2 or SEQ ID NO:3. Some embodiments include a plant plant, plant part, plant organ, plant seed, and/or plant cell comprising a heterologous nucleic acid that hybridizes to another nucleic acid having SEQ ID NO:2 or SEQ ID NO:3 under high-stringency conditions. In particular examples, the plant, plant part, plant organ, plant seed, and/or plant cell comprising a heterologous nucleic acid that hybridizes to another nucleic acid having SEQ ID NO:2 or SEQ ID NO:3 under high-stringency conditions comprises a polypeptide encoded by the heterologous nucleic acid that confers glyphosate tolerance (or increases glyphosate tolerance) to the plant, plant part, plant organ, plant seed, and/or plant cell.

In further embodiments, the disclosure relates to methods of generating a plant, plant part, plant organ, plant seed, and/or plant cell resistant to glyphosate comprising: transforming a plant, plant part, plant organ, plant seed, and/or plant cell with a nucleic acid encoding a polypeptide having at least 90% identity to SEQ ID NO:1; and expressing the nucleic acid so as to produce the polypeptide having at least 90% identity to SEQ ID NO:1.

Other embodiments include vectors comprising a nucleic acid encoding a polypeptide having at least 90% identity to SEQ ID NO:1. Particular examples include vectors comprising a nucleic acid encoding a polypeptide having at least 95% identity to SEQ ID NO:1. For example, a vector may comprise a nucleic acid sequence having at least 90% identity to SEQ ID NO:2 or SEQ ID NO:3.

Particular embodiments include glyphosate tolerant plants and plant cells expressing a heterologous polypeptide having at least 90% identity to SEQ ID NO:1.

Additional embodiments include methods for controlling weeds in a field or area under cultivation containing glyphosate-resistant plants, wherein such a method may comprise: planting a plant or a plant seed comprising a nucleic acid encoding a heterologous polypeptide having at least 90% identity to SEQ ID NO:1 in the field or area under cultivation; and applying to the field or area under cultivation a sufficient amount of glyphosate to control weeds in the field without significantly affecting the plant.

In some embodiments, the disclosure relates to regenerable cells for use in tissue culture of plants resistant to glyphosate. Such a tissue culture may be capable of regenerating plants having the physiological and morphological characteristics of the foregoing glyphosate-resistant plants, and also of regenerating plants having substantially the same genotype as the glyphosate-resistant plants. Regenerable cells in such tissue cultures may be, for example, embryos, protoplasts, meristematic cells, callus, pollen, leaves, anthers, roots, root tips, flowers, seeds, pods, and stems. Particular embodiments relate to plants regenerated from a tissue culture according to the foregoing.

In some embodiments, the disclosure relates to cells that are not regenerable to produce plants, for example for use in producing plant cell lines resistant to glyphosate. In other embodiments, the disclosure relates to plants comprising in part such cells.

In certain embodiments, the present disclosure relates to the application of multiple herbicides to crops planted in an area under cultivation. An over the top application of glyphosate in addition to multiple herbicides takes advantage of the different herbicide properties, so that weed control is provided with an improved combination of flexibility and economy. For example, individual herbicides may have different longevities in the area under cultivation; i.e., some herbicides may persist and be effective for a relatively long time after they are applied to the area, while other herbicides may be quickly broken down into other and/or non-active compounds. An improved herbicide application system according to particular embodiments allows the use of glyphosate and multiple herbicides so that a grower can tailor the selection of particular herbicides for use in a particular situation.

In other embodiments, the present disclosure relates to methods and compositions for making and using a plant that is tolerant to more than one herbicide or class or subclass of herbicide, as described below. In particular embodiments, a plant is provided that is tolerant to both glyphosate and at least one other herbicide (or class or subclass of herbicide) or chemical (or class or subclass of chemical) (e.g., fungicides, insecticides, plant growth regulators and the like). Such plants may find use, for example, in methods comprising treatment of crop plants with multiple herbicides. Thus, the disclosure provides herbicide-resistant plants which tolerate treatment with an herbicide or combination of herbicides (including a combination of herbicides that each act through a different mode of herbicidal activity) or which tolerate treatment with a combination of at least one herbicide and at least one other chemical. In this manner, the disclosure describes improved methods of growing crop plants in which weeds are selectively controlled.

An herbicide-resistant plant according to some embodiments may comprise a nucleic acid molecule that encodes a heterologous polypeptide that confers tolerance to glyphosate and a nucleic acid molecule encoding a polypeptide that confers tolerance to 2,4-dichlorophenoxyacetic acid (2,4-D). According to the foregoing paragraphs, plants are provided that comprise at least a third nucleic acid molecule encoding a polypeptide imparting to the plant a trait selected from the group consisting of an herbicide tolerance trait; an insect resistance trait; an agronomic trait; a disease resistance trait; a modified fatty acid trait; and a reduced phytate trait.

In some examples, an herbicide-resistant plant comprises a heterologous nucleic acid molecule encoding a polypeptide that confers tolerance to glyphosate and a nucleic acid molecule encoding a polypeptide that confers tolerance to glufosinate. Some examples include an herbicide-resistant plant comprising a nucleic acid molecule encoding a polypeptide imparting to the plant a trait selected from the group consisting of an herbicide tolerance trait; an insect resistance trait; an agronomic trait; a disease resistance trait; a modified fatty acid trait; and a reduced phytate trait.

In particular examples, a herbicide-resistant plant comprises a heterologous nucleic acid molecule encoding a polypeptide that confers tolerance to glyphosate and a nucleic acid molecule encoding a polypeptide that confers tolerance to a herbicide that inhibits acetolactate synthase (ALS) (Lee et al. (1988) EMBO J. 7:1241), also known as acetohydroxyacid synthase (AHAS) enzyme (Mild et al. (1990) Theor. Appl. Genet. 80:449). Some examples include an herbicide-resistant plant comprising a nucleic acid molecule encoding a polypeptide imparting to the plant a trait selected from the group consisting of an herbicide tolerance trait; an insect resistance trait; an agronomic trait; a disease resistance trait; a modified fatty acid trait; and a reduced phytate trait.

In some embodiments, a nucleic acid may be combined (or "stacked") in a plant with any other nucleic acid molecule, for example and without limitation, to provide additional resistance or tolerance to glyphosate or another herbicide, to provide resistance to select insects or diseases, to provide nutritional enhancements, to provide improved agronomic characteristics, and to provide a protein or other product useful in feed, food, industrial uses, pharmaceutical uses, and/or other uses. Examples include the stacking of two or more nucleic acids of interest within a plant genome. Such a "gene stack" may be accomplished via conventional plant breeding using two or more events, transformation of a plant with a construct that contains the sequences of interest, re-transformation of a transgenic plant, or addition of new traits through targeted integration via homologous recombination. Particular examples of such a stack include any combination of the following: a dgt-28 nucleic acid; a Cry34Ab1 nucleic acid; a Cry35Ab1 nucleic acid; a Cry1F nucleic acid; a Cry1Ac nucleic acid; an aad-12 nucleic acid; an aad-1 nucleic acid; a pat nucleic acid; and a DSM-2 nucleic acid.

In addition to the exemplary aspects and embodiments described above, further aspects and embodiments will become apparent by study of the following descriptions.

BRIEF DESCRIPTION OF THE FIGURES

FIG. 1 includes a partial sequence alignment of exemplary EPSP synthase enzymes (i.e., DGT-28, DGT-32, DGT-33, and others). All three of these exemplary DGT enzymes share a conserved alanine at the aroA EPSP synthase enzyme amino acid position 96. The location of this amino acid is indicated by an asterisk, and the amino acid residue is underlined.

FIG. 2 includes an alignment of exemplary DGT enzymes (i.e., DGT-1, DGT-3, and DGT-7). The location of a mutated amino acid residue that was changed from a glycine to an alanine is indicated by the first asterisk. The location of a second mutated amino acid residue that was changed from a threonine to an isoleucine is indicated by the second asterisk. The location of a third mutated amino acid residue that was changed from a proline to a serine is indicated by the third asterisk.

DETAILED DESCRIPTION

I. Overview

Figure 3:
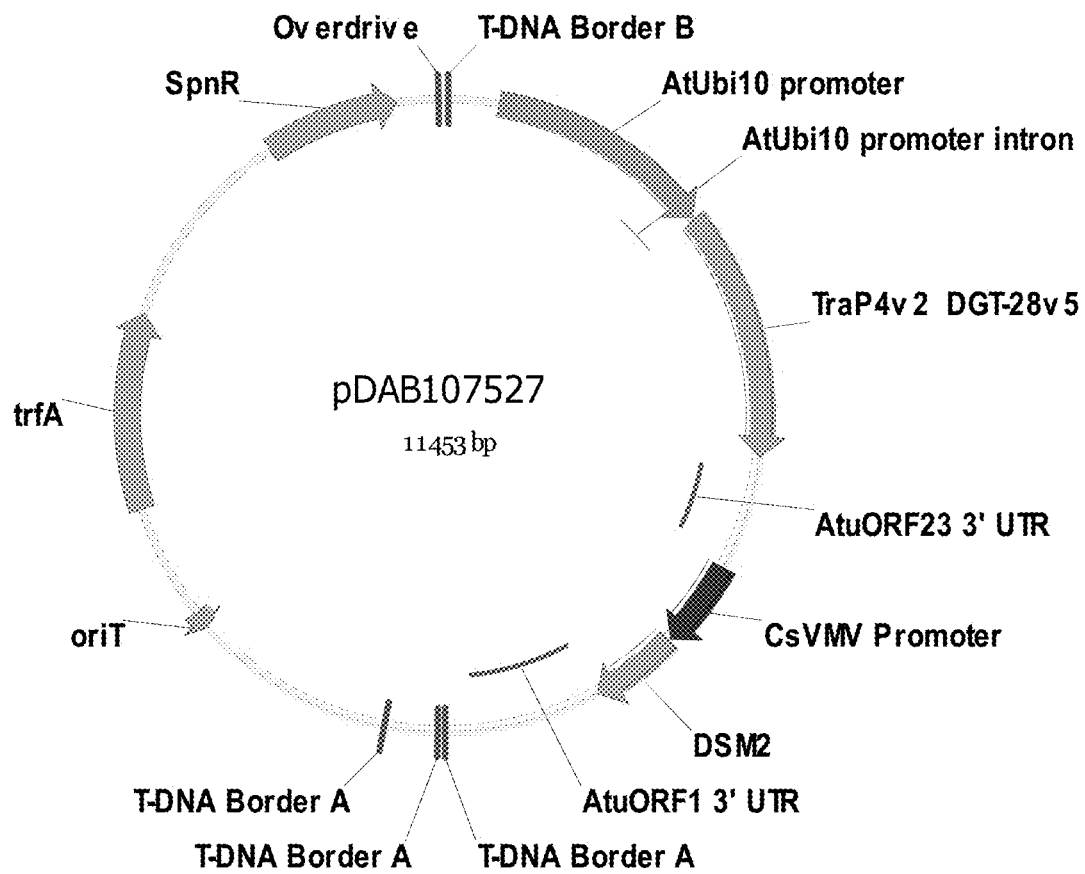
FIGS. 3-30 include maps of various exemplary plasmids: pDAB 107527 (FIG. 3); pDAB105530 (FIG. 4); pDAB105531 (FIG. 5); pDAB105532 (FIG. 6); pDAB105533 (FIG. 7); pDAB105534 (FIG. 8); pDAB4104 (FIG. 9); pDAB102715 (FIG. 10); pDAB107532 (FIG. 11); pDAB107534 (FIG. 12); pDAB102785 (FIG. 13); pDAB100445 (FIG. 14); pDAB102946 (FIG. 15); pDAB100469 (FIG. 16); pDAB102028 (FIG. 17); pDAB102029 (FIG. 18); pDAB102032 (FIG. 19); pDAB102034 (FIG. 20); pDAB100429 (FIG. 21); pDAB100442 (FIG. 22); pDAB100430 (FIG. 23); pDAB102036 (FIG. 24); pDAB102038 (FIG. 25); pDAB102040 (FIG. 26); pDAB102042 (FIG. 27); pDAB107712 (FIG. 28); pDAB107713 (FIG. 29); and pDAB107714 (FIG. 30).

Disclosed herein are novel polypeptides involved in metabolism of N-(phosphonomethyl) glycine, and nucleic acids encoding such polypeptides. In some examples, such a polypeptide confers (or increases) tolerance to glyphosate in a plant cell wherein the polypeptide is heterologously expressed, for example, without adversely affecting the binding of EPSP synthase with its natural substrate, phosphoenolpyruvate (PEP).

II. Terms

In order to further clarify the breadth of this disclosure, the following specific definitions, terms, and abbreviations are provided.

Unless specifically defined otherwise, all technical and scientific terms used herein have the same meaning as commonly understood by one of ordinary skill in the art. Unless otherwise clear from the context in which it appears, a singular term shall include pluralities, and plural terms are understood to include the singular. Thus, the indefinite articles "a" and "an," as used preceding an element or component are non-restrictive regarding the number of instances (i.e., occurrences) of the element or component. Where ranges of numerical values are provided herein (e.g., "less than about X," "less than X," and "for example, $X_1$ . . . and $X_2$"), the ranges are understood to include all values and ranges of values included within the provided range, as if these included values and ranges had been expressly recited.

All publications, patents, and other references mentioned herein are incorporated by reference in their entireties for all purposes, as if each individual publication or patent application were specifically and individually indicated to be incorporated by reference, unless only specific sections of patents or patent publications are indicated to be incorporated by reference.

As used herein, the terms "comprising," "including," "having," and "containing," and variations thereof, are open-ended (i.e., non-exclusive). For example, a composition or method that comprises a list of elements is not necessarily limited to only those elements. Such a composition or method may (or may not) include other elements not expressly listed or inherent to the composition or method. Further, unless expressly stated to the contrary, "or" is used in the inclusive (and not the exclusive) sense. For example, a condition "A or B" is satisfied by any of the following: A is true (or present) and B is false (or not present); A is false (or not present) and B is true (or present); and both A and B are true (or present).

Plant: As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

Herbicide resistance/tolerance: When referring to plants that are resistant or tolerant to glyphosate, it is meant that an application of an amount of glyphosate on the plant does not significantly affect or kill the plant, wherein a wild-type plant of the same species would be significantly affected and/or killed by the application of the amount of glyphosate.

A plant may be naturally tolerant to a particular herbicide, or a plant may be rendered herbicide tolerant as a result of genetic engineering, such as for example, selective breeding; genetic transformation; and/or the introduction of a transgene within the genome of the plant. A "glyphosate resistant plant" refers to a plant containing a polypeptide or nucleic acid molecule that confers herbicide tolerance when provided to a heterologous plant or other organism expressing it (i.e., that makes a plant or other organism herbicide-tolerant).

A plant that is resistant or tolerant to glyphosate may show some minimal impact from the application of glyphosate to the plant. For instance, there can be an alteration in the normal growth and development of the plant, wherein the plant may exhibit signs or symptoms that are associated with stress or disease. Such a minimal impact resulting from the application of glyphosate to plants that are resistant or tolerant to glyphosate is in contrast to the adverse impact that results from application of glyphosate to plants that are susceptible to glyphosate. One of skill in the art can distinguish between plants that are resistant to glyphosate and plants that are susceptible to glyphosate. Application of glyphosate to plants comprising a nucleic acid that confers glyphosate tolerance results in significantly less impact than application of the same amount of glyphosate to a plant of the same species that does not comprise a nucleic acid molecule that confers tolerance to glyphosate.

A plant that is tolerant to an herbicide or other chemical shows improved tolerance in comparison to an appropriate control plant. Damage resulting from herbicide or other chemical treatment may be assessed by evaluating any parameter of plant growth or well-being. Such parameters are known to those of skill in the art, and their selection is within the discretion of the skilled person. Plant damage can be assessed by visual inspection and/or by statistical analysis of one or more suitable parameter(s) of plant growth or well-being in individual plants or a group(s) of plants. Thus, damage may be assessed by evaluating parameters including, for example and without limitation: plant height; plant weight; leaf color; leaf length; flowering; fertility; silking; yield; and seed production. Damage may also be assessed by evaluating the time elapsed to a particular stage of development (e.g., silking, flowering, and pollen shed), or the time elapsed until a plant has recovered from treatment with a particular chemical and/or herbicide.

In making damage assessments, values may be assigned to particular degrees of damage so that statistical analysis or quantitative comparisons may be made. The use of ranges of values to describe particular degrees of damage is known in the art, and any suitable range or scale may be used. For example, herbicide injury scores (also called tolerance scores) may be assigned. Accordingly, herbicide tolerance may also indicated by other ratings in this scale, where an appropriate control plant (or group of control plants) exhibits a statistically lower score on the scale in response to an herbicide treatment than a group of subject plants.

Damage caused by an herbicide or other chemical can be assessed at various times after a plant has been treated with an herbicide. Often, damage is assessed at about the time that the control plant exhibits maximum damage. Sometimes, damage is assessed after a period of time over which a control plant that was not treated with herbicide or other chemical has measurably grown and/or developed in comparison to the size or stage at which the treatment was administered. Damage may be assessed at any of many suitable times, for example, at 12 hours; at 1, 2, 3, 4, 5, 6, 7, 8, 9, 10, 11, 12, 13, and/or 14 days; at 3 and/or 4 weeks; or longer, after a subject plant was treated with herbicide. Any time of assessment is suitable as long as it permits detection of a difference in response to a treatment of test and control plants.

A herbicide does not "significantly affect" a plant when it either has no effect on the plant, when it has some effect on the plant from which the plant later recovers, or when it has an effect on the plant that is detrimental but which is offset, for example, by the impact of the particular herbicide on weeds. Thus, for example, a crop plant may not be "significantly affected" by a herbicide or other treatment if the plant exhibits less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1% decrease in at least one suitable parameter that is indicative of plant health and/or productivity, in comparison to an appropriate control plant (e.g., an untreated plant of the same species). In particular embodiments, a plant is tolerant to a herbicide or other chemical if it shows damage in comparison to an appropriate control plant that is less than the damage exhibited by the control plant by at least 40%, 45%, 50%, 55%, 60%, 65%, 70%, 75%, 80%, 90%, 100%, 150%, 200%, 250%, 300%, 400%, 500%, 600%, 700%, 800%, 900%, or 1000% or more. A crop plant that is not significantly affected by an herbicide or other treatment may exhibit a decrease in at least one parameter, but the decrease is temporary in nature, and the plant recovers fully within, for example, about 1 week, about 2 weeks, about 3 weeks, about 4 weeks, or about 6 weeks. In particular embodiments, a plant that is tolerant to a herbicide or other chemical may be characterized by the fact that the plant is not significantly affected by application of the herbicide or other chemical.

Suitable parameters that are indicative of plant health and/or productivity include, for example and without limitation: plant height; plant weight; leaf length; time elapsed to a particular stage of development; flowering; yield; and seed production. The evaluation of a parameter may be performed by visual inspection and/or by statistical analysis of the parameter. Once evaluated in a subject plant and a control plant, a comparison may be made so as to determine if the subject plant is significantly affected by the herbicide or other treatment. if it.

Appropriate control plants that may be used to determine resistance to an herbicide (or other chemical) include plants of the same species that do not comprise a putative heterologous herbicide tolerance nucleic acid and/or polypeptide, and plants that do comprise the putative heterologous herbicide tolerance nucleic acid and/or polypeptide, but which have not been treated with the herbicide.

Herbicide: A "herbicide" is a chemical that causes temporary or permanent injury to a plant. Non-limiting examples of herbicides are listed and discussed in further detail elsewhere herein. A herbicide may be incorporated into a plant or its cells, or it may act on the plant or cells without being incorporated. An "active ingredient" is a chemical in a herbicide formulation that is responsible for the phytotoxicity of the formulation. Active ingredients in commercial herbicide formulations are typically identified as an active ingredient on the product label. Product label information is available from the U.S. Environmental Protection Agency, and is updated online at oaspub.epa.gov/pestlabl/ppls.own. Product label information is also available online at www.cdms.net.

When used in regard to an herbicide, the term "acid equivalent" refers to the rate or quantity as the herbicidal active parent acid.

Isolated: An "isolated" biological component (such as a nucleic acid or polypeptide) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid: The terms "polynucleotide," "nucleic acid," and "nucleic acid molecule" are used interchangeably herein, and encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single- and double-stranded DNA; DNA that is a mixture of single- and double-stranded regions; single- and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product.

As used herein, the term "coding sequence" refers to a nucleic acid sequence that encodes a specific amino acid sequence. A "regulatory sequence" refers to a nucleotide sequence located upstream (e.g., 5' non-coding sequences), within, or downstream (e.g., 3' non-coding sequences) of a coding sequence, which influence the transcription, RNA processing or stability, or translation of the associated coding sequence. Regulatory sequences include, for example and without limitation: promoters; translation leader sequences; introns; polyadenylation recognition sequences; RNA processing sites; effector binding sites; and stem-loop structures.

As used herein, the term "codon degeneracy" refers to redundancy in the genetic code that permits variation of a particular nucleotide sequence without affecting the amino acid sequence of the encoded polypeptide. Since each codon consists of three nucleotides, and the nucleotides comprising DNA are restricted to four specific bases, there are 64 possible combinations of nucleotides, 61 of which encode amino acids (the remaining three codons encode signals ending translation). As a result, many amino acids are designated by more than one codon. For example, the amino acids alanine and proline are coded for by four triplets, serine and arginine by six, whereas tryptophan and methionine are coded by just one triplet. The "genetic code" that shows which codons encode which amino acids is commonly known in the art. The degeneracy therein allows for the bases of a DNA to vary over a wide range without altering the amino acid sequence of the proteins encoded by the DNA.

In some embodiments herein, when designing a coding sequence for improved expression in a host cell, the gene is designed such that the frequency of codon usage therein approaches the frequency of the preferred codon usage of the host cell. Accordingly, the term "codon-optimized" refers to genes or coding sequences of nucleic acids for transformation of various hosts, wherein codons in the gene or coding sequence has been altered to reflect the typical codon usage of the host organism without altering the polypeptide encoded by the nucleic acid. In examples, such optimization includes replacing at least one, more than one, a significant number, and/or all of the codons in the gene or coding sequence with one or more codons that are more frequently used in the genes of that organism.

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored or designed for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available on the internet at kazusa.or.jp/codon/, and these tables can be adapted in a number of ways. See Nakamura et al. (2000) Nucl. Acids Res. 28:292. By utilizing a codon usage table, one of skill in the art can apply the frequencies corresponding to a given species to any given polypeptide sequence, to design and produce a synthetic nucleic acid fragment of a codon-optimized coding region which encodes the polypeptide, but which uses codons optimal for the species. Codon bias is reflected in the mean base composition of protein coding regions. For example, organisms having genomes with relatively low G+C contents utilize more codons having A or T in the third position of synonymous codons, whereas those having higher G+C contents utilize more codons having G or C in the third position. Further, it is thought that the presence of "minor" codons within an mRNA may reduce the absolute translation rate of that mRNA, especially when the relative abundance of the charged tRNA corresponding to the minor codon is low. An extension of this reasoning is that the diminution of translation rate by individual minor codons would be at least additive for multiple minor codons. Therefore, mRNAs having high relative contents of minor codons would have correspondingly low translation rates. This rate could be reflected by correspondingly low levels of the encoded protein.

The codon bias can be calculated as the frequency at which a single codon is used relative to the codons for all amino acids. Alternatively, the codon bias may be calculated as the frequency at which a single codon is used to encode a particular amino acid, relative to all the other codons for that amino acid (synonymous codons).

The term "percent identity" (or "% identity") refers to a relationship between two or more polypeptide sequences (or polynucleotide sequences), as determined by comparing the sequences. The percent identity may express the degree of sequence relatedness between polypeptide (or polynucleotide) sequences, as may be determined by the match between strings of such sequences. In general, identity refers to an exact nucleotide-to-nucleotide or amino acid-to-amino acid correspondence of two polynucleotides or polypeptide sequences, respectively. The percent identity of two sequences, whether nucleic acid or amino acid sequences, is the number of exact matches between two aligned sequences divided by the length of the shorter sequences and multiplied by 100. See Russell and Barton (1994) J. Mol. Biol. 244: 332-50.

Techniques for aligning nucleic acid and amino acid sequences and determining identity are known in the art, and include, for example and without limitation, those provided in: *Computational Molecular Biology* (1988) (Lesk, A. M., Ed.) Oxford University, NY; *Biocomputing: Informatics and Genome Projects* (1993) (Smith, D. W., Ed.) Academic, NY; *Computer Analysis of Sequence Data, Part I* (1994) (Griffin, A. M., and Griffin, H. G., Eds.) Humania, N.J.; *Sequence Analysis in Molecular Biology* (1987) (von Heinje, G., Ed.) Academic, NY; and *Sequence Analysis Primer* (1991) (Gribskov, M. and Devereux, J., Eds.) Stockton, N.Y. A technique for determining the percent identity between two sequences may include providing the nucleotide sequence of an mRNA or gene and/or providing or inferring the amino acid sequence encoded thereby, and comparing the sequence(s) to a second nucleotide and/or amino acid sequence. Genomic sequences can also be determined and compared in this fashion.

In addition, methods for aligning nucleic acid and amino acid sequences and determining identity are incorporated in various publicly available computer software programs. Sequence alignments and percent identity calculations can be performed, for example, using the AlignX™ program of the Vector NTI® suite (Invitrogen, Carlsbad, Calif.) or MegAlign™ program of the LASERGENE™ bioinformatics computing suite (DNASTAR™ Inc., Madison, Wis.). Multiple alignment of sequences may be performed using the Clustal™ method, which encompasses several varieties of an alignment algorithm, including Clustal™ V and Clustal™ W (Higgins and Sharp (1989) CABIOS 5:151-3; Higgins et al. (1992) Comput. Appl. Biosci. 8:189-91). For multiple alignments in Clustal™ V, default values that may be used include GAP PENALTY=10 and GAP LENGTH PENALTY=10. Default parameters for multiple alignment in Clustal™ W include (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). Default parameters for pairwise alignments and calculation of percent identity between protein sequences that may be used in a Clustal™ method are KTUPLE=1, GAP PENALTY=3, WINDOW=5, and DIAGONALS SAVED=5. For nucleic acids, these default parameters may be KTUPLE=2, GAP PENALTY=5, WINDOW=4, and DIAGONALS SAVED=4. After alignment of sequences using a Clustal™ program, it is possible to obtain a "percent identity" by viewing the "sequence distances" table in the same program.

In some embodiments, a nucleic acid encodes a polypeptide having a sequence identity (when compared to a reference polypeptide; e.g., a DGT polypeptide) of, for example and without limitation: at least about 55%; at least about 60%; at least about 65%; at least about 70%; at least about 75%; at least about 80%; at least about 85%; at least about 90%; and at least about 95%, has the same or similar function as the reference polypeptide. Accordingly, any integer percentage of identity from, for example, 55% to 100% may be useful in describing particular nucleic acids herein, for example and without limitation: 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. Certain nucleic acid fragments not only have the foregoing sequence identity, but may encode a polypeptide having, for example and without limitation: at least 50 amino acids; at least 100 amino acids; at least 150 amino acids; at least 200 amino acids; and at least 250 amino acids. Particular embodiments include a nucleic acid having at least about 90% identity to SEQ ID NO:1 (e.g., at least 89% identity; at least about 90% identity; at least about 91% identity; at least about 92% identity; at least about 93% identity; at least about 94% identity; at least about 95% identity; at least about 96% identity; at least about 97% identity; at least about 98% identity; at least about 99% identity; and at least about 99.5% identity).

The term "sequence analysis software" refers to a computer algorithm or software program that is useful for the analysis of nucleotide or amino acid sequences. "Sequence analysis software" may be commercially available or independently developed. Non-limiting examples of sequence analysis software includes: the GCG suite of programs (Wisconsin Package Version 9.0, Genetics Computer Group (GCG), Madison, Wis.); BLASTP™, BLASTN™, and BLASTX™ (Altschul et al. (1990) J. Mol. Biol. 215:403-10); DNASTAR™ (DNASTAR™, Inc. Madison, Wis.); Sequencher™ (Gene Codes Corporation, Ann Arbor, Mich.); and the FASTA™ program incorporating the Smith-Waterman algorithm (Pearson (1994) *Comput. Methods Genome Res.* [*Proc. Int. Symp.*], Meeting Date 1992 (Suhai and Sandor, Eds.), Plenum: New York, N.Y., pp. 111-20). Where sequence analysis software has been used to analyze a nucleotide or amino acid sequence herein, the results of the analysis shown have been generated using default values of the program referenced, unless otherwise specified. As used herein, the term "default values" refers to a set of values or parameters that originally loads with the sequence analysis software when it is first initialized.

Hybridization: A nucleic acid comprising all or part of a nucleotide sequence may be used as a probe that selectively "hybridizes" to nucleotide sequences present in a population of cloned genomic DNA fragments or cDNA fragments (e.g., genomic or cDNA libraries from a chosen organism) that have a significant amount of sequence identity to the probe sequence. A hybridization probe may be a genomic DNA fragment; a plasmid DNA fragment; a cDNA fragment; an RNA fragment; a PCR amplified DNA fragment; an oligonucleotide; or other polynucleotide, and a probe may be labeled with a detectable group (e.g., $^{32}$P), or any other detectable marker. Thus, for example and without limitation, a probe for hybridization may be made by labeling a synthetic oligonucleotide that specifically hybridizes to a nucleic acid herein (e.g., a nucleic acid having at least about 90% identity to SEQ ID NO:1). Methods for preparation of probes for hybridization, and for construction of cDNA and genomic libraries, are known in the art. Sambrook et al. (1989) *Molecular Cloning: A Laboratory Manual*, Second Edition, Cold Spring Harbor Laboratory Press, Cold Spring Harbor, N.Y. An extensive guide to the hybridization of nucleic acids can be found in Sambrook et al. (1989), supra; and Ausubel et al. (1997) *Short Protocols in Molecular Biology*, Third Edition, Wiley, N.Y., New York, pp. 2-40.

In some embodiments, nucleic acid hybridization (e.g., to amplified DNA) may be used to identify the presence of a transgenic event in a sample. Nucleic acid molecules or fragments thereof are capable of "specifically hybridizing" to another nucleic acid molecule under certain circumstances. In some examples, a nucleic acid specifically hybridizes under stringent conditions to a target nucleic acid. As used herein, two nucleic acid molecules are said to be capable of specifically hybridizing to one another if the two molecules are capable of forming an anti-parallel, double-stranded nucleic acid structure under stringent (e.g., high-stringency) conditions.

A nucleic acid is said to be the "complement" of another nucleic acid molecule if the two nucleic acid molecules exhibit complete sequence complementarity. As used herein, nucleic acids are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al. (1989), supra.

Two molecules are said to exhibit "minimal complementarity" if they can hybridize to one another with sufficient stability to permit them to remain annealed to one another under at least conventional "low-stringency" conditions. Conventional low-stringency conditions are also described by Sambrook et al. (1989), supra. In order for a nucleic acid molecule to serve as a primer or probe, it need only exhibit the minimal complementarity of sequence to be able to form a stable double-stranded structure under the particular solvent and salt concentrations employed.

Factors that affect the stringency of hybridization are well-known to those of skill in the art and include, for example: temperature; pH; ionic strength; and concentration of organic solvents (e.g., formamide and dimethylsulfoxide). As is known to those of skill in the art, hybridization stringency is increased by higher temperatures, lower ionic strength, and lower solvent concentrations. Stringent conditions may also be achieved with the addition of destabilizing agents such as formamide.

The term "stringent condition" or "stringency conditions" is defined with regard to the hybridization of one nucleic acid to another target nucleic acid (i.e., to a nucleic acid molecule comprising a particular nucleotide sequence of interest) by the specific hybridization procedure discussed in Sambrook et al. (1989), supra (at 9.52-9.55). See also Sambrook et al. (1989) at 9.47-9.52 and 9.56-9.58.

Specificity in many applications is related to the conditions of post-hybridization washes, wherein factors include the ionic strength and temperature of the wash solution. For DNA-DNA hybrids, the thermal melting point ($T_m$) can be approximated from the equation:

$$T_m = 81.5° C. + 16.6(\log M) + 0.41(\% \ GC) - 0.61(\% \ \text{form}) - 500/L, \quad (1)$$

where M is the molarity of monovalent cations, % GC is the percentage of guanosine and cytosine nucleotides in the DNA, % form is the percentage of formamide in the hybridization solution, and L is the length of the hybrid in base pairs. Meinkoth and Wahl (1984) Anal. Biochem. 138:267-84.

The $T_m$ is the temperature (under a particular ionic strength and pH) at which 50% of a complementary target sequence hybridizes to a perfectly matched probe. The $T_m$ is reduced by about 1° C. for each 1% of mismatching. Thus, $T_m$, hybridization, and/or wash conditions can be adjusted for sequences of the desired identity to hybridize. For example, if hybridization of sequences with 90% identity are sought, the $T_m$ can be decreased 10° C. (under a particular ionic strength and pH). Stringent conditions may, for example, be selected to be about 5° C. lower than the thermal melting point ($T_m$) for a specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11 to 20° C. lower than the $T_m$.

In some examples, stringent conditions are those in which the salt concentration is less than about 1.5 M Na$^+$ (e.g., about 0.01 to 1.0 M Na$^+$) at pH 7.0 to 8.3, and the temperature is at least about 30° C. for short nucleic acids (e.g., 10 to 50 nucleotides in length) and at least about 60° C. for long probes (e.g., greater than 50 nucleotides in length). Exemplary low stringency conditions include hybridization with a buffer solution of 30 to 35% formamide, 1.0 M NaCl, 0.1% sodium dodecyl sulfate (SDS) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 0.1% SDS at 37° C., and a wash in 0.5× to 1×SSC at 55 to 60° C. Exemplary high stringency conditions include hybridization in about 50% formamide, about 1.0 M Na salt, about 0.1% SDS at about 37° C., and a wash in about 0.1×SSC at about 60 to 65° C.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide," and the foregoing terms are used interchangeably with "polypeptide" herein. A polypeptide may be isolated from a natural biological source or produced by recombinant technology, but a specific polypeptide is not necessarily translated from a specific nucleic acid. A polypeptide may be generated in any appropriate manner, including for example and without limitation, by chemical synthesis.

Endogenous and Heterologous: As used herein, the term "native" refers to the form of a polynucleotide, gene or polypeptide that is found in nature with its own regulatory sequences, if present. The term "endogenous" refers to the native form of the polynucleotide, gene or polypeptide in its natural location in the organism or in the genome of the organism.

In contrast, the term "heterologous" refers to a polynucleotide, gene or polypeptide that is not normally found at its location in the reference (host) organism. For example, a heterologous nucleic acid may be a nucleic acid that is normally found in the reference organism at a different genomic location. By way of further example, a heterologous nucleic acid may be a nucleic acid that is not normally found in the reference organism. A host organism comprising a hetereologous polynucleotide, gene or polypeptide may be produced by introducing the heterologous polynucleotide, gene or polypeptide into the host organism. In particular examples, a heterologous polynucleotide comprises a native coding sequence, or portion thereof, that is reintroduced into a source organism in a form that is different from the corresponding native polynucleotide. In particular examples, a heterologous gene comprises a native coding sequence, or portion thereof, that is reintroduced into a source organism in a form that is different from the corresponding native gene. For example, a heterologous gene may include a native coding sequence that is a portion of a chimeric gene including non-native regulatory regions that is reintroduced into the native host. In particular examples, a heterologous polypeptide is a native polypeptide that is reintroduced into a source organism in a form that is different from the corresponding native polypeptide.

A heterologous gene or polypeptide may be a gene or polypeptide that comprises a functional polypeptide or nucleic acid sequence encoding a functional polypeptide that is fused to another genes or polypeptide to produce a chimeric or fusion polypeptide, or a gene encoding the same. Genes and proteins of particular embodiments include specifically exemplified full-length sequences and portions, segments, fragments (including contiguous fragments and internal and/or terminal deletions compared to the full-length molecules), variants, mutants, chimerics, and fusions of these sequences.

Modification: As used herein, the term "modification" may refer to a change in a particular reference polynucleotide that results in reduced, substantially eliminated, or eliminated activity of a polypeptide encoded by the reference polynucleotide. A modification may also refer to a change in a reference polypeptide that results in reduced, substantially eliminated, or eliminated activity of the reference polypeptide. Alternatively, the term "modification" may refer to a change in a reference polynucleotide that results in increased or enhanced activity of a polypeptide encoded by the reference polynucleotide, as well as a change in a reference polypeptide that results in increased or enhanced activity of the reference polypeptide. Changes such as the foregoing may be made by any of several methods well-known in the art including, for example and without limitation: deleting a portion of the reference molecule; mutating the reference molecule (e.g., via spontaneous mutagenesis, via random mutagenesis, via mutagenesis caused by mutator genes, and via transposon mutagenesis); substituting a portion of the reference molecule; inserting an element into the reference molecule; down-regulating expression of the reference molecule; altering the cellular location of the reference molecule; altering the state of the reference molecule (e.g., via methylation of a reference polynucleotide, and via phosphorylation or ubiquitination of a reference polypeptide); removing a cofactor of the reference molecule; introduction of an antisense RNA/DNA targeting the reference molecule; introduction of an interfering RNA/DNA targeting the reference molecule; chemical modification of the reference molecule; covalent modification of the reference molecule; irradiation of the reference molecule with UV radiation or X-rays; homologous recombination that alters the reference molecule; mitotic recombination that alters the reference molecule; replacement of the promoter of the reference molecule; and/or combinations of any of the foregoing.

Guidance in determining which nucleotides or amino acid residues may be modified in a specific example may be found by comparing the sequence of the reference polynucleotide or polypeptide with that of homologous (e.g., homologous yeast or bacterial) polynucleotides or polypeptides, and maximizing the number of modifications made in regions of high homology (conserved regions) or consensus sequences.

Derivative and Variant: The term "derivative," as used herein, refers to a modification of an exemplary sequence herein. Such modifications include the substitution, insertion, and/or deletion of one or more bases of a coding sequence herein that preserve, slightly alter, or increase the function of the coding sequence in a crop species. Such derivatives can be readily determined by one skilled in the art, for example and without limitation, by using computer modeling techniques for predicting and optimizing sequence structure. The term "derivative" thus also includes heterologous nucleic acids comprising a sequence having substantial sequence identity with an exemplary sequence herein, such that they may have the same, slightly altered, or increased functionality for use in expressing DGT-28 in a crop plant.

As used herein, the term "variant" refers to a polypeptide differing from an exemplary polypeptide herein by amino acid insertions, deletions, mutations, and/or substitutions, as may be introduced using, for example and without limitation, recombinant DNA techniques. Guidance in determining which amino acid residues may be replaced, added, or deleted within a reference amino acid sequence may be found by comparing the sequence of the particular reference polypeptide with that of homologous polypeptides, and minimizing the number of amino acid sequence changes made in regions of high homology (conserved regions), or by replacing amino acids with a consensus sequence. A variant polypeptide may have substituted amino acids, and yet retain the functional activity of the reference polypeptide. "Variant" genes comprise a nucleotide sequence that encodes the same polypeptide as a reference gene or an equivalent polypeptide that has an activity equivalent or similar to the reference polypeptide.

In some embodiments, variant genes can be used to produce variant proteins, and recombinant hosts can be used to produce the variant proteins. For example, variant genes and proteins can be constructed that comprise contiguous residues (amino acid or nucleotide) of any exemplified sequence herein. A variant gene or protein may have, for example and without limitation: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, and 293 contiguous residues (amino acid or nucleotide) that correspond to a segment (of the same size) in the exemplified sequence. Similarly sized segments, especially those for conserved regions, can also be used as probes and/or primers.

It is understood by those of skill in the art that many levels of sequence identity are useful in identifying polypeptides (e.g., from other species) that have the same or similar function or activity as a reference polypeptide. In some embodiments, a variant polypeptide having a sequence identity (when compared to a reference polypeptide; e.g., a DGT-28 polypeptide) of, for example and without limitation: at least about 55%; at least about 60%; at least about 65%; at least about 70%; at least about 75%; at least about 80%; at least about 85%; at least about 90%; and at least about 95%, has the same or similar function as the reference polypeptide.

Strategies for designing and constructing variant genes and proteins that comprise contiguous residues of a particular molecule can be determined by obtaining and examining the structure of a protein of interest (e.g., atomic 3-D (three dimensional) coordinates from a crystal structure and/or a molecular model). In some examples, a strategy may be directed to certain segments of a protein that are ideal for modification, such as surface-exposed segments, and not internal segments that are involved with protein folding and essential 3-D structural integrity. U.S. Pat. No. 5,605,793, for example, relates to methods for generating additional molecular diversity by using DNA reassembly after random or focused fragmentation. This can be referred to as gene "shuffling," which typically involves mixing fragments (of a desired size) of two or more different DNA molecules, followed by repeated rounds of renaturation. This process may improve the activity of a protein encoded by a subject gene. The result may be a chimeric protein having improved activity, altered substrate specificity, increased enzyme stability, altered stereospecificity, or other characteristics.

An amino acid "substitution" can be the result of replacing one amino acid in a reference sequence with another amino acid having similar structural and/or chemical properties (i.e., conservative amino acid substitution), or it can be the result of replacing one amino acid in a reference sequence with an amino acid having different structural and/or chemical properties (i.e., non-conservative amino acid substitution). Amino acids can be placed in the following structural and/or chemical classes: non-polar; uncharged polar; basic; and acidic. Accordingly, "conservative" amino acid substitutions can be made on the basis of similarity in polarity, charge, solubility, hydrophobicity, hydrophilicity, or the amphipathic nature of the residues involved. For example, non-polar (hydrophobic) amino acids include glycine, alanine, leucine, isoleucine, valine, proline, phenylalanine, tryptophan, and methionine; uncharged (neutral) polar amino acids include serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions can be made by selecting the differences in the polarity, charge, solubility, hydrophobicity, hydrophilicity, or amphipathic nature of any of these amino acids. "Insertions" or "deletions" can be within the range of variation as structurally or functionally tolerated by the recombinant proteins.

In some embodiments, a variant protein is "truncated" with respect to a reference, full-length protein. In some examples, a truncated protein retains the functional activity of the reference protein. By "truncated" protein, it is meant that a portion of a protein may be cleaved off, for example, while the remaining truncated protein retains and exhibits the desired activity after cleavage. Cleavage may be achieved by any of various proteases. Furthermore, effectively cleaved proteins can be produced using molecular biology techniques, wherein the DNA bases encoding a portion of the protein are removed from the coding sequence, either through digestion with restriction endonucleases or other techniques available to the skilled artisan. A truncated protein may be expressed in a heterologous system, for example, E. coli, baculoviruses, plant-based viral systems, and yeast. Truncated proteins conferring herbicide tolerance may be confirmed by using the heterologous system expressing the protein in a herbicide tolerance bioassay, such as described herein. It is well-known in the art that truncated proteins can be successfully produced so that they retain the functional activity of the full-length reference protein. For example, Bt proteins can be used in a truncated (core protein) form. See, e.g., Hofte and Whiteley (1989) Microbiol. Rev. 53(2):242-55; and Adang et al. (1985) Gene 36:289-300.

In some cases, especially for expression in plants, it can be advantageous to use truncated genes that express truncated proteins. Truncated genes may encode a polypeptide comprised of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein.

The variant genes and proteins that retain the function of the reference sequence from which they were designed may be determined by one of skill in the art, for example, by assaying recombinant variants for activity. If such an activity assay is known and characterized, then the determination of functional variants requires only routine experimentation.

Specific changes to the "active site" of an enzyme may be made to affect the its inherent functionality with respect to activity or stereospecificity. See Muller et. al. (2006) Protein Sci. 15(6):1356-68. For example, the known tauD structure has been used as a model dioxygenase to determine active site residues while bound to its inherent substrate, taurine. See Elkins et al. (2002) Biochemistry 41(16):5185-92. Further information regarding sequence optimization and designability of enzyme active sites can be found in Chakrabarti et al. (2005) Proc. Natl. Acad. Sci. USA 102(34):12035-40.

Various structural properties and three-dimensional features of a protein may be changed without adversely affecting the activity/functionality of the protein. Conservative amino acid substitutions can be made that do not adversely affect the activity and/or three-dimensional configuration of the molecule ("tolerated" substitutions). Variant proteins can also be designed that differ at the sequence level from the reference protein, but which retain the same or similar overall essential three-dimensional structure, surface charge distribution, and the like. See, e.g., U.S. Pat. No. 7,058,515; Larson et al. (2002) Protein Sci. 11:2804-13; Crameri et al.

(1997) Nat. Biotechnol. 15:436-8; Stemmer (1994) Proc. Natl. Acad. Sci. USA 91:10747-51; Stemmer (1994) Nature 370:389-91; Stemmer (1995) Bio/Technology 13:549-53; Crameri et al. (1996) Nat. Med. 2:100-3; and Crameri et al. (1996) Nat. Biotechnol. 14: 315-9.

Computational design of 5' or 3' UTRs (e.g., synthetic hairpins) that are suitable for use in an expression construct (e.g., a DGT-28 expression construct) may also be performed, and may be used to design elements within nucleic acids of some embodiments herein. Computer modeling and UTRs and computer modeling techniques for use in predicting/evaluating 5' and 3' UTR derivatives include, for example and without limitation: MFoLd™ version 3.1 (available from Genetics Corporation Group, Madison, Wis.; see Zucker et al. "Algorithms and Thermodynamics for RNA Secondary Structure Prediction: A Practical Guide," in *RNA Biochemistry and Biotechnology*, 11-43, J. Barciszewski & B. F. C. Clark, eds., NATO ASI Series, Kluwer Academic Publishers, Dordrecht, N L, 1999; Zucker et al. (1999) J. Mol. Biol. 288:911-40; Zucker et al. "RNA Secondary Structure Prediction," in *Current Protocols in Nucleic Acid Chemistry*, S. Beaucage, D. E. Bergstrom, G. D. Glick, and R. A. Jones eds., John Wiley & Sons, New York, 11.2.1-11.2.10, 2000); and COVE™ (RNA structure analysis using covariance models (stochastic context free grammar methods)) v.2.4.2 (Eddy and Durbin (1994) Nucl. Acids Res. 22:2079-88), which is freely distributed as source code and which can be downloaded by accessing the website, genetics.wustl.edu/eddy/software/; and FOLDALIGN™ (see Gorodkin et al. (1997) Nucleic Acids Res. 25(18):3724-32 and Gorodkin et al. (1997) Proceedings International Conference on Intelligent Systems for Molecular Biology ISMB International Conference on Intelligent Systems for Molecular Biology 5:120-123), also freely distributed and available for downloading at the website, foldalign.ku.dk/software/index.html.

Promoter: The term "promoter" refers to a DNA sequence capable of controlling the expression of a nucleic acid coding sequence or functional RNA. In examples, the controlled coding sequence is located 3' to a promoter sequence. A promoter may be derived in its entirety from a native gene, a promoter may be comprised of different elements derived from different promoters found in nature, or a promoter may even comprise synthetic DNA segments. It is understood by those skilled in the art that different promoters can direct the expression of a gene in different tissues or cell types, or at different stages of development, or in response to different environmental or physiological conditions. Examples of all of the foregoing promoters are known and used in the art to control the expression of heterologous nucleic acids. Promoters that direct the expression of a gene in most cell types at most times are commonly referred to as "constitutive promoters." Furthermore, while those in the art have (in many cases unsuccessfully) attempted to delineate the exact boundaries of regulatory sequences, it has come to be understood that DNA fragments of different lengths may have identical promoter activity. The promoter activity of a particular nucleic acid may be assayed using techniques familiar to those in the art.

Operably linked: The term "operably linked" refers to an association of nucleic acid sequences on a single nucleic acid, wherein the function of one of the nucleic acid sequences is affected by another. For example, a promoter is operably linked with a coding sequence when the promoter is capable of effecting the expression of that coding sequence (e.g., the coding sequence is under the transcriptional control of the promoter). A coding sequence may be operably linked to a regulatory sequence in a sense or antisense orientation.

Expression: The term "expression," as used herein, may refer to the transcription and stable accumulation of sense (mRNA) or antisense RNA derived from a DNA. Expression may also refer to translation of mRNA into a polypeptide. As used herein, the term "overexpression" refers to expression that is higher than endogenous expression of the same gene or a related gene. Thus, a heterologous gene is "overexpressed" if its expression is higher than that of a comparable endogenous gene.

Transformation: As used herein, the term "transformation" refers to the transfer and integration of a nucleic acid or fragment thereof into a host organism, resulting in genetically stable inheritance. Host organisms containing a transforming nucleic acid are referred to as "transgenic," "recombinant," or "transformed" organisms. Known methods of transformation include, for example: *Agrobacterium tumefaciens*- or *A. rhizogenes*-mediated transformation; calcium phosphate transformation; polybrene transformation; protoplast fusion; electroporation; ultrasonic methods (e.g., sonoporation); liposome transformation; microinjection; transformation with naked DNA; transformation with plasmid vectors; transformation with viral vectors; biolistic transformation (microparticle bombardment); silicon carbide WHISKERS-mediated transformation; aerosol beaming; and PEG-mediated transformation.

Introduced: As used herein, the term "introduced" (in the context of introducing a nucleic acid into a cell) includes transformation of a cell, as well as crossing a plant comprising the nucleic acid with a second plant, such that the second plant contains the nucleic acid, as may be performed utilizing conventional plant breeding techniques. Such breeding techniques are known in the art. For a discussion of plant breeding techniques, see Poehlman (1995) *Breeding Field Crops,* 4th Edition, AVI Publication Co., Westport Conn.

Backcrossing methods may be used to introduce a nucleic acid into a plant. This technique has been used for decades to introduce traits into plants. An example of a description of backcrossing (and other plant breeding methodologies) can be found in, for example, Poelman (1995), supra; and Jensen (1988) *Plant Breeding Methodology*, Wiley, New York, N.Y. In an exemplary backcross protocol, an original plant of interest (the "recurrent parent") is crossed to a second plant (the "non-recurrent parent") that carries the a nucleic acid be introduced. The resulting progeny from this cross are then crossed again to the recurrent parent, and the process is repeated until a converted plant is obtained, wherein essentially all of the desired morphological and physiological characteristics of the recurrent parent are recovered in the converted plant, in addition to the nucleic acid from the non-recurrent parent.

Plasmid/vector: The terms "plasmid" and "vector," as used herein, refer to an extra chromosomal element that may carry one or more gene(s) that are not part of the central metabolism of the cell. Plasmids and vectors typically are circular double-stranded DNA molecules. However, plasmids and vectors may be linear or circular nucleic acids, of a single- or double-stranded DNA or RNA, and may be derived from any source, in which a number of nucleotide sequences have been joined or recombined into a unique construction that is capable of introducing a promoter fragment and a coding DNA sequence along with any appropriate 3' untranslated sequence into a cell. In examples, plasmids and vectors may comprise autonomously replicating sequences, genome integrating sequences, and/or phage or nucleotide sequences.

III. DGT-28 and DGT-28-Encoding Sequences

Some embodiments herein provide an isolated polypeptide having at least about 90% identity (e.g., 89%, at least 90%, at least 91%, at least 92%, at least 93%, at least 94%, at least 95%, at least 96%, at least 97%, at least 98%, and at least 99% identity) to SEQ ID NO:1. Such a polypeptide is referred to herein as a DGT-28 polypeptide. Some embodiments herein provide a nucleic acid encoding a polypeptide having at least about 90% identity to SEQ ID NO:1. Particular examples of such a nucleic acid are referred to herein as a "dgt-28" nucleic acid. Dgt-28 nucleic acids may be useful in any of a wide variety of applications (e.g., introducing glyphosate resistance) in which modified glyphosate metabolism is desired in a plant cell.

Particular examples of dgt-28 nucleic acids provided for illustrative purposes herein are SEQ ID NOs:2 and 3. Accordingly, some embodiments provide a nucleic acid comprising a nucleotide sequence having at least about 80% sequence identity (e.g., 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, and at least 99% identity) to SEQ ID NO:2 or SEQ ID NO:3, wherein the nucleic acid encodes a polypeptide having at least about 90% identity to SEQ ID NO:1. Particular examples of dgt-28 nucleic acids include nucleic acids that specifically hybridize to a nucleic acid having SEQ ID NO:2 or SEQ ID NO:3 under stringent (e.g., highly-stringent) conditions.

In some embodiments, codon-optimized dgt-28 nucleic acids are provided. For example, to obtain high expression of a heterologous gene in a plant it may be desirable to design and reengineer the gene so that it is more efficiently expressed in a cell of the plant. This strategy may be particularly desirable in the circumstance where a bacterial gene is desired to be expressed in a plant cell.

Thus, some examples herein provide a plant-optimized gene encoding a DGT-28 protein, and methods for the desing thereof, to generate a DNA sequence that can be expressed optimally in dicotyledonous or monocotyledonous plants, and in which the sequence modifications do not hinder translation or transcription. Design of an optimized dgt-28 gene for expression of the same DGT-28 protein in both monocotyledonous and dicotyledonous plants is exemplified herein with a reengineering of the protein coding region of this gene for optimal expression. Exemplary plant-optimized dgt-28 nucleic acids herein include SEQ ID NO:2 and SEQ ID NO:3.

In engineering a gene encoding a DGT-28 protein for expression in dicotyledonous or monocotyledonous plants (e.g., cotton, canola, tobacco, corn, soybean, wheat and rice), the codon bias of the prospective host plant(s) may be determined, for example, through use of publicly available DNA sequence databases to find information about the codon distribution of plant genomes or the protein coding regions of various plant genes.

In designing coding regions in a nucleic acid for plant expression, the primary ("first choice") codons preferred by the plant should be determined, as well may be the second, third, fourth, etc. choices of preferred codons when multiple choices exist. A new DNA sequence can then be designed which encodes the amino acid sequence of the same peptide (e.g., a DGT-28 protein), but the new DNA sequence differs from the original DNA sequence by the substitution of plant (first preferred, second preferred, third preferred, or fourth preferred, etc.) codons to specify the amino acid at each position within the amino acid sequence.

The new sequence may then be analyzed for restriction enzyme sites that might have been created by the modifications. The identified sites may be further modified by replacing the codons with first, second, third, or fourth choice preferred codons. Other sites in the sequence that could affect transcription or translation of the gene of interest are stem-loop structures, exon:intron junctions (5' or 3'), poly A addition signals, and RNA polymerase termination signals; these sites may be removed by the substitution of plant codons. The sequence may be further analyzed and modified to reduce the frequency of TA or CG doublets. In addition to the doublets, G or C sequence blocks that have more than about six residues that are the same can affect transcription or translation of the sequence. Therefore, these blocks may be modified by replacing the codons of first or second choice, etc. with the next preferred codon of choice.

SEQ ID NO: 2 (dgt-28 (v5)) was optimized for expression in dicotyledonous plants. SEQ ID NO: 3 (dgt-28 (v6)) was optimized for expression in monocotyledonous plants. The codon usage in these synthetic sequences was selected based upon preferred codon usage; i.e., the expression products of each are encoded by codons having a bias toward either monocot or dicot plant usage, and deleterious sequences and superfluous restriction sites were removed to increase the efficiency of transcription/translation of the DGT-28 polypeptide and to facilitate DNA manipulation steps.

Likewise, the nucleic acid molecule of SEQ ID NO: 4 (dgt-28 (v1)) was optimized to improve expression in *Escherichia coli*. Codon usage in SEQ ID NO:4 was selected based upon preferred *E. coli* codon usage; the expressed protein is encoded by codons having a bias toward *E. coli* usage. During the redesign, deleterious sequences and superfluous restriction sites were removed to increase the efficiency of transcription/translation of the DGT-28 coding sequence and to facilitate DNA manipulation steps. Thus, expression of DGT-28 from a nucleic acid comprising SEQ ID NO:4 in *E. coli* may result in robust protein expression, for example, for enzymatic characterization of DGT-28.

Once an optimized (e.g., a plant-optimized) DNA sequence has been designed on paper, or in silico, actual DNA molecules may be synthesized in the laboratory to correspond in sequence precisely to the designed sequence. Such synthetic nucleic acid molecule molecules can be cloned and otherwise manipulated exactly as if they were derived from natural or native sources.

A nucleic acid herein may be cloned into a vector for transformation into prokaryotic or eukaryotic cells for replication and/or expression. Vectors may be prokaryotic vectors; e.g., plasmids, or shuttle vectors, insect vectors, or eukaryotic vectors. A nucleic acid herein may also be cloned into an expression vector, for example, for administration to a plant cell. In certain applications, it may be preferable to have vectors that are functional in *E. coli* (e.g., production of protein for raising antibodies, DNA sequence analysis, construction of inserts, obtaining quantities of nucleic acids).

To express a DGT-28 protein in a cell, a nucleic acid encoding the protein is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001);

Kriegler, *Gene Transfer and Expression: A Laboratory Manual* (1990); and *Current Protocols in Molecular Biology* (Ausubel et al., supra.). Bacterial expression systems for expressing a nucleic acid herein are available in, for example, *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The particular expression vector used to transport the genetic information into the cell is selected with regard to the intended use of the DGT-28 protein (e.g., expression in plants, animals, bacteria, fungus, and protozoa). Standard bacterial and animal expression vectors are known in the art and are described in detail, for example, U.S. Patent Publication 20050064474A1 and International Patent Publications WO 05/084190, WO05/014791 and WO03/080809. Standard transfection methods can be used to produce bacterial cell lines that express large quantities of protein, which can then be purified using standard techniques.

The selection of a promoter used to direct expression of a nucleic acid herein depends on the particular application. A number of promoters that direct expression of a gene in a plant may be employed in embodiments herein. Such promoters can be selected from constitutive, chemically-regulated, inducible, tissue-specific, and seed-preferred promoters. For example, a strong constitutive promoter suited to the host cell may be used for expression and purification of DGT-28 proteins. Non-limiting examples of plant promoters include promoter sequences derived from *A. thaliana* ubiquitin-10 (ubi-10) (Callis, et al., 1990, *J. Biol. Chem.*, 265: 12486-12493); *A. tumefaciens* mannopine synthase (Δmas) (Petolino et al., U.S. Pat. No. 6,730,824); and/or Cassava Vein Mosaic Virus (CsVMV) (Verdaguer et al., 1996, Plant Molecular Biology 31:1129-1139).

Constitutive promoters include, for example, the core Cauliflower Mosaic Virus 35S promoter (Odell et al. (1985) Nature 313:810-812); Rice Actin promoter (McElroy et al. (1990) Plant Cell 2:163-171); Maize Ubiquitin promoter (U.S. Pat. No. 5,510,474; Christensen et al. (1989) Plant Mol. Biol. 12:619-632 and Christensen et al. (1992) Plant Mol. Biol. 18:675-689); pEMU promoter (Last et al. (1991) Theor. Appl. Genet. 81:581-588); ALS promoter (U.S. Pat. No. 5,659,026); Maize Histone promoter (Chabouté et al. Plant Molecular Biology, 8:179-191 (1987)); and the like.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form, which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically, the protein factor that binds specifically to an inducible regulatory element to activate transcription is present in an inactive form which is then directly or indirectly converted to the active form by the inducer. A plant cell containing an inducible regulatory element may be exposed to an inducer by externally applying the inducer to the cell or plant such as by spraying, watering, heating or similar methods.

Any inducible promoter can be used in embodiments herein. See Ward et al. Plant Mol. Biol. 22: 361-366 (1993). Inducible promoters include, for example and without limitation: ecdysone receptor promoters (U.S. Pat. No. 6,504,082); promoters from the ACE1 system which respond to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); Tet repressor from Tn10 (Gatz et al., Mol. Gen. Genet. 227: 229-237 (1991); promoters from a steroid hormone gene, the transcriptional activity of which is induced by a glucocorticosteroid hormone, Schena et al., Proc. Natl. Acad. Sci. U.S.A. 88: 10421 (1991) and McNellis et al., (1998) Plant J. 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-la promoter, which is activated by salicylic acid (see Ono S, Kusama M, Ogura R, Hiratsuka K., "Evaluation of the Use of the Tobacco PR-la Promoter to Monitor Defense Gene Expression by the Luciferase Bioluminescence Reporter System," Biosci Biotechnol Biochem. 2011 Sep. 23; 75(9):1796-800). Other chemical-regulated promoters of interest include tetracycline-inducible and tetracycline-repressible promoters (see, for example, Gatz et al., (1991) Mol. Gen. Genet. 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; the light-inducible promoter derived from the pea rbcS gene or pea psaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138); a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991).

Stress inducible promoters include salt/water stress-inducible promoters such as P5CS (Zang et al. (1997) Plant Sciences 129:81-89); cold-inducible promoters, such as cor15a (Hajela et al. (1990) Plant Physiol. 93:1246-1252), cor15b (Wilhelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), and ci21A (Schneider et al. (1997) Plant Physiol. 113:335-45); drought-inducible promoters, such as Trg-31 (Chaudhary et al. (1996) Plant Mol. Biol. 30:1247-57) and rd29 (Kasuga et al. (1999) Nature Biotechnology 18:287-291); osmotic inducible promoters, such as Rab17 (Vilardell et al.

(1991) Plant Mol. Biol. 17:985-93) and osmotin (Raghothama et al. (1993) Plant Mol Biol 23:1117-28); heat inducible promoters, such as heat shock proteins (Barros et al. (1992) Plant Mol. 19:665-75; Marrs et al. (1993) Dev. Genet. 14:27-41), smHSP (Waters et al. (1996) J. Experimental Botany 47:325-338); and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the *Agrobacterium* pMAS promoter (Guevara-Garcia et al. (1993) Plant J. 4(3):495-505) and the *Agrobacterium* ORF13 promoter (Hansen et al., (1997) Mol. Gen. Genet. 254(3):337-343).

Tissue-preferred promoters may be utilized to target enhanced transcription and/or expression within a particular plant tissue. Examples of these types of promoters include seed-preferred expression, such as that provided by the phaseolin promoter (Bustos et al. 1989. *The Plant Cell* Vol. 1, 839-853), and the maize globulin-1 gene, Belanger, et al. 1991 Genetics 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al. 1994. T-DNA tagging of a seed coat-specific cryptic promoter in tobacco. Plant J. 4: 567-577), the P-gene promoter from corn (Chopra et al. 1996. Alleles of the maize P gene with distinct tissue specificities encode Myb-homologous proteins with C-terminal replacements. Plant Cell 7:1149-1158, Erratum in Plant Cell.1997, 1:109), the globulin-1 promoter from corn (Belenger and Kriz.1991. Molecular basis for Allelic Polymorphism of the maize Globulin-1 gene. Genetics 129: 863-972), and promoters that direct expression to the seed coat or hull of corn kernels, for example the pericarp-specific glutamine synthetase promoter (Muhitch et al., 2002. Isolation of a Promoter Sequence From the Glutamine Synthetase$_{1-2}$ Gene Capable of Conferring Tissue-Specific Gene Expression in Transgenic Maize. Plant Science 163:865-872).

In addition to the promoter, an expression vector typically contains a transcription unit or expression cassette that contains all the additional elements required for the expression of the nucleic acid in host cells, either prokaryotic or eukaryotic. A typical expression cassette thus contains a promoter operably-linked, e.g., to a nucleic acid sequence encoding the protein, and signals required, e.g., for efficient polyadenylation of the transcript, transcriptional termination, ribosome binding sites, or translation termination. Additional elements of the cassette may include, e.g., enhancers and heterologous splicing signals.

Other components of the vector may be included, also depending upon intended use of the gene. Examples include selectable markers, targeting or regulatory sequences, transit peptide sequences such as the optimized transit peptide sequence (see U.S. Pat. No. 5,510,471) stabilizing sequences such as RB7 MAR (see Thompson and Myatt, (1997) *Plant Mol. Biol.*, 34: 687-692 and WO9727207) or leader sequences, introns etc. General descriptions and examples of plant expression vectors and reporter genes can be found in Gruber, et al., "Vectors for Plant Transformation" in *Methods in Plant Molecular Biology and Biotechnology*, Glick et al. eds; CRC Press pp. 89-119 (1993).

The selection of an appropriate expression vector will depend upon the host and the method of introducing the expression vector into the host. The expression cassette may include, at the 3' terminus of a heterologous nucleotide sequence of interest, a transcriptional and translational termination region functional in plants. The termination region can be native with the DNA sequence of interest or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp7831-7846 (nos)); see also Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al. Nucleic Acids Res. 17:7891-7903 (1989); Joshi et al. Nucleic Acid Res. 15:9627-9639 (1987).

An expression cassette may contain a 5' leader sequence. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154:9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987).

The construct may also contain sequences that enhance translation and/or mRNA stability such as introns. An example of one such intron is the first intron of gene II of the histone H3.III variant of *Arabidopsis thaliana*. Chaubet et al. Journal of Molecular Biology, 225:569-574 (1992).

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (see Lebrun et al. U.S. Pat. No. 5,510,417), Zea mays Brittle-1 chloroplast transit peptide (Nelson et al. Plant Physiol 117(4):1235-1252 (1998); Sullivan et al. Plant Cell 3(12):1337-48; Sullivan et al., Planta (1995) 196(3):477-84; Sullivan et al., J. Biol. Chem. (1992) 267(26):18999-9004) and the like. In addition, chimeric chloroplast transit peptides are known in the art, such as the Optimized Transit Peptide (see, U.S. Pat. No. 5,510,471). Additional chloroplast transit peptides have been described previously in U.S. Pat. Nos. 5,717,084; 5,728,925. One skilled in the art will readily appreciate the many options available in expressing a product to a particular organelle. For example, the barley alpha amylase sequence is often used to direct expression to the endoplasmic reticulum. Rogers, J. Biol. Chem. 260:3731-3738 (1985).

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, stable integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno or Kozak sequences), modification of nucleic acid molecules to correspond to the codon usage of the host cell, and deletion of sequences that destabilize transcripts.

Reporter or marker genes for selection of transformed cells or tissues or plant parts or plants may be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, 1983; Meijer et al., Plant Mol. Biol. 16:807-820, 1991); neomycin phosphotransferase, which confers resistance to the aminoglycosides neomycin, kanamycin and paromycin (Herrera-Estrella, EMBO J. 2:987-995, 1983 and Fraley et al. Proc. Natl. Acad. Sci USA 80:4803 (1983)); hygromycin phosphotransferase, which confers resistance to hygromycin (Marsh, Gene 32:481-485, 1984; see also Waldron et al., Plant Mol. Biol. 5:103-108, 1985; Zhijian et al., Plant Science 108:219-227, 1995); trpB, which allows cells to utilize indole in place of tryptophan; hisD, which allows cells to utilize histinol in place of histidine (Hartman, Proc. Natl. Acad. Sci., USA 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.); and deaminase from *Aspergillus terreus*, which confers resistance to Blasticidin S (Tamura, Biosci. Biotechnol. Biochem. 59:2336-2338, 1995).

Additional selectable markers include, for example, a mutant acetolactate synthase, which confers imidazolinone or sulfonylurea resistance (Lee et al., EMBO J. 7:1241-1248, 1988), a mutant psbA, which confers resistance to atrazine (Smeda et al., Plant Physiol. 103:911-917, 1993), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, 1983); streptomycin (Jones et al., Mol. Gen. Genet. 210:86-91, 1987); spectinomycin (Bretagne-Sagnard et al., Transgenic Res. 5:131-137, 1996); bleomycin (Hille et al., Plant Mol. Biol. 7:171-176, 1990); sulfonamide (Guerineau et al., Plant Mol. Biol. 15:127-136, 1990); bromoxynil (Stalker et al., Science 242:419-423, 1988); glyphosate (Shaw et al., Science 233:478-481, 1986); phosphinothricin (DeBlock et al., EMBO J. 6:2513-2518, 1987), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) Gene 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. In a preferred embodiment, the marker used is beta-carotene or provitamin A (Ye et al, Science 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, The Plant Cell (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., Plant Cell (1996) 8: 1171-1179; Scheffler et al. Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al. Proc. Natl. Acad. Sci USA (1991) 88:4587-4591; Grotewold et al., Cell (1994) 76:543-553; Sidorenko et al., Plant Mol. Biol. (1999) 39:11-19); the bronze locus genes (Ralston et al., Genetics (1988) 119:185-197; Nash et al., Plant Cell (1990) 2(11): 1039-1049), among others.

Further examples of suitable markers include the cyan fluorescent protein (CYP) gene (Bolte et al. (2004) J. Cell Science 117: 943-54 and Kato et al. (2002) Plant Physiol 129: 913-42), the yellow fluorescent protein gene (PHI-YFP™ from Evrogen; see Bolte et al. (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al. (2002) Biotechniques 2(2):286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available and known to one skilled in the art.

IV. Cells and Organisms Comprising DGT-28

In some embodiments, a cell and/or organism (e.g., a plant cell or plant) is provided that comprises a heterologous polypeptide having at least 90% identity to SEQ ID NO:1. In particular embodiments, a cell and/or organism is provided that comprises a heterologous nucleic acid encoding a polypeptide having at least 90% identity to SEQ ID NO:1; e.g., a dgt-28 nucleic acid. Some embodiments include a cell and/or organism comprising a heterologous nucleic acid that hybridizes to another nucleic acid having SEQ ID NO:2 or SEQ ID NO:3 under high-stringency conditions.

A plant cell, plant part, and/or plant may be genetically modified to comprise a heterologous polypeptide (e.g., a DGT-28 protein) and/or heterologous nucleic acid (e.g., a dgt-28 nucleic acid) by any of several methods of introducing a heterologous molecule known in the art. In particular embodiments herein, a heterologous molecule is introduced into a plant cell, plant part, and/or plant by a method selected from, for example and without limitation: transformation and selective breeding (e.g., backcross breeding).

Any plant species or plant cell may be genetically modified to comprise a heterologous polypeptide and/or nucleic acid herein. In some embodiments, the plant cell that is so genetically modified is not capable of regeneration to produce a plant. In some embodiments, plants which are genetically modified in accordance with the present disclosure (e.g., plant host cells) includes, but is not limited to, a higher plant, a dicotyledonous plant, a monocotyledonous plants, a consumable plant, a crop plant, and a plant utilized for its oils (e.g., an oilseed plant). Such plants include, for example and without limitation: alfalfa; soybean; cotton; rapeseed (canola); linseed; corn; rice; brachiaria; wheat; safflower; sorghum; sugarbeet; sunflower; tobacco; and grasses (e.g., turf grass). In particular examples, a genetically modified plant cell or plant herein includes, for example and without limitation: *Brassica napus*; indian mustard (*Brassica juncea*); Ethiopian mustard (*Brassica carinata*); turnip (*Brassica rapa*); cabbage (*Brassica oleracea*); *Glycine max; Linum usitatissimum; Zea mays; Carthamus tinctorius; Helianthus annuus; Nicotiana tabacum; Arabidopsis thaliana*, Brazil nut (*Betholettia excelsa*); castor bean (*Ricinus communis*); coconut (*Cocus nucifera*); coriander (*Coriandrum sativum*); *Gossypium* spp.; groundnut (*Arachis hypogaea*); jojoba (*Simmondsia chinensis*); oil palm (*Elaeis guineeis*); olive (*Olea eurpaea*); *Oryza sativa*; squash (*Cucurbita maxima*); barley (*Hordeum vulgare*); sugarcane (*Saccharum officinarum*); *Triticum* spp. (including *Triticum durum* and *Triticum aestivum*); and duckweed (*Lemnaceae* sp.). In some embodiments, the plant may have a particular genetic background, as for elite cultivars, wild-type cultivars, and commercially distinguishable varieties.

Nucleic acids introduced into a plant cell may be used to confer desired traits on essentially any plant. A wide variety of plants and plant cell systems may be engineered for the desired physiological and agronomic characteristics described herein using a nucleic acid encoding a DGT polypeptide and various transformation methods. Embodiments herein may use any of many methods for the transformation of plants (and production of genetically modified plants) that are known in the art. Numerous methods for plant transformation have been developed, including biological and physical transformation protocols for dicotyledenous plants, as well as monocotyledenous plants (See, e.g., Goto-Fumiyuki et al. (1999) Nat. Biotechnol. 17:282-6; Mild et al. (1993) *Methods in Plant Molecular Biology and Biotechnology* (Glick, B. R. and Thompson, J. E., Eds.), CRC Press, Inc., Boca Raton, Fla., pp. 67-88). In addition, vectors and in vitro culture methods for plant cell and tissue transformation and regeneration of plants are described, for example, in Gruber et al. (1993), supra, at pp. 89-119.

Plant transformation techniques available for introducing a nucleic acid into a plant host cell include, for example and without limitation: transformation with disarmed T-DNA using *Agrobacterium tumefaciens* or *A. rhizogenes* as the transformation agent; calcium phosphate transfection; polybrene transformation; protoplast fusion; electroporation (D'Halluin et al. (1992) Plant Cell 4:1495-505); ultrasonic methods (e.g., sonoporation); liposome transformation; microinjection; contact with naked DNA; contact with plasmid vectors; contact with viral vectors; biolistics (e.g., DNA particle bombardment (see, e.g., Klein et al. (1987) Nature 327:70-3) and microparticle bombardment (Sanford et al. (1987) Part. Sci. Technol. 5:27; Sanford (1988) Trends Biotech. 6:299, Sanford (1990) Physiol. Plant 79:206; and Klein et al. (1992) Biotechnology 10:268); silicon carbide WHISKERS-mediated transformation (Kaeppler et al. (1990) Plant Cell Rep. 9:415-8); nanoparticle transformation (see, e.g., U.S. Patent Publication No. US2009/0104700A1); aerosol beaming; and polyethylene glycol (PEG)-mediated uptake. In specific examples, a heterologous nucleic acid may be introduced directly into the genomic DNA of a plant cell.

A widely utilized method for introducing an expression vector into a plant is based on the natural transformation system of *Agrobacterium*. Horsch et al. (1985) Science 227:1229. *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado (1991) Crit. Rev. Plant. Sci. 10:1. Details regarding *Agrobacterium* vector systems and methods for *Agrobacterium*-mediated gene transfer are also available in, for example, Gruber et al., supra, Mild et al., supra, Moloney et al. (1989) Plant Cell Reports 8:238, and U.S. Pat. Nos. 4,940,838 and 5,464,763.

If *Agrobacterium* is used for the transformation, the DNA to be inserted typically is cloned into special plasmids; either into an intermediate vector or a binary vector. Intermediate vectors cannot replicate themselves in *Agrobacterium*. The intermediate vector may be transferred into *A. tumefaciens* by means of a helper plasmid (conjugation). The Japan Tobacco Superbinary system is an example of such a system (reviewed by Komari et al. (2006) *Methods in Molecular Biology* (K. Wang, ed.) No. 343; *Agrobacterium Protocols*, $2^{nd}$ Edition, Vol. 1, Humana Press Inc., Totowa, N.J., pp. 15-41; and Komori et al. (2007) Plant Physiol. 145:1155-60). Binary vectors can replicate themselves both in *E. coli* and in *Agrobacterium*. Binary vectors comprise a selection marker gene and a linker or polylinker which are framed by the right and left T-DNA border regions. They can be transformed directly into *Agrobacterium* (Holsters, 1978). The *Agrobacterium* comprises a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) Nuc. Acid Res. 12:8711-21) or the co-cultivation procedure (Horsch et al. (1985) Science 227:1229-31). Generally, the *Agrobacterium* transformation system is used to engineer dicotyledonous plants. Bevan et al. (1982) Ann. Rev. Genet 16:357-84; Rogers et al. (1986) Methods Enzymol. 118:627-41. The *Agrobacterium* transformation system may also be used to transform, as well as transfer, nucleic acids to monocotyledonous plants and plant cells. See U.S. Pat. No. 5,591,616; Hernalsteen et al. (1984) EMBO J 3:3039-41; Hooykass-Van Slogteren et al. (1984) Nature 311:763-4; Grimsley et al. (1987) Nature 325:1677-9; Boulton et al. (1989) Plant Mol. Biol. 12:31-40; and Gould et al. (1991) Plant Physiol. 95:426-34.

The genetic manipulations of a recombinant host herein may be performed using standard genetic techniques and screening, and may be carried out in any host cell that is suitable to genetic manipulation. In some embodiments, a recombinant host cell may be any organism or microorganism host suitable for genetic modification and/or recombinant gene expression. In some embodiments, a recombinant host may be a plant. Standard recombinant DNA and molecular cloning techniques used here are well-known in the art and are described in, for example and without limitation: Sambrook et al. (1989), supra; Silhavy et al. (1984) *Experiments with Gene Fusions*, Cold Spring Harbor Laboratory Press, Cold Spring Harbor, N.Y.; and Ausubel et al. (1987) *Current Protocols in Molecular Biology*, Greene Publishing Assoc. and Wiley-Interscience, New York, N.Y.

Following the introduction of a nucleic acid into a plant cell, the plant cell may be grown, and upon emergence of differentiating tissue such as shoots and roots, mature plants can be generated. In some embodiments, a plurality of plants can be generated. Methodologies for regenerating plants are known to those of ordinary skill in the art and can be found, for example, in: Plant Cell and Tissue Culture, 1994, Vasil and Thorpe Eds. Kluwer Academic Publishers and in: Plant Cell Culture Protocols (Methods in Molecular Biology 111, 1999 Hall Eds Humana Press). Genetically modified plants described herein may be cultured in a fermentation medium or grown in a suitable medium such as soil. In some embodiments, a suitable growth medium for higher plants may be any growth medium for plants, including, but not limited to, soil, sand, any other particulate media that support root growth (e.g., vermiculite, perlite, etc.) or hydroponic culture, as well as suitable light, water and nutritional supplements that facilitate the growth of the higher plant.

Transformed plant cells which are produced by any of the above transformation techniques can be cultured to regenerate a whole plant that possesses the transformed genotype, and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

In other embodiments, the plant cells which are transformed are not capable of regeneration to produce a plant. Such cells may be employed, for example, in developing a plant cell line having the relevant phenotype, for example, herbicide resistance.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Such selection and screening methodologies are well known to those skilled in the art.

A transgenic plant containing a heterologous molecule herein can be produced through selective breeding, for example, by sexually crossing a first parental plant comprising the molecule, and a second parental plant, thereby producing a plurality of first progeny plants. A first progeny plant may then be selected that is resistant to a selectable marker (e.g., glyphosate, resistance to which may be conferred upon the progeny plant by the heterologous molecule herein). The first progeny plant may then by selfed, thereby producing a plurality of second progeny plants. Then, a second progeny plant may be selected that is resistant to the selectable marker. These steps can further include the backcrossing of the first progeny plant or the second progeny plant to the second parental plant or a third parental plant.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

A nucleic acid may also be introduced into a predetermined area of the plant genome through homologous recombination. Methods to stably integrate a polynucleotide sequence within a specific chromosomal site of a plant cell via homologous recombination have been described within the art. For instance, site specific integration as described in US Patent Application Publication No. 2009/0111188 A1 involves the use of recombinases or integrases to mediate the introduction of a donor polynucleotide sequence into a chromosomal target. In addition, International Patent Application No. WO 2008/021207, describes zinc finger mediated-homologous recombination to stably integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to stably integrate a polynucleotide sequence into a specific chromosomal site. Finally, the use of meganucleases for targeting donor polynucleotides into a specific chromosomal location was described in Puchta et al., PNAS USA 93 (1996) pp. 5055-5060).

Other various methods for site specific integration within plant cells are generally known and applicable (Kumar et al., Trends in Plant Sci. 6(4) (2001) pp. 155-159). Furthermore, site-specific recombination systems that have been identified in several prokaryotic and lower eukaryotic organisms may be applied for use in plants. Examples of such systems include, but are not limited too; the R/RS recombinase system from the pSR1 plasmid of the yeast Zygosaccharomyces rouxii (Araki et al. (1985) J. Mol. Biol. 182: 191-203), and the Gin/gix system of phage Mu (Maeser and Kahlmann (1991) Mol. Gen. Genet. 230: 170-176).

In some embodiments, a heterologous nucleic acid encoding a polypeptide having at least 90% identity to SEQ ID NO:1 may be optionally combined with another nucleic acid in the host cell and/or organism. For example, in certain embodiments, the heterologous nucleic acid encoding a polypeptide having at least 90% identity to SEQ ID NO:1 may be combined or "stacked" with another that provides additional resistance or tolerance to glyphosate or another herbicide, and/or another that provides resistance to select insects or diseases and/or nutritional enhancements, and/or improved agronomic characteristics, and/or another that provides proteins or other products useful in feed, food, industrial, pharmaceutical or other uses. The "stacking" of two or more nucleic acid sequences of interest within a plant genome may be accomplished, for example, via conventional plant breeding using two or more events, transformation of a plant with a construct(s) that contain the nucleic acids, re-transformation of a transgenic plant, or addition of new traits through targeted integration via homologous recombination.

Nucleic acids that may be "stacked" with a heterologous nucleic acid encoding a polypeptide having at least 90% identity to SEQ ID NO:1 include, for example and without limitation:

Genes or Coding Sequence (e.g., iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to Cladosporium fulvum (Jones et al., 1994 Science 266:789), tomato Pto gene, which encodes a protein kinase, for resistance to Pseudomonas syringae pv. tomato (Martin et al., 1993 Science 262:1432), and Arabidopsis RSSP2 gene for resistance to Pseudomonas syringae (Mindrinos et al., 1994 Cell 78:1089).

(B) A Bacillus thuringiensis protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several Clivia miniata mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in Diploptera punctata (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to Pseudomonas solanacearum.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., 1988 EMBOJ. 7:1241), which is also known as AHAS enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3 Cl2phenyl)propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992) Proc. Nat. Acad. Sci. USA 89:2624.

(B) Decreased phytate content
(1) Introduction of a phytase-encoding gene, such as the *Aspergillus niger* phytase gene (Van Hartingsveldt et al., 1993 Gene 127:87), enhances breakdown of phytate, adding more free phosphate to the transformed plant.
(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., 1988) J. Bacteriol. 170:810, *Bacillus subtilis* levansucrase gene (Steinmetz et al., 1985 Mol. Gen. Genel. 200:220), *Bacillus licheniformis* α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:10450).

Various assays can be employed in connection with the nucleic acid molecule of certain embodiments of the disclosure. The following techniques are useful in a variety of situations, and in one embodiment, are useful in detecting the presence of the nucleic acid molecule and/or the polypeptide encoded in a plant cell. For example, the presence of the molecule can be determined in a variety of ways, including using a primer or probe of the sequence, ELISA assay to detect the encoded protein, a Western blot to detect the protein, or a Northern or Southern blot to detect RNA or DNA. Enzymatic assays for detecting enzyme DGT-28 can be employed. Further, an antibody which can detect the presence of the DGT-28 protein can be generated using art recognized procedures. Additional techniques, such as in situ hybridization, enzyme staining, and immunostaining, also may be used to detect the presence or expression of the recombinant construct in specific plant organs and tissues. A transgene may be selectively expressed in some tissues of the plant or at some developmental stages, or the transgene may be expressed in substantially all plant tissues, substantially along its entire life cycle. However, any combinatorial expression mode is also applicable.

Southern analysis is a commonly used detection method, wherein DNA is cut with restriction endonucleases and fractionated on an agarose gel to separate the DNA by molecular weight and then transferring to nylon membranes. It is then hybridized with the probe fragment which was radioactively labeled with $^{32}P$ (or other probe labels) and washed in an SDS solution.

Likewise, Northern analysis deploys a similar protocol, wherein RNA is cut with restriction endonucleases and fractionated on an agarose gel to separate the RNA by molecular weight and then transferring to nylon membranes. It is then hybridized with the probe fragment which was radioactively labeled with $^{32}P$ (or other probe labels) and washed in an SDS solution. Analysis of the RNA (e.g., mRNA) isolated from the tissues of interest can indicate relative expression levels. Typically, if the mRNA is present or the amount of mRNA has increased, it can be assumed that the corresponding transgene is being expressed. Northern analysis, or other mRNA analytical protocols, can be used to determine expression levels of an introduced transgene or native gene.

In the Western analysis, instead of isolating DNA/RNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997); Towbin et al. (1979) "Electrophoretic transfer of proteins from polyacrylamide gels to nitrocellulose sheets: procedure and some applications" Proc Natl Acad Sci USA 76(9): 4350-4354; Renart et al. "Transfer of proteins from gels to diazobenzyloxymethyl-paper and detection with antisera: a method for studying antibody specificity and antigen structure" Proc Natl Acad Sci USA 76(7): 3116-3120.

The nucleic acids herein, or segments thereof, may be used to design primers for PCR amplification. In performing PCR amplification, a certain degree of mismatch can be tolerated between primer and template. Mutations, insertions, and deletions can be produced in a given primer by methods known to an ordinarily skilled artisan.

Another example of method detection is the pyrosequencing technique as described by Winge (Innov. Pharma. Tech. 00:18-24, 2000). In this method, an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

Certain embodiments relate to processes of making crosses using a plant of an embodiment of this disclosure as at least one parent. For example, particular embodiments relate to an $F_1$ hybrid plant having as one or both parents any of the plants exemplified herein. Other embodiments relate to seed produced by such $F_1$ hybrids. Still other embodiments relate to a method for producing an $F_1$ hybrid seed by crossing an exemplified plant with a different (e.g. in-bred parent) plant and harvesting the resultant hybrid seed. Other embodiments relate to an exemplified plant that is either a female parent or a male parent. Characteristics of the resulting plants may be improved by careful consideration of the parent plants.

V. Glyphosate Tolerance Mediated by DGT-28

Polypeptides having at least 90% sequence identity to SEQ ID NO:1 may have EPSPS enzymatic activity. Thus, polypeptides having at least 90% identity to SEQ ID NO:1, nucleic acids encoding a polypeptide having at least 90% identity to SEQ ID NO:1 (e.g., SEQ ID NOs:2-4), and a nucleic acids that hybridize to a nucleic acid having SEQ ID NO:2 or SEQ ID NO:3 under high-stringency conditions may be used in some embodiments to confer glyphosate tolerance to an cell or organism (e.g., a plant cell or plant). Providing a plant or plant cell that is resistant to glyphosate herbicide formulations may be useful in a variety of applications, where those plant cells having such resistance can tolerate exposure to a sufficient amount of glyphosate that is used to control at least some weeds in an area under cultivation.

Glyphosate, a composition comprising N-(phosphonomethyl) glycine, is a widely used component in herbicides. Glyphosate is typically formulated as a salt in an aqueous liquid concentrate, a solid concentrate, an emulsion or a microemulsion. Glyphosate can be applied over-the-top of plants from emergence throughout the various stages of plant development.

Glyphosate tolerant plant varieties used in combination with glyphosate herbicidal formulations have become the standard program for weed management in crop production in the United States and throughout the world. The primary advantage to growers in using a glyphosate tolerance trait is that it allows simple and convenient application of glyphosate; a broad spectrum, post-emergence herbicide, to control unwanted plants and grasses (i.e., "weeds") with excellent crop safety and less dependence on pre-plant herbicide applications. Other benefits include a better fit into no-till and reduced tillage systems. Glyphosate tolerant crops have expanded the options for weed management and made the practice of weed control much easier, less expensive and more flexible. Growers have reported making fewer trips across fields to apply herbicides as well as making fewer cultivation trips, which conserves fuel and reduces soil erosion. Glyphosate-tolerant crops, therefore, decrease the environmental risks posed by herbicides, while at the same time increasing the efficacy of necessary chemical weed control.

Accordingly, some embodiments herein provide for selectively controlling weeds in an area under cultivation containing a plant comprising a polypeptide having at least 90% identity to SEQ ID NO:1, a nucleic acid encoding a polypeptide having at least 90% identity to SEQ ID NO:1, and/or a nucleic acid that hybridizes to a nucleic acid having SEQ ID NO:2 or SEQ ID NO:3 under high-stringency conditions, wherein the plant has increased glyphosate tolerance when compared to a plant of the same species that does not comprise the polypeptide and/or nucleic acid(s). In some examples, a method provided herein comprises applying a sufficient amount of a herbicidal glyphosate to the crop foliage and weeds to control growth of the weeds.

Particular embodiments herein provide a method for killing or controlling weeds or unwanted vegetation in an area under cultivation containing a crop (e.g., a plant comprising a polypeptide having at least 90% identity to SEQ ID NO:1, a nucleic acid encoding a polypeptide having at least 90% identity to SEQ ID NO:1, and/or a nucleic acid that hybridizes to a nucleic acid having SEQ ID NO:2 or SEQ ID NO:3 under high-stringency conditions). In some examples, the method comprises applying glyphosate to the crop and/or the area under cultivation; for example, applying an amount of the glyphosate to foliage of the crop plant, and simultaneously to weeds growing in close proximity to such plants, wherein the amount is sufficient to result in control of the weeds or unwanted vegetation, while leaving the crop plant substantially unharmed.

A glyphosate composition may be applied to plants at an application rate sufficient to give desired biological results, for example, control of weed growth without significantly affecting glyphosate tolerant crop plants. These application rates are usually expressed as amount of glyphosate per unit area treated, e.g., grams per hectare (g/ha). What constitutes a "significant effect" varies according to the standards and practice of those who investigate, develop, market and use compositions, and the selection of application rates that are significantly effective for a composition is within the skill of those skilled in the art.

In certain examples, the amount of the glyphosate composition applied per unit area to give 85% control of a weed species as measured by growth reduction or mortality is used to define an application rate. The selection of a number of glyphosate herbicide application rates sufficient to control weeds in an area under cultivation is within the skill of the ordinary agricultural scientist. Those of skill in the art will likewise recognize that individual plant conditions, weather and growing conditions, as well as the specific active ingredients and their weight ratio in the composition, may influence the degree of herbicidal effectiveness in a particular application.

In some embodiments, an aqueous glyphosate composition can be applied to the foliar tissues of plants to kill or control the growth of a wide variety of unwanted plants, including annual and perennial grass and broadleaf weed species, by applying to the foliar tissues of the plants aqueous glyphosate compositions. The relative amount of glyphosate present in a contemplated herbicidal composition (e.g., a particulate solid concentrate, liquid concentrate, ready-to-use composition, and tank-mix composition) may vary depending upon many factors including, for example, the weed species to be controlled and the method of application. Generally speaking, however, the concentration of glyphosate, and optionally a surfactant and/or some other adjuvant or additive (as described elsewhere herein) used in the herbicidal composition is sufficient to control weeds within an area under cultivation.

An herbicidal spray composition may be applied as an aqueous solution or dispersion, whether the composition is manufactured ready for application, or results from the further dilution of a liquid glyphosate concentrate or the addition of water to a particulate solid glyphosate concentrate. However, the term "aqueous," as used herein, includes compositions comprising some small amount of non-aqueous solvent, so long as the predominant solvent present is water. An herbicidal spray compositions may be applied to the foliage of the plants to be treated through any of the appropriate methods that are well known to those having skill in the art, including aerial application and ground application techniques (e.g., a ground boom, a hand sprayer, and a rope-wick).

In some examples, a liquid concentrate composition is formulated to include glyphosate in a concentration of at least about 50 grams, at least about 75 grams, or at least about 100, 125, 150, 175, 200, 225, 250, 275, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690 or 700 grams (acid equivalent or a.e.) per liter, or more. The glyphosate concentration range may be, for example, from about 50 to about 680 grams (a.e.) per liter (gpl), from about 100 to about 600 gpl, from about 250 to about 600 gpl, and from about 360 to about 540 gpl.

When expressed as a weight percentage based on the total weight of the glyphosate concentrate, a liquid concentrate may comprise, for example, at least about 10 wt. % glyphosate (a.e.), at least about 15 wt. %, and at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, or 68 wt. %, or more. The glyphosate concentration range may be, for example, from about 10 wt. % to about 70 wt. % a.e., from about 20 wt. % to about 68 wt. %, or from about 25 wt. % to about 45 wt. %.

If the glyphosate is applied as a ready-to-use composition, the glyphosate concentration may be, for example, from about 1 wt. % to about 3 wt. % a.e., and from about 1 wt. % to about 2 wt. %.

Spray compositions may be formulated for application of, for example, at least about 1 gallon of spray composition per acre, at least about 2, 3, 4, 5, 6, 7, 8, 9, 10, 11, 12, 13, 14, 15, 16, 17, 18, 19, or 20 gallons per acre, and more. The spray volume of the spray composition may range, for example, from about 1 gallon to about 100 gallons per acre, from about 2 gallons to about 40 gallons per acre, and from about 2 gallons to about 5 gallons per acre for an aerial application, and from about 5 gallons to about 20 gallons per acre for a ground application.

In some examples, a liquid concentrate formulation having an aqueous phase wherein glyphosate is present predominantly in the form of a salt, and a non-aqueous phase optionally containing a second herbicidal active ingredient that is relatively water-insoluble, may be employed. Such formulations may include, for example, emulsions (including macroemulsions and microemulsions, water-in-oil, oil-in-water and water-in-oil-in-water types), suspensions, and suspoemulsions. The non-aqueous phase may comprise in certain instances a microencapsulated component (e.g., a microencapsulated herbicide). In formulations having a non-aqueous phase, the concentration of glyphosate a.e. in the composition as a whole may nonetheless be within the particular exemplary ranges recited herein for aqueous concentrate formulations.

Suitable salt forms of glyphosate which may be used in accordance with any of the formulations include, for example, alkali metal salts, for example sodium and potassium salts, ammonium salts, di-ammonium salts such as dimethylammonium, alkylamine salts, for example dimethylamine and isopropylamine salts, alkanolamine salts, for example ethanolamine salts, alkylsulfonium salts, for example trimethylsulfonium salts, sulfoxonium salts, and mixtures or combinations thereof. Examples of commercial formulations of glyphosate include, without restriction: GLYPHOMAX™, GLYPHOMAX™ XRT, GLYPHOMAX™ PLUS, DURANGO™ ROUNDUP™ ULTRA, ROUNDUP™ ULTRAMAK, ROUNDUP™ CT, ROUNDUP™ EXTRA, ROUNDUP™ BIOACTIVE, ROUNDUP™ BIOFORCE, RODEO™, POLARIS™ SPARK™ ACCORD™ SP, ACCORD™ XRT, and ACCORD™ CONCENTRATE, all of which contain glyphosate as its isopropylammonium salt (IPA); ROUNDUP™ DRY and RIVAL™, which contain glyphosate as its ammonium salt; ROUNDUP™ GEOFORCE, a sodium glyphosate formulation; TOUCHDOWN™, a glyphosate trimesium salt formulation, TOUCHDOWN™ IQ, a glyphosate diammonium salt formulation, TOUCHDOWN™ TOTAL IQ, a potassium glyphosate formulation, and ROUNDUP™ WEATHERMAX, a potassium glyphosate formulation. Glyphosate formulations may include safening agents, surfactants, and/or adjuvants.

If desired, the user may mix one or more adjuvants with a glyphosate composition and the water of dilution when preparing a formulation for application. Such adjuvants may include additional surfactant and/or an inorganic salt (e.g., ammonium sulfate) with the aim of further enhancing herbicidal efficacy.

If desired, the user may also employ appropriate safeners in a glyphosate formulation to further protect plants and/or to add cross resistance to more herbicides. Safeners are chemical agents that reduce the phytotoxicity of herbicides to crop plants by a physiological or molecular mechanism, without compromising weed control efficacy. Safeners typically act to increase a plant's immune system by activating/expressing cP450. Exemplary safeners include, for example and without limitation: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, and oxabetrinil.

Safeners may be used for the protection of large-seeded grass crops, for example and without limitation, corn, grain sorghum, and wet-sown rice, against preplant-incorporated or preemergence-applied herbicides of the thiocarbamate and chloroacetanilide families. Safeners also have been developed to protect winter cereal crops such as wheat against postemergence applications of aryloxyphenoxypropionate and sulfonylurea herbicides. The use of safeners for the protection of corn and rice against sulfonylurea, imidazolinone, cyclohexanedione, isoxazole, and triketone herbicides is also well-established.

Plant activators (a new class of compounds that protect plants by activating their defense mechanisms) may also be used in embodiments herein. Exemplary plant activators include acibenzolar and probenazole.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1

Materials and Methods

Embodiments of the present disclosure are further described in the following examples, which are offered by way of illustration, and are not intended to limit the invention in any manner.

A single amino acid mutation (G96A) in the *Escherichia coli* 5-enolpyruvylshikimate 3-phosphate synthase enzyme (EPSP synthase) can result in glyphosate insensitivity (Padgette et al., (1991); Eschenburg et al., (2002); Priestman et al., (2005); Haghani et al., (2008)). While this mutation confers tolerance to glyphosate, it is also known to adversely affect binding of EPSP synthase with its natural substrate, phosphoenolpyruvate (PEP). The resulting change in substrate binding efficiency can render a mutated enzyme unsuitable for providing in planta tolerance to glyphosate.

The NCBI Genbank database was screened in silico for EPSP synthase protein and polynucleotide sequences that naturally contain an alanine at an analogous position within the EPSP synthase enzyme as that of the G96A mutation which was introduced into the *E. coli* version of the enzyme (Padgette et al., (1991); Eschenburg et al., (2002); Priestman et al., (2005); Haghani et al., (2008)).

Figure 1:
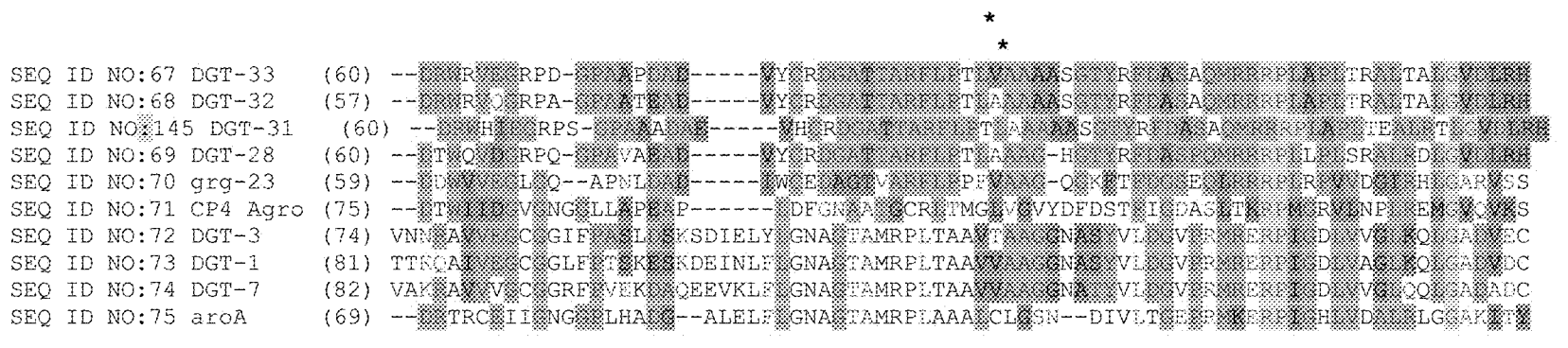

One enzyme that was identified to contain a natural alanine at this position was DGT-28 (GENBANK ACC NO: ZP_06917240.1) from *Streptomyces sviceus* ATCC29083. Further in silico data mining revealed three other unique *Streptomyces* enzymes with greater homology to DGT-28; DGT-31 (GENBANK ACC NO: YP_004922608.1); DGT-32 (GENBANK ACC NO: ZP_04696613); and DGT-33 (GENBANK ACC NO: NC_010572). Each of these enzymes contains a natural alanine at an analogous position within the EPSP synthase enzyme as that of the G96A mutation that was introduced into the *E. coli* version of the enzyme. FIG. 1.

Because EPSP synthase proteins from different organisms are of different lengths, the numbering of the mutation for the *E. coli* version of the EPSP synthase enzyme does not necessarily correspond with the numbering of the mutation for the EPSP synthase enzymes from the other organisms. These identified EPSP synthase enzymes were not previously characterized in regard to glyphosate tolerance or PEP substrate affinity. Furthermore, these EPSP synthase enzymes represent a new class of EPSP synthase enzymes and do not contain any sequence motifs that have been used to characterize previously described Class I (plant derived sequences further described in U.S. Pat. No. RE39247), II (bacterially derived sequences further described in U.S. Pat. No. RE39247), and III (bacterially derived sequences further described in International Patent Application WO 2006/110586) EPSP synthase enzymes.

The novel DGT-28, DGT-31, DGT-32, and DGT-33 enzymes were characterized for glyphosate tolerance and PEP substrate affinity by comparison to Class I EPSP synthase enzymes. The following Class I enzymes; DGT-1 from *Glycine max*, DGT-3 from *Brassica napus* (GENBANK ACC NO: P17688), and DGT-7 from *Triticum aestivum* (GENBANK ACC NO: EU977181) were for comparison. The Class I EPSP synthase enzymes and mutant variants thereof were synthesized and evaluated. A mutation introduced into the plant EPSP synthase enzymes consisted of the Glycine to Alanine mutation made within the EPSP synthase enzyme at a similar location as that of the G96A mutation from the *E. coli* version of the enzyme. In addition, Threonine to Isoleucine and Proline to Serine mutations were introduced within these Class I EPSP synthase enzymes at analogous positions as that of amino acid 97 (T to I) and amino acid 101 (P to S) in the EPSP synthase of *E. coli* as described in Funke et al., (2009).

FIG. 1 depicts a partial sequence alignment of DGT-28, DGT-31, DGT-32, and DGT-33 to other EPSP synthase enzymes. All four DGT enzymes share a conserved alanine at the aroA EPSP synthase enzyme amino acid position 96. The location of this amino acid is indicated by an asterisk, and the amino acid residue is underlined.

Figure 2:
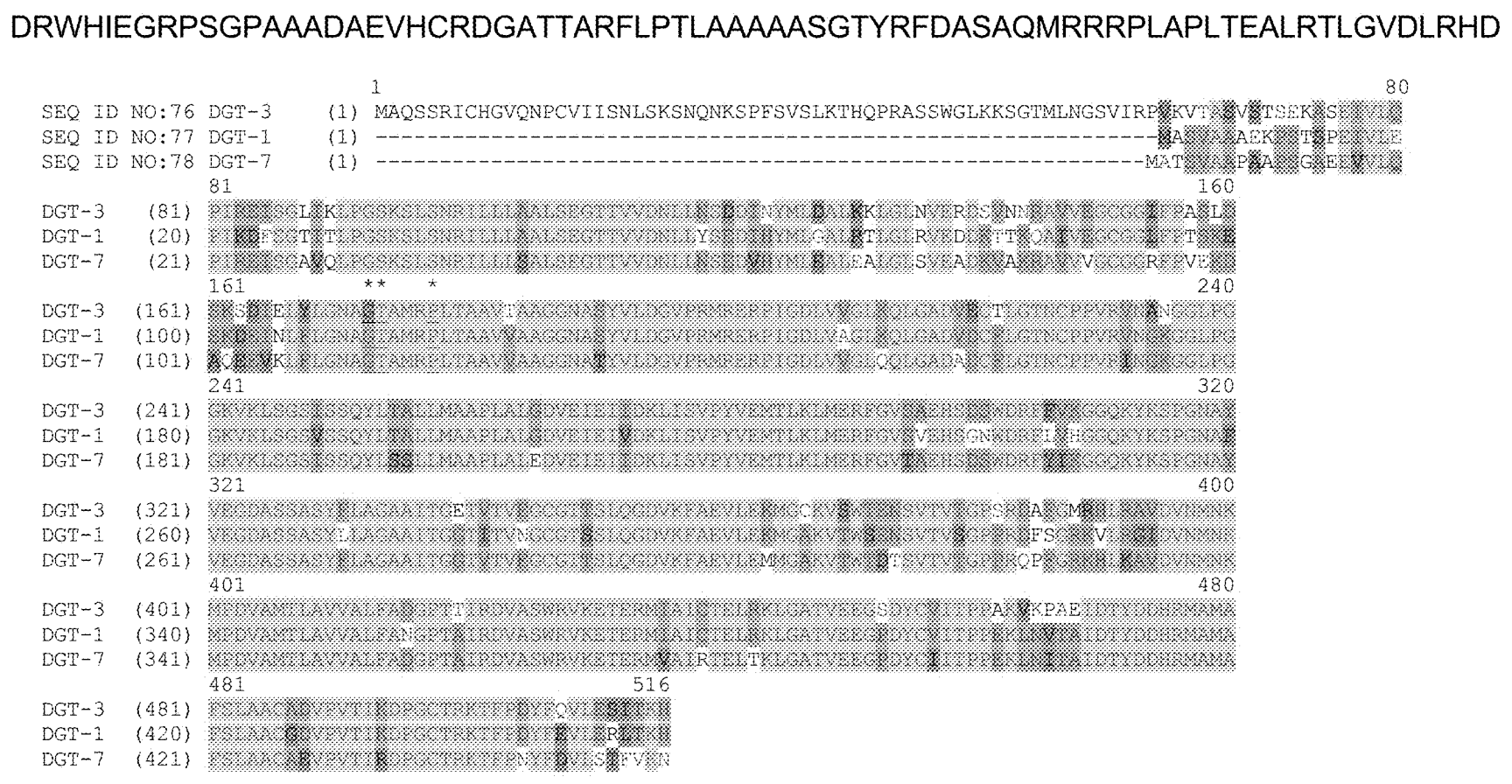

FIG. 2 shows an alignment of the DGT-1, DGT-3, and DGT-7 enzymes. The location of the amino acid residue that was mutated from glycine to alanine is indicated by the first asterisk. The location of the amino acid residue which was mutated from threonine to isoleucine is indicated by the second asterisk. The location of the third amino acid residue that was mutated from proline to serine is indicated by the third asterisk. These mutations were introduced into different versions of DGT-1, DGT-3, and DGT-7. The different versions (v1, v2, v3 . . . vN) of the genes that contain the mutations are described in more detail below.

Example 2

Optimization of Sequence for Expression in Plants and Bacteria

Plant Optimization.

Codon bias for dicots and monocots (maize) was calculated as the frequency at which a single codon is used relative to the codons for all amino acids. Table 1. Alternatively, the codon bias may be calculated as the frequency at which a single codon is used to encode a particular amino acid, relative to all the other codons for that amino acid (synonymous codons). In designing coding regions for plant expression, the primary ("first choice") codons preferred by the plant were determined, as well as the second, third, fourth, etc. choices of preferred codons when multiple choices existed.

Analysis of the DGT-28 coding sequence from *S. sviceus* revealed the presence of several sequence motifs that were believed to be detrimental to optimal plant expression, as well as a non-optimal codon composition for expression in dicotyledonous and monocotyledonous plants.

TABLE 1

Synonymous codon representation from coding regions of monocotyledonous (maize %) and dicotyledonous (dicot %) plant genes are shown in Columns D, E, I, and J. Values for a balanced-biased codon representation set for a plant-optimized synthetic gene design are in Columns C and H.

| A<br>Amino Acid | B<br>Codon | C<br>Weighted Average | D<br>Maize % | E<br>Dicot % | F<br>Amino Acid | G<br>Codon | H<br>Weighted Average | I<br>Maize % | J<br>Dicot % |
|---|---|---|---|---|---|---|---|---|---|
| ALA (A) | GCA | 25.5 | 18 | 25 | LEU (L) | CTA | DNU | 8 | 8 |
| 100 | GCC | 35.6 | 34 | 27 | 100 | CTC | 34.3 | 26 | 19 |
|  | GCG | DNU | 24 | 6 |  | CTG | DNU | 29 | 9 |
|  | GCT | 39.0 | 24 | 42 |  | CTT | 34.3 | 17 | 28 |
| ARG (R) | AGA | 27.4 | 15 | 30 |  | TTA | DNU | 5 | 10 |
| 100 | AGG | 31.5 | 26 | 25 |  | TTG | 31.4 | 15 | 26 |
|  | CGA | DNU | 9 | 8 | LYS (K) | AAA | 30.6 | 22 | 39 |
|  | CGC | 21.7 | 24 | 11 | 100 | AAG | 69.4 | 78 | 61 |
|  | CGG | DNU | 15 | 4 | MET (M) | ATG | 100 | 100 | 100 |
|  | CGT | 19.4 | 11 | 21 | PHE (F) | TTC | 63.2 | 71 | 55 |
| ASN (N) | AAC | 61.4 | 68 | 55 | 100 | TTT | 36.8 | 29 | 45 |
| 100 | AAT | 38.6 | 32 | 45 | PRO (P) | CCA | 41.4 | 26 | 42 |
| ASP (D) | GAC | 52.6 | 63 | 42 | 100 | CCC | 25.3 | 24 | 17 |
| 100 | GAT | 47.4 | 37 | 58 |  | CCG | DNU | 28 | 9 |
| CYS (C) | TGC | 61.8 | 68 | 56 |  | CCT | 33.3 | 22 | 32 |
| 100 | TGT | 38.2 | 32 | 44 | SER (S) | AGC | 26.0 | 23 | 18 |
| END | TAA |  | 20 | 48 | 100 | AGT | DNU | 9 | 14 |
| 100 | TAG |  | 21 | 19 |  | TCA | 22.4 | 16 | 19 |
|  | TGA |  | 59 | 33 |  | TCC | 26.3 | 23 | 18 |
| GLN (Q) | CAA | 48.4 | 38 | 59 |  | TCG | DNU | 14 | 6 |
| 100 | CAG | 51.6 | 62 | 41 |  | TCT | 25.4 | 15 | 25 |
| GLU (E) | GAA | 38.8 | 29 | 49 | THR (T) | ACA | 28.0 | 21 | 27 |
| 100 | GAG | 61.2 | 71 | 51 | 100 | ACC | 39.5 | 37 | 30 |
| GLY (G) | GGA | 28.5 | 19 | 38 |  | ACG | DNU | 22 | 8 |
| 101 | GGC | 29.0 | 42 | 16 |  | ACT | 32.5 | 20 | 35 |
|  | GGG | 16.0 | 20 | 12 | TRP (W) | TGG | 100 | 100 | 100 |
|  | GGT | 26.6 | 20 | 33 | TYR (Y) | TAC | 65.0 | 73 | 57 |
| HIS (H) | CAC | 54.1 | 62 | 46 | 100 | TAT | 35.0 | 27 | 43 |
| 100 | CAT | 45.9 | 38 | 54 | VAL (V) | GTA | DNU | 8 | 12 |
| ILE (I) | ATA | 15.9 | 14 | 18 | 100 | GTC | 28.7 | 32 | 20 |
|  | ATC | 47.9 | 58 | 37 |  | GTG | 38.0 | 39 | 29 |
|  | ATT | 36.4 | 28 | 45 |  | GTT | 33.3 | 21 | 39 |

*DNU = Do Not Use

To engineer the plant-optimized genes encoding a DGT-28 protein, DNA sequences were designed to encode the amino acid sequences, utilizing a redundant genetic code established from the codon bias table compiled from the protein coding sequences for the particular host plants. In Table 1, Columns D and I present the distributions (in % of usage for all codons for that amino acid) of synonymous codons for each amino acid, as found in the coding regions of monocotyledonous (maize) plants. Columns E and J present the distributions (in % of usage for all codons for that amino acid) of synonymous codons for each amino acid, as found in the coding regions of dicotyledonous plants. Some synonymous codons for some amino acids are found only rarely in plant genes (e.g. CGG). Usually, a codon was considered to be rarely used if it is represented at about 10% or less of the time to encode the relevant amino acid in genes of either plant type (indicated by DNU in Columns C and H of Table 1). To balance the distribution of the remaining codon choices for an amino acid, a Weighted Average representation for each codon was calculated, using the formula:

$$\text{Weighted Average \% of } C1 = 1/(\% C1 + \% C2 + \% C3 + \text{etc.}) \times \% C1 \times 100, \quad (1)$$

where C1 is the codon in question, and % C2, % C3, etc. represent the averages of the % values for dicots of remaining synonymous codons (average % values for the relevant codons are taken from Columns C and H of Table 1.

The Weighted Average % value for each codon is given in Columns C and H of Table 1.

Using the foregoing procedure, a new DNA sequence that encodes essentially the amino acid sequence of the DGT-28 protein was designed for optimal expression in dicotyledonous plants, using a balanced codon distribution of frequently used codons found in dicotyledonous plant genes. A second DNA sequence that encodes essentially the amino acid sequence of the DGT-28 protein was designed for optimal expression in monocotyledonous plants, using a balanced codon distribution of frequently used codons found in monocotyledonous plant genes. The two new DNA sequences differed from the original DNA sequences encoding dgt-28 by the substitution of plant (first preferred, second preferred, third preferred, or fourth preferred) codons to specify the appropriate amino acid at each position within the protein amino acid sequence.

Design of the plant-optimized DNA sequences were initiated by reverse-translation of the protein sequences of the DGT-28 protein sequence (Genbank Accession No: ZP_06917240.1). SEQ ID NO:1 was reverse-translated using a dicot codon bias table constructed from Table 1; Columns E and J. A second reverse-translation of SEQ ID NO:1 was completed using a monocot codon bias table constructed from Table 1; Columns D and I.

The initial reverse-translation sequences were then modified by compensating codon changes (while retaining overall weighted average codon representation) to remove or add restriction enzyme recognition sites, remove highly stable intrastrand secondary structures, and remove other sequences that might be detrimental to cloning manipulations or expression of the engineered gene in plants. The DNA sequence was then re-analyzed for restriction enzyme recognition sites that might have been created by the modifications. The identified sites were further modified by replacing the relevant codons with first, second, third, or fourth choice preferred codons. Other sites in the sequences that could affect transcription or translation of the gene of interest include the exon:intron junctions (5' or 3'), poly A addition signals, and RNA polymerase termination signals. The modified sequences were further analyzed and further modified to reduce the frequency of TA or CG doublets, and to increase the frequency of TG or CT doublets. In addition to these doublets, sequence blocks that have more than about six consecutive residues of [G+C] or [A+T] can affect transcription or translation of the sequence. Therefore, these sequence blocks were also modified by replacing the codons of first or second choice, etc. with other preferred codons of choice. Rarely used codons were not included to a substantial extent in the gene design, being used only when necessary to accommodate a different design criterion than codon composition, per se (e.g., addition or deletion of restriction enzyme recognition sites).

The newly-designed, dicotyledonous plant optimized dgt-28 v5 polynucleotide sequence is listed in SEQ ID NO:2. The newly-designed, monocotyledonous plant optimized dgt-28 v6 polynucleotide sequence is listed in SEQ ID NO:3; this sequence was slightly modified by including an alanine at the second amino acid position to introduce a restriction enzyme site. The resulting DNA sequences have a higher degree of codon diversity, a desirable base composition, contains strategically placed restriction enzyme recognition sites, and lacks sequences that might interfere with transcription of the gene, or translation of the product mRNA.

Synthesis of DNA fragments comprising SEQ ID NO:2 and SEQ ID NO:3 containing additional sequences, such as 6-frame stops (stop codons located in all six reading frames that are added to the 3' end of the coding sequence), and a 5' restriction site for cloning were performed by commercial suppliers (DNA2.0, Menlo Park, Calif.). The synthetic nucleic acid molecule was then cloned into expression vectors and transformed into plants or bacteria as described in the Examples below.

Similar codon optimization strategies were used to design dgt-1, dgt-3 v2 (G173A), dgt-3 v3 (G173A; P178S), dgt-3 v4 (T174I; P178S), dgt-7 v4 (T168I; P172S), dgt-32 v3, dgt-33 v3, and dgt-33 v3. The codon optimized version of these genes are listed as SEQ ID NO:5, SEQ ID NO:6, SEQ ID NO:7, SEQ ID NO:8, SEQ ID NO:9, SEQ ID NO:10, SEQ ID NO:11, and SEQ ID NO:144, respectively.

Bacterial Optimization.

Figure 16:
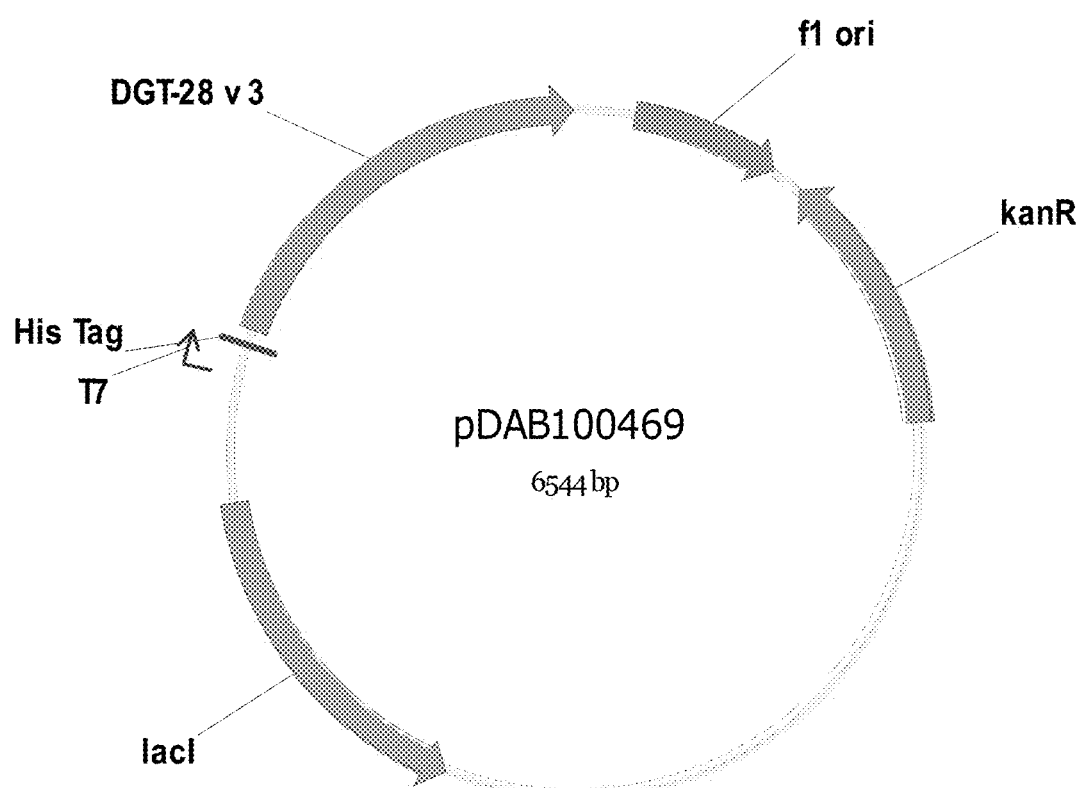

A new DNA sequence that encodes the DGT-28 protein of SEQ ID NO:1 that is optimized for expression in *Escherichia coli* cells was designed. Design of the *E. coli*-optimized DNA sequence was initiated by reverse translation of the protein sequence of SEQ ID NO:1, using a proprietary codon optimization protocol from GeneArt (Regensburg, Germany). The initial sequence was modified by compensating codon changes (while retaining overall weighted average representation) to remove or add restriction enzyme recognition sites, and remove highly stable intrastrand secondary structures and other sequences that might be detrimental to cloning manipulations or expression of the engineered gene. An example of such detrimental sequence to avoid within a coding region is a 16S ribosomal RNA binding sequence ("Shine-Dalgarno sequence") such as AGGAGG, which could encode, for example, two consecutive arginine amino acids, but which might also serve as an intragenic (and therefore undesirable) translation initiation signal. The *E. coli*-biased dgt-28 DNA sequence (dgt-28 v1) that encodes the protein of SEQ ID NO:1 is given as SEQ ID NO:4.

To facilitate cloning and to ensure efficient translation initiation, a 5' terminal NdeI restriction enzyme recognition sequence was placed upstream of the ATG translation start codon. Also to facilitate cloning, and to ensure proper translation termination, bases encoding two TAA translation stop codons and an XhoI restriction enzyme recognition site were included at the 3' end of the coding region. Synthesis of a DNA fragment comprising SEQ ID NO: 4 was performed by the commercial supplier, GeneArt™.

Similar *E. coli* codon optimization strategies were used to design dgt-1 v5, dgt-1 v6 (G112A), dgt-1 v7 (G112A; P117S), dgt-1 v8 (T113I; P117S), dgt-3 v6 (G105A), dgt-3 v7 (G105A; P112S), dgt-3 v8 (T106I; P112S), dgt-7 v5, dgt-7 v6 (G113A), dgt-7 v7 (G113A; P117S), dgt-7 v8 (T114I; P117S), dgt-32 v5, and dgt-33 v5. The dgt-1, dgt-3, and dgt-7 sequence versions were modified by the removal of the chloroplast targeting sequence. The *E. coli*-codon optimized version of these genes are listed as SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24, respectively.

Example 3

Vectors for Bacterial Expression of Glyphosate Tolerance Genes

Construction of pET Expression Vector, dgt-28 for *E. coli* Expression. For in vitro testing, the dgt-28 v1 *E. coli* optimized gene sequence (SEQ ID NO:4) was synthesized and cloned by GeneArt™ for synthesis and cloning. The synthesized dgt-28 v1 gene sequence was cloned into the pET28 expression vector via added Nde I and Xho I restriction sites. The resulting construction introduced an N-terminal 6×His tag and was labeled as pDAB 100445. FIG. 14.

Site Directed Mutagenesis of Dgt-28 v1.

Site directed mutagenesis was carried out on dgt-28 v1 to assess the role of the alanine at position 84 in providing tolerance to glyphosate. This natural alanine was mutated to glycine to determine if the change would lower the enzyme's tolerance to glyphosate or affinity for PEP. This amino acid residue was selected, as it corresponds with the G96A mutation which was introduced into the *E. coli* EPSP synthase as previously described.

The Quick Change II™ kit from Stratagene™ (Santa Clara, Calif.) was used to perform the mutagenesis. PCR reactions were set up according to the QuickChange™ protocol using pDAB 100445 (dgt-28 v1) as template DNA. The construct containing the mutated dgt-28 v2 gene sequence was designated pDAB 102946 (FIG. 15) and confirmed via DNA sequencing. The following primers were designed to make the amino acid switch:

```
DGT28 MutF
(SEQ ID NO: 25; 5' gATgTTTATTgCCgTgATggTggAACCACC
gCACgTTTTC)

DGT28 MutR
(SEQ ID NO: 26; 5' gAAAACgTgCggIggITCCACCATCACgg
CAATAAACATC)
```

A second round of mutagenesis was carried out on dgt-28 v2 in an attempt to further lower its tolerance to glyphosate. A second mutation, T172A, was introduced to the already mutagenized dgt-28 v2. The reciprocal alanine to threonine mutation of EPSP synthase at this position was previously described in Haghani et al., (2008), wherein it resulted in insensitivity to glyphosate. The end result was the production of a double A84G, T172A mutant which was designated as dgt-28 v3. PCR reactions were set up according to the QuickChange™ protocol using pDAB 102946 (dgt-28 v2) as template DNA. The construct containing the mutated dgt-28 v3 gene sequence was designated pDAB 100469 (FIG. 16). The following primers were used to produce the T172A mutation:

```
DGT28 Mut2F
(SEQ ID NO: 27; 5' gggTCCgCTggCACgTCAgggTCTgCgTAT
TCg)

DGT28 Mut2R
(SEQ ID NO: 28; 5' CgAATACgCAgACCCTgACgTgCCAgCggA
CCCAgCAgC)
```

Additional Constructions, pET Expression Vector for *E. coli* Expression.

Figure 17:
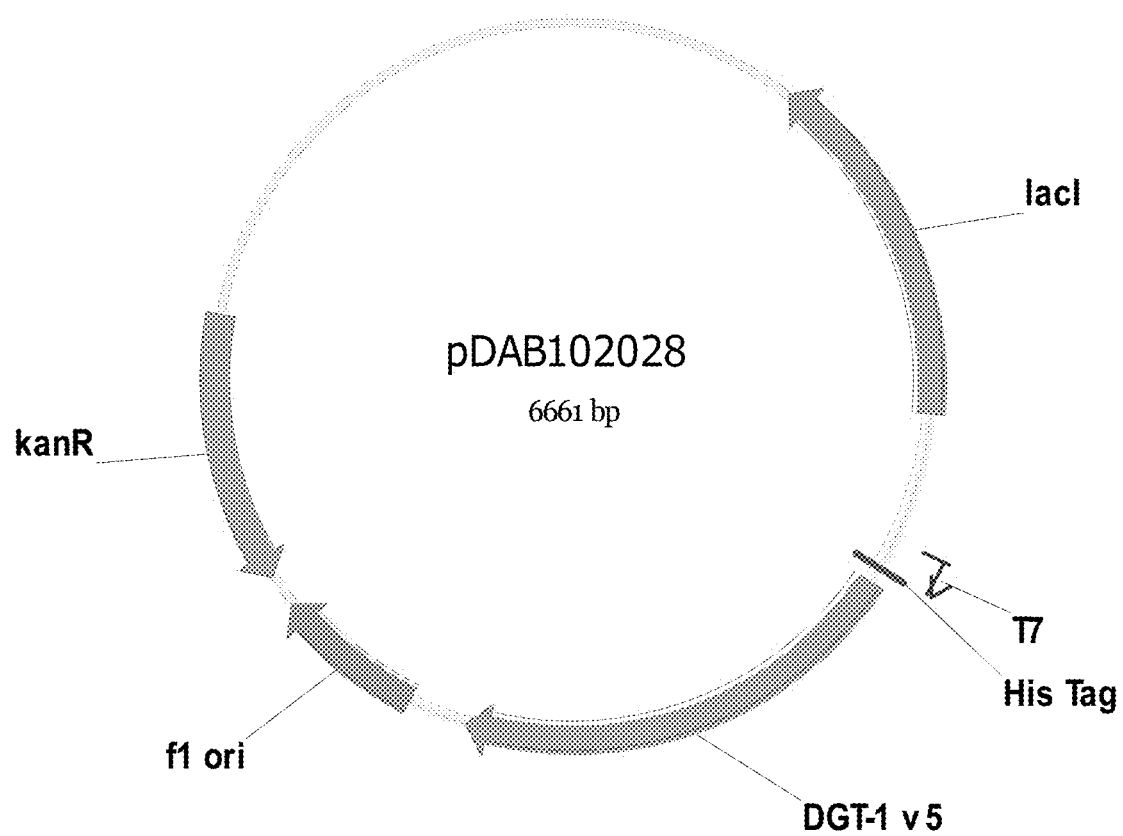
Figure 18:
Figure 19:
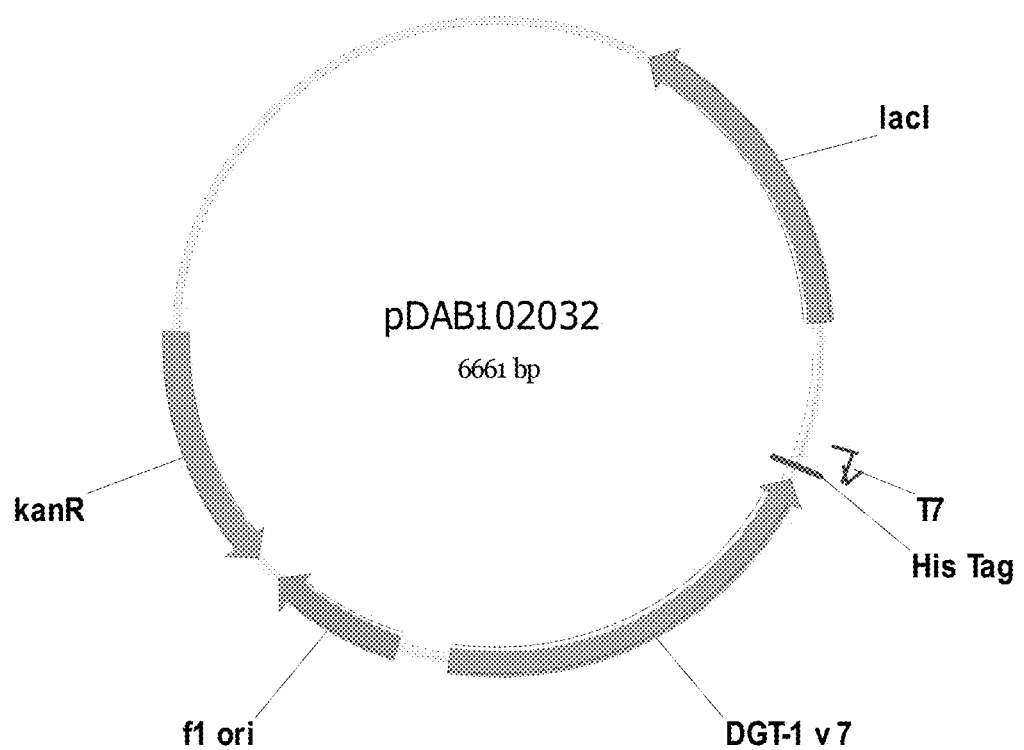
Figure 20:
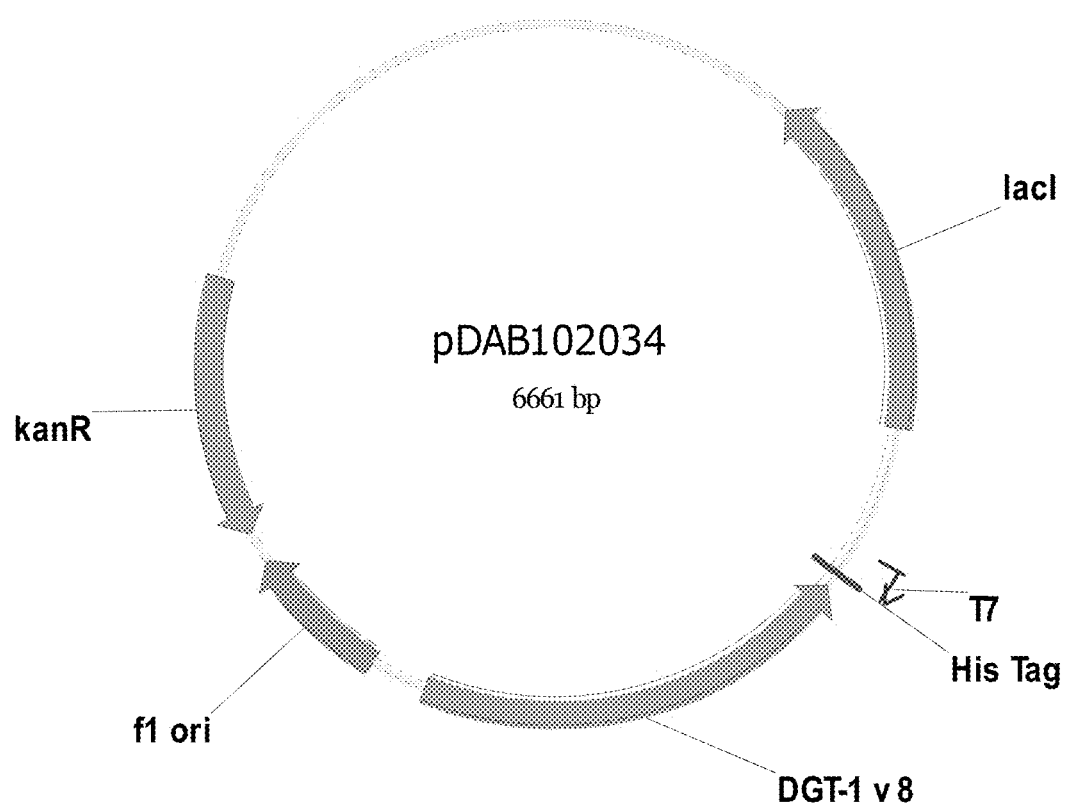
Figure 21:
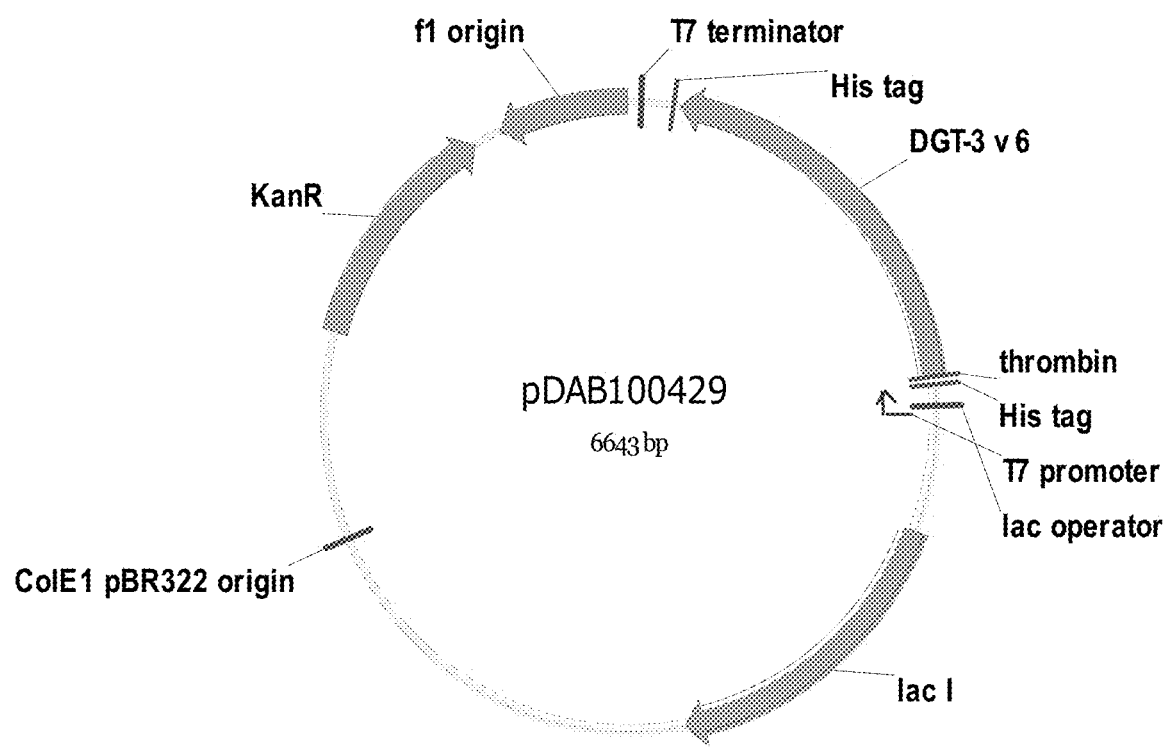
Figure 22:
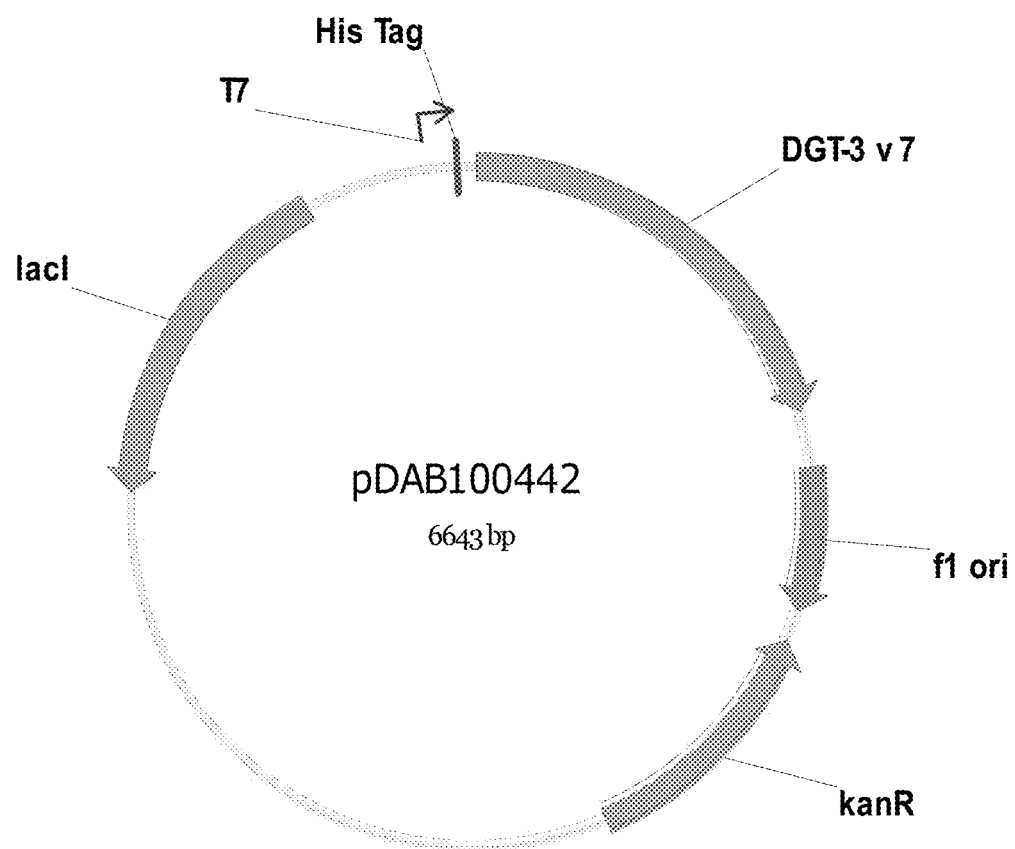
Figure 23:
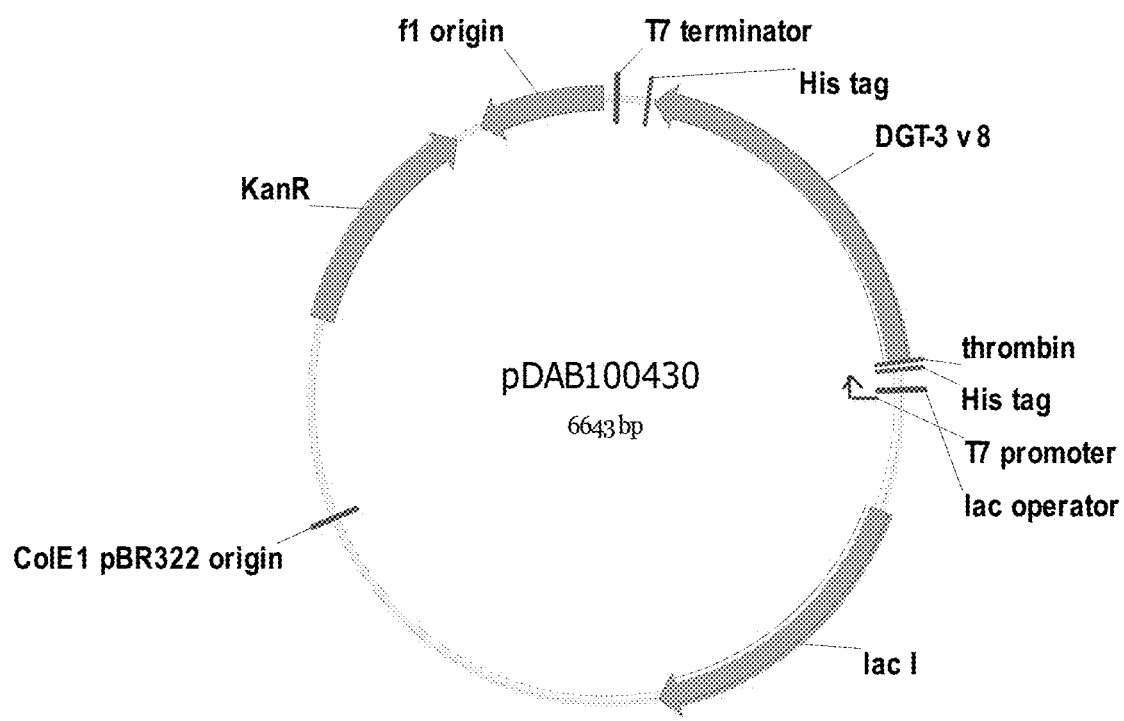
Figure 24:
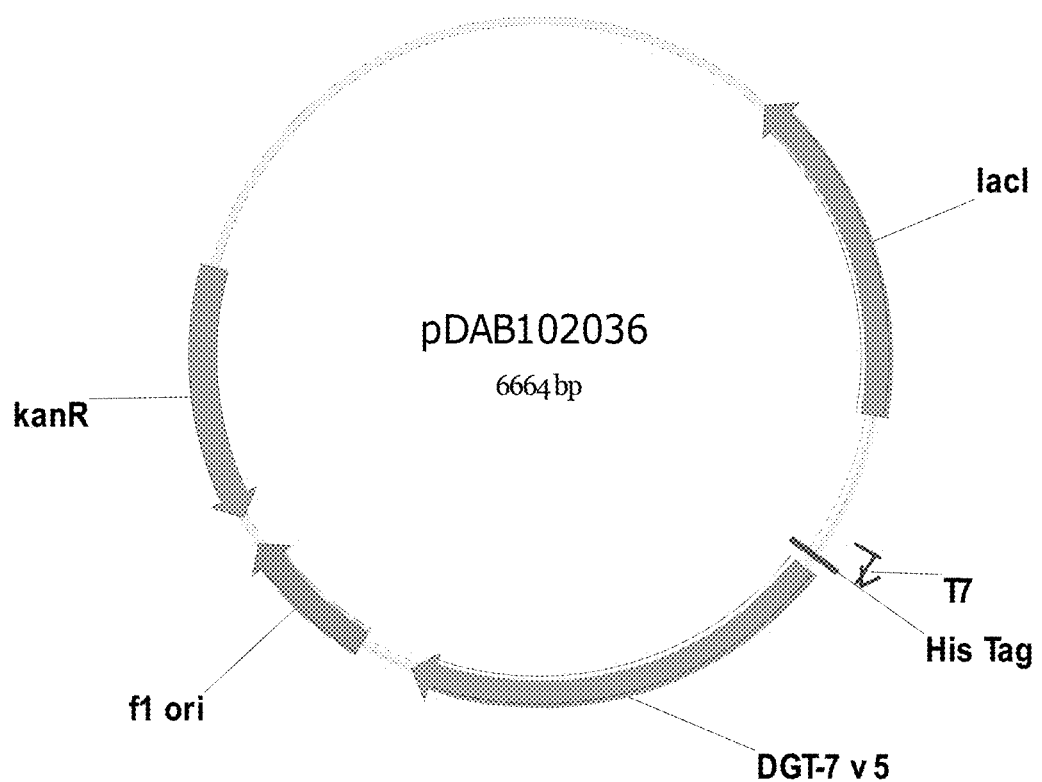
Figure 25:
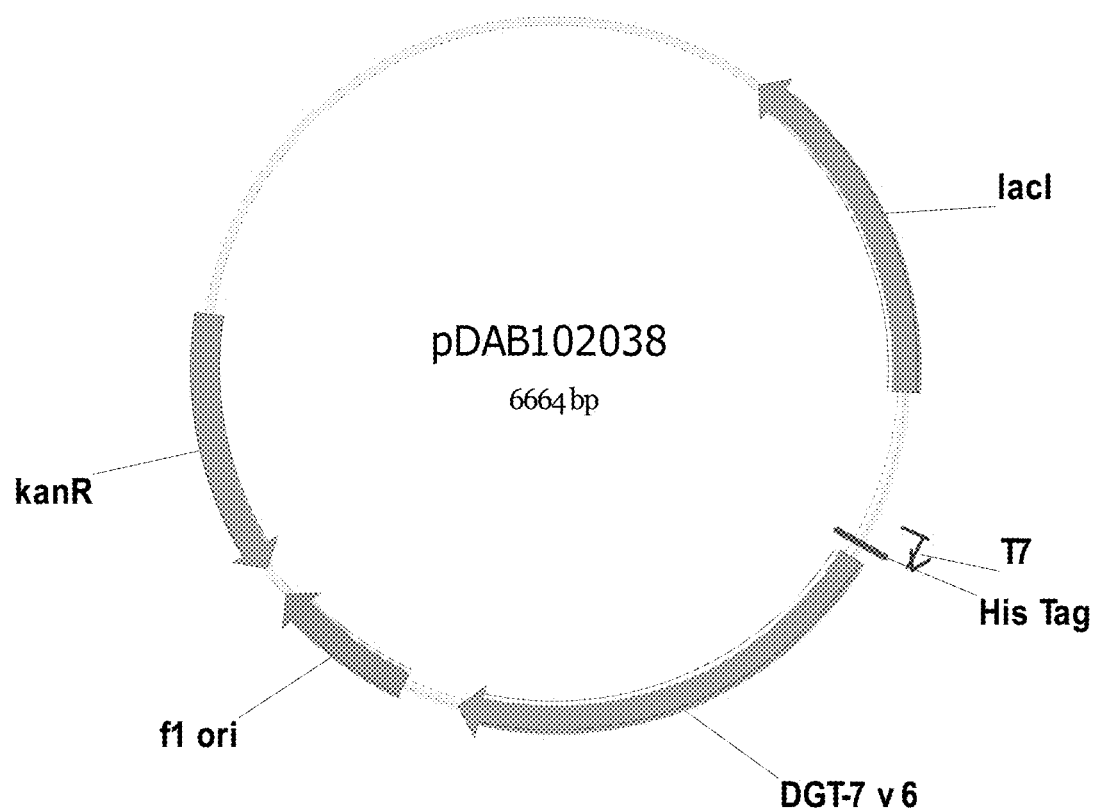
Figure 26:
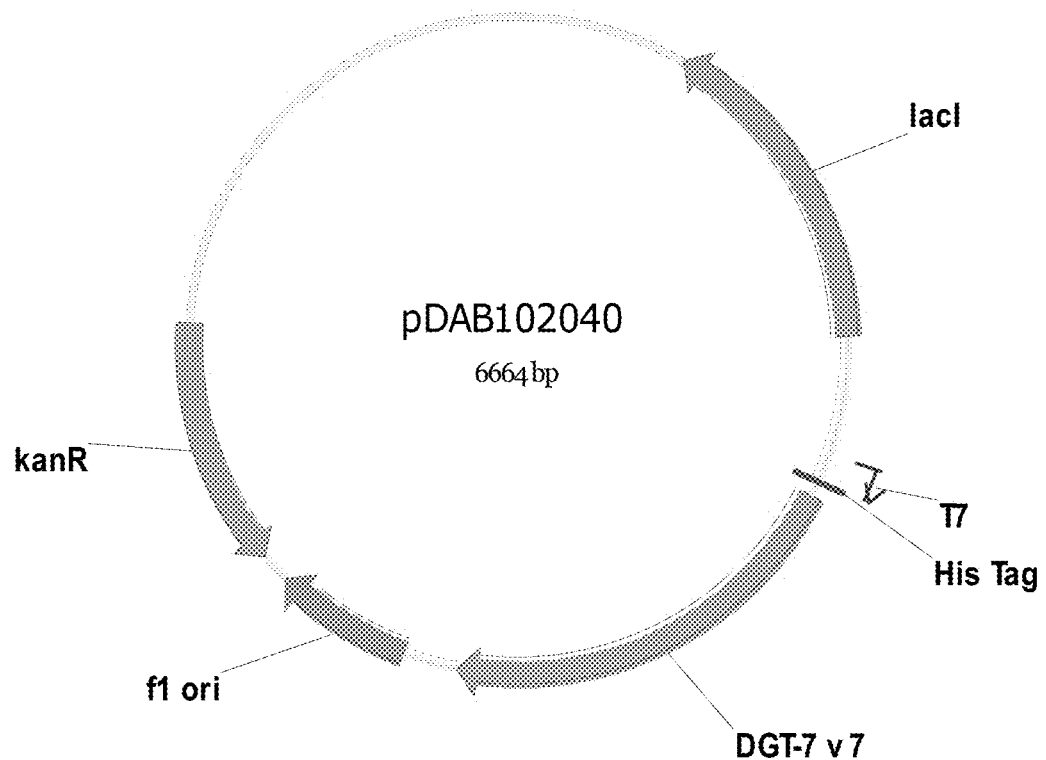
Figure 27:
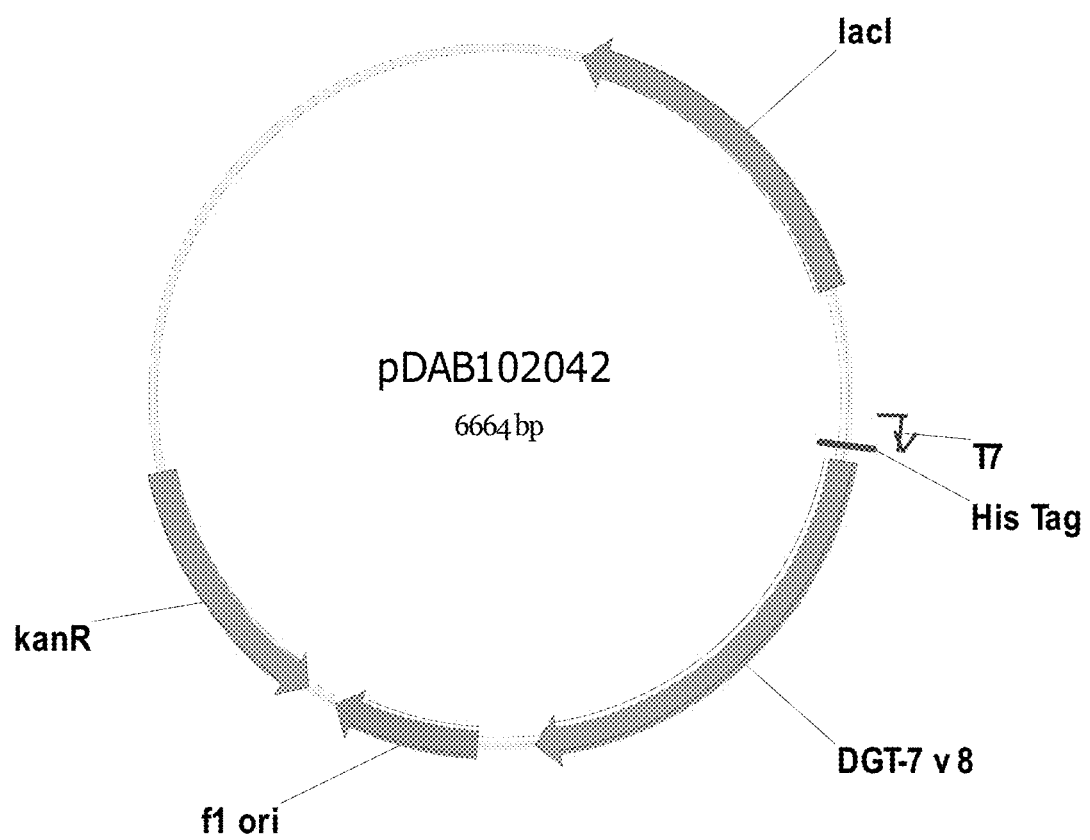

For in vitro testing, the dgt-1 v5, dgt-1 v6, dgt-1 v7, dgt-1 v8, dgt-3 v6, dgt-3 v7, dgt-3 v8, dgt-7 v5, dgt-7 v6, dgt-7 v7, dgt-7 v8, dgt-32 v5, and dgt-33 v5 gene sequences were synthesized and cloned (GeneArt™). The synthesized genes were cloned into the pET28 expression vector. The resulting constructions were labeled as pDAB 102028 (FIG. 17) containing dgt-1 v5, pDAB 102029 (FIG. 18) containing dgt-1 v6, pDAB102032 (FIG. 19) containing dgt-1 v7, pDAB102034 (FIG. 20) containing dgt-1 v8, pDAB100429 (FIG. 21) containing dgt-3 v6, pDAB100442 (FIG. 22) containing dgt-3 v7, pDAB100430 (FIG. 23) containing dgt-3 v8, pDAB102036 (FIG. 24) containing dgt-7 v5, pDAB102038 (FIG. 25) containing dgt-7 v6, pDAB102040 (FIG. 26) containing dgt-7 v7, and pDAB 102042 (FIG. 27) containing dgt-7 v8.

Cloning of DGT-32, and DGT-33.

Figure 11:
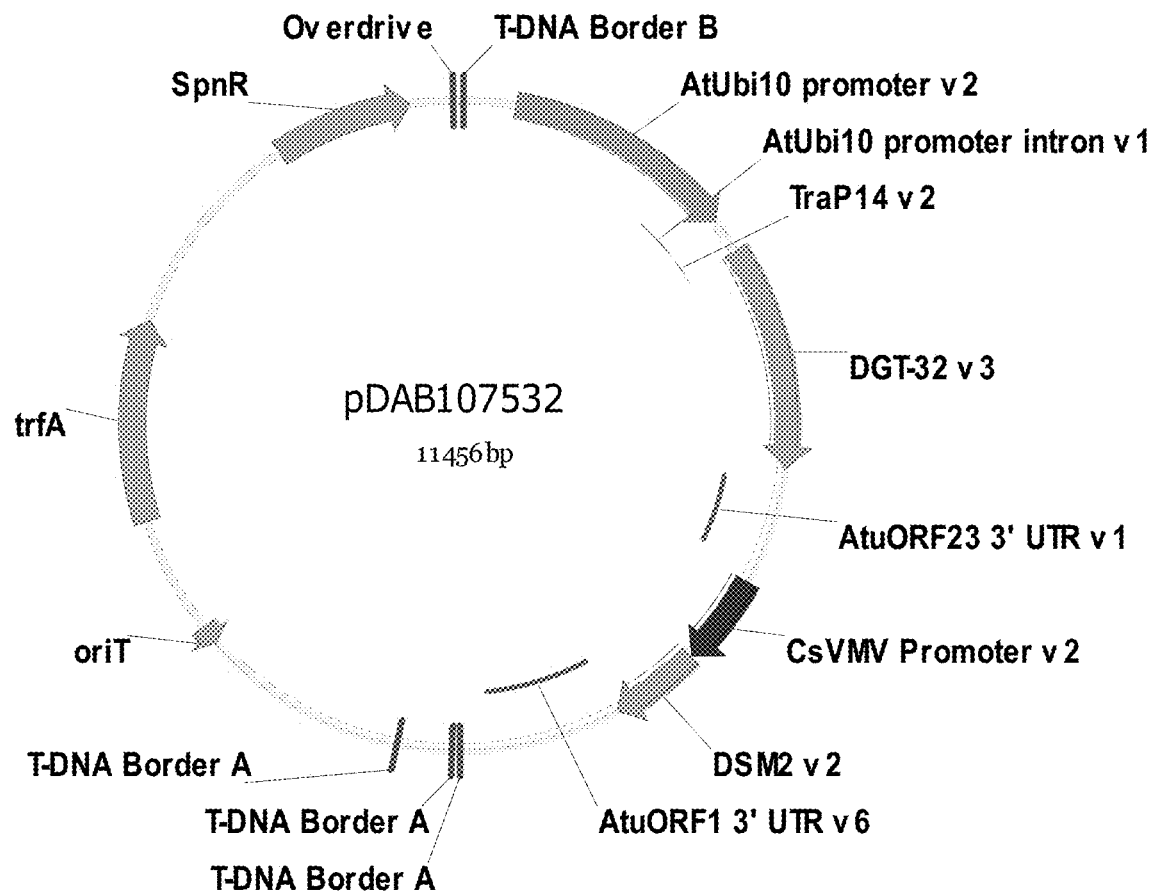
Figure 12:
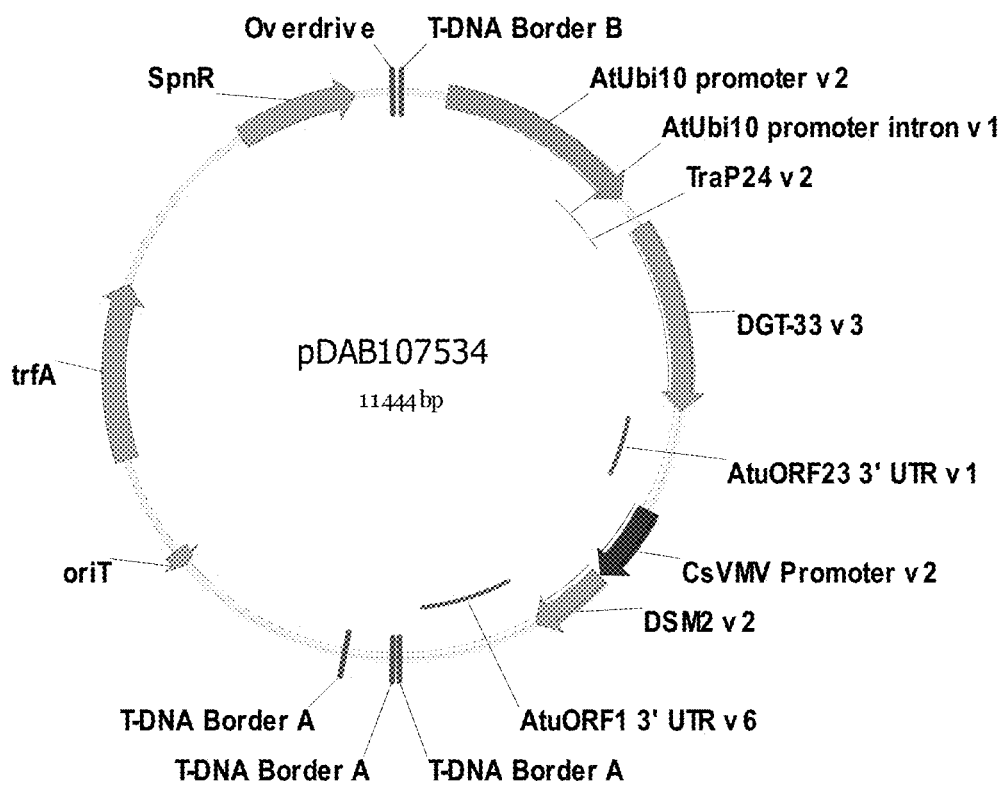

For in vitro testing, the following plant optimized genes; dgt-32 v3, and dgt-33 v3 were amplified out of the binary vectors pDAB 107532 (FIG. 11) and pDAB 107534 (FIG. 12), respectively. The following primer sets were used:

```
pMALDGT32F
(SEQ ID NO: 29; CATATGACCGTTATTGAAATTCCGGG)
and pMALDGT32R
(SEQ ID NO: 30; GATATCCTATTATTAACGACCTTCCAG)
for dgt-32,
and pMALDGT33F
(SEQ ID NO: 31; CATATGGGTGCAGTTACCGTTATTGA), pMALDGT33R
(SEQ ID NO: 32; GATATCCTATTATTATGCCTGCGGAC)
for dgt-33.
```

Figure 29:
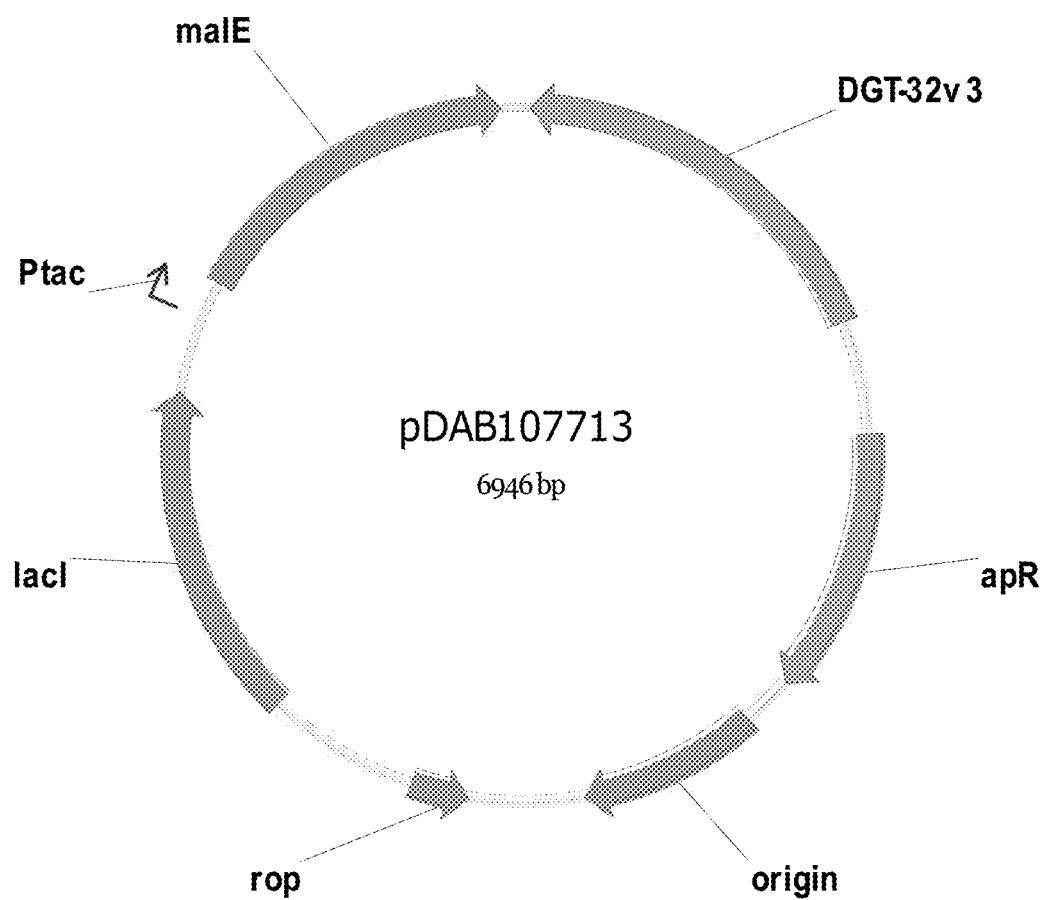
Figure 30:
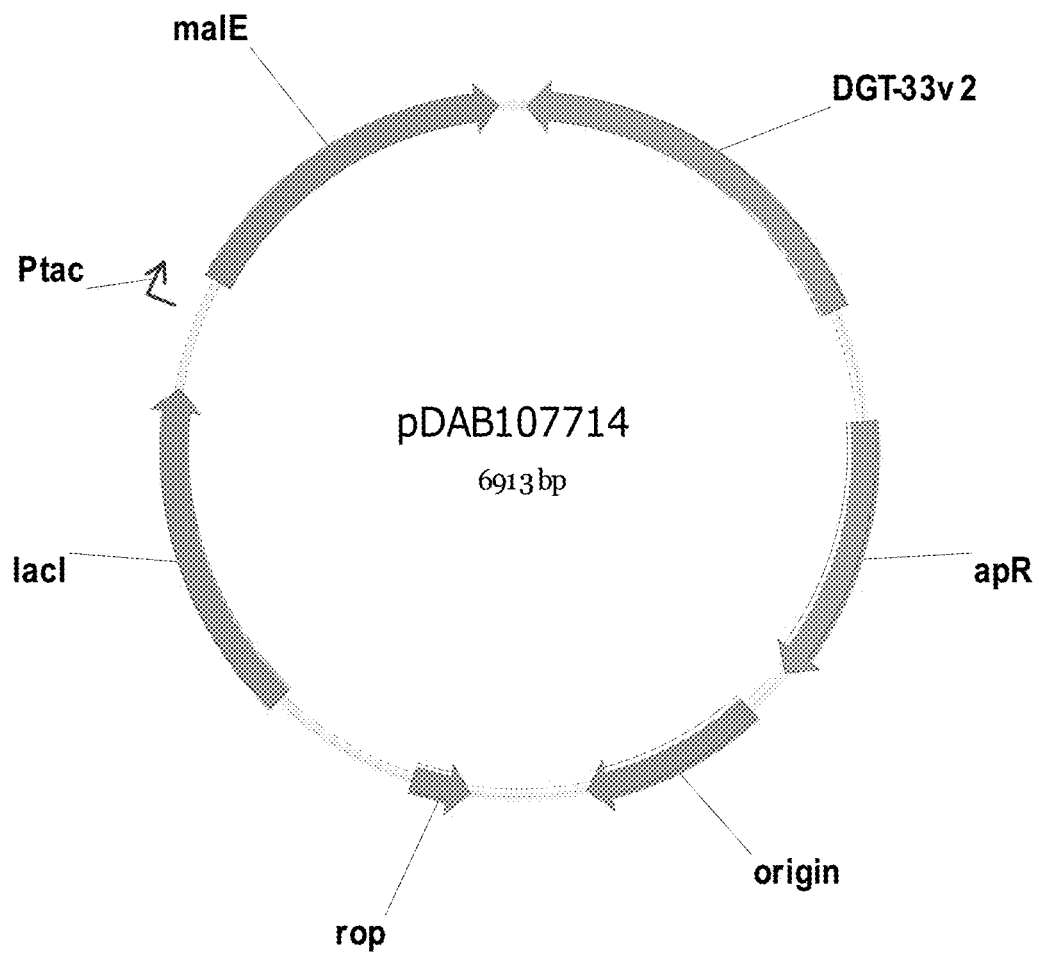

Amplified sequences were then subcloned into pMAL-c5× so that each gene was an in-frame fusion with the malE coding sequence. The final expression constructs were pDAB107713 (FIG. 29) containing dgt-32 v3, and pDAB107714 (FIG. 30) containing dgt-33 v3.

Example 4

In-Vitro Biochemical Enzymatic Kinetic Assay

Overexpression and Purification of Recombinant DGT Enzymes.

Recombinant DGT proteins were overexpressed in Rosetta2™ (DE3) cells (Novagen™, Madison, Wis.) from the constructs described above. A single colony was used to inoculate 50 mL starter cultures of LB containing chloramphenicol (25 µg/mL) and kanamycin (50 µg/mL) which were cultivated overnight at 37° C. The overnight cultures were used to inoculate 1 L of LB containing chloramphenicol (25 µg/mL) and kanamycin (50 µg/mL). The cultures were grown at 37° C. to an $O.D._{600}$=0.6 then placed in an ice water bath for 10 minutes. Expression of the target proteins was achieved by addition of IPTG to a final concentration of 500 µM.

Induction was allowed to proceed overnight at 20° C. followed by harvesting via centrifugation at 8,000 rpm for 20 minutes. The cell pellets were stored at −80° C. until required for purification. All purification steps were carried out at 4° C. Cell pellets from 1 L cultures were resuspended in 20-30 mL Buffer A (50 mM HEPES pH 7.5, 150 mM KCl, 2 mM DTT, 1 mM EDTA, 20 mM imidazole, and 5% glycerol). COMPLETE™ protease inhibitor cocktail (1 tablet/50 mL, Roche, Indianapolis, Ind.) and lysozyme (1 mg/mL, Sigma-Aldrich, St. Louis, Mo.) were then added and the suspension was stirred for 20 minutes. Cell lysis was performed using a Branson™ Sonifier™ 250 (3×60 second bursts) followed by removal of the cell debris by centrifugation at 16,000 rpm for 45 minutes.

DGT enzymes were purified to homogeneity in one step via immobilized metal affinity chromatography (IMAC) using a 5 mL HisTrap FF crude column. The column was equilibrated in Buffer A and the sample was loaded in the same buffer. The column was then washed with 10 column volumes of Buffer A followed by elution in a 0-100% Buffer B (50 mM HEPES pH 7.5, 200 mM KCl, 2 mM DTT, 1 mM EDTA, 500 mM imidazole, and 5% glycerol) linear gradient over 25 column volumes. Fractions containing target protein, as judged by SDS-PAGE analysis, were concentrated to 2.5 mL using a Millipore ultracentrifugation device equipped with a 10 kDa molecular weight cut-off (MWCO). The purified DGT enzymes were buffer exchanged using PD-10 columns (GE Healthcare) into 50 mM HEPES pH 7.5, 150 mM KCl, 2 mM DTT, and 5% glycerol and subsequently concentrated ~1 mL. Samples were typically diluted 1:50 and the UV-visible spectrum was recorded from 240-700 nm on a Cary50™ Bio UV-visible spectrophotometer. A theoretical extinction coefficient was then used to calculate the protein concentration based on the absorbance at 280 nm (ExPASy, Geneva, Switzerland).

Expression and Purification of Recombinant DGT-32 and DGT-33 Fusions.

Figure 28:
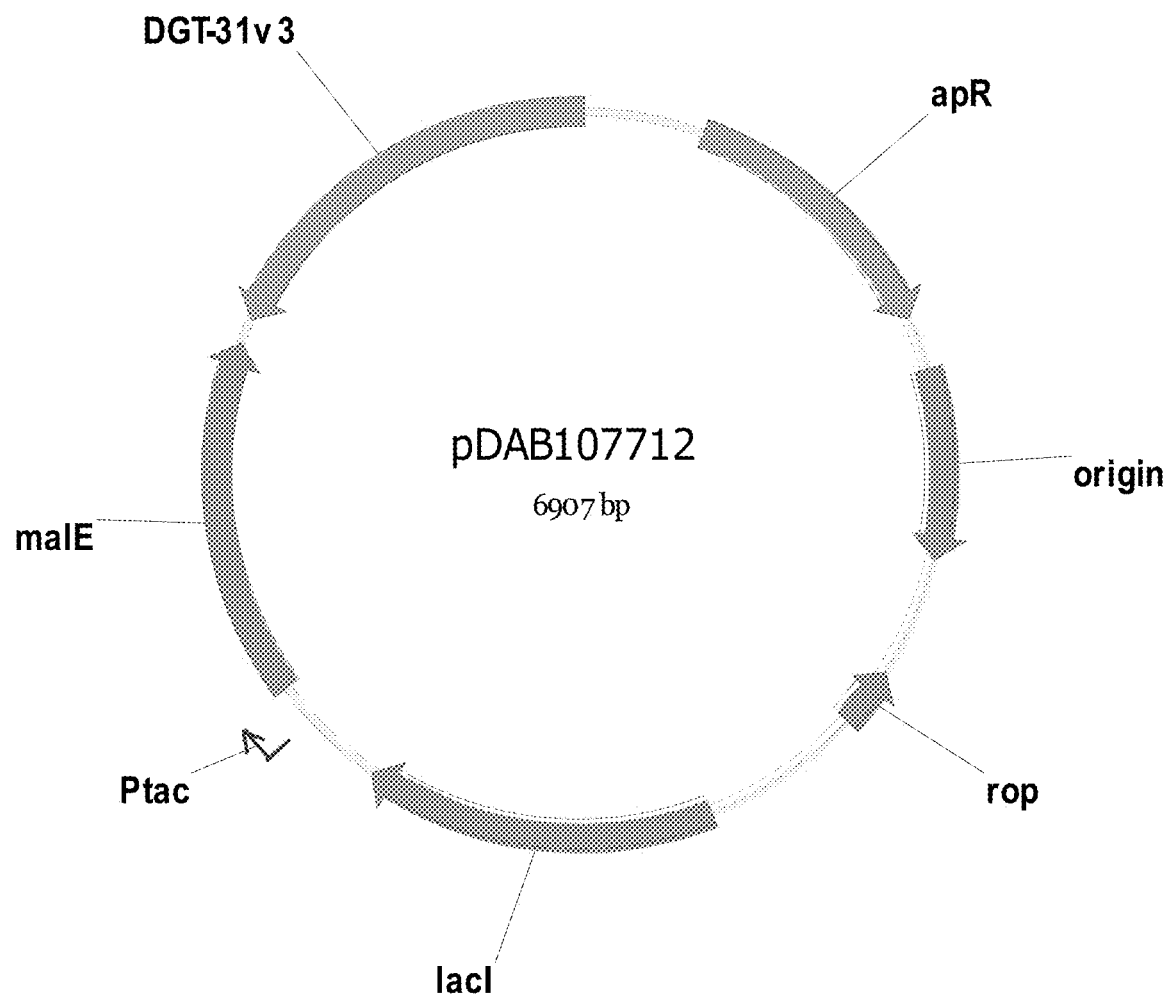

The DGT-32 and DGT-33 enzymes were constructed to contain a maltose fusion tag located at the amino terminus of the enzyme. *Escherichia coli* cells transformed with pDAB 107712 (FIG. 28), pDAB 107713, and pDAB 107714 were isolated and confirmed. A single colony of each bacterial strain was used to inoculate 50 mL of LB media containing 100 µg/µL carbenicillin and 25 µg/µL chloramphenicol. The starter culture was grown overnight at 37° C. and subsequently used to inoculate 600 mL of LB media supplemented with 0.2% glucose, 100 µg/µL carbenicillin, and 25 chloramphenicol. The cultures were grown at 37° C. to an $OD_{600}$=0.4 at which time IPTG was added to a final concentration of 50 µM IPTG. The cultures were induced for 15 hours at 18° C. The following day the cultures were harvested by centrifugation at 8,000 rpm for 20 minutes to pellet the cells. The cell paste was stored at −80° C. until required for purification.

Frozen pellets were resuspended in 20-30 mL buffer A (50 mM HEPES pH 7.5, 100 mM KCl, 1 mM EDTA, 5% glycerol, and 1 mM DTT) and 1 tablet of protease inhibitor (Roche Complete). Once the pellet was completely resolubilized 1 mg/mL of lysozyme was added and the sample was mixed at 4° C. for 15-20 minutes. Following the incubation with the lysozyme the sample was transferred to a 50 mL centrifuge tube and placed on ice. The sample was then sonicated for 1 minute intervals followed by 4 minutes of cooling. This step was repeated two more times for a total of three sonication cycles. Cell debris was removed by centrifugation at 16,500 rpm for 45 minutes and the supernatant was loaded into a 50 mL injection loop. The crude lysate was applied to an amylose column, washed for 7 column volumes with buffer A, and eluted in 100% buffer B (Buffer A and 10 mM maltose). Target protein was pooled and concentrated to 2.5 mL using a 30 kDa MWCO centricon. The purified protein was buffer exchanged into 50 mM HEPES pH 7.5, 100 mM KCl, and 5% glycerol using a PD-10 gel filtration column. Protein concentrations were determined via Bradford assay using BSA as a standard. The pure protein was frozen in liquid nitrogen and stored at −80° C.

In Vitro Kinetic Characterization of Plant and Bacterial DGT Enzymes.

The enzyme activities of wild-type (WT) and mutant DGTs were measured by inorganic phosphate ($P_i$) production in a modified procedure described by Lanzetta et al. (1979) Anal. Bioch. 100:95-7. Assays were performed in 96-well plate format in a total of 50 µL on a Spectra-Max 190 plate reader (Molecular Devices, Sunnyvale, Calif.). Typical assays contained 50 mM HEPES pH 7.5, 150 mM KCl, 2 mM DTT, and 1 mM S3P. PEP and glyphosate concentrations were varied as indicated. Glyphosate was obtained from Sigma as the free acid and was resuspended in ddH$_2$O. Glyphosate was solubilized by addition of KOH until the mixture was at a neutral pH. Assays were initiated by addition of the DGT enzyme at concentrations that varied between 0.01-1 µM. Reactions were terminated by the addition of 235 µL of a 3:1 mixture of malachite green:ammonium molybdate solution. After complete color development (~1 minute), the absorbance change at 660 nm was recorded and the amount of $P_i$ formed was calculated from a standard curve. Control reactions lacking enzyme were used to correct for background absorbance. High concentrations of PEP (>2 mM) and glyphosate (>30 mM) contribute a significant amount of background absorbance using this detection method. The data were fitted to the Michaelis-Menten equation which allowed for the determination of $K_m$ and $V_{max}$ (Equation 3) while IC$_{50}$ was determined from Equation 4, where y is the relative activity and s is the Hill coefficient. Data were analyzed using GraFit™ version 5 software (Erithacus Software Limited, Horley, U.K.).

$$v = \frac{V_{max} \cdot [S]}{K_m + [S]} \quad (3)$$

$$y = \frac{100\%}{1 + \left(\frac{x}{IC_{50}}\right)^s} \quad (4)$$

The IC$_{50}$ value for a competitive inhibitor will change dependent on the concentration of substrate, therefore the IC$_{50}$ values in Table 2 were obtained at 1 mM PEP and at 60 µM PEP (an estimate of the intracellular PEP concentrations in plants). Only IC$_{50}$ values measured at the same concentration of PEP should be compared (K. determinations for DGT-32 and DGT-33 were determined at 100 µM PEP). Additionally, IC$_{50}$ values of highly tolerant enzymes could not accurately be determined by the method of Lanzetta and were therefore estimated based on relative activity.

Kinetics of Plant DGTs.

Figure 31:
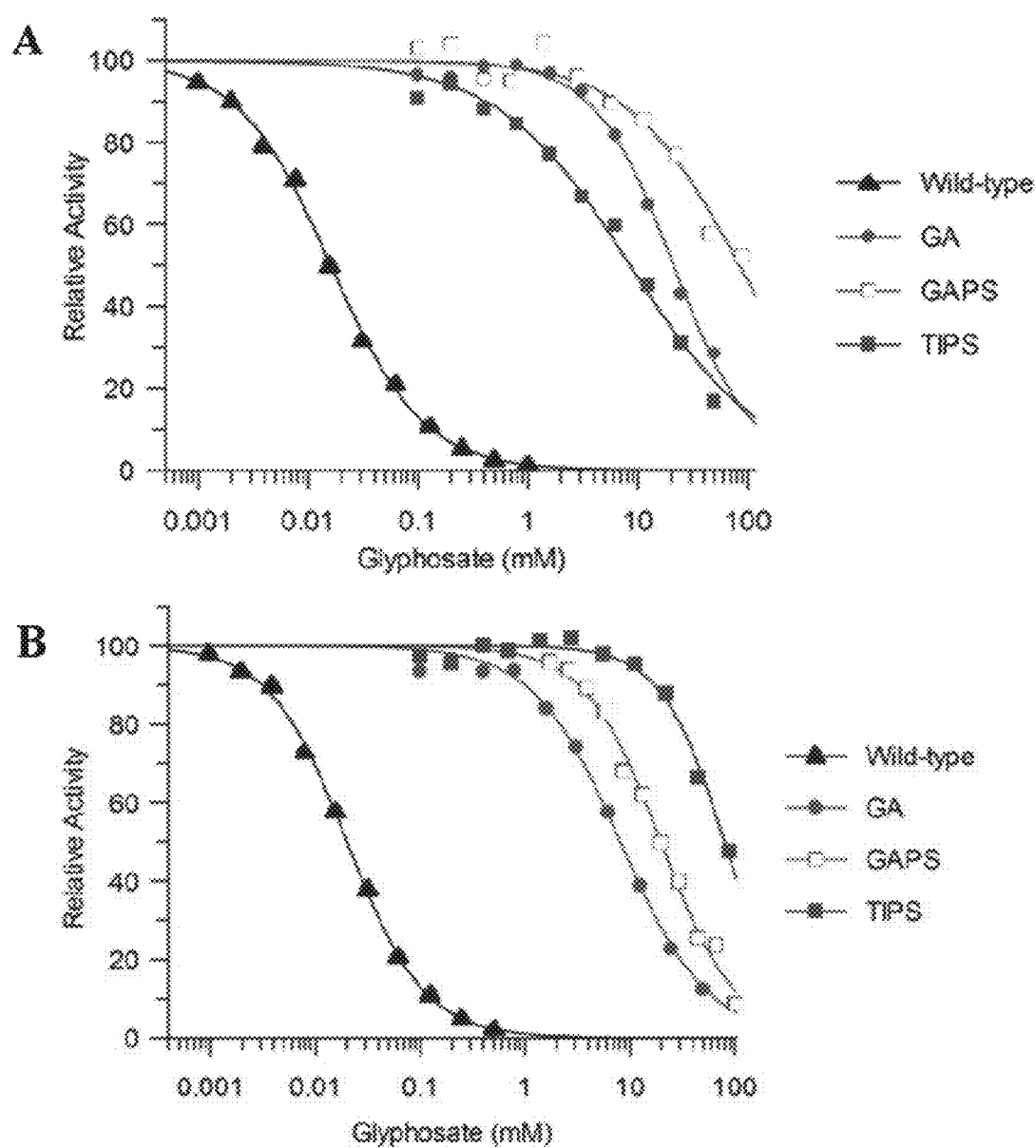
FIG. 31 includes $IC_{50}$ values obtained after introduction of various mutations within DGT-1 (A) and DGT-7 (B) using 1 mM PEP. For both FIG. 31(A) and FIG. 31(B) $IC_{50}$ curves, closed triangles represent wild-type, closed circles represent GA mutants, open squares represent GAPS mutants, and closed squares represent TIPS mutants.

Two enzymes with un-mutated native sequences, DGT-1 v5 and DGT-7 v5, were tested first to establish baseline parameters for glyphosate sensitivity. Both proteins displayed low K$_m$ values for PEP (~70 µM) and were sensitive to glyphosate with IC$_{50}$ values of ~20 µM (Table 2) at 1 mM PEP. As observed for DGT-1 v6, DGT-3 v6, and DGT-7 v6, a single point mutation from G to A significantly improved tolerance to glyphosate (IC$_{50}$ values of 8-21 mM) but also increased the K$_m$ for PEP by ~8-fold. The double mutation (GAPS), for all plant derived DGTs (DGT-1 v7, DGT-3 v7, and DGT-7 v7), also enhanced glyphosate tolerance, but once again resulted in a considerable elevation in the PEP K$_m$. Table 2. The TIPS mutants (DGT-1 v8, DGT-3 v8, and DGT-7 v8) were tolerant to modest concentrations of glyphosate β-6 mM) but in contrast to the GA and GAPS mutants, the K$_m$ levels remained close to the wild-type proteins between 60-200 µM. FIG. 31 demonstrates the shifts in glyphosate tolerance for DGT-1 (A) and DGT-7 (B) upon introduction of the specified mutations. The PEP concentration was held at 1 mM for the experiments resulting in the data shown in FIG. 31, which likely led to the elevated IC$_{50}$ (>80 mM) for DGT-7 v8. Further procedures were carried out to determine if lower levels of PEP altered the relative tolerance to glyphosate. Physiologically relevant levels of PEP range from 5-60 µM. With 60 µM PEP, the IC$_{50}$ value decreased significantly (3.6 mM), suggesting the initial determination was influenced by excess PEP, as expected from Michaelis-Menten kinetics and noted in Table 2.

FIG. 31 shows IC$_{50}$ values obtained after introduction of various mutations within DGT-1 (A) and DGT-7 (B) using 1 mM PEP. For both A and B IC$_{50}$ curves closed triangles represent wild-type, closed circles represent GA mutants, open squares represent GAPS mutants, and closed squares represent TIPS mutants.

TABLE 2

Steady-state kinetic parameters for DGT enzymes. IC$_{50}$ values greater than 50 are estimates due to limitations of the method used.
*IC$_{50}$ for glyphosate was determined at 100 µM PEP.

| | | Protein | Sequence Version | IC$_{50}$ (mM Glyphosate) | | $K_M^{PEP}$ (µM) | $K_{cat}/K_m$ (M$^{-1}$ s$^{-1}$) |
| --- | --- | --- | --- | --- | --- | --- | --- |
| | | | | IC$_{50}$ at 1 mM PEP | IC$_{50}$ at 60 µM PEP | | |
| Plant Enzymes | Soybean | DGT-1 v5 | Native | 0.0 | 0.0 | 73.0 | 7.41E+04 |
| | | DGT-1 v6 | GA | 21.1 | 17.3 | 608.2 | 1.34E+04 |
| | | DGT-1 v7 | GA PS | >80.0 | >80.0 | 1291.2 | 6.67E+03 |
| | | DGT-1 v8 | TI PS | 13.3 | 5.9 | 151.4 | 1.23E+04 |

TABLE 2-continued

Steady-state kinetic parameters for DGT enzymes. $IC_{50}$ values greater than 50 are estimates due to limitations of the method used.
*$IC_{50}$ for glyphosate was determined at 100 μM PEP.
$IC_{50}$ (mM Glyphosate)

|  | Protein | Sequence Version | $IC_{50}$ at 1 mM PEP | $IC_{50}$ at 60 μM PEP | $K_M^{PEP}$ (μM) | $K_{cat}/K_m$ ($M^{-1} s^{-1}$) |
|---|---|---|---|---|---|---|
| Canola | DGT-3 v6 | GA | 15.8 | 8.7 | 1073.4 | 1.39E+04 |
|  | DGT-3 v7 | GA PS | >50.0 | 42.0 | 2728.3 | 2.28E+03 |
|  | DGT-3 v8 | TI PS | 13.3 | 4.8 | 196.8 | 3.29E+04 |
| Wheat | DGT-7 v5 | Native | 0.0 | 0.0 | 75.6 | 2.15E+05 |
|  | DGT-7 v6 | GA | 8.1 | 15.1 | 538.2 | 1.61E+04 |
|  | DGT-7 v7 | GA PS | 19.7 | 15.4 | 1103.2 | 1.46E+04 |
|  | DGT-7 v8 | TIPS | >80.0 | 3.6 | 60.5 | 1.36E+04 |
| Bacterial Enzymes | DGT-28v1 | Native | >80.0 | >80.0 | 91.6 | 1.32E+05 |
|  | DGT-28 v2 | AG | >50.0 | 2.2 | 161.5 | 6.86E+04 |
|  | DGT-28 v3 | AGTA | >50.0 | 5.2 | 27.3 | 6.01E+02 |
|  | DGT-32 | Native | — | >50.0* | 139.8 | 1.30E+03 |
|  | DGT-33 | Native | — | >50.0* | 114.2 | 2.40E+03 |

Kinetics of Bacterial DGTs.

Of the bacterial enzymes, DGT-28 v1 possesses the most favorable overall kinetic parameters (Elevated $IC_{50}$ and $K_{cat}$/Km values). The enzyme was tolerant to glyphosate at concentrations >80 mM and displayed a catalytic efficiency of $1.32 \times 10^5$ $M^{-1}s^{-1}$. The A→G mutation in DGT-28 v2 lowered the $IC_{50}$ to 2.17 mM (at 60 μM PEP) and caused a slight elevation in the Km for PEP (161 μM). This mutant enzyme retains the high catalytic efficiency seen in DGT-28 v1. Even with a lowered $IC_{50}$, this mutated enzyme is suitable for providing tolerance to glyphosate in planta in certain applications. The data suggest that in this new class of EPSP synthase, the alanine is not the sole determinant for tolerance to glyphosate. To explore other possible determinants an additional variant, DGT-28 v3 (A84G T172A double mutant), was constructed. This enzyme displayed lowered tolerance to glyphosate with an $IC_{50}$ value of 5.15 mM (at 60 μM PEP). The decrease in $IC_{50}$ for DGT-28 v3 was accompanied by a 200-fold decrease in catalytic efficiency, suggesting the second mutation led to unintended effects (Table 2). The higher identity DGT-28 v1 homologues (~75% amino acid identity), DGT-32 and DGT-33, had low Km's for PEP (~114-139 however catalytic efficiencies were 100-fold lower than DGT-28 v1. This drop in catalytic efficiency is likely derived from the maltose binding protein (MBP) fusion. The enzymes are also insensitive to glyphosate displaying $IC_{50}$ values of greater than 50 mM. As a result of these in vitro assays, which indicated that the various DGT enzymes provided tolerance to glyphosaste, the DGT enzymes were tested in planta.

Example 5

Cloning of Plant Transformation Vectors

Plant Binary Vector Construction.

Standard cloning methods were used in the construction of entry vectors containing a chloroplast transit peptide polynucleotide sequence joined to dgt-28 as an in-frame fusion. The entry vectors containing a transit peptide (TraP) fused to dgt-28 were assembled using the IN-FUSION™ Advantage Technology (Clontech, Mountain View, Calif.). As a result of the fusion, the first amino acid, methionine, was removed from dgt-28. Transit peptides TraP4 v2 (SEQ ID NO:33), TraP5 v2 (SEQ ID NO:34), TraP8 v2 (SEQ ID NO:35), TraP9 v2 (SEQ ID NO:36), TraP12 v2 (SEQ ID NO:37), and TraP13 v2 (SEQ ID NO:38) were each synthesized by DNA2.0 (Menlo Park, Calif.) and fused to the 5' end fragment of dgt-28, up to and including a unique Accl restriction endonuclease recognition site.

Binary plasmids which contained the various TraP and dgt-28 expression cassettes were driven by the *Arabidopsis thaliana* Ubiquitin 10 promoter (AtUbi10 v2; Callis, et al., (1990) *J. Biol. Chem.*, 265: 12486-12493) and flanked by the *Agrobacterium tumefaciens* open reading frame twenty-three 3' untranslated region (AtuORF23 3' UTR v1; U.S. Pat. No. 5,428,147).

The assembled TraP and dgt-28 expression cassettes were engineered using GATEWAY® Technology (Invitrogen, Carlsbad, Calif.) and transformed into plants via *Agrobacterium*-mediated plant transformation. Restriction endonucleases were obtained from New England BioLabs (NEB; Ipswich, Mass.) and T4 DNA Ligase (Invitrogen) was used for DNA ligation. Gateway reactions were performed using GA TEWAY® LR CLONASE® enzyme mix (Invitrogen) for assembling one entry vector into a single destination vector which contained the selectable marker cassette Cassava Vein Mosaic Virus promoter (CsVMV v2; Verdaguer et al., (1996) *Plant Mol. Biol.*, 31: 1129-1139)—DSM-2 (U.S. Pat. App. No. 2007/086813)—*Agrobacterium tumefaciens* open reading frame one 3' untranslated region (AtuORF1 3' UTR v6; Huang et al., (1990) *J. Bacteriol.* 172:1814-1822). Plasmid preparations were performed using NUCLEO-SPIN® Plasmid Kit (Macherey-Nagel Inc., Bethlehem, Pa.) or the Plasmid Midi Kit (Qiagen) following the instructions of the suppliers. DNA fragments were isolated using QIA-quick™ Gel Extraction Kit (Qiagen) after agarose Tris-acetate gel electrophoresis.

Colonies of all assembled plasmids were initially screened by restriction digestion of miniprep DNA. Plasmid DNA of selected clones was sequenced by a commercial sequencing vendor (Eurofins™ MWG Operon, Huntsville, Ala.). Sequence data were assembled and analyzed using the SEQUENCHER™ software (Gene Codes Corp., Ann Arbor, Mich.).

Figure 4:
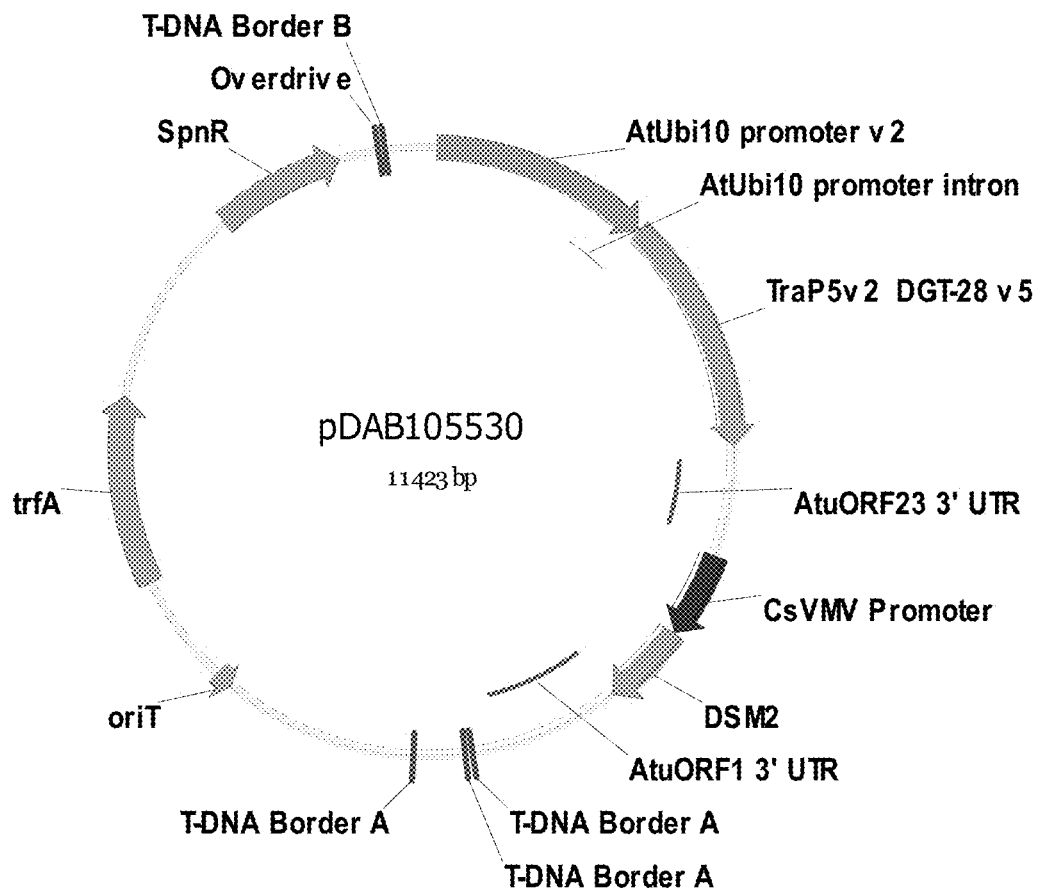
Figure 5:
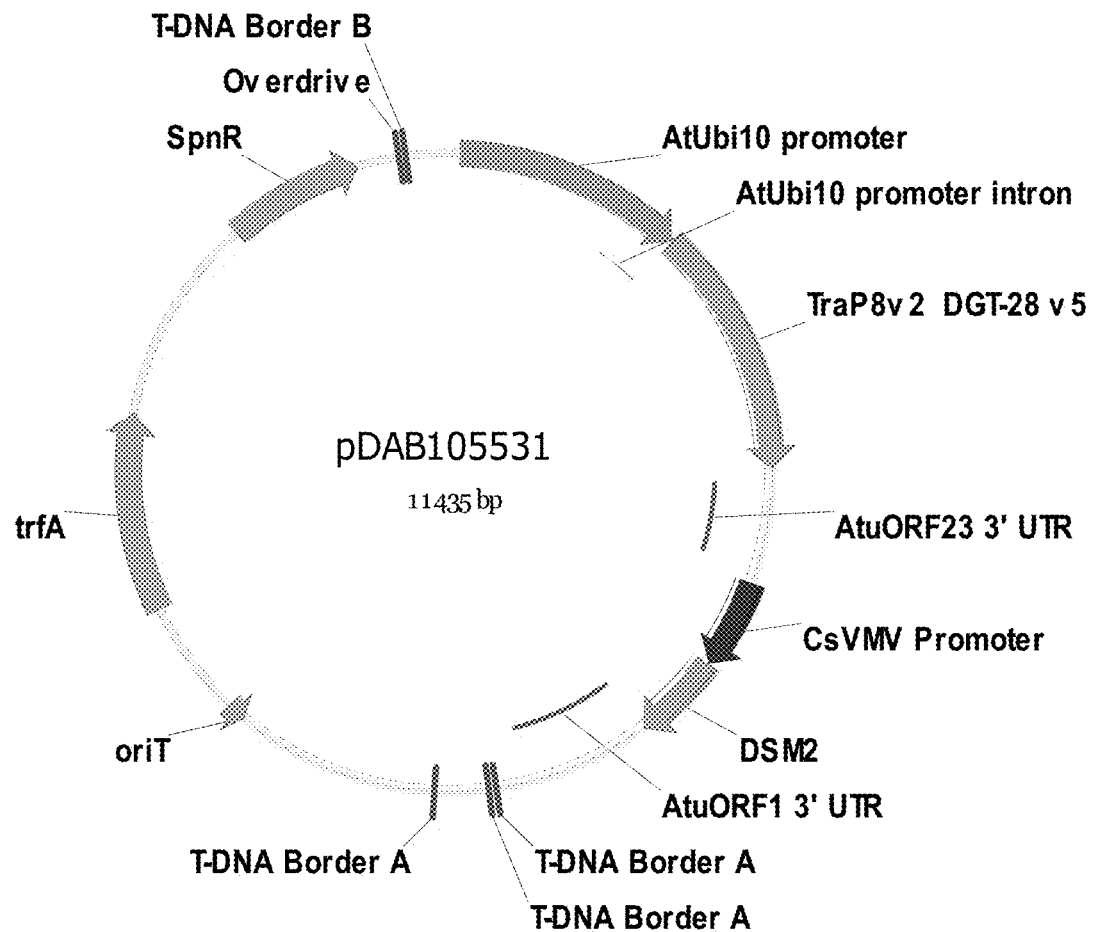
Figure 6:
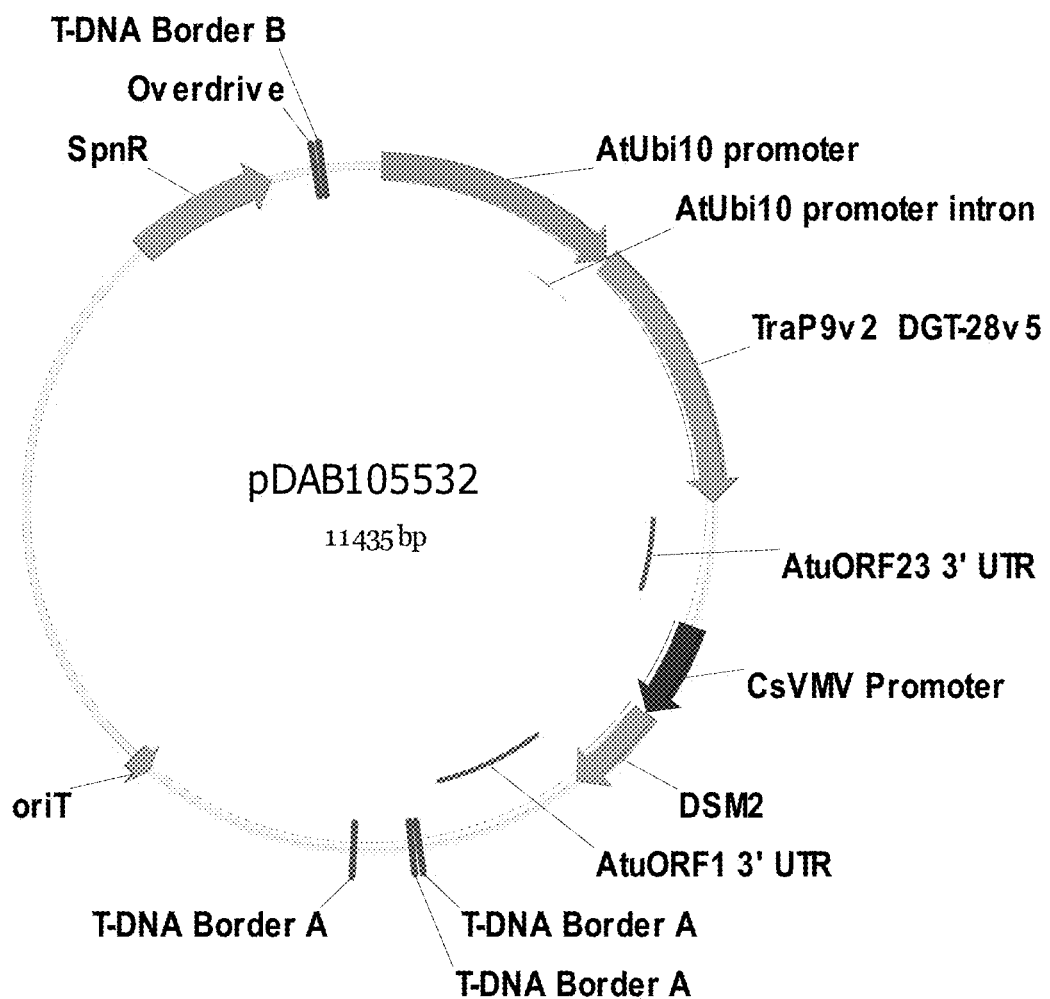
Figure 7:
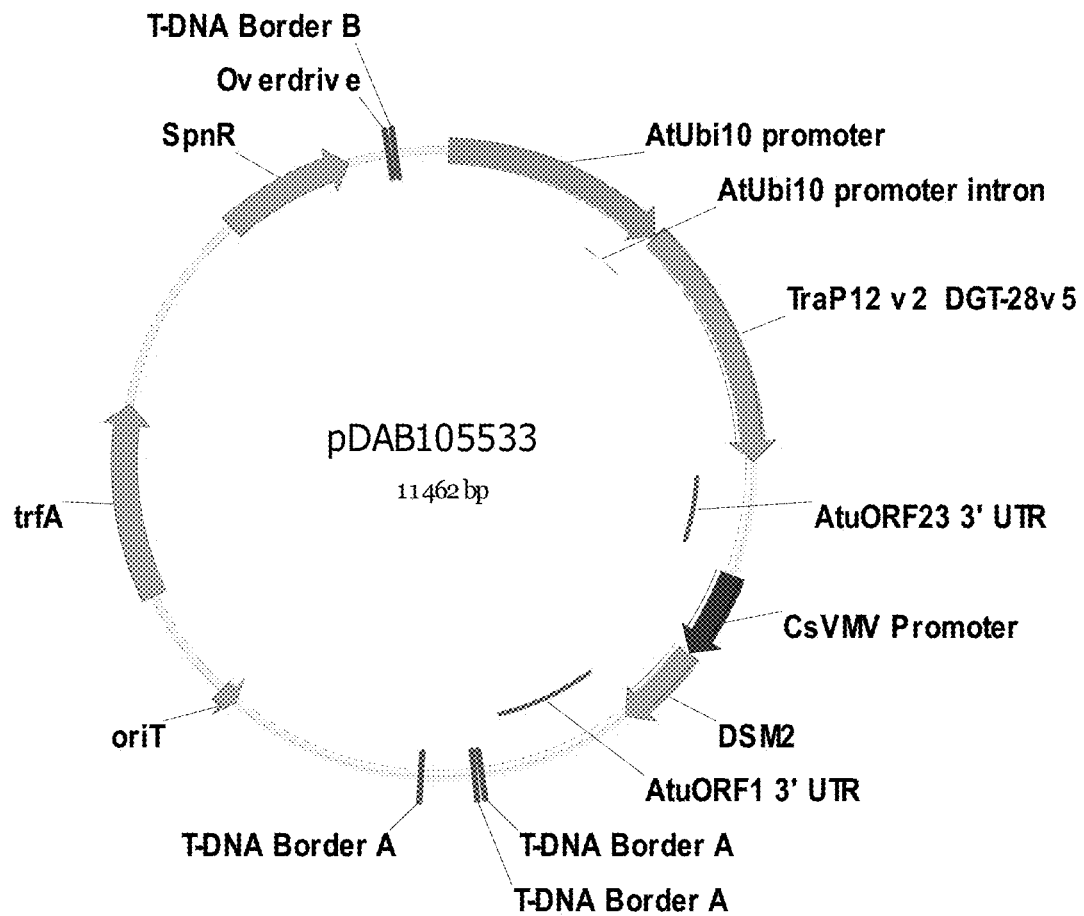
Figure 8:
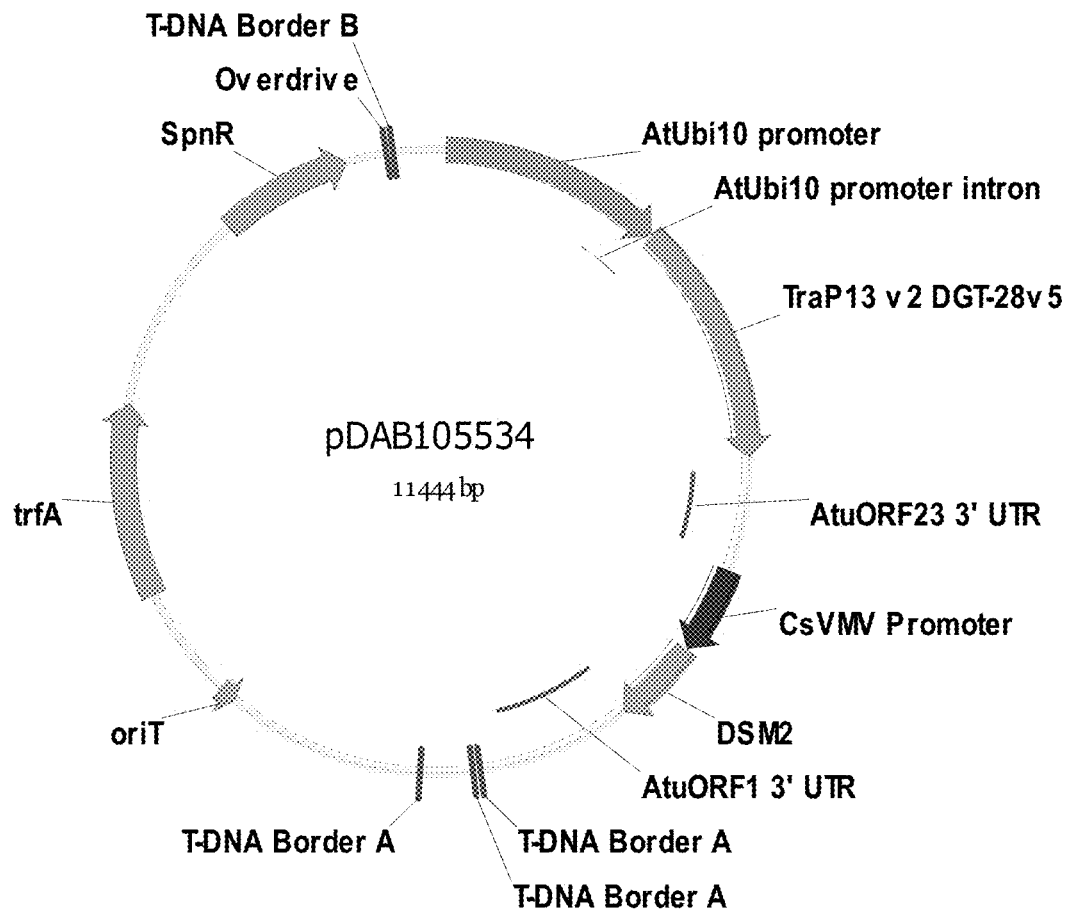

The following binary constructs express the various TraP: dgt-28 fusion gene sequences: pDAB107527 (FIG. 3) contains TraP4 v2:dgt-28 v5 (SEQ ID NO:79); pDAB105530 (FIG. 4) contains TraP5 v2: dgt-28 v5 (SEQ ID NO:80); pDAB105531 (FIG. 5) contains TraP8 v2: dgt-28 v5 (SEQ ID NO:81); PDAB105532 (FIG. 6) contains TraP9 v2: dgt-28 v5 (SEQ ID NO:82); pDAB105533 (FIG. 7) contains TraP12 v2: dgt-28 v5 (SEQ ID NO:83); and pDAB105534 (FIG. 8) contains TraP13 v2:dgt-28 v5 (SEQ ID NO:84). The dgt-28 v5 sequence of pDAB 105534 was modified wherein the first codon (GCA) was changed to (GCT).

Additional Plant Binary Vector Construction.

Cloning strategies similar to those described above were used to construct binary plasmids which contain dgt-31, dgt-32, dgt-33, dgt-1, dgt-3, and dgt-7.

Figure 54:
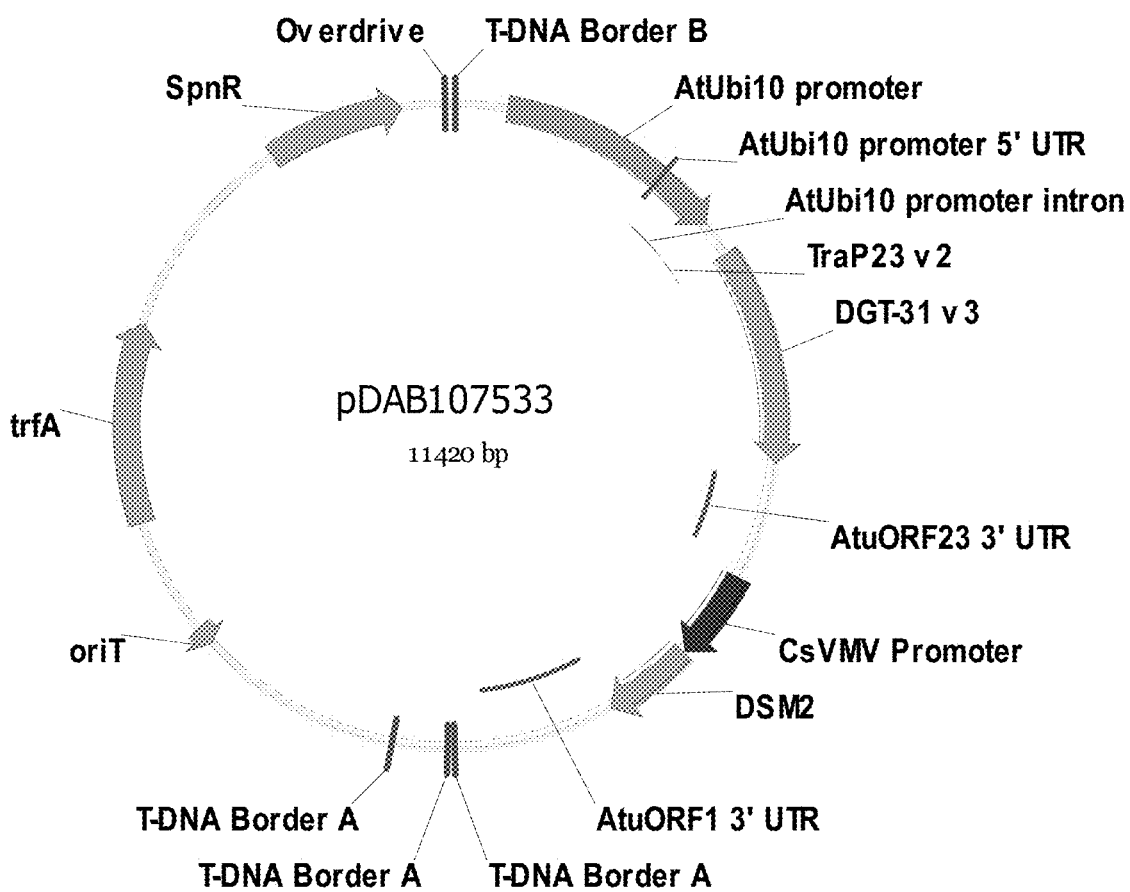

The microbially derived genes; dgt-31, dgt-32, and dgt-33, were fused with different chloroplast transit peptides than previously described. The following chloroplast transit peptides were used; TraP14 v2 (SEQ ID NO:39), TraP23 v2 (SEQ ID NO:40), TraP24 v2 (SEQ ID NO:41). pDAB107532 (FIG. 11) contains dgt-32 v3 fused to TraP14 v2 (SEQ ID NO:42), pDAB 107534 (FIG. 12) contains dgt-33 v3 fused to TraP24 v2 (SEQ ID NO:43), and pDAB 1017533 (FIG. 54) contains dgt-33 v1 fused to TraP23 v2 (SEQ ID NO:143). The dgt expression cassettes were driven by the *Arabidopsis thaliana* Ubiquitin 10 promoter (AtUbi10 promoter v2) and flanked by the *Agrobacterium tumefaciens* open reading frame twenty-three 3' untranslated region (AtuORF23 3' UTR v1). A DSM-2 selectable marker cassette containing Cassava Vein Mosaic Virus promoter (CsVMV v2)—DSM-2—*Agrobacterium tumefaciens* open reading frame one 3' untranslated region (AtuORF1 3' UTR v6) was also present in the binary vector.

Additional binaries are constructed wherein dgt-31 v3, dgt-32 v3, and dgt-33 v3 are fused to the previously described chloroplast transit peptide sequences. For example, the TraP8 v2 sequence is fused to dgt-31 v3, dgt-32 v3, and dgt-33 v3, and cloned into binary vectors as described above.

Figure 9:
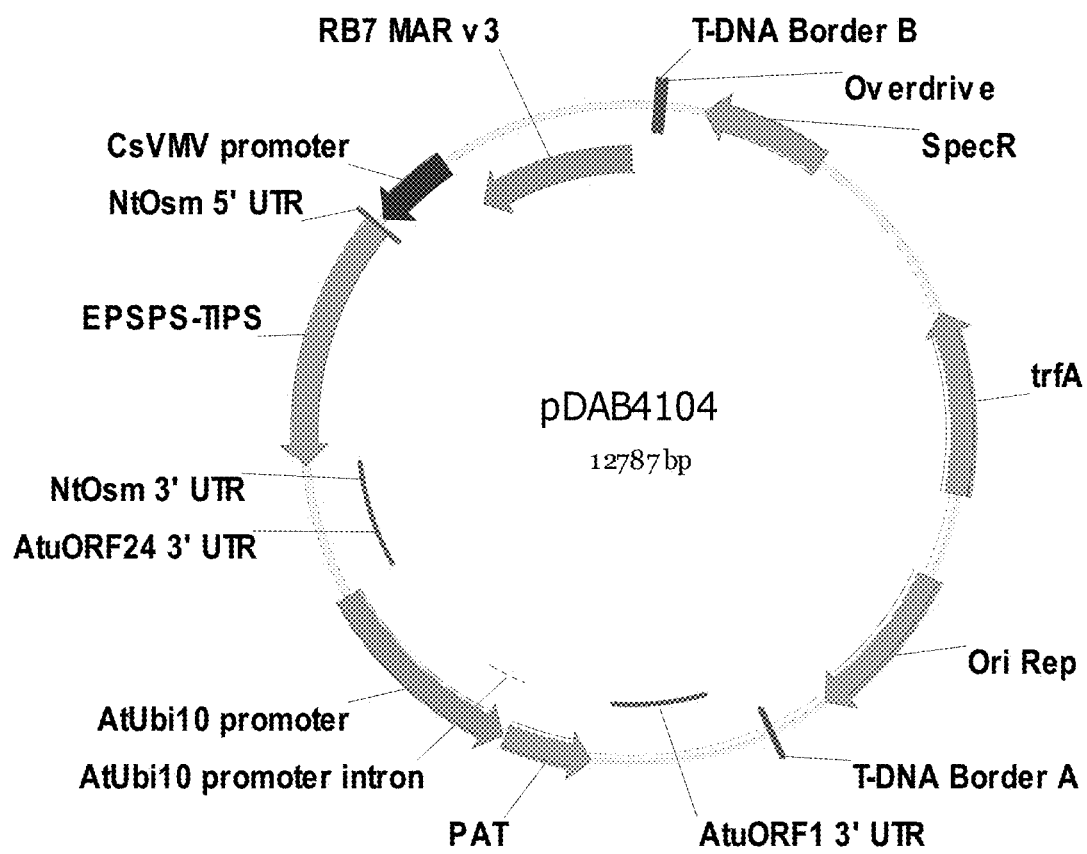
Figure 10:
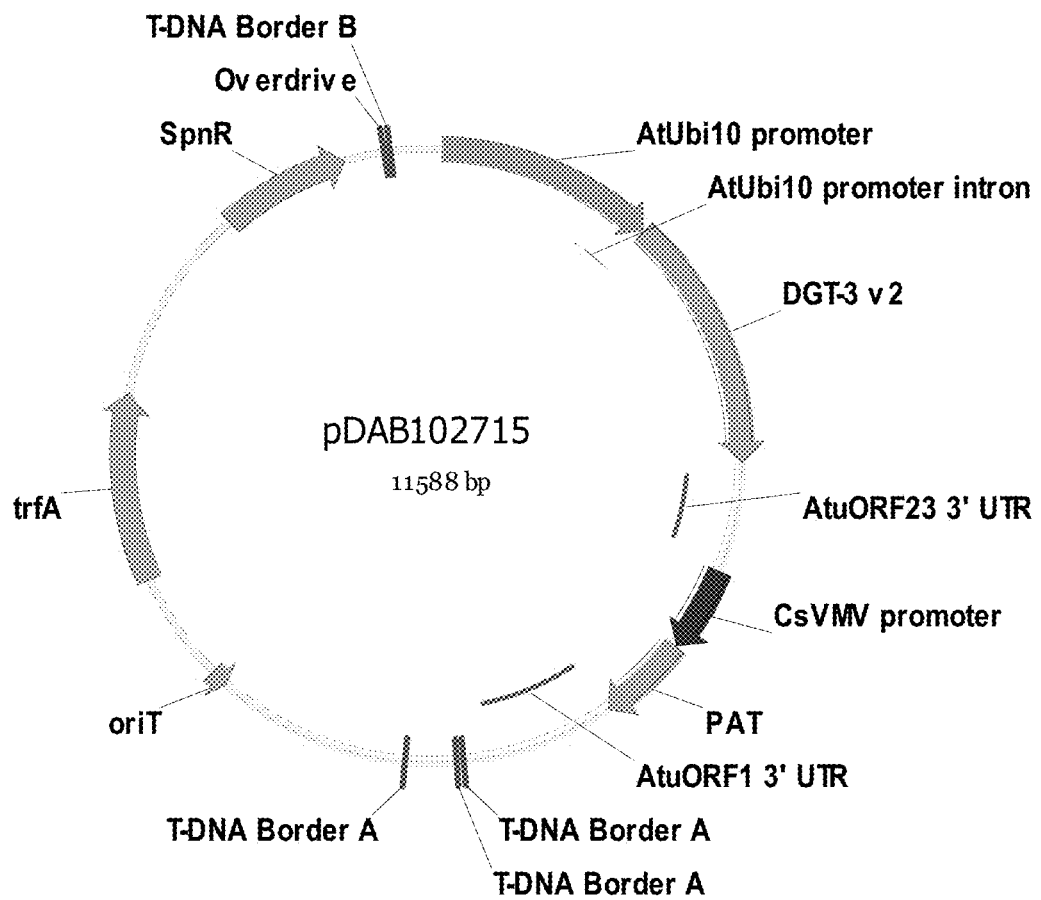
Figure 13:
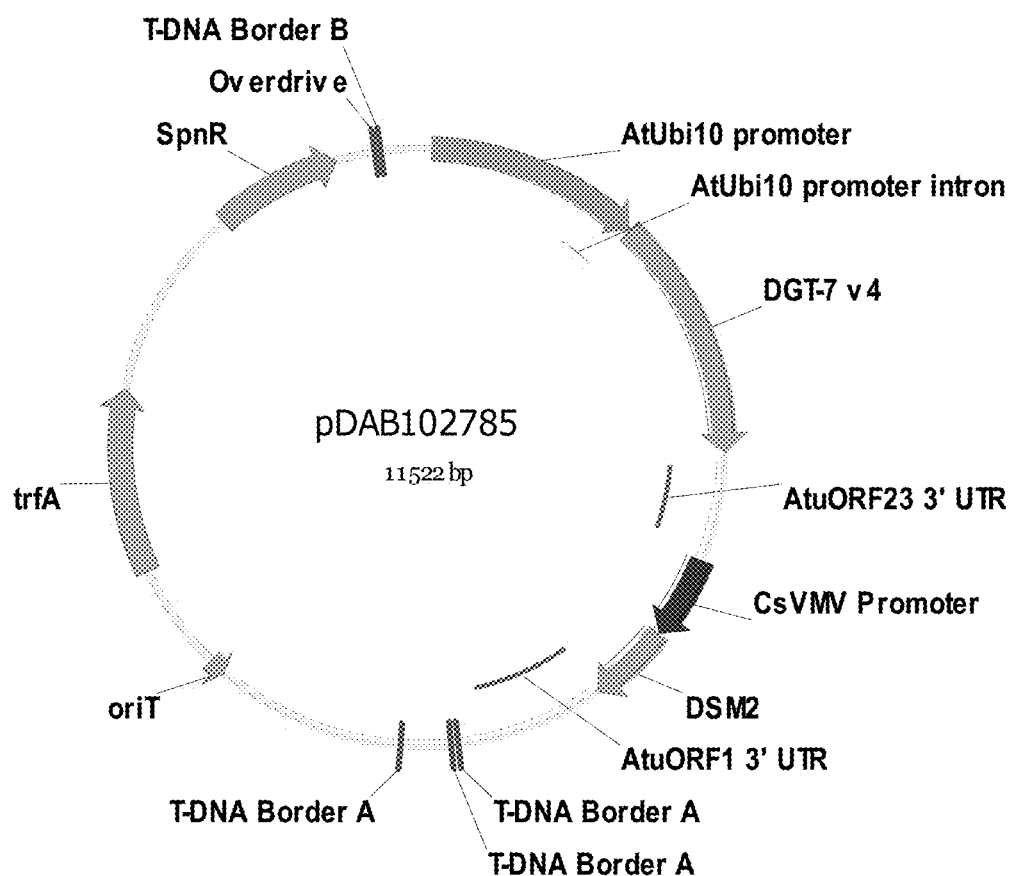
Figure 14:
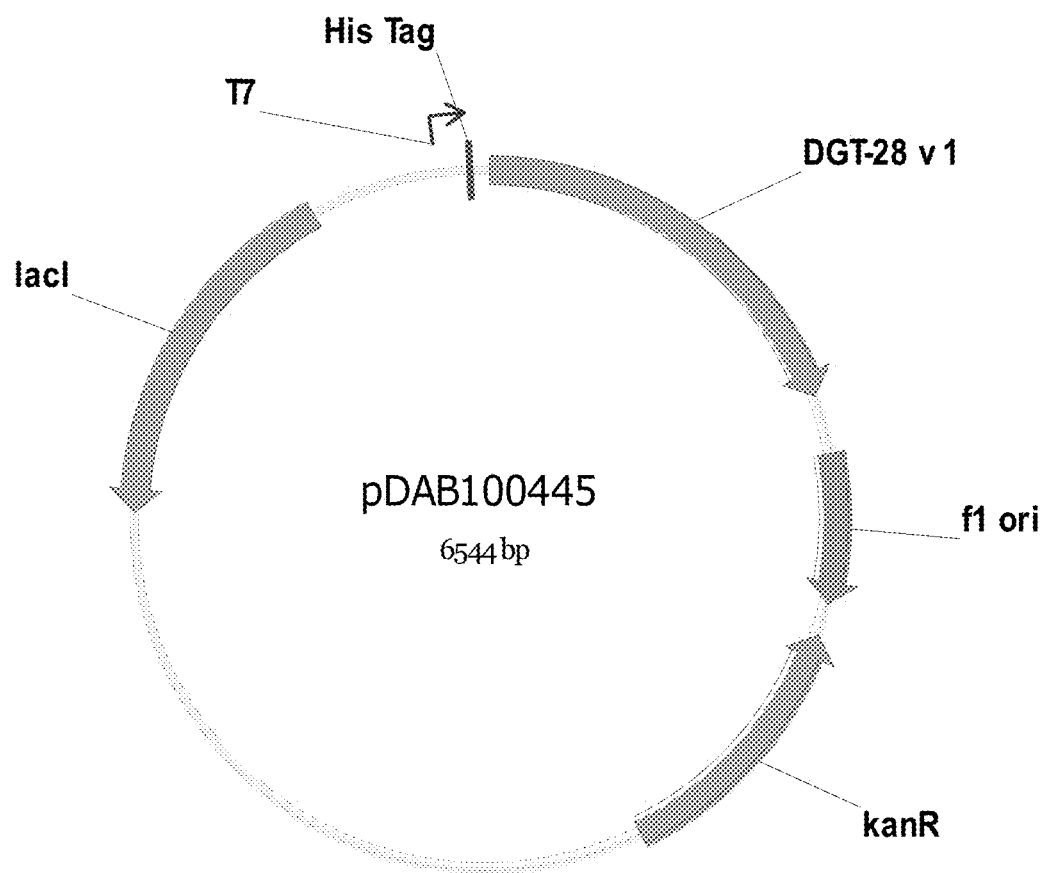
Figure 15:
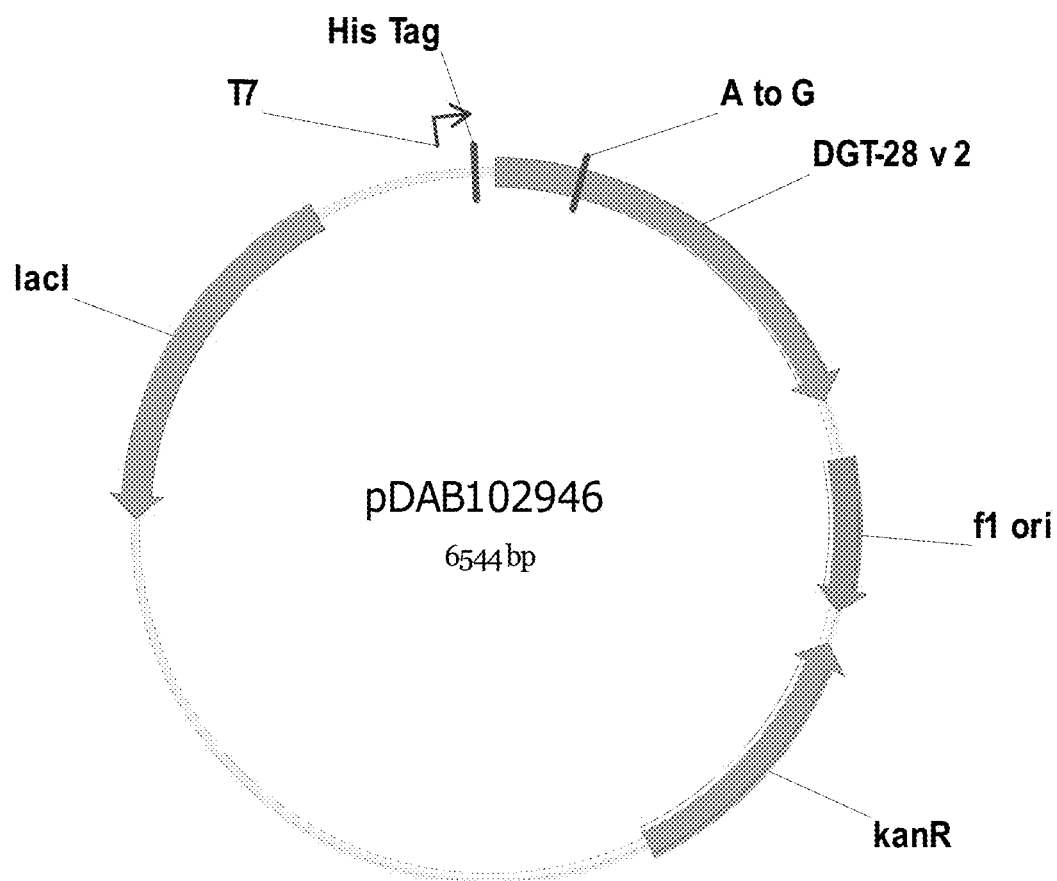
Figure 45:
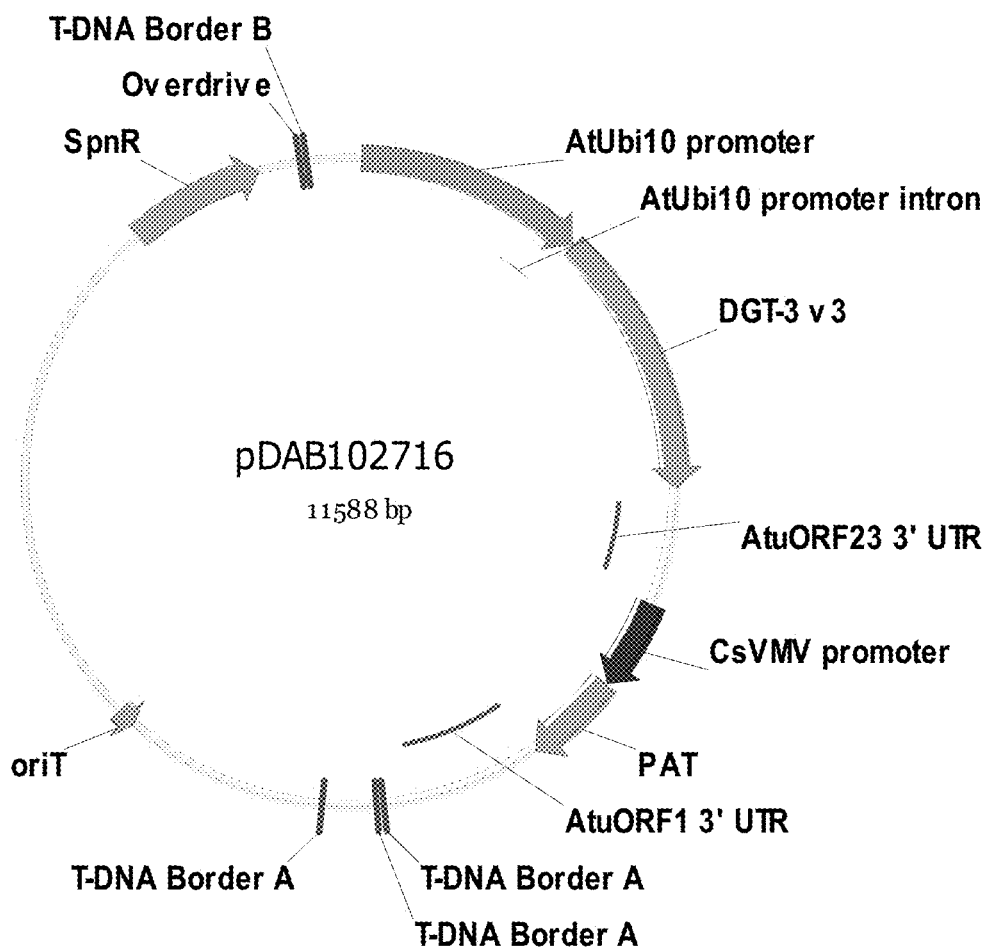
Figure 46:
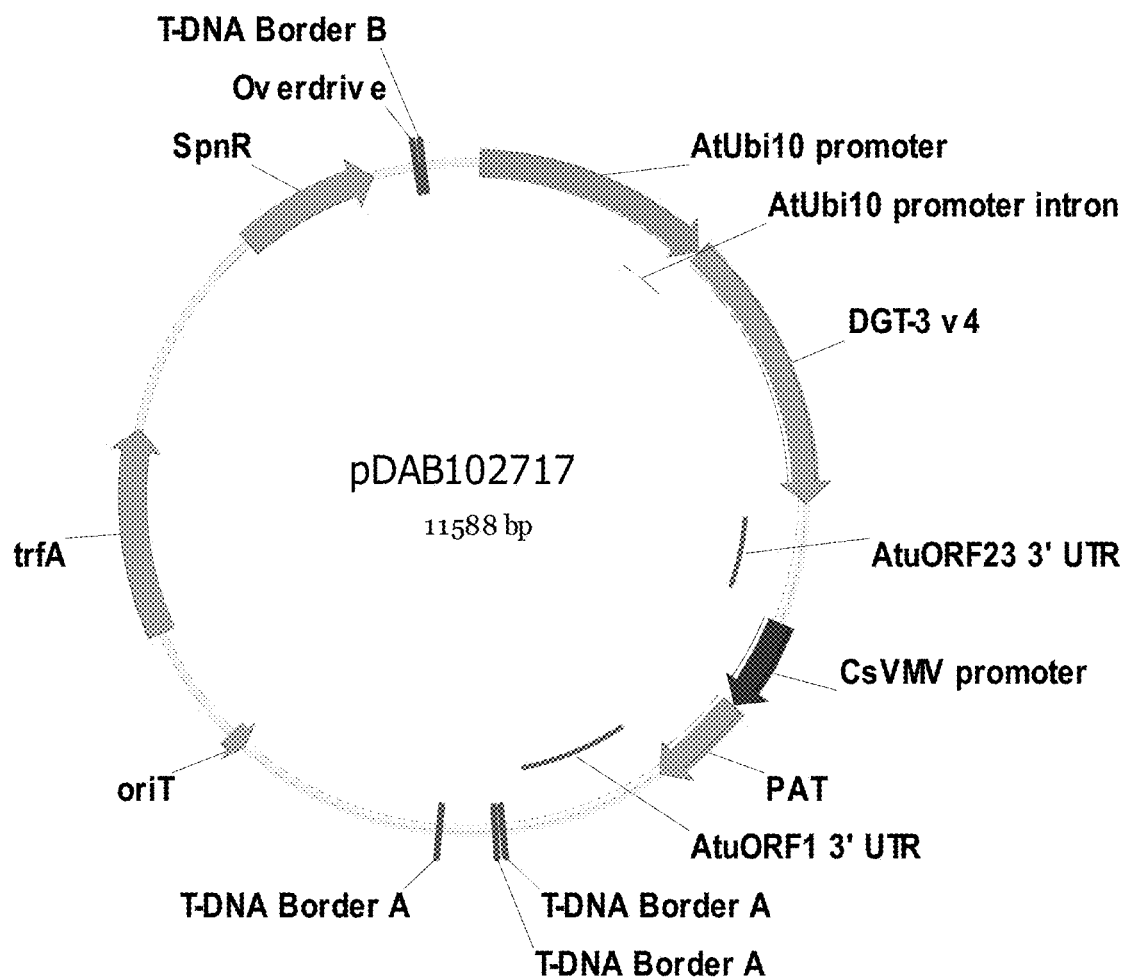
Figure 47:
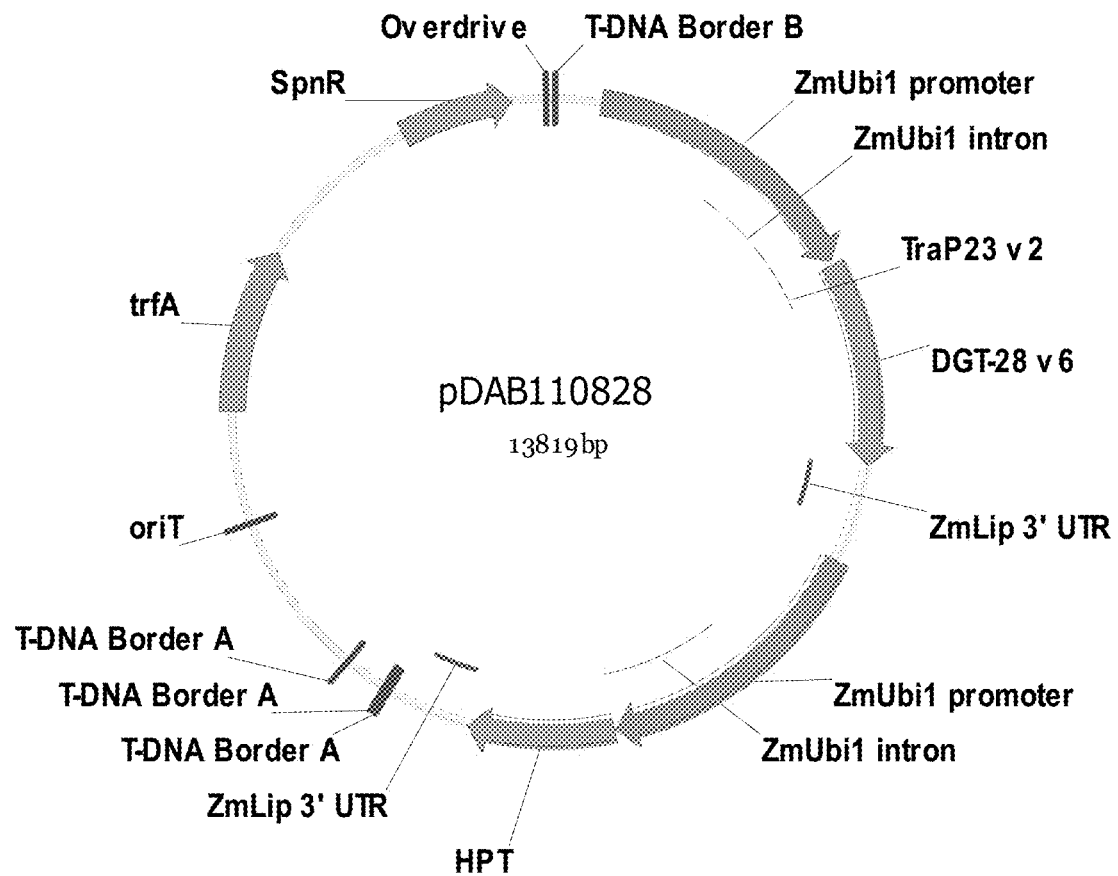
Figure 48:
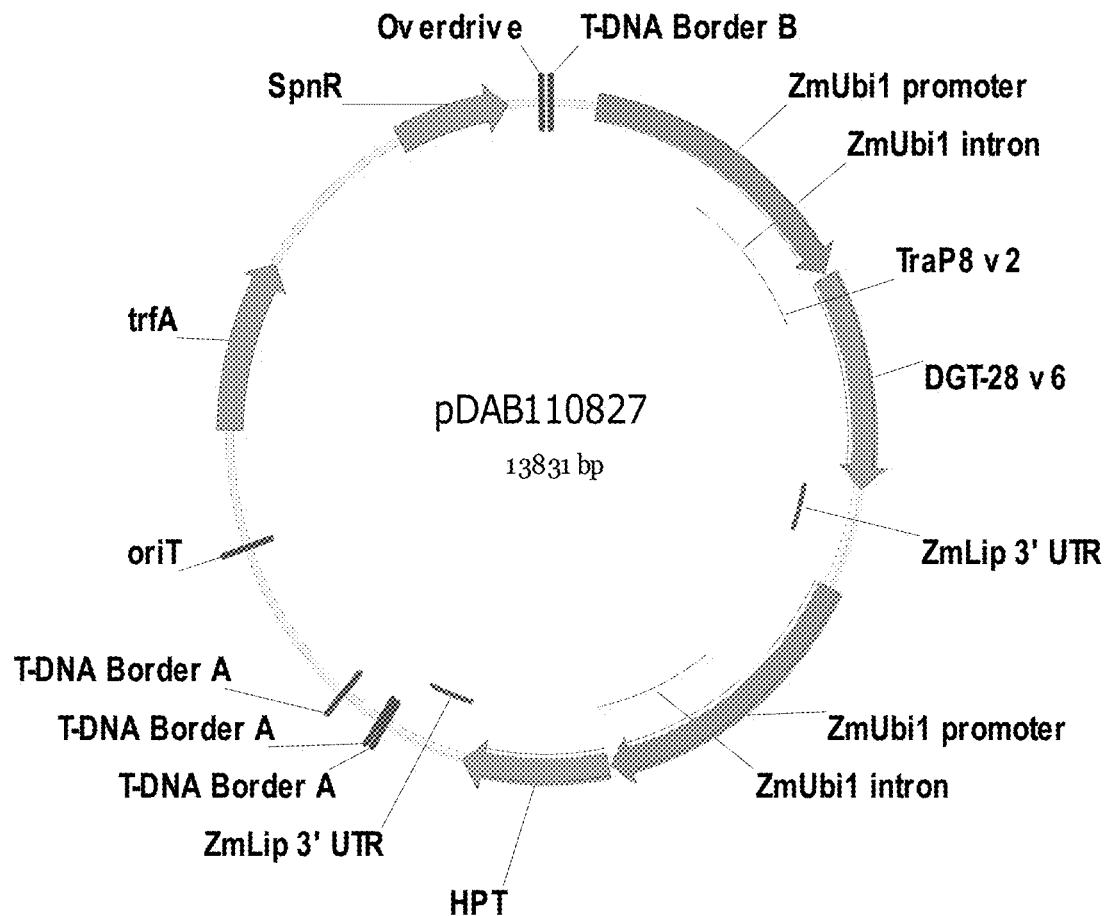
Figure 49:
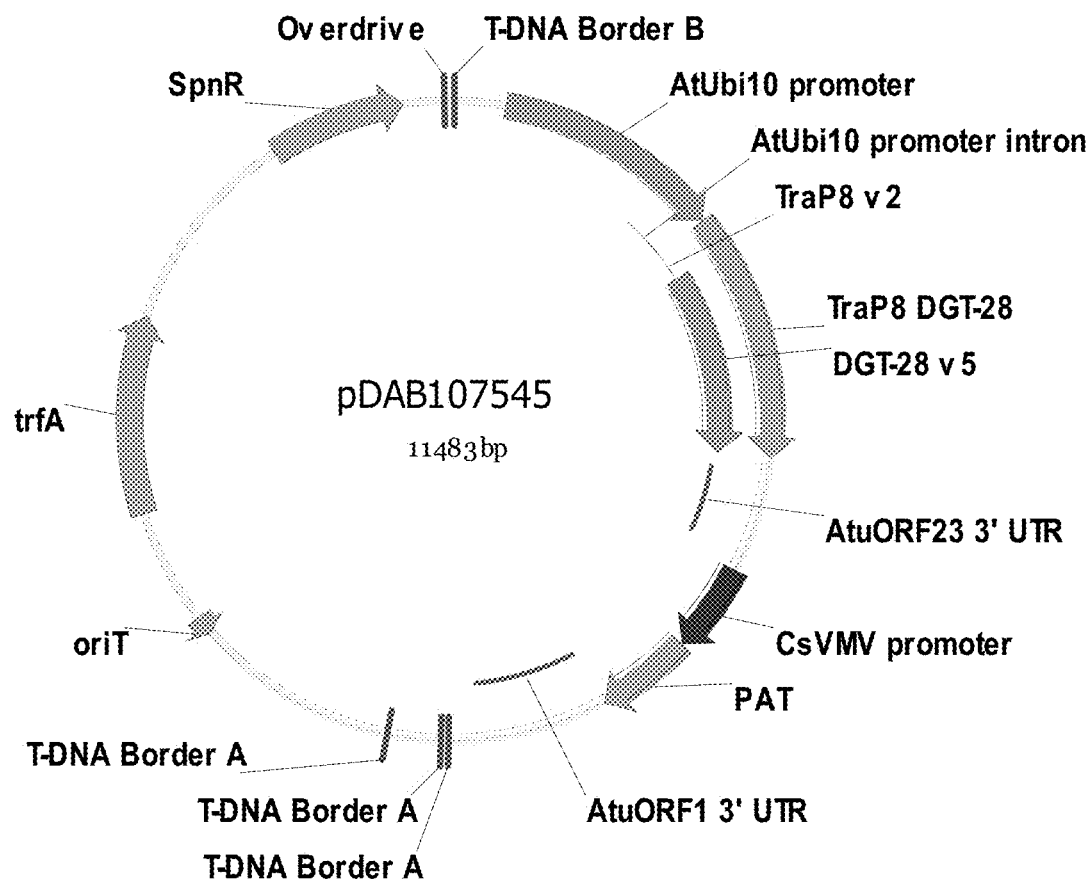
Figure 50:
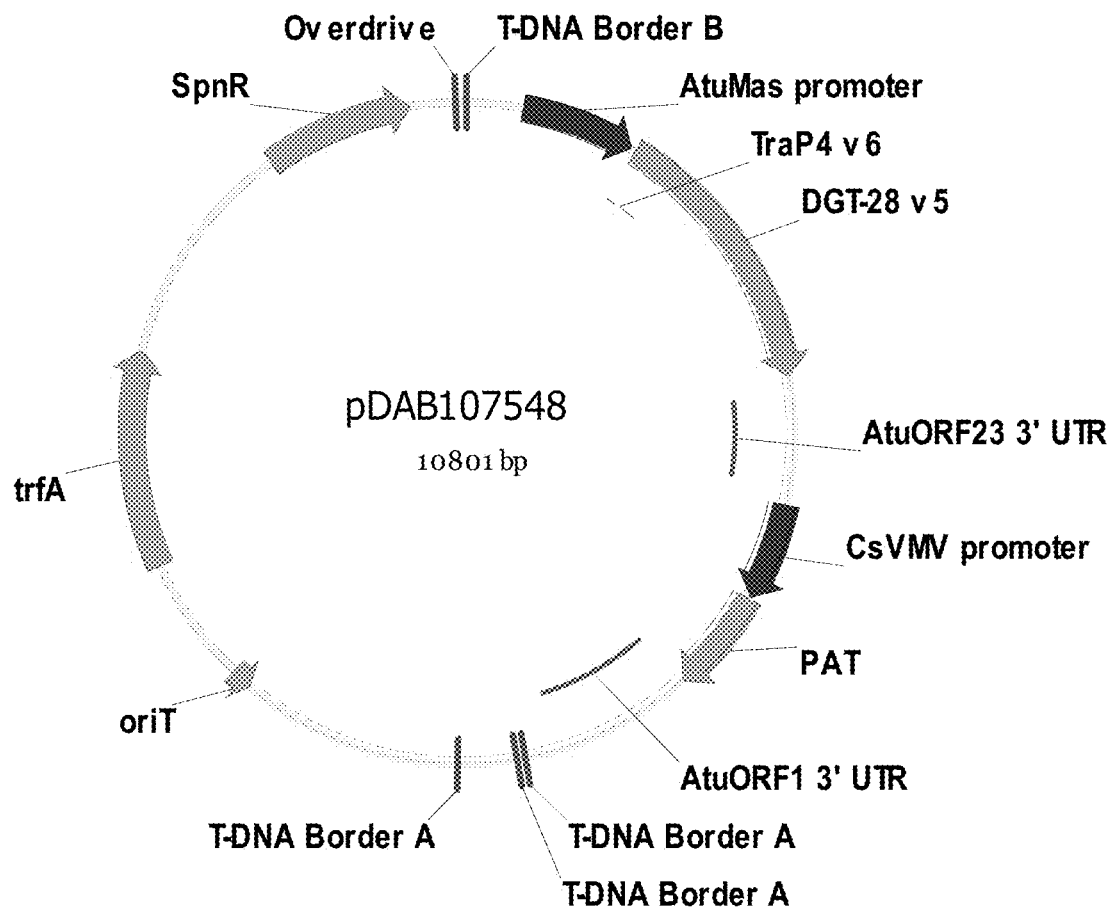
Figure 51:
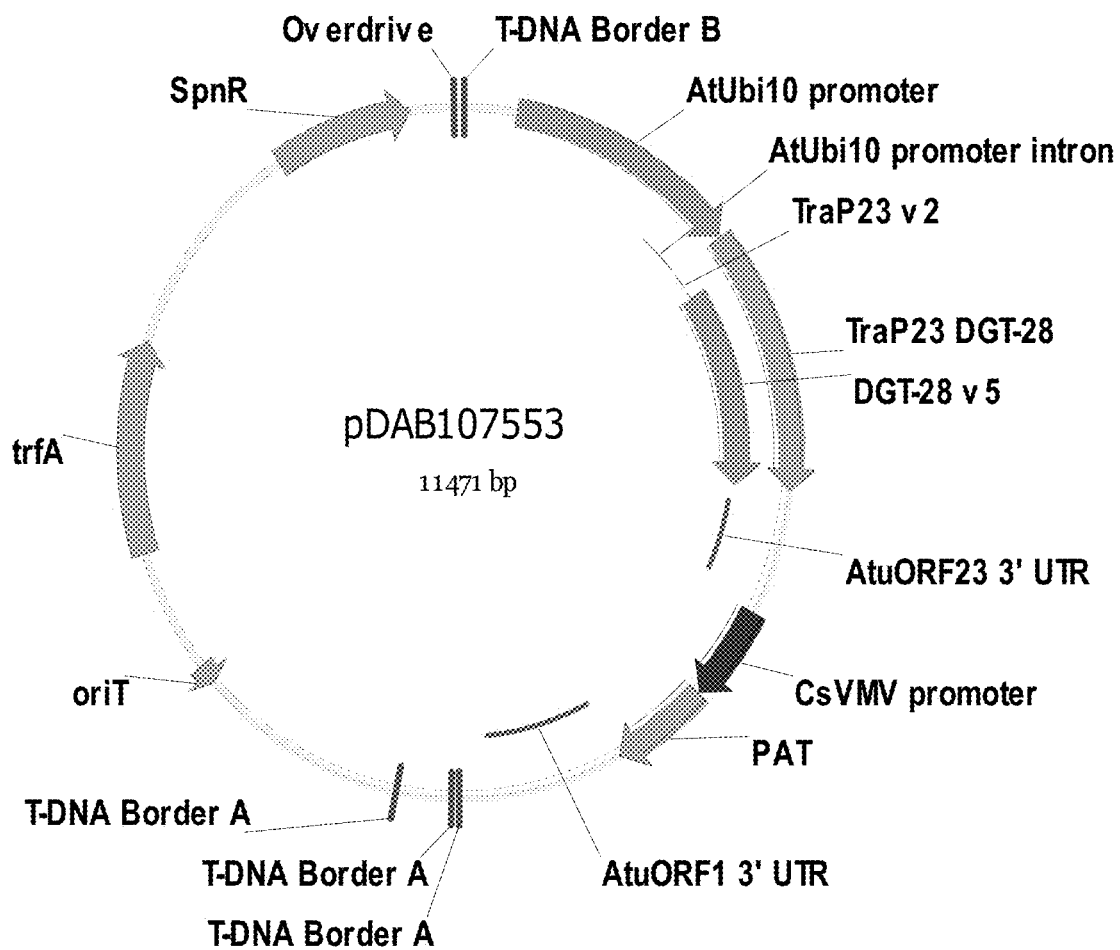
Figure 52:
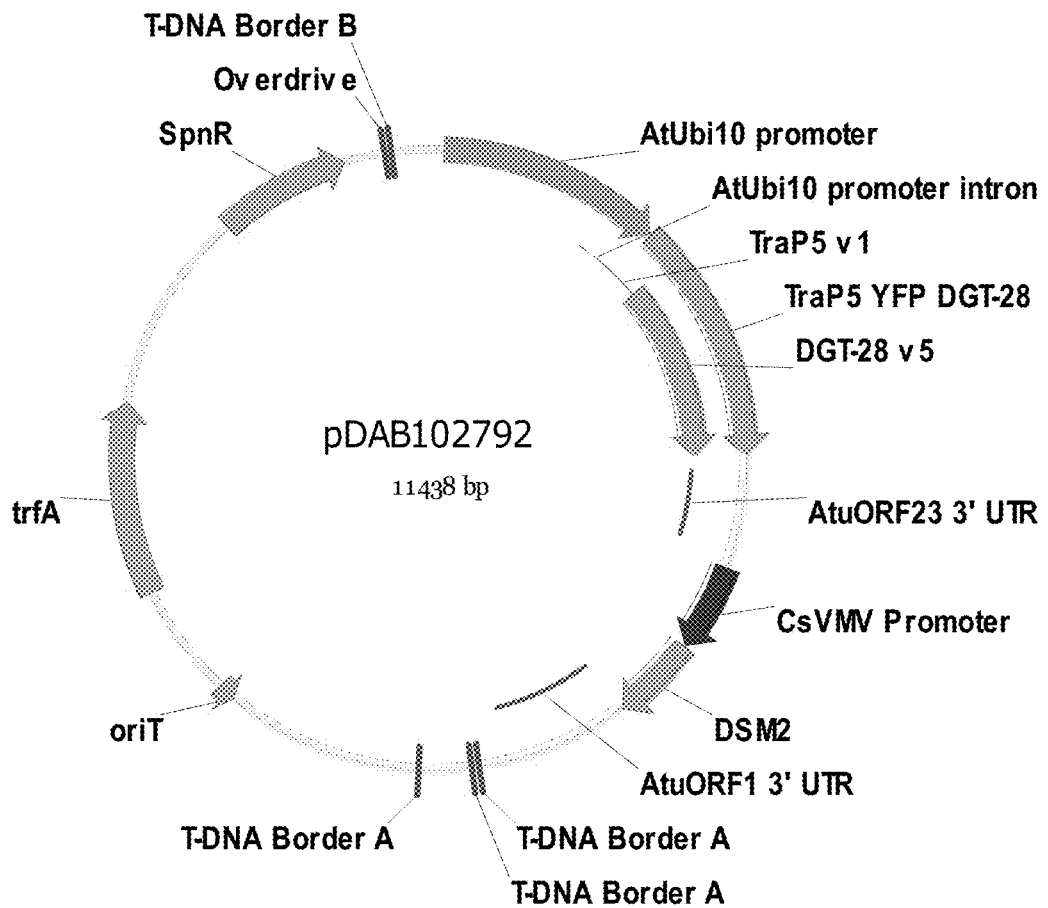
Figure 53:
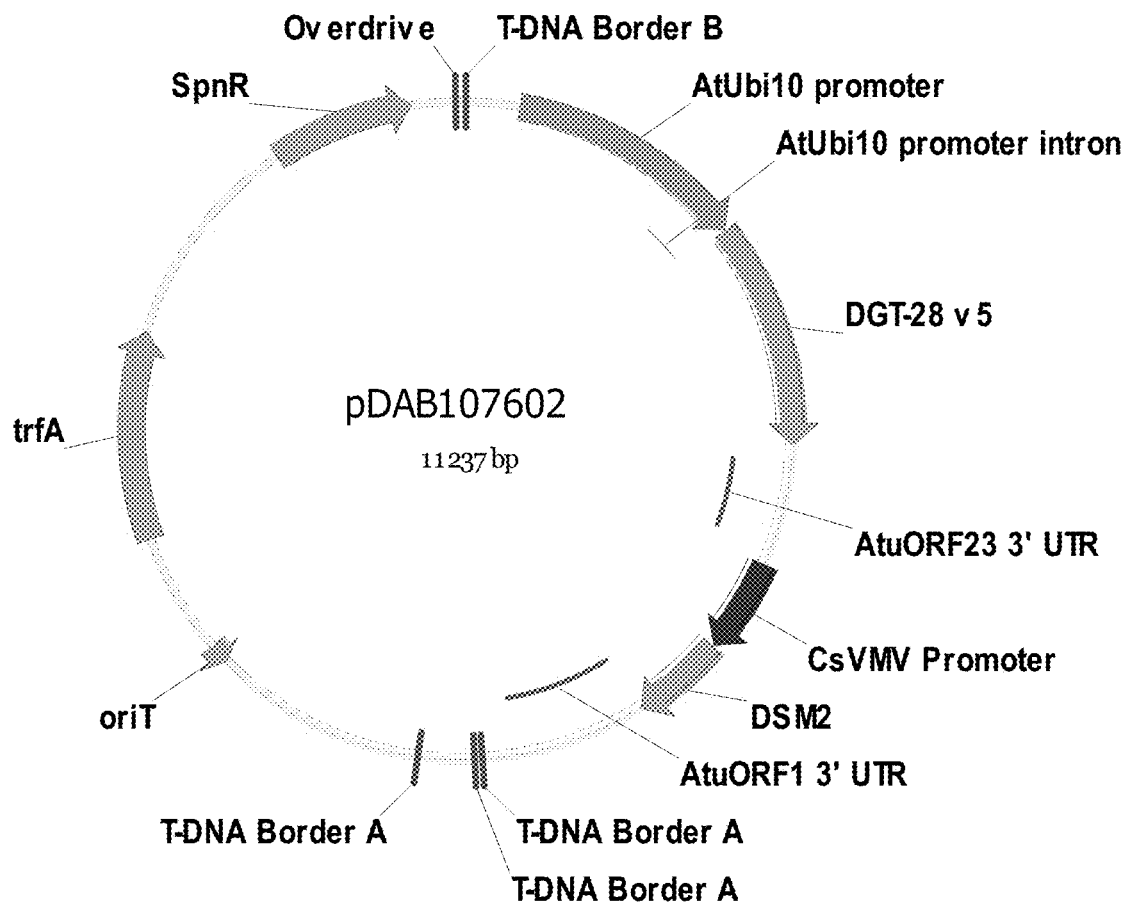

Binary vectors containing the Class I genes (dgt-1, dgt-3, and dgt-7) were constructed. The following binary vectors were constructed and transformed into plants: pDAB4104 (FIG. 9), which contains the dgt-1 v4 sequence as described in U.S. Patent Application Publication No. 2011/0124503, which is flanked by the *Nicotiana tabacum* Osmotin sequences as described in U.S. Patent Application Publication No. 2009/0064376; pDAB102715 (FIG. 10); pDAB102716 (FIG. 45); pDAB102717 (FIG. 46); and pDAB102785 (FIG. 13). The various TraP chloroplast transit peptides that were fused to dgt-28, dgt-31, dgt-32, and dgt-33 were not added to the Class I genes, as these plant derived sequences possess native plant chloroplast transit peptides. These vectors are described in further detail in Table 3.

TABLE 3

Description of the binary vectors which contain a Class I EPSP synthase gene (i.e., dgt-1, dgt-3, or dgt-7).

| Name | Description | EPSPS mutation |
|---|---|---|
| pDAB4104 | RB7 MAR v2 :: CsVMV promoter v2/NtOsm 5' UTR v2/dgt-1 v4/NtOsm 3' UTR v2/ AtuORF24 3' UTR v2 :: AtUbi10 promoter v4/pat v3/AtuORF1 3'UTR v3 binary vector | TI PS |
| pDAB102715 | AtUbi10 promoter v2/dgt-3 v2/AtuORF23 3'UTR v1 :: CsVMV promoter v2/pat v9/ AtuORF1 3'UTR v6 binary vector | GA |
| pDAB102716 | AtUbi10 promoter v2/dgt-3 v3/AtuORF23 3'UTR v1 :: CsVMV promoter v2/pat v9/ AtuORF1 3'UTR v6 binary vector | GA PS |
| pDAB102717 | AtUbi10 promoter v2/dgt-3 v4/AtuORF23 3'UTR v1 :: CsVMV promoter v2/pat v9/ AtuORF1 3'UTR v6 binary vector | TI PS |

TABLE 3-continued

Description of the binary vectors which contain a Class I EPSP synthase gene (i.e., dgt-1, dgt-3, or dgt-7).

| Name | Description | EPSPS mutation |
|---|---|---|
| pDAB102785 | AtUbi10 promoter v2/dgt-7 v4/AtuORF23 3'UTR :: CsVMV promoter v2/DSM-2 v2/ AtuORF1 3'UTR v6 binary vector | TI PS |

Example 6

Transformation into *Arabidopsis* and Selection

*Arabidopsis thaliana* Transformation.

*Arabidopsis* was transformed using the floral dip method from Clough and Bent (1998). A selected *Agrobacterium* colony containing one of the binary plasmids described above was used to inoculate one or more 100 mL pre-cultures of YEP broth containing spectinomycin (100 mg/L) and kanamycin (50 mg/L). The culture was incubated overnight at 28° C. with constant agitation at 225 rpm. The cells were pelleted at approximately 5000×g for 10 minutes at room temperature, and the resulting supernatant discarded. The cell pellet was gently resuspended in 400 mL dunking media containing: 5% (w/v) sucrose, 10 µg/L 6-benzylaminopurine, and 0.04% Silwet™ L-77. Plants approximately 1 month old were dipped into the media for 5-10 minutes with gentle agitation. The plants were laid down on their sides and covered with transparent or opaque plastic bags for 2-3 hours, and then placed upright. The plants were grown at 22° C., with a 16-hour light/8-hour dark photoperiod. Approximately 4 weeks after dipping, the seeds were harvested.

Selection of Transformed Plants.

Freshly harvested $T_1$ seed [containing the dgt and DSM-2 expression cassettes] was allowed to dry for 7 days at room temperature. $T_1$ seed was sown in 26.5×51-cm germination trays, each receiving a 200 mg aliquot of stratified $T_1$ seed (~10,000 seeds) that had previously been suspended in 40 mL of 0.1% agarose solution and stored at 4° C. for 2 days to complete dormancy requirements and ensure synchronous seed germination.

Sunshine Mix LP5 was covered with fine vermiculite and subirrigated with Hoagland's solution until wet, then allowed to gravity drain. Each 40 mL aliquot of stratified seed was sown evenly onto the vermiculite with a pipette and covered with humidity domes for 4-5 days. Domes were removed 1 day prior to initial transformant selection using glufosinate postemergence spray (selecting for the co-transformed DSM-2 gene).

Seven days after planting (DAP) and again 11 DAP, $T_1$ plants (cotyledon and 2-4-1 f stage, respectively) were sprayed with a 0.2% solution of Liberty herbicide (200 g ai/L glufosinate, Bayer Crop Sciences, Kansas City, Mo.) at a spray volume of 10 mL/tray (703 L/ha) using a DeVilbiss compressed air spray tip to deliver an effective rate of 280 g ai/ha glufosinate per application. Survivors (plants actively growing) were identified 4-7 days after the final spraying and transplanted individually into 3-inch pots prepared with potting media (Metro Mix 360). Transplanted plants were reared in the greenhouse (22±5° C., 50±30% RH, 14 h light:10 dark, minimum 500 µE/m$^2$s$^1$ natural+ supplemental light). Molecular confirmation analysis was completed on the surviving $T_1$ plants to confirm that the glyphosate tolerance gene had stably integrated into the genome of the plants.

Molecular Confirmation.

The presence of the dgt-28 and DSM-2 transgenes within the genome of *Arabidopsis* plants that were transformed with pDAB 107527, pDAB 105530, pDAB105531, pDAB105532, pDAB105533, or pDAB105534 was confirmed. The presence of these polynucleotide sequences was confirmed via hydrolysis probe assays, gene expression cassette PCR (also described as plant transcription unit PCR-PTU PCR), Southern blot analysis, and Quantitative Reverse Transcription PCR analyses.

The $T_1$ *Arabidopsis* plants were initially screened via a hydrolysis probe assay, analogous to TAQMAN™, to confirm the presence of the DSM-2 and dgt-28 transgenes. Events were screened via gene expression cassette PCR to determine whether the dgt expression cassette completely integrated into the plant genomes without rearrangement. The data generated from these studies were used to determine the transgene copy number and identify select *Arabidopsis* events for self fertilization and advancement to the $T_2$ generation. The advanced $T_2$ *Arabidopsis* plants were also screened via hydrolysis probe assays to confirm the presence and to estimate the copy number of the DSM-2 and dgt genes within the plant chromosome. Finally, a Southern blot assay was used to confirm the estimated copy number on a subset of the $T_1$ *Arabidopsis* plants.

Similar assays were used to confirm the presence of the dgt-1 transgene from plants transformed with pDAB4101, the presence of the dgt-32 transgene from plants transformed with pDAB 107532, the presence of the dgt-33 transgene from plants transformed with pDAB 107534, the presence of the dgt-3 transgene from plants transformed with pDAB 102715, the presence of the dgt-3 transgene from plants transformed with pDAB 102716, the presence of the dgt-3 transgene from plants transformed with pDAB 102717, and the presence of the dgt-7 transgene from plants transformed with pDAB 102785.

Hydrolysis Probe Assay.

Copy number was determined in the $T_1$ and $T_2$ *Arabidopsis* plants using the hydrolysis probe assay described below. Plants with varying numbers of transgenes were identified and advanced for subsequent glyphosate tolerance studies.

Tissue samples were collected in 96-well plates and lyophilized for 2 days. Tissue maceration was performed with a KLECO™ tissue pulverizer and tungsten beads (Environ Metal INC., Sweet Home, Oregon). Following tissue maceration, the genomic DNA was isolated in high-throughput format using the Biosprint™ 96 Plant kit (Qiagen™, Germantown, Md.) according to the manufacturer's suggested protocol. Genomic DNA was quantified by QUANT-IT™ PICO GREEN DNA ASSAY KIT (Molecular Probes, Invitrogen, Carlsbad, Calif.). Quantified genomic DNA was adjusted to around 2 ng/µL for the hydrolysis probe assay using a BIOROBOT3000™ automated liquid handler (Qiagen, Germantown, Md.). Transgene copy number determination by hydrolysis probe assay was performed by real-time PCR using the LIGHTCYCLER® 480 system (Roche Applied Science, Indianapolis, Ind.). Assays were designed for DSM-2, dgt-28 and the internal reference gene, TAFII15 (Genbank ID: NC 003075; Duarte et al., (201) *BMC Evol. Biol.,* 10:61).\

For amplification, LIGHTCYCLER® 480 Probes Master mix (Roche Applied Science, Indianapolis, Ind.) was prepared at a 1×final concentration in a 10 µL volume multiplex reaction containing 0.1 µM of each primer for DSM-2 and dgt-28, 0.4 µM of each primer for TAFII15 and 0.2 µM of each probe. Table 4. A two-step amplification reaction was performed with an extension at 60° C. for 40 seconds with fluorescence acquisition. All samples were run and the averaged Cycle threshold (Ct) values were used for analysis of each sample. Analysis of real time PCR data was performed using LightCycler™ software release 1.5 using the relative quant module and is based on the ΔΔCt method. For this, a sample of genomic DNA from a single copy calibrator and known 2 copy check were included in each run. The copy number results of the hydrolysis probe screen were determined for the $T_1$ and $T_2$ transgenic *Arabidopsis* plants.

TABLE 4

Primer and probe Information for hydrolysis probe assay of DSM-2, dgt-28 and internal reference gene (TAFII15).

| Primer Name | Sequence |
|---|---|
| DSM2A (SEQ ID NO: 44) | 5' AGCCACATCCCAGTAACGA 3' |
| DSM2S (SEQ ID NO: 45) | 5' CCTCCCTCTTTGACGCC3' |
| DSM2 Cy5 probe (SEQ ID NO: 46) | 5' CAGCCCAATGAGGCATCAGC 3' |
| DGT28F (SEQ ID NO: 47) | 5' CTTCAAGGAGATTTGGGATTTGT 3' |
| DGT28R (SEQ ID NO: 48) | 5' GAGGGT CGGCATCGTAT 3' |
| UPL154 probe | Cat# 04694406001 (Roche, Indianapolis, IN) |
| TAFFY-HEX probe (SEQ ID NO: 49) | 5' AGAGAAGTTTCGACGGATTTCGGGC 3' |
| TAFII15-F (SEQ ID NO: 50) | 5' GAGGATTAGGGTTTCAACGGAG 3' |
| TAFII15-R (SEQ ID NO: 51) | 5' GAGAATTGAGCTGAGACGAGG 3' |

Dgt-28 Integration Confirmation Via Southern Blot Analysis.

Southern blot analysis was used to establish the integration pattern of the inserted T-strand DNA fragment and identify events which contained dgt-28. Data were generated to demonstrate the integration and integrity of the transgene inserts within the *Arabidopsis* genome. Southern blot data were used to identify simple integration of an intact copy of the T-strand DNA. Detailed Southern blot analysis was conducted using a PCR amplified probe specific to the dgt-28 gene expression cassette. The hybridization of the probe with genomic DNA that had been digested with specific restriction enzymes identified genomic DNA fragments of specific molecular weights, the patterns of which were used to identify full length, simple insertion $T_1$ transgenic events for advancement to the next generation.

Tissue samples were collected in 2 mL conical tubes (Eppendorf™) and lyophilized for 2 days. Tissue maceration was performed with a KLECKO™ tissue pulverizer and tungsten beads. Following tissue maceration, the genomic DNA was isolated using a CTAB isolation procedure. The genomic DNA was further purified using the Qiagen™ Genomic Tips kit. Genomic DNA was quantified by Quant-IT™ Pico Green DNA assay kit (Molecular Probes, Invitrogen, Carlsbad, Calif.). Quantified genomic DNA was adjusted to 4 μg for a consistent concentration.

For each sample, 4 μg of genomic DNA was thoroughly digested with the restriction enzyme SwaI (New England Biolabs, Beverley, Mass.) and incubated at 25° C. overnight, then NsiI was added to the reaction and incubated at 37° C. for 6 hours. The digested DNA was concentrated by precipitation with Quick Precipitation Solution™ (Edge Biosystems, Gaithersburg, Md.) according to the manufacturer's suggested protocol. The genomic DNA was then resuspended in 25 μL of water at 65° C. for 1 hour. Resuspended samples were loaded onto a 0.8% agarose gel prepared in 1×TAE and electrophoresed overnight at 1.1 V/cm in 1×TAE buffer. The gel was sequentially subjected to denaturation (0.2 M NaOH/0.6 M NaCl) for 30 minutes, and neutralization (0.5 M Tris-HCl (pH 7.5)/1.5 M NaCl) for 30 minutes.

Transfer of DNA fragments to nylon membranes was performed by passively wicking 20×SSC solution overnight through the gel onto treated IMMOBILON™ NY+ transfer membrane (Millipore, Billerica, Mass.) by using a chromatography paper wick and paper towels. Following transfer, the membrane was briefly washed with 2×SSC, cross-linked with the STRATALINKER™ 1800 (Stratagene, LaJolla, Calif.), and vacuum baked at 80° C. for 3 hours.

Blots were incubated with pre-hybridization solution (Perfect Hyb plus, Sigma, St. Louis, Mo.) for 1 hour at 65° C. in glass roller bottles using a model 400 hybridization incubator (Robbins Scientific, Sunnyvale, Calif.). Probes were prepared from a PCR fragment containing the entire coding sequence. The PCR amplicon was purified using QIAEX™ II gel extraction kit and labeled with $\alpha^{32}$P-dCTP via the Random RT Prime IT™ labeling kit (Stratagene, La Jolla, Calif.). Blots were hybridized overnight at 65° C. with denatured probe added directly to hybridization buffer to approximately 2 million counts per blot per mL. Following hybridization, blots were sequentially washed at 65° C. with 0.1×SSC/0.1% SDS for 40 minutes. Finally, the blots were exposed to storage phosphor imaging screens and imaged using a Molecular Dynamics Storm 860™ imaging system.

The Southern blot analyses completed in this study were used to determine the copy number and confirm that selected events contained the dgt-28 transgene within the genome of *Arabidopsis*.

Dgt-28 Gene Expression Cassette Confirmation Via PCR Analysis.

The presence of the dgt-28 gene expression cassette contained in the $T_1$ plant events was detected by an end point PCR reaction. Primers (Table 5) specific to the AtUbi10 promoter v2 and AtuORF23 3'UTR v1 regions of the dgt-28 gene expression cassette were used for detection.

TABLE 5

Oligonucleotide primers used for dgt-28 gene expression cassette confirmation.

| Primer Name | Sequence |
| --- | --- |
| Forward oligo (SEQ ID NO: 52) | 5' CTGCAGGTCAACGGATCAGGATAT 3' |
| Reverse oligo (SEQ ID NO: 53) | 5' TGGGCTGAATTGAAGACATGCTCC 3' |

The PCR reactions required a standard three step PCR cycling protocol to amplify the gene expression cassette. All of the PCR reactions were completed using the following PCR conditions: 94° C. for three minutes followed by 35 cycles of 94° C. for thirty seconds, 60° C. for thirty seconds, and 72° C. for three minutes. The reactions were completed using the EX-TAQ™ PCR kit (TaKaRa Biotechnology Inc. Otsu, Shiga, Japan) per manufacturer's instructions. Following the final cycle, the reaction was incubated at 72° C. for 10 minutes. TAE agarose gel electrophoresis was used to determine the PCR amplicon size. PCR amplicons of an expected size indicated the presence of a full length gene expression cassette was present in the genome of the transgenic *Arabidopsis* events.

Dgt-28 Relative Transcription Confirmation Via Quantitative Reverse Transcription PCR Analysis.

Tissue samples of dgt-28 transgenic plants were collected in 96-well plates and frozen at 80° C. Tissue maceration was performed with a KLECO™ tissue pulverizer and tungsten beads (Environ Metal INC., Sweet Home, Oregon). Following tissue maceration, the Total RNA was isolated in high-throughput format using the Qiagen™ Rneasy 96 kit (Qiagen™, Germantown, Md.) according to the manufacturer's suggested protocol which included the optional DnaseI treatment on the column. This step was subsequently followed by an additional DnaseI (Ambion™ Austin, Tex.) treatment of the eluted total RNA. cDNA synthesis was carried out using the total RNA as template with the High Capacity cDNA Reverse Transcription™ kit (Applied Biosystems, Austin, Tex.) following the manufacturer's suggested procedure with the addition of the oligonucleotide, TVN. Quantification of expression was completed by hydrolysis probe assay and was performed by real-time PCR using the LIGHTCYCLER®480 system (Roche Applied Science, Indianapolis, Ind.). Assays were designed for dgt-28 and the internal reference gene "unknown protein" (Genbank Accession Number: AT4G24610) using the LIGHTCYCLER® Probe Design Software 2.0. For amplification, LIGHTCYCLER®480 Probes Master mix (Roche Applied Science, Indianapolis, Ind.) was prepared at 1× final concentration in a 10 μL volume singleplex reaction containing 0.4 μM of each primer, and 0.2 μM of each probe. Table 6.

TABLE 6

PCR primers used for quantitative reverse transcription PCR analysis of dgt-28.

| Primer Name | Sequence |
|---|---|
| AT26410LP (SEQ ID NO: 54) | 5' CGTCCACAAAGCTGAATGTG 3' |
| AT26410RP (SEQ ID NO: 55) | 5' CGAAGTCATGGAAGCCACTT 3 ' |
| UPL146 | Cat# 04694325001 (Roche, Indianapolis, IN) |
| DGT28F (SEQ ID NO: 56) | 5' CTTCAAGGAGATTTGGGATTTGT 3 ' |
| DGT28R (SEQ ID NO: 57) | 5' GAGGGTCGGCATCGTAT 3' |
| UPL154 probe | Cat# 04694406001 (Roche, Indianapolis, IN) |

A two-step amplification reaction was performed with an extension at 60° C. for 40 seconds with fluorescence acquisition. All samples were run in triplicate and the averaged Cycle threshold (Ct) values were used for analysis of each sample. A minus reverse transcription reaction was run for each sample to ensure that no gDNA contamination was present. Analysis of real time PCR data was performed based on the ΔΔCt method. This assay was used to determine the relative expression of dgt-28 in transgenic *Arabidopsis* events which were determined to be hemizygous and homozygous. The relative transcription levels of the dgt-28 mRNA ranged from 2.5 fold to 207.5 fold higher than the internal control. These data indicate that dgt-28 transgenic plants contained a functional dgt-28 gene expression cassette, and the plants were capable of transcribing the dgt-28 transgene.

Western Blotting Analysis.

DGT-28 was detected in leaf samples obtained from transgenic *Arabidopsis thaliana* plants. Plant extracts from dgt-28 transgenic plants and DGT-28 protein standards were incubated with NUPAGE® LDS sample buffer (Invitrogen, Carlsbad, Calif.) containing DTT at 90° C. for 10 minutes and electrophoretically separated in an acrylamide precast gel. Proteins were then electro-transferred onto nitrocellulose membrane using the manufacturer's protocol. After blocking with the WESTERNBREEZE® Blocking Mix (Invitrogen) the DGT-28 protein was detected by anti-DGT-28 antiserum followed by goat anti-rabbit phosphatase. The detected protein was visualized by chemiluminescence substrate BCIP/NBT Western Analysis Reagent (KPL, Gaithersburg, Md.). Production of an intact DGT-28 protein via Western blot indicated that the dgt-28 transgenic plants which were assayed expressed the DGT-28 protein.

Example 7

Glyphosate Tolerance

Transgenic $T_1$ *Arabidopsis* plants containing the dgt-28 transgene were sprayed with differing rates of glyphosate. Elevated rates were applied in this study to determine the relative levels of resistance (105, 420, 1,680 or 3,360 g ae/ha). A typical 1×usage rate of glyphosate that will control non-transformed *Arabidopsis* is 420 g ae/ha. Glyphosate formulations with the addition of ammonium sulfate were applied to the $T_1$ plants with a track sprayer calibrated at 187 L/ha. The $T_1$ *Arabidopsis* plants that were used in this study were variable copy number for the dgt-28 transgene. The low copy dgt-28 $T_1$ *Arabidopsis* plants were self-pollinated and used to produce $T_2$ plants. Table 7 shows the comparison of dgt-28 transgenic plants, drawn to a glyphosate herbicide resistance gene, dgt-1, and wildtype controls. Table 8 shows the comparison of dgt-32, and dgt-33 drawn to a glyphosate herbicide resistance gene, dgt-1, and wildtype controls. Table 9 shows the comparison of the novel bacterial EPSP synthase enzymes to the Class I EPSP synthase enzymes and the controls at a glyphosate rate of 1,680 g ae/ha.

Results of Glyphosate Selection of Transformed Dgt-28 *Arabidopsis* Plants.

The *Arabidopsis* $T_1$ transformants were first selected from the background of untransformed seed using a glufosinate selection scheme. Three flats or 30,000 seed were analyzed for each $T_1$ construct. The $T_1$ plants selected above were molecularly characterized and representative plants with variable copy number were subsequently transplanted to individual pots and sprayed with various rates of commercial glyphosate as previously described. The response of these plants is presented in terms of % visual injury 2 weeks after treatment (WAT). Data are presented in a table which shows individual plants exhibiting little or no injury (<20%), moderate injury (20-40%), or severe injury (>40%). An arithmetic mean and standard deviation is presented for each construct used for *Arabidopsis* transformation. The range in individual response is also indicated in the last column for each rate and transformation. Wild-type, non-transformed *Arabidopsis* (c.v. Columbia) served as a glyphosate sensitive control.

The level of plant response varied. This variance can be attributed to the fact each plant represents an independent transformation event and thus the copy number of the gene of interest varies from plant to plant. It was noted that some plants which contained the transgene were not tolerant to glyphosate; a thorough analysis to determine whether these plants expressed the transgene was not completed. It is likely that the presence of high copy numbers of the transgene within the $T_1$ *Arabidopsis* plants resulted in transgene silencing or other epigenetic effects which resulted in sensitivity to glyphosate, despite the presence of the dgt-28 transgene.

An overall population injury average by rate is presented in Table 9 for rates of glyphosate at 1,680 g ae/ha to demonstrate the significant difference between the plants transformed with dgt-3, dgt-7, dgt-28, dgt-32, and dgt-33 versus the dgt-1 and wild-type controls.

The tolerance provided by the novel bacterial EPSP synthases varied depending upon the specific enzyme. DGT-28, DGT-32, and DGT-33 unexpectedly provided significant tolerance to glyphosate. The dgt genes imparted herbicide resistance to individual $T_1$ *Arabidopsis* plants across all transit peptides tested. As such, the use of additional chloroplast transit peptides (i.e., TraP8-dgt-32 or TraP8-dgt-33) would provide protection to glyphosate with similar injury levels as reported within a given treatment.

TABLE 7 dgt-28 transformed T₁ *Arabidopsis* response to a range of glyphosate rates applied postemergence, compared to a dgt-1 (T₄) homozygous resistant population, and a non-transformed control. Visual % injury 14 days after application.

| Averages | % Injury | | | % Injury | | |
|---|---|---|---|---|---|---|
| | <20% | 20-40% | >40% | Ave | Std dev | Range (%) |
| pDAB107527: TraP4 v2 -- dgt-28 v5 | | | | | | |
| 0 g ae/ha glyphosate | 4 | 0 | 0 | 0.0 | 0.0 | 0 |
| 105 g ae/ha glyphosate | 4 | 0 | 0 | 3.8 | 7.5 | 0-15 |
| 420 g ae/ha glyphosate | 2 | 1 | 1 | 28.8 | 28.1 | 0-65 |
| 1680 g ae/ha glyphosate | 0 | 2 | 2 | 55.0 | 26.8 | 35-85 |
| 3360 g ae/ha glyphosate | 0 | 2 | 2 | 43.8 | 18.0 | 30-70 |
| pDAB105530: TraP5 v2 - dgt-28 v5 | | | | | | |
| 0 g ae/ha glyphosate | 6 | 0 | 0 | 0.0 | 0.0 | 0 |
| 105 g ae/ha glyphosate | 2 | 2 | 2 | 39.3 | 37.4 | 8-100 |
| 420 g ae/ha glyphosate | 1 | 4 | 1 | 33.0 | 26.6 | 8-85 |
| 1680 g ae/ha glyphosate | 0 | 4 | 2 | 47.5 | 27.5 | 25-85 |
| 3360 g ae/ha glyphosate | 0 | 0 | 6 | 76.7 | 13.7 | 50-85 |
| pDAB105531: TraP8 v2 -- dgt-28 v5 | | | | | | |
| 0 g ae/ha glyphosate | 4 | 0 | 0 | 0.0 | 0.0 | 0 |
| 105 g ae/ha glyphosate | 3 | 1 | 0 | 10.8 | 10.4 | 0-25 |
| 420 g ae/ha glyphosate | 3 | 0 | 1 | 22.8 | 18.6 | 8-50 |
| 1680 g ae/ha glyphosate | 4 | 0 | 0 | 5.3 | 3.8 | 0-8 |
| 3360 g ae/ha glyphosate | 0 | 4 | 0 | 29.3 | 6.8 | 22-35 |
| pDAB105532: TraP9 v2 -- dgt-28 v5 | | | | | | |
| 0 g ae/ha glyphosate | 4 | 0 | 0 | 0.0 | 0.0 | 0 |
| 105 g ae/ha glyphosate | 3 | 0 | 1 | 17.5 | 28.7 | 0-60 |
| 420 g ae/ha glyphosate | 1 | 1 | 2 | 39.5 | 25.1 | 18-70 |
| 1680 g ae/ha glyphosate | 3 | 0 | 1 | 26.3 | 36.1 | 5-80 |
| 3360 g ae/ha glyphosate | 3 | 0 | 1 | 25.8 | 32.9 | 8-75 |
| pDAB105533: TraP12 v2 -- dgt-28 v5 | | | | | | |
| 0 g ae/ha glyphosate | 5 | 0 | 0 | 0.0 | 0.0 | 0 |
| 105 g ae/ha glyphosate | 4 | 1 | 0 | 10.0 | 10.0 | 0-25 |
| 420 g ae/ha glyphosate | 1 | 1 | 3 | 53.6 | 34.6 | 8-85 |
| 1680 g ae/ha glyphosate | 4 | 1 | 0 | 11.0 | 8.2 | 0-20 |
| 3360 g ae/ha glyphosate | 0 | 2 | 3 | 55.0 | 25.5 | 25-80 |
| pDAB105534: TraP13 v2 -- dgt-28 v5 | | | | | | |
| 0 g ae/ha glyphosate | 5 | 0 | 0 | 0.0 | 0.0 | 0 |
| 105 g ae/ha glyphosate | 4 | 0 | 1 | 14.0 | 20.6 | 0-50 |
| 420 g ae/ha glyphosate | 3 | 1 | 1 | 17.6 | 19.5 | 0-50 |
| 1680 g ae/ha glyphosate | 3 | 0 | 2 | 39.0 | 47.1 | 5-100 |
| 3360 g ae/ha glyphosate | 2 | 2 | 1 | 31.2 | 22.3 | 18-70 |
| pDAB4104: dgt-1 (transformed control) | | | | | | |
| 0 g ae/ha glyphosate | 5 | 0 | 0 | 0.0 | 0.0 | 0 |
| 105 g ae/ha glyphosate | 0 | 0 | 4 | 80.0 | 0.0 | 80 |
| 420 g ae/ha glyphosate | 0 | 0 | 4 | 80.0 | 0.0 | 80 |
| 1680 g ae/ha glyphosate | 0 | 0 | 4 | 80.0 | 0.0 | 80 |
| 3360 g ae/ha glyphosate | 0 | 0 | 4 | 81.3 | 2.5 | 80-85 |
| WT (non-transformed control) | | | | | | |
| 0 g ae/ha glyphosate | 5 | 0 | 0 | 0.0 | 0.0 | 0 |
| 105 g ae/ha glyphosate | 0 | 0 | 4 | 100.0 | 0.0 | 100 |
| 420 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

TABLE 8 dgt-32, and dgt-33 transformed T₁ *Arabidopsis* response to a range of
glyphosate rates applied postemergence, compared to a dgt-1 (T₄) homozygous
resistant population, and a non-transformed control. Visual % injury 14 days after application.

| Averages | % Injury <20% | % Injury 20-40% | % Injury >40% | Ave | Std dev | % Injury Range (%) |
|---|---|---|---|---|---|---|
| pDAB107532: TraP14 v2 - dgt-32 v3 | | | | | | |
| 0 g ae/ha glyphosate | 4 | 0 | 0 | 0.0 | 0.0 | 0 |
| 105 g ae/ha glyphosate | 4 | 0 | 0 | 0.0 | 0.0 | 0 |
| 420 g ae/ha glyphosate | 2 | 0 | 2 | 30.0 | 29.4 | 0-60 |
| 1680 g ae/ha glyphosate | 3 | 0 | 1 | 17.5 | 21.8 | 5-50 |
| 3360 g ae/ha glyphosate | 0 | 3 | 1 | 35.0 | 30.0 | 20-80 |
| pDAB107534: TraP24 v2 -- dgt-33 v3 | | | | | | |
| 0 g ae/ha glyphosate | 4 | 0 | 0 | 0.0 | 0.0 | 0 |
| 105 g ae/ha glyphosate | 2 | 2 | 0 | 21.3 | 14.9 | 5-40 |
| 420 g ae/ha glyphosate | 1 | 1 | 2 | 46.3 | 30.9 | 5-70 |
| 1680 g ae/ha glyphosate | 1 | 0 | 3 | 62.5 | 38.8 | 5-90 |
| 3360 g ae/ha glyphosate | 1 | 0 | 3 | 62.0 | 36.0 | 8-80 |
| pDAB4104: dgt-1 (transformed control) | | | | | | |
| 0 g ae/ha glyphosate | 4 | 0 | 0 | 0.0 | 0.0 | 0 |
| 105 g ae/ha glyphosate | 0 | 2 | 3 | 42.5 | 15.0 | 20-50 |
| 420 g ae/ha glyphosate | 0 | 1 | 2 | 38.8 | 11.1 | 25-50 |
| 1680 g ae/ha glyphosate | 0 | 0 | 4 | 79.0 | 19.4 | 50-90 |
| 3360 g ae/ha glyphosate | 0 | 0 | 4 | 50.0 | 0.0 | 50 |
| WT (non-transformed control) | | | | | | |
| 0 g ae/ha glyphosate | 4 | 0 | 0 | 0.0 | 0.0 | 0 |
| 105 g ae/ha glyphosate | 0 | 0 | 4 | 85.0 | 0.0 | 85 |
| 420 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

TABLE 9 dgt-28, dgt-32, dgt-33, dgt-3, and dgt-7 transformed T₁ *Arabidopsis*
response to glyphosate applied postemergence at 1,680 g ae/ha, compared to a dgt-1 (T₄)
homozygous resistant population, and a non-transformed control. Visual % injury 14 days after
application.

| | | | % Injury <20% | % Injury 20-40% | % Injury >40% | Ave | Std dev | % Injury Range (%) |
|---|---|---|---|---|---|---|---|---|
| Bacterial Enzymes | pDAB107527 | TraP4 v2 -- dgt-28 v5 | 0 | 2 | 2 | 55.0 | 26.8 | 35-85 |
| | pDAB105530 | TraP5 v2 - dgt-28 v5 | 0 | 4 | 2 | 47.5 | 27.5 | 25-85 |
| | pDAB105531 | TraP8 v2 - dgt-28 v5 | 4 | 0 | 0 | 5.3 | 3.8 | 0-8 |
| | pDAB105532 | TraP9 v2 - dgt-28 v5 | 3 | 0 | 1 | 26.3 | 36.1 | 5-80 |
| | pDAB105533 | Trap12 v2 - dgt-28 v5 | 4 | 1 | 0 | 11.0 | 8.2 | 0-20 |
| | pDAB105534 | TraP13 v2 - dgt-28 v5 | 3 | 0 | 2 | 39.0 | 47.1 | 5-100 |
| | pDAB107532 | TraP14 v2 - dgt-32 v3 | 3 | 0 | 1 | 17.5 | 21.8 | 5-50 |
| | pDAB107534 | TraP24 v2 -- dgt-33 v3 | 1 | 0 | 3 | 62.5 | 38.8 | 5-90 |
| Class I Enzymes | pDAB102715 | dgt-3 v2 | 4 | 0 | 3 | 42 | 48 | 0-100 |
| | pDAB102716 | dgt-3 v3 | 2 | 1 | 0 | 14 | 23 | 0-40 |
| | pDAB102717 | dgt-3 v4 | 3 | 2 | 1 | 28 | 35 | 10-100 |
| | pDAB102785 | dgt-7 v4 | 0 | 1 | 1 | 45 | 21 | 30-60 |
| | pDAB4104 | dgt-1 (transformed control) | 0 | 0 | 4 | 80.0 | 0.0 | 80 |
| | — | WT (non-transformed control) | 0 | 0 | 4 | 100.0 | 0.0 | 100 |

Dgt-28 as a Selectable Marker.

The use of dgt-28 as a selectable marker for glyphosate selection agent is tested with the *Arabidopsis* transformed plants described above. Approximately 50 $T_4$ generation *Arabidopsis* seed (homozygous for dgt-28) are spiked into approximately 5,000 wildtype (sensitive to glyphosate) seed. The seeds are germinated and plantlets are sprayed with a selecting dose of glyphosate. Several treatments of glyphosate are compared; each tray of plants receives either one or two application timings of glyphosate in one of the following treatment schemes: 7 DAP (days after planting), 11 DAP, or 7 followed by 11 DAP. Since all plants also contain a glufosinate resistance gene in the same transformation vector, dgt-28 containing plants selected with glyphosate can be directly compared to DSM-2 or pat containing plants selected with glufosinate.

Glyphosate treatments are applied with a DeVilbiss™ spray tip as previously described. Transgenic plants containing dgt-28 are identified as "resistant" or "sensitive" 17 DAP. Treatments of 26.25-1680 g ae/ha glyphosate applied 7 and 11 days after planting (DAP), show effective selection for transgenic *Arabidopsis* plants that contain dgt-28. Sensitive and resistant plants are counted and the number of glyphosate tolerant plants is found to correlate with the original number of transgenic seed containing the dgt-28 transgene which are planted. These results indicate that dgt-28 can be effectively used as an alternative selectable marker for a population of transformed *Arabidopsis*.

Heritability.

Confirmed transgenic $T_1$ *Arabidopsis* events were self-pollinated to produce $T_2$ seed. These seed were progeny tested by applying Ignite™ herbicide containing glufosinate (200 g ae/ha) to 100 random $T_2$ siblings. Each individual $T_2$ plant was transplanted to 7.5-cm square pots prior to spray application (track sprayer at 187 L/ha applications rate). The $T_1$ families ($T_2$ plants) segregated in the anticipated 3 Resistant: 1 Sensitive model for a dominantly inherited single locus with Mendelian inheritance as determined by Chi square analysis (P>0.05). The percentage of $T_1$ families that segregated with the expected Mendelian inheritance are illustrated in Table 10, and demonstrate that the dgt-28 trait is passed via Mendelian inheritance to the $T_2$ generation. Seed were collected from 5 to 15 $T_2$ individuals ($T_3$ seed). Twenty-five $T_3$ siblings from each of 3-4 randomly-selected $T_2$ families were progeny tested as previously described. Data showed no segregation and thus demonstrated that dgt-28 and dgt-3 are stably integrated within the chromosome and inherited in a Mendelian fashion to at least three generations.

TABLE 10

Percentage of $T_1$ families ($T_2$ plants) segregating as single Mendelian inheritance for a progeny test of 100 plants.

| Gene of Interest | T1 Families Tested Segregating at 1 Locus (%) |
| --- | --- |
| dgt-3 v2 | 64% |
| dgt-3 v3 | 60% |
| dgt-3 v4 | 80% |
| dgt-7 v4 | 63% |
| TraP5 v2 - dgt-28 v5 | 100% |
| TraP8 v2 - dgt-28 v5 | 100% |
| TraP9 v2 - dgt-28 v5 | 100% |
| TraP12 v2 - dgt-28 v5 | 50% |
| TraP13 v2 - dgt-28 v5 | 75% |
| yfp Transgenic Control Plants | 100% |

$T_2$ *Arabidopsis* Data.

The second generation plants ($T_2$) of selected $T_1$ *Arabidopsis* events which contained low copy numbers of the dgt-28 transgene were further characterized for glyphosate tolerance. Glyphosate was applied as described previously. The response of the plants is presented in terms of % visual injury 2 weeks after treatment (WAT). Data are presented as a histogram of individuals exhibiting little or no injury (<20%), moderate injury (20-40%), or severe injury (>40%). An arithmetic mean and standard deviation are presented for each construct used for *Arabidopsis* transformation. The range in individual response is also indicated in the last column for each rate and transformation. Wild-type, non-transformed *Arabidopsis* (cv. Columbia) served as a glyphosate sensitive control. In the $T_2$ generation hemizygous and homozygous plants were available for testing for each event and therefore were included for each rate of glyphosate tested. Hemizygous plants contain two different alleles at a locus as compared to homozygous plants which contain the same two alleles at a locus. Variability of response to glyphosate is expected in the $T_2$ generation as a result of the difference in gene dosage for hemizygous as compared to homozygous plants. The variability in response to glyphosate is reflected in the standard deviation and range of response.

In the $T_2$ generation both single copy and multi-copy dgt-28 events were characterized for glyphosate tolerance. Within an event, single copy plants showed similar levels of tolerance to glyphosate. Characteristic data for a single copy $T_2$ event are presented in Table 11. Events containing dgt-28 linked with TraP5 v2 did not provide robust tolerance to glyphosate as compared with the dgt-28 constructs which contained other TraP transit peptides. However, the dgt-28 TraP5 constructs did provide a low level of glyphosate tolerance as compared to the non-transformed Columbia control. There were instances when events that were shown to contain two or more copies of dgt-28 were more susceptible to elevated rates of glyphosate (data not shown). This increase in sensitivity to glyphosate is similar to the data previously described for the $T_1$ plants which also contained high copy numbers of the dgt-28 transgene. It is likely that the presence of high copy numbers of the transgene within the *Arabidopsis* plants result in transgene silencing or other epigenetic effects which resulted in sensitivity to glyphosate, despite the presence of the dgt-28 transgene.

These events contained dgt-28 linked with TraP5 v2 (pDAB105530), TraP12 v2 (pDAB105533) and TraP13 v2 (pDAB105534).

Figure 32:
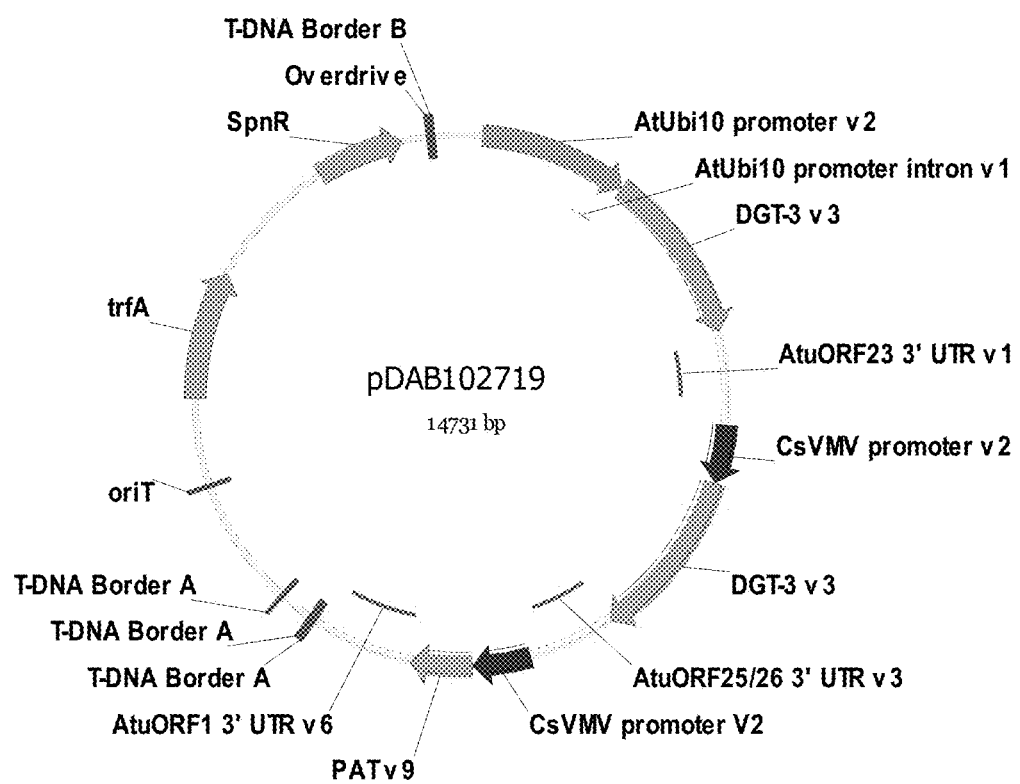
FIGS. 32-54 include maps of various exemplary plasmids: pDAB102719 (FIG. 32); pDAB102718 (FIG. 33); pDAB107663 (FIG. 34); pDAB107664 (FIG. 35); pDAB107665 (FIG. 36); pDAB107666 (FIG. 37); pDAB109812 (FIG. 38); pDAB101556 (FIG. 39); pDAB107698 (FIG. 40); pDAB108384 (FIG. 41); pDAB108385 (FIG. 42); pDAB108386 (FIG. 43); pDAB108387 (FIG. 44); pDAB102716 (FIG. 45); pDAB102717 (FIG. 46); pDAB110828 (FIG. 47); pDAB110827 (FIG. 48); pDAB107545 (FIG. 49); pDAB107548 (FIG. 50); pDAB107553 (FIG. 51); pDAB102792 (FIG. 52); pDAB107602 (FIG. 53); and pDAB 107533 (FIG. 54).
Figure 33:
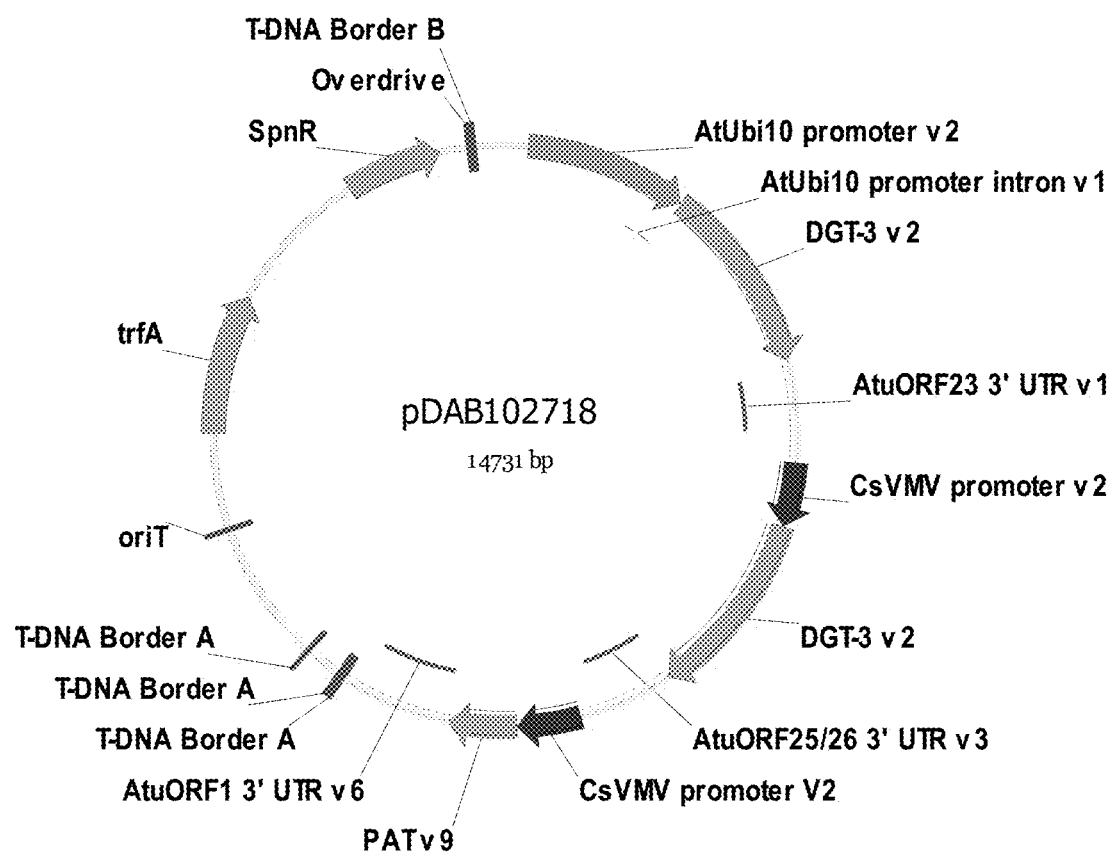
Figure 34:
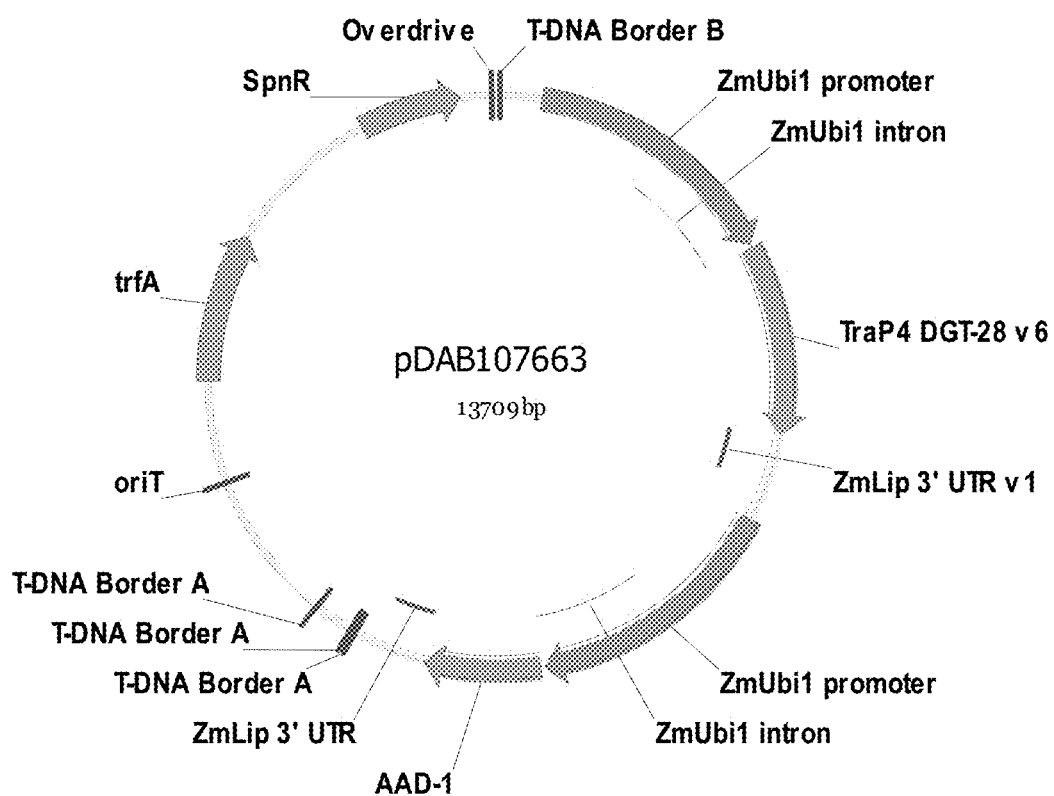
Figure 35:
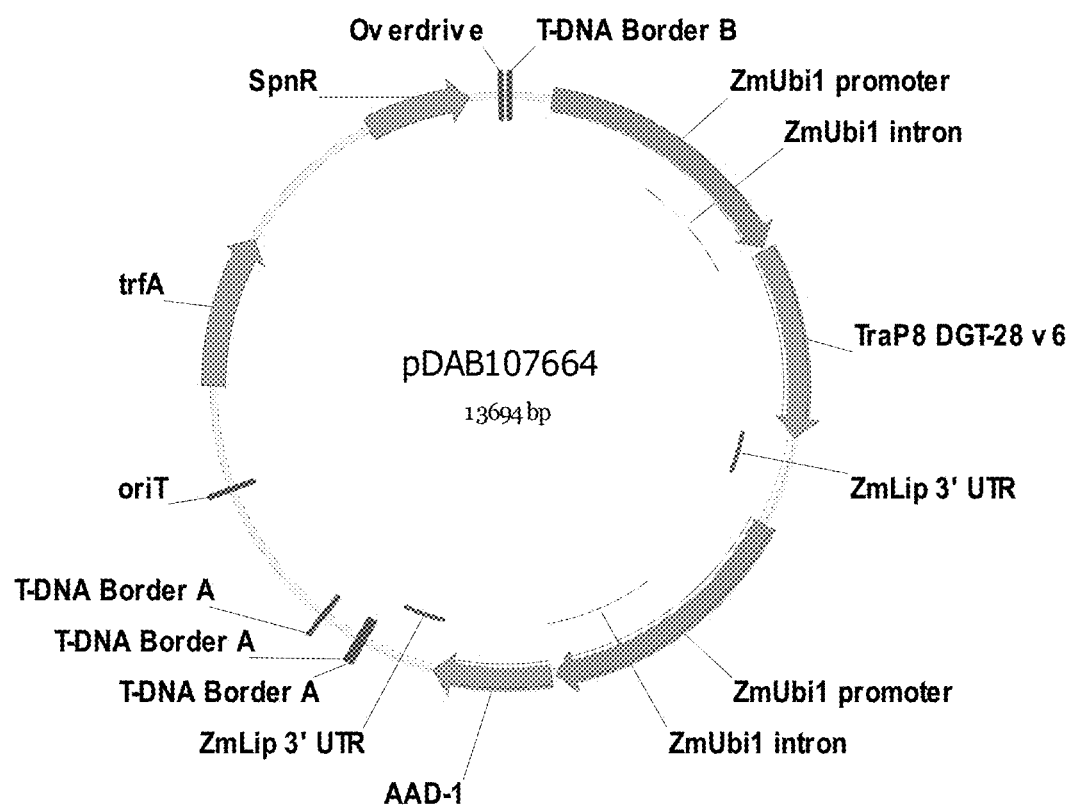
Figure 36:
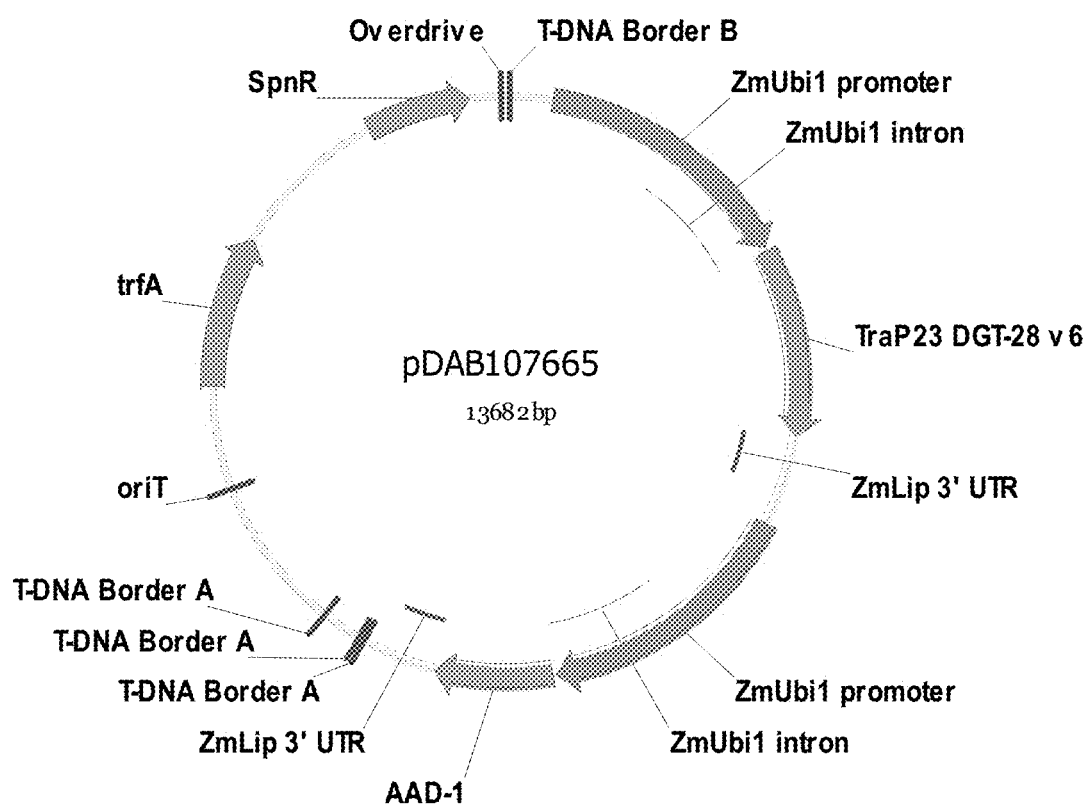
Figure 37:
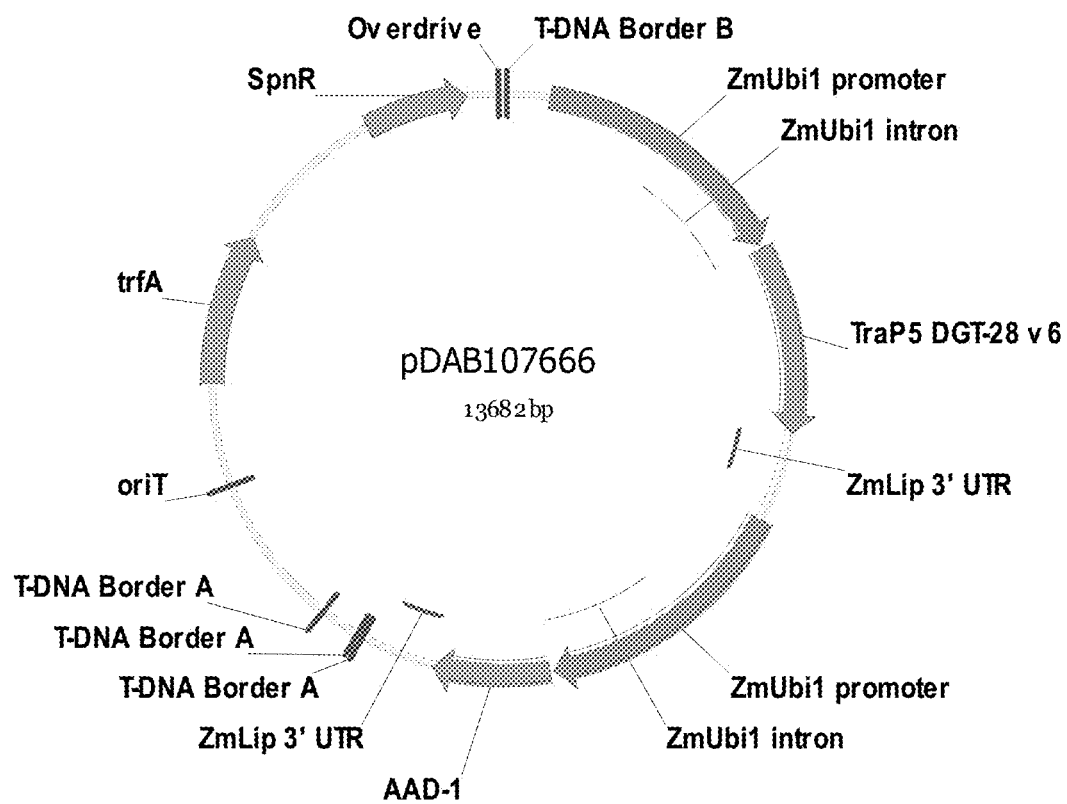
Figure 38:
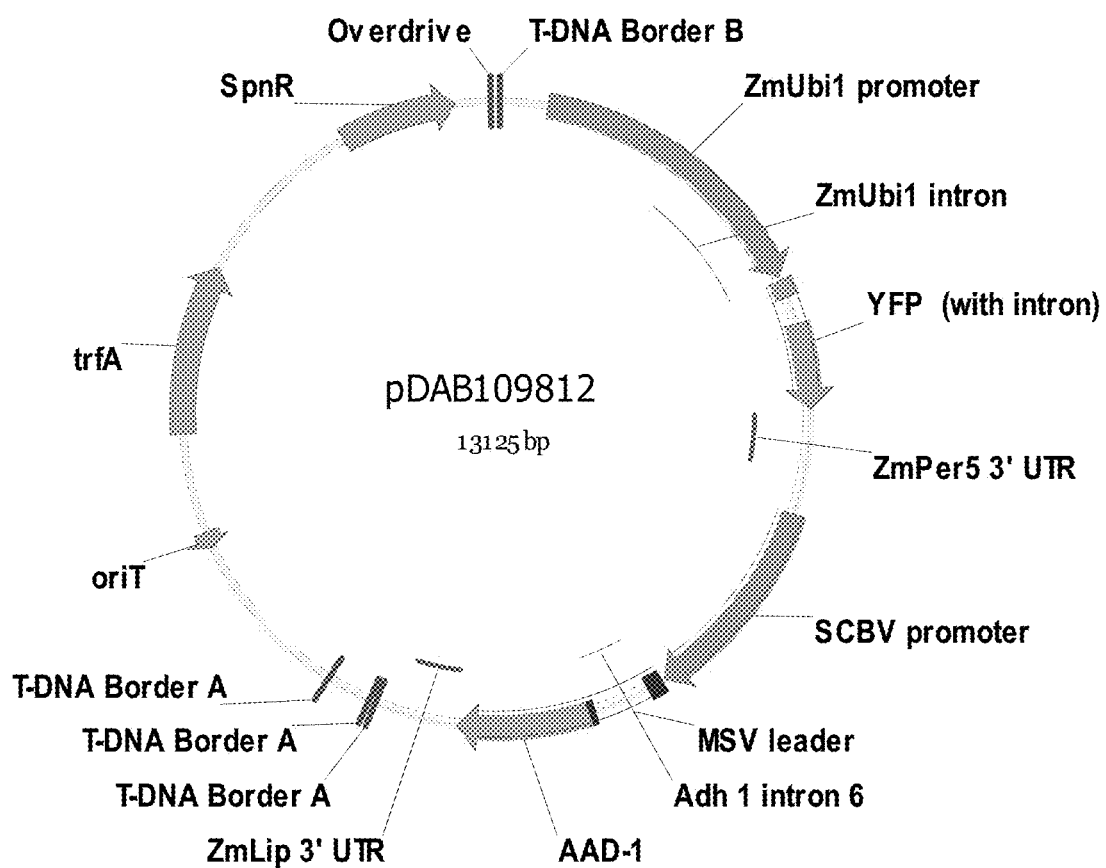
Figure 39:
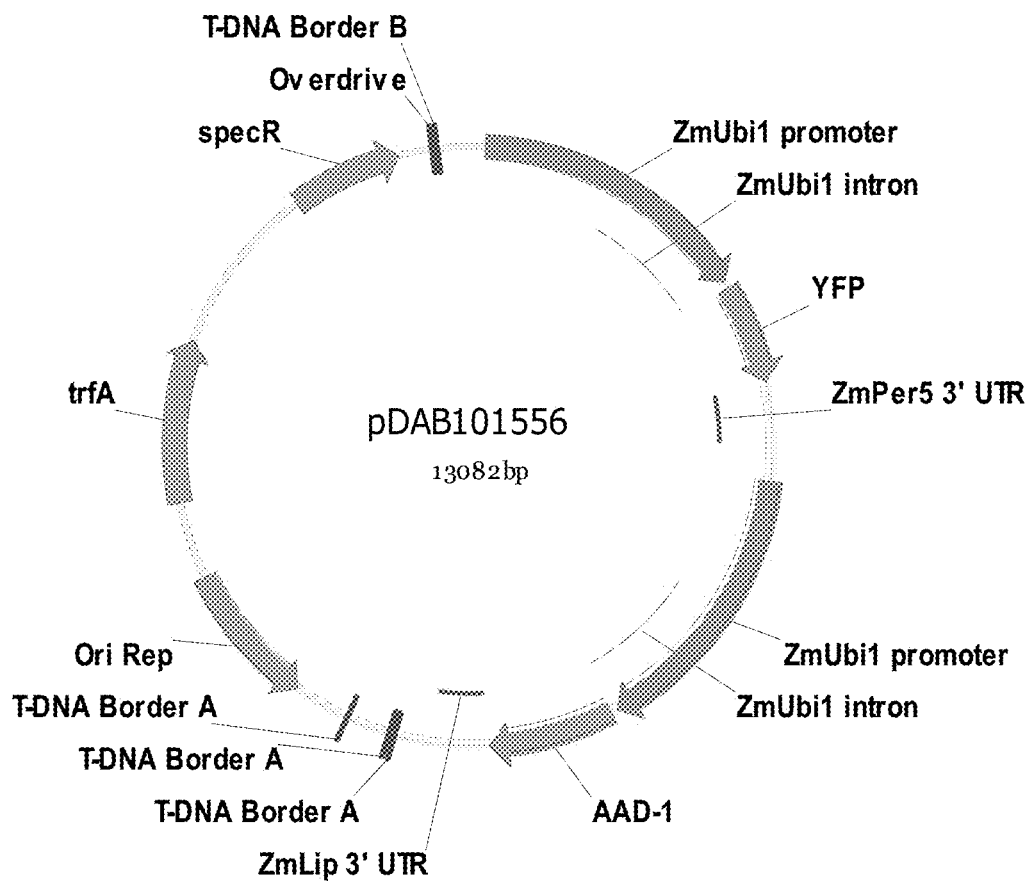
Figure 40:
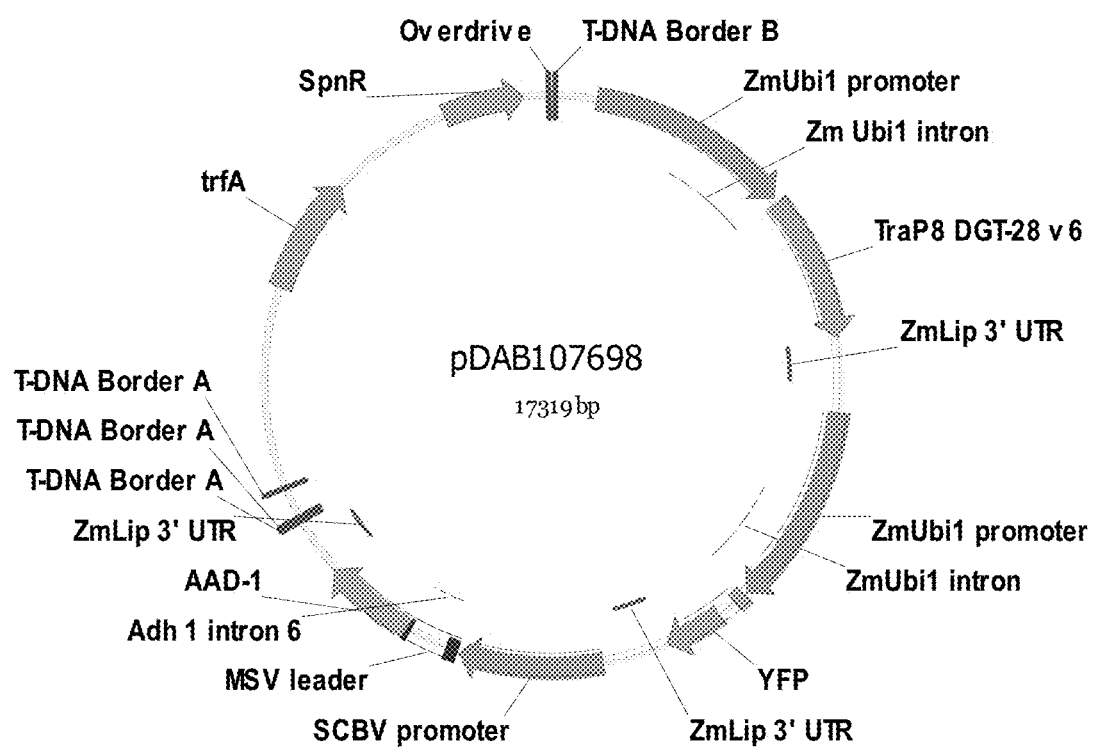
Figure 41:
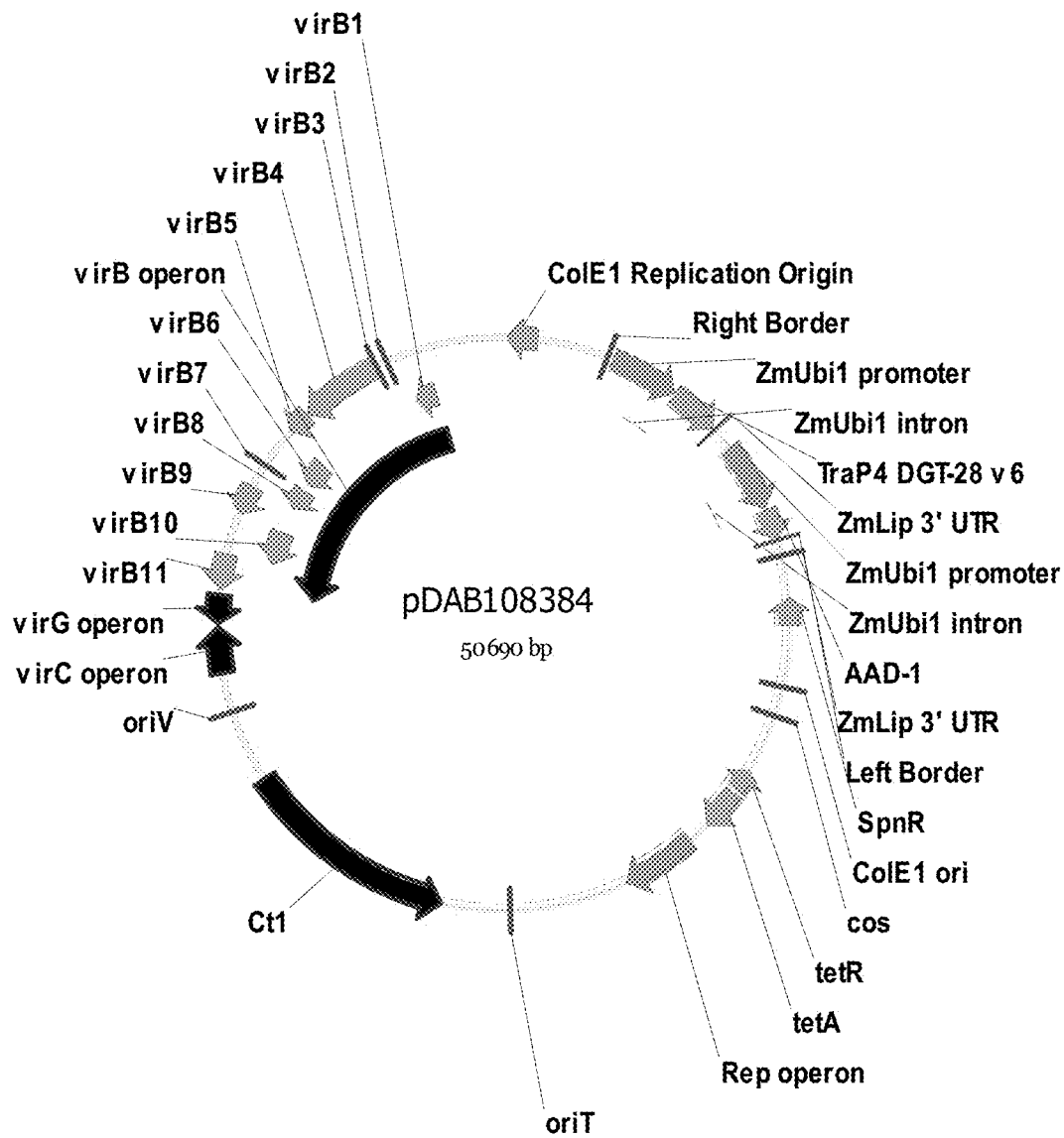
Figure 42:
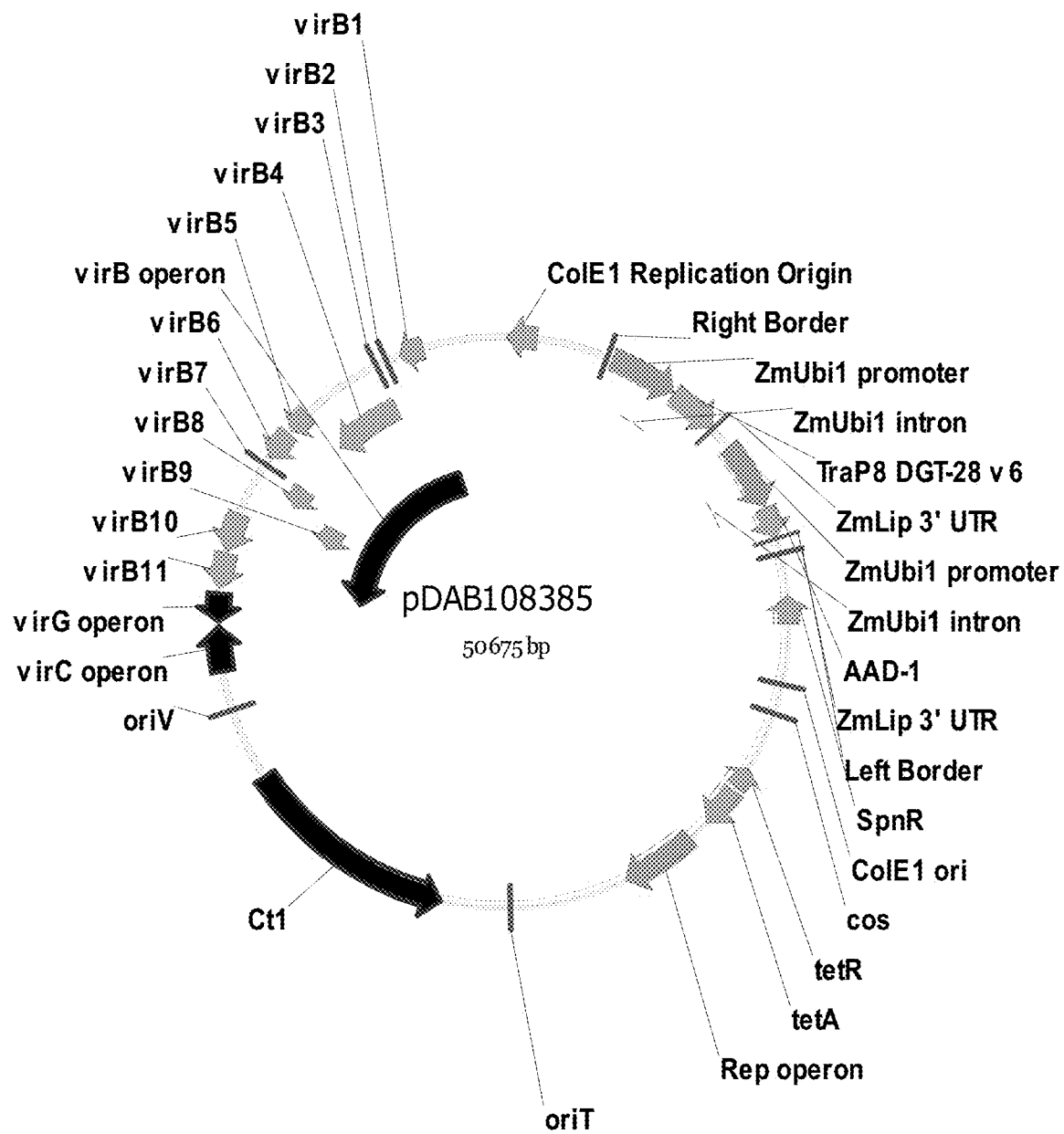
Figure 43:
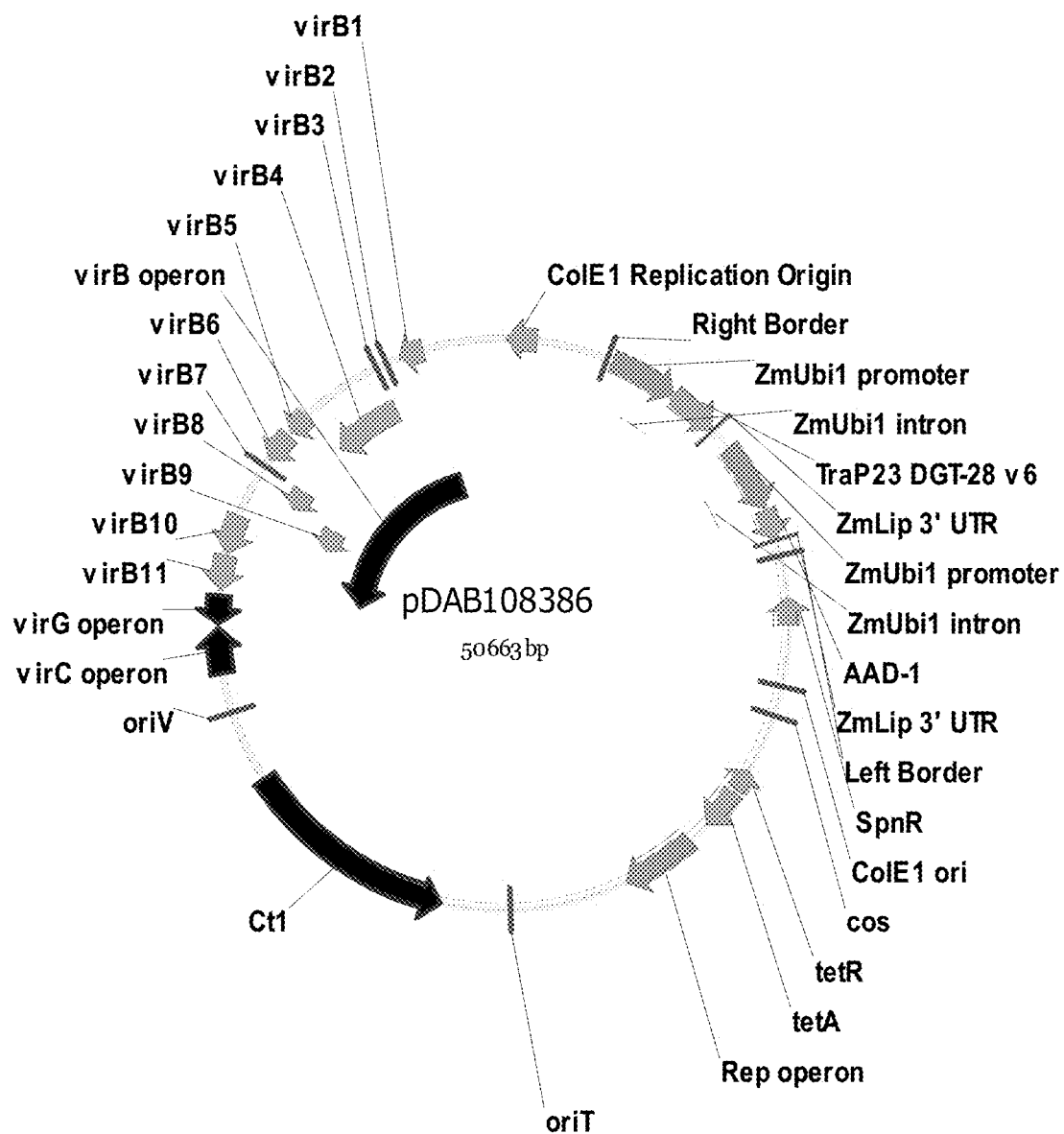
Figure 44:
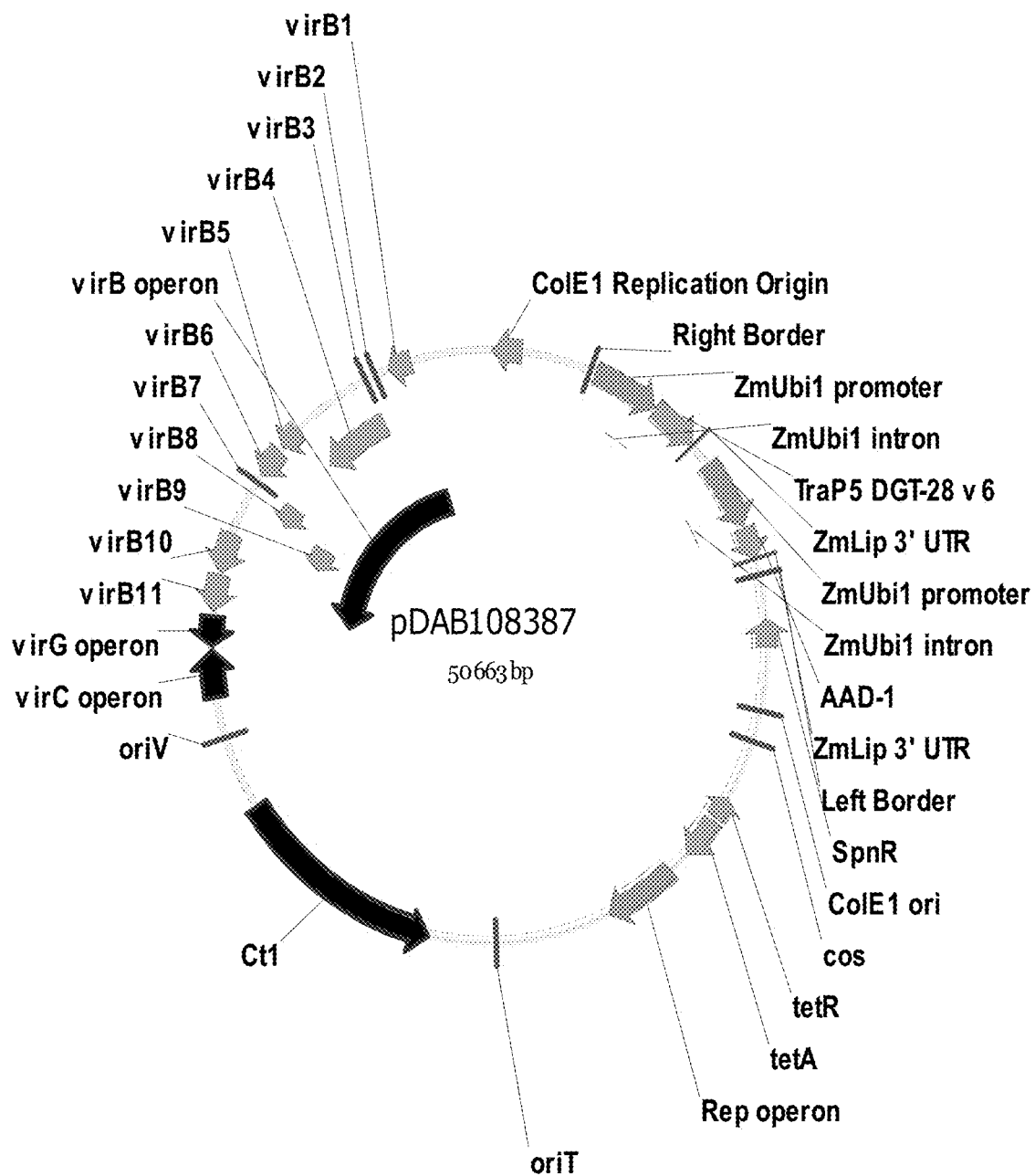

In addition to dgt-28, $T_2$ *Arabidopsis* events transformed with dgt-3 are presented in Table 12. As described for the dgt-28 events in Table 11, the data table contains a representative event that is characteristic of the response to glyphosate for each construct. For the dgt-3 characterization, constructs containing a single PTU (plant transformation unit) with the dgt-3 gene being driven by the AtUbi10 promoter (pDAB102716, FIG. 45 and pDAB102715, FIG. 10) were compared to constructs with the same gene containing 2 PTUs of the gene (pDAB 102719, FIG. 32;

pDAB102718, FIG. 33). The constructs which contained 2 PTU used the AtUbi10 promoter to drive one copy of the gene and the CsVMV promoter to drive the other copy. The use of the double PTU was incorporated to compare the dgt-3 transgenic plants with dgt-28 transgenic plants which contained two copies of the transgene. Data demonstrated that single copy $T_2$ dgt-3 events with only a single PTU were more susceptible to glyphosate than single copy dgt-28 events tested, but were more tolerant than the non-transformed control. $T_1$ families containing 2 PTUs of the dgt-3 gene provided a higher level of visual tolerance to glyphosate compared to the 1 PTU constructs. In both instances the $T_1$ families were compared to the dgt-1 and wildtype controls. $T_2$ data demonstrate that dgt-28 provides robust tolerance as single copy events.

TABLE 11

Response of selected individual $T_2$ *Arabidopsis* events containing dgt-28 to glyphosate applied postemergence at varying rates, compared to a dgt-1 ($T_4$) homozygous resistant population, and a non-transformed control. Visual % injury 14 days after application.

| | % Injury | | | % Injury | | |
|---|---|---|---|---|---|---|
| 1 copy | <20% | 20-40% | >40% | Ave | Std dev | Range (%) |
| pDAB105530: TraP5 v2 - dgt-28 v5 | | | | | | |
| 0 g ae/ha glyphosate | 4 | 0 | 0 | 0.0 | 0.0 | 0 |
| 420 g ae/ha glyphosate | 0 | 0 | 4 | 75.0 | 17.8 | 50-90 |
| 840 g ae/ha glyphosate | 0 | 0 | 4 | 80.0 | 20.0 | 50-90 |
| 1680 g ae/ha glyphosate | 0 | 0 | 4 | 75.0 | 10.8 | 60-85 |
| 3360 g ae/ha glyphosate | 0 | 0 | 4 | 76.3 | 4.8 | 70-80 |
| pDAB105531: TraP8 v2 - dgt-28 v5 | | | | | | |
| 0 g ae/ha glyphosate | 4 | 0 | 0 | 0.0 | 0.0 | 0 |
| 420 g ae/ha glyphosate | 4 | 0 | 0 | 0.5 | 1.0 | 0-2 |
| 840 g ae/ha glyphosate | 4 | 0 | 0 | 1.3 | 2.5 | 0-5 |
| 1680 g ae/ha glyphosate | 4 | 0 | 0 | 7.5 | 5.0 | 5-15 |
| 3360 g ae/ha glyphosate | 4 | 0 | 0 | 7.5 | 6.5 | 0-15 |
| pDAB105532: TraP9 v2 - dgt-28 v5 | | | | | | |
| 0 g ae/ha glyphosate | 4 | 0 | 0 | 0.0 | 0.0 | 0 |
| 420 g ae/ha glyphosate | 4 | 0 | 0 | 2.0 | 4.0 | 0-8 |
| 840 g ae/ha glyphosate | 4 | 0 | 0 | 9.0 | 2.0 | 8-12 |
| 1680 g ae/ha glyphosate | 4 | 0 | 0 | 7.3 | 4.6 | 2-12 |
| 3360 g ae/ha glyphosate | 4 | 0 | 0 | 11.0 | 1.2 | 10-12 |
| pDAB105533: TraP12 v2 - dgt-28 v5 | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 0.0 | 0.0 | 0 |
| 3360 g ae/ha glyphosate | 3 | 1 | 0 | 13.3 | 7.9 | 8-25 |
| pDAB105534: TraP13 v2 - dgt-28 v5 | | | | | | |
| 0 g ae/ha glyphosate | 4 | 0 | 0 | 0.0 | 0.0 | 0 |
| 420 g ae/ha glyphosate | 3 | 1 | 0 | 5.0 | 10.0 | 0-20 |
| 840 g ae/ha glyphosate | 3 | 1 | 0 | 5.0 | 10.0 | 0-20 |
| 1680 g ae/ha glyphosate | 2 | 2 | 0 | 10.0 | 11.5 | 0-20 |
| 3360 g ae/ha glyphosate | 2 | 2 | 0 | 15.0 | 12.2 | 5-30 |
| WT (non-transformed control) | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |
| pDAB4104: dgt-1 (transformed control) | | | | | | |
| 0 g ae/ha glyphosate | 4 | 0 | 0 | 0.0 | 0.0 | 0 |
| 420 g ae/ha glyphosate | 0 | 4 | 0 | 37.5 | 2.9 | 35-40 |
| 840 g ae/ha glyphosate | 0 | 0 | 4 | 45.0 | 0.0 | 45 |
| 1680 g ae/ha glyphosate | 0 | 0 | 4 | 47.5 | 2.9 | 45-50 |
| 3360 g ae/ha glyphosate | 0 | 0 | 4 | 50.0 | 0.0 | 50 |

TABLE 12

Response of selected $T_2$ Arabidopsis events transformed with dgt-3 to glyphosate applied postemergence at varying rates. Visual % injury 14 days after application.

|  | % Injury | | | % Injury | | |
|---|---|---|---|---|---|---|
| 1 copy seg | <20% | 20-40% | >40% | Ave | Std dev | Range (%) |
| pDAB102716: dgt-3 v3 (1 PTU) | | | | | | |
| 0 g ae/ha glyphosate | 4 | 0 | 0 | 0 | 0 | 0 |
| 420 g ae/ha glyphosate | 1 | 1 | 2 | 39 | 25 | 15-65 |
| 840 g ae/ha glyphosate | 0 | 2 | 2 | 50 | 23 | 30-70 |
| 1680 g ae/ha glyphosate | 0 | 1 | 3 | 69 | 19 | 40-80 |
| 3360 g ae/ha glyphosate | 0 | 0 | 4 | 79 | 6 | 70-85 |
| pDAB102719: dgt-3 v3 (2 PTU) | | | | | | |
| 0 g ae/ha glyphosate | 4 | 0 | 0 | 0 | 0 | 0 |
| 420 g ae/ha glyphosate | 0 | 4 | 0 | 20 | 0 | 20 |
| 840 g ae/ha glyphosate | 0 | 3 | 1 | 38 | 5 | 35-45 |
| 1680 g ae/ha glyphosate | 3 | 1 | 0 | 15 | 7 | 10-25 |
| 3360 g ae/ha glyphosate | 2 | 2 | 0 | 21 | 8 | 15-30 |
| pDAB102715: dgt-3 v2 (1 PTU) | | | | | | |
| 0 g ae/ha glyphosate | 4 | 0 | 0 | 0 | 0 | 0 |
| 420 g ae/ha glyphosate | 2 | 2 | 0 | 26 | 16 | 10-40 |
| 840 g ae/ha glyphosate | 0 | 2 | 2 | 55 | 17 | 40-70 |
| 1680 g ae/ha glyphosate | 0 | 2 | 2 | 56 | 22 | 35-75 |
| 3360 g ae/ha glyphosate | 0 | 0 | 4 | 65 | 17 | 50-80 |
| pDAB102718: dgt-3 v2 (2 PTU) | | | | | | |
| 0 g ae/ha glyphosate | 4 | 0 | 0 | 0 | 0 | 0 |
| 420 g ae/ha glyphosate | 4 | 0 | 0 | 5 | 7 | 0-15 |
| 840 g ae/ha glyphosate | 2 | 2 | 0 | 23 | 10 | 15-35 |
| 1680 g ae/ha glyphosate | 3 | 0 | 1 | 20 | 20 | 5-50 |
| 3360 g ae/ha glyphosate | 1 | 1 | 2 | 36 | 22 | 15-60 |

$T_3$ Arabidopsis Data.

The third generation plants (T3) of selected $T_2$ Arabidopsis events which contained low copy numbers of the dgt-28 transgene were further characterized for glyphosate tolerance. Twenty-five plants per line were selected with glufosinate as previously described and lines from every construct tested did not segregate for the selectable marker gene. Glyphosate was applied as described previously. The response of the plants is presented in terms of % visual injury 2 weeks after treatment (WAT). Data are presented as a histogram of individuals exhibiting little or no injury (<20%), moderate injury (20-40%), or severe injury (>40%). An arithmetic mean and standard deviation are presented for each construct used for Arabidopsis transformation. The range in individual response is also indicated in the last column for each rate and transformation. Wild-type, non-transformed Arabidopsis (cv. Columbia) served as a glyphosate sensitive control.

TABLE 13

Response of selected individual $T_3$ Arabidopsis events containing dgt-28 to glyphosate applied postemergence at varying rates, compared to a dgt-1 ($T_4$) homozygous resistant population, and a non-transformed control. Visual % injury 14 days after application.

| | % Injury Range (No. Replicates) | | | % Injury Analysis | | |
|---|---|---|---|---|---|---|
| Application Rate | <20% | 20-40% | >40% | Ave | Std dev | Range (%) |
| dgt-28 (pDAB107602) | | | | | | |
| 0 g ae/ha glyphosate | 4 | 0 | 0 | 0.0 | 0.0 | 0 |
| 420 g ae/ha glyphosate | 0 | 0 | 4 | 73.8 | 2.5 | 70-75 |
| 840 g ae/ha glyphosate | 0 | 0 | 4 | 71.3 | 7.5 | 60-75 |
| 1680 g ae/ha glyphosate | 0 | 0 | 4 | 77.5 | 2.9 | 75-80 |
| 3360 g ae/ha glyphosate | 0 | 0 | 4 | 77.5 | 2.9 | 75-80 |
| TraP4::dgt-28 (pDAB107527) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 5.0 | 0.0 | 5 |
| 1680 g ae/ha glyphosate | 4 | 0 | 0 | 10.0 | 0.0 | 10 |
| 3360 g ae/ha glyphosate | 1 | 3 | 0 | 18.8 | 2.5 | 15-20 |
| TraP5 v1::dgt-28 (pDAB102792) | | | | | | |
| 0 g ae/ha glyphosate | 4 | 0 | 0 | 0.0 | 0.0 | 0 |
| 420 g ae/ha glyphosate | 3 | 0 | 0 | 0.0 | 0.0 | 0 |
| 840 g ae/ha glyphosate | 3 | 0 | 0 | 0.0 | 0.0 | 0 |

TABLE 13-continued

Response of selected individual T₃ Arabidopsis events containing dgt-28 to glyphosate applied postemergence at varying rates, compared to a dgt-1 (T₄) homozygous resistant population, and a non-transformed control. Visual % injury 14 days after application.

| | | | | | | |
|---|---|---|---|---|---|---|
| 1680 g ae/ha glyphosate | 3 | 0 | 0 | 6.0 | 1.7 | 5-8 |
| 3360 g ae/ha glyphosate | 2 | 0 | 0 | 6.5 | 2.1 | 5-8 |

| TraP5 v2::dgt-28 (pDAB105530) | % Injury Range (No. Replicates) | | | % Injury Analysis | | |
|---|---|---|---|---|---|---|
| Averages | <20% | 20-40% | >40% | Ave | Std dev | Range (%) |
| 0 g ae/ha glyphosate | 4 | 0 | 0 | 0.0 | 0.0 | 0 |
| 420 g ae/ha glyphosate | 4 | 0 | 0 | 6.0 | 1.7 | 5-8 |
| 840 g ae/ha glyphosate | 4 | 0 | 0 | 8.0 | 0.0 | 8 |
| 1680 g ae/ha glyphosate | 4 | 0 | 0 | 14.3 | 1.5 | 12-15 |
| 3360 g ae/ha glyphosate | 1 | 3 | 0 | 18.7 | 2.5 | 15-20 |

| | % Injury Range (No. Replicates) | | | % Injury Analysis | | |
|---|---|---|---|---|---|---|
| Application Rate | <20% | 20-40% | >40% | Ave | Std dev | Range (%) |
| TraP8 v2::dgt-28 (pDAB105531) | | | | | | |
| 0 g ae/ha glyphosate | 4 | 0 | 0 | 0.0 | 0.0 | 0 |
| 420 g ae/ha glyphosate | 4 | 0 | 0 | 2.5 | 5.0 | 0-10 |
| 840 g ae/ha glyphosate | 4 | 0 | 0 | 3.3 | 3.9 | 0-8 |
| 1680 g ae/ha glyphosate | 4 | 0 | 0 | 2.5 | 2.9 | 0-5 |
| 3360 g ae/ha glyphosate | 4 | 0 | 0 | 7.3 | 6.4 | 2-15 |
| TraP9 v2::dgt-28 (pDAB105532) | | | | | | |
| 0 g ae/ha glyphosate | 4 | 0 | 0 | 0.0 | 0.0 | 0 |
| 420 g ae/ha glyphosate | 4 | 0 | 0 | 1.3 | 2.5 | 0-5 |
| 840 g ae/ha glyphosate | 4 | 0 | 0 | 1.8 | 2.4 | 0-5 |
| 1680 g ae/ha glyphosate | 4 | 0 | 0 | 0.0 | 0.0 | 0 |
| 3360 g ae/ha glyphosate | 4 | 0 | 0 | 10.0 | 4.4 | 5-15 |
| TraP12 v2::dgt-28 (pDAB105533) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 3.8 | 7.5 | 0-15 |
| 3360 g ae/ha glyphosate | 4 | 0 | 0 | 6.3 | 4.8 | 0-10 |
| TraP13 v2::dgt-28 (pDAB105534) | | | | | | |
| 0 g ae/ha glyphosate | 4 | 0 | 0 | 0.0 | 0.0 | 0 |
| 420 g ae/ha glyphosate | 2 | 2 | 0 | 10.0 | 11.5 | 0-20 |
| 840 g ae/ha glyphosate | 4 | 0 | 0 | 1.3 | 2.5 | 0-5 |
| 1680 g ae/ha glyphosate | 4 | 0 | 0 | 2.8 | 1.5 | 2-5 |
| 3360 g ae/ha glyphosate | 4 | 0 | 0 | 8.0 | 0.0 | 8 |
| TraP23::dgt-28 (pDAB107553) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 7.8 | 2.1 | 5-10 |
| 3360 g ae/ha glyphosate | 4 | 0 | 0 | 10.8 | 3.0 | 8-15 |
| WT (non-transformed control) | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

Selection of Transformed Plants.

Freshly harvested T₁ seed [dgt-31, dgt-32, and dgt-33 v1 gene] were allowed to dry at room temperature and shipped to Indianapolis for testing. T₁ seed was sown in 26.5×51-cm germination trays (T.O. Plastics Inc., Clearwater, Minn.), each receiving a 200 mg aliquots of stratified T₁ seed (~10,000 seed) that had previously been suspended in 40 mL of 0.1% agarose solution and stored at 4° C. for 2 days to complete dormancy requirements and ensure synchronous seed germination.

Sunshine Mix LP5 (Sun Gro Horticulture Inc., Bellevue, Wash.) was covered with fine vermiculite and subirrigated with Hoagland's solution until wet, then allowed to gravity drain. Each 40 mL aliquot of stratified seed was sown evenly onto the vermiculite with a pipette and covered with humidity domes (KORD™ Products, Bramalea, Ontario, Canada) for 4-5 days. Domes were removed once plants had germinated prior to initial transformant selection using glufosinate postemergence spray (selecting for the co-transformed dsm-2 gene).

Six days after planting (DAP) and again 10 DAP, T₁ plants (cotyledon and 2-4-1 f stage, respectively) were sprayed with a 0.1% solution of IGNITE™ herbicide (280 g ai/L glufosinate, Bayer Crop Sciences, Kansas City, Mo.) at a spray volume of 10 mL/tray (703 L/ha) using a DeVilbiss™ compressed air spray tip to deliver an effective rate of 200 g ae/ha glufosinate per application. Survivors (plants actively growing) were identified 4-7 days after the final spraying. Surviving plants were transplanted individually into 3-inch pots prepared with potting media (Metro Mix 360™). Plants reared in the greenhouse at least 1 day prior to tissue sampling for copy number analyses.

T₁ plants were sampled and copy number analysis for the dgt-31, dgt-32, and dgt-33 v1 gene were completed. T₁ plants were then assigned to various rates of glyphosate so that a range of copies were among each rate. For *Arabidopsis*, 26.25 g ae/ha glyphosate is an effective dose to distinguish sensitive plants from ones with meaningful levels of resistance. Elevated rates were applied to determine relative levels of resistance (105, 420, 1680, or 3360 g ae/ha). Table 15 shows the comparisons drawn to dgt-1.

All glyphosate herbicide applications were made by track sprayer in a 187 L/ha spray volume. Glyphosate used was of the commercial Durango dimethylamine salt formulation (480 g ae/L, Dow AgroSciences, LLC). Low copy $T_1$ plants that exhibited tolerance to either glufosinate or glyphosate were further accessed in the $T_2$ generation.

The first *Arabidopsis* transformations were conducted using dgt-31, dgt-32, and dgt-33 v1. $T_1$ transformants were first selected from the background of untransformed seed using a glufosinate selection scheme. Three flats or 30,000 seed were analyzed for each $T_1$ construct. Transformation frequency was calculated and results of T1 dgt-31, dgt-32, and dgt-33 constructs are listed in Table 14.

TABLE 14

Transformation frequency of T1 dgt-31, dgt-32, and dgt-33 *Arabidopsis* constructs selected with glufosinate for selection of the selectable marker gene DSM-2.

| Construct | Cassette | Transformation Frequency (%) |
|---|---|---|
| pDAB107532 | AtUbi10/TraP14 dgt-32 v1 | 0.47 |
| pDAB107533 | AtUbi10/TraP23 dgt-31 v1 | 0.36 |
| pDAB107534 | AtUbi10/TraP24 dgt-33 v1 | 0.68 |

$T_1$ plants selected above were subsequently transplanted to individual pots and sprayed with various rates of commercial glyphosate. Table 15 compares the response of dgt-31, dgt-32, and dgt-33 v1 and control genes to impart glyphosate resistance to *Arabidopsis* $T_1$ transformants. Response is presented in terms of % visual injury 2 WAT. Data are presented as a histogram of individuals exhibiting little or no injury (<20%), moderate injury (20-40%), or severe injury (>40%). An arithmetic mean and standard deviation is presented for each treatment. The range in individual response is also indicated in the last column for each rate and transformation. Wild-type non-transformed *Arabidopsis* (cv. Columbia) served as a glyphosate sensitive control. The DGT-31 (v1) gene with transit peptide TraP23 imparted slight herbicide tolerance to individual $T_1$ *Arabidopsis* plants compared to the negative control, but the gene exhibited improved tolerance with transit peptide TraP8. Both DGT-32 and DGT-33 demonstrated robust tolerance to glyphosate at the rates tested with TraP8 and with their respective differing chloroplast transit peptide (TraP14 and TraP24 respectively). Within a given treatment, the level of plant response varied greatly, which can be attributed to the fact each plant represents an independent transformation event and thus the copy number of the gene of interest varies from plant to plant. Of important note, at each glyphosate rate tested, there were individuals that were more tolerant than others. An overall population injury average by rate is presented in Table 15 to demonstrate the significant difference between the plants transformed with dgt-31, dgt-32, and dgt-33 v1 versus the dgt-1 v1 or Wild-type controls.

TABLE 15 dgt-31, dgt-32, and dgt-33 v1 transformed $T_1$ *Arabidopsis* response to a range of glyphosate rates applied postemergence, compared to a dgt-1 (T4) homozygous resistant population, or a non-transformed control. Visual % injury 2 weeks after treatment.

| Averages | % Injury <20% | 20-40% | >40% | % Injury Ave | Std. Dev. | Range (%) |
|---|---|---|---|---|---|---|
| TraP23 dgt-31 | | | | | | |
| 0 g ae/ha glyphosate | 4 | 0 | 0 | 0.0 | 0.0 | 0 |
| 105 g ae/ha | 0 | 0 | 4 | 81.3 | 2.5 | 80-85 |
| 420 g ae/ha | 0 | 0 | 4 | 97.3 | 4.9 | 90-100 |
| 1680 g ae/ha | 0 | 0 | 4 | 90.0 | 7.1 | 85-100 |
| 3360 g ae/ha | 0 | 0 | 4 | 91.3 | 6.3 | 85-100 |
| TraP14 dgt-32 | | | | | | |
| 0 g ae/ha glyphosate | 4 | 0 | 0 | 0.0 | 0.0 | 0 |
| 105 g ae/ha | 4 | 0 | 0 | 0.0 | 0.0 | 0 |
| 420 g ae/ha | 2 | 0 | 2 | 30.0 | 29.4 | 0-60 |
| 1680 g ae/ha | 3 | 0 | 1 | 17.5 | 21.8 | 5-50 |
| 3360 g ae/ha | 0 | 3 | 1 | 35.0 | 30.0 | 20-80 |
| TraP24 dgt-33 | | | | | | |
| 0 g ae/ha glyphosate | 4 | 0 | 0 | 0.0 | 0.0 | 0 |
| 105 g ae/ha | 2 | 2 | 0 | 21.3 | 14.9 | 5-40 |
| 420 g ae/ha | 1 | 1 | 2 | 46.3 | 30.9 | 5-70 |
| 1680 g ae/ha | 1 | 0 | 3 | 62.5 | 38.8 | 5-90 |
| 3360 g ae/ha | 1 | 0 | 3 | 62.0 | 36.0 | 8-80 |
| TraP8 dgt-31 | | | | | | |
| 0 g ae/ha glyphosate | 4 | 0 | 0 | | 0.0 | 0.0 |
| 105 g ae/ha glyphosate | 0 | 1 | 3 | | 43.8 | 17.0 |
| 420 g ae/ha glyphosate | 1 | 2 | 1 | | 43.8 | 32.5 |
| 1680 g ae/ha glyphosate | 0 | 1 | 3 | | 71.3 | 27.8 |
| 3360 g ae/ha glyphosate | 0 | 0 | 4 | | 81.3 | 8.5 |
| TraP8 dgt-32 | | | | | | |
| 0 g ae/ha glyphosate | 4 | 0 | 0 | | 0.0 | 0.0 |
| 105 g ae/ha glyphosate | 4 | 0 | 0 | | 0.0 | 0.0 |

TABLE 15-continued dgt-31, dgt-32, and dgt-33 v1 transformed $T_1$ Arabidopsis response to a range of glyphosate rates applied postemergence, compared to a dgt-1 (T4) homozygous resistant population, or a non-transformed control. Visual % injury 2 weeks after treatment.

| Averages | % Injury <20% | % Injury 20-40% | % Injury >40% | Ave | Std. Dev. | Range (%) |
|---|---|---|---|---|---|---|
| 420 g ae/ha glyphosate | 4 | 0 | 0 | | 7.5 | 5.0 |
| 1680 g ae/ha glyphosate | 3 | 1 | 0 | | 10.8 | 9.6 |
| 3360 g ae/ha glyphosate | 4 | 0 | 0 | | 12.8 | 3.2 |
| TraP8 dgt-33 | | | | | | |
| 0 g ae/ha glyphosate | 4 | 0 | 0 | | 0.0 | 0.0 |
| 105 g ae/ha glyphosate | 4 | 0 | 0 | | 0.0 | 0.0 |
| 420 g ae/ha glyphosate | 4 | 0 | 0 | | 2.5 | 3.8 |
| 1680 g ae/ha glyphosate | 4 | 0 | 0 | | 6.3 | 2.5 |
| 3360 g ae/ha glyphosate | 3 | 1 | 0 | | 20.0 | 13.5 |
| dgt-1 (transformed control) | | | | | | |
| 0 g ae/ha glyphosate | 4 | 0 | 0 | 0.0 | 0.0 | 0 |
| 105 g ae/ha | 0 | 1 | 3 | 42.5 | 15.0 | 20-50 |
| 420 g ae/ha | 0 | 2 | 2 | 38.8 | 11.1 | 25-50 |
| 1680 g ae/ha | 0 | 0 | 4 | 79.0 | 19.4 | 50-90 |
| 3360 g ae/ha | 0 | 0 | 4 | 50.0 | 0.0 | 50 |
| WT (non-transformed control) | | | | | | |
| 0 g ae/ha glyphosate | 4 | 0 | 0 | 0.0 | 0.0 | 0 |
| 105 g ae/ha | 0 | 0 | 4 | 100.0 | 0.0 | 100 |
| 420 g ae/ha | 0 | 0 | 4 | 100.0 | 0.0 | 100 |
| 1680 g ae/ha | 0 | 0 | 4 | 100.0 | 0.0 | 100 |
| 3360 g ae/ha | 0 | 0 | 4 | 100.0 | 0.0 | 100 |
| TraP23 dgt-31 | | | | | | |
| 0 g ae/ha glyphosate | 4 | 0 | 0 | 0.0 | 0.0 | 0 |
| 105 g ae/ha | 0 | 0 | 4 | 81.3 | 2.5 | 80-85 |
| 420 g ae/ha | 0 | 0 | 4 | 97.3 | 4.9 | 90-100 |
| 1680 g ae/ha | 0 | 0 | 4 | 90.0 | 7.1 | 85-100 |
| 3360 g ae/ha | 0 | 0 | 4 | 91.3 | 6.3 | 85-100 |
| TraP14 dgt-32 | | | | | | |
| 0 g ae/ha glyphosate | 4 | 0 | 0 | 0.0 | 0.0 | 0 |
| 105 g ae/ha | 4 | 0 | 0 | 0.0 | 0.0 | 0 |
| 420 g ae/ha | 2 | 0 | 2 | 30.0 | 29.4 | 0-60 |
| 1680 g ae/ha | 3 | 0 | 1 | 17.5 | 21.8 | 5-50 |
| 3360 g ae/ha | 0 | 3 | 1 | 35.0 | 30.0 | 20-80 |
| TraP24 dgt-33 | | | | | | |
| 0 g ae/ha glyphosate | 4 | 0 | 0 | 0.0 | 0.0 | 0 |
| 105 g ae/ha | 2 | 2 | 0 | 21.3 | 14.9 | 5-40 |
| 420 g ae/ha | 1 | 1 | 2 | 46.3 | 30.9 | 5-70 |
| 1680 g ae/ha | 1 | 0 | 3 | 62.5 | 38.8 | 5-90 |
| 3360 g ae/ha | 1 | 0 | 3 | 62.0 | 36.0 | 8-80 |
| dgt-1 (transformed control) | | | | | | |
| 0 g ae/ha glyphosate | 4 | 0 | 0 | 0.0 | 0.0 | 0 |
| 105 g ae/ha | 0 | 1 | 3 | 42.5 | 15.0 | 20-50 |
| 420 g ae/ha | 0 | 2 | 2 | 38.8 | 11.1 | 25-50 |
| 1680 g ae/ha | 0 | 0 | 4 | 79.0 | 19.4 | 50-90 |
| 3360 g ae/ha | 0 | 0 | 4 | 50.0 | 0.0 | 50 |
| WT (non-transformed control) | | | | | | |
| 0 g ae/ha glyphosate | 4 | 0 | 0 | 0.0 | 0.0 | 0 |
| 105 g ae/ha | 0 | 0 | 4 | 100.0 | 0.0 | 100 |
| 420 g ae/ha | 0 | 0 | 4 | 100.0 | 0.0 | 100 |
| 1680 g ae/ha | 0 | 0 | 4 | 100.0 | 0.0 | 100 |
| 3360 g ae/ha | 0 | 0 | 4 | 100.0 | 0.0 | 100 |

Example 8

Dgt-32 and Dgt-33 as Selectable Markers dgt-32 and dgt-33 v1 are used as selectable markers with glyphosate as the selection agent. The performance of these markers is analyzed with transformed *Arabidopsis*. Approximately 50 $T_4$ generation *Arabidopsis* seed (homozygous for dgt-32 and dgt-33 v1) are spiked into approximately 5,000 wild-type (sensitive) seed. Several treatments are compared, each tray of plants receiving either one or two application timings of glyphosate in one of the following treatment schemes: 7 DAP, 11 DAP, or 7 followed by 11 DAP. Since all individuals also contain the dsm-2 gene in the same transformation vector, dgt-32 and dgt-33 selected with glyphosate are able to be directly compared to dsm-2 selected with glufosinate.

Treatments are applied with a DeVilbiss™ spray tip. Plants are identified as Resistant or Sensitive 17 DAP. Treatments of 26.25-280 g ae/ha 2,4-D applied 7 and 11 days after planting (DAP), are equally effective in selection frequency. These results indicate that dgt-32 and dgt-33 v1 can be effectively used as a selectable marker.

Heritability.

A variety of $T_1$ events were self-pollinated to produce $T_2$ seed. These seed were progeny tested by applying IGNITE™ (200 g ae/ha) to 100 random $T_2$ siblings. Each individual $T_2$ plant was transplanted to 7.5-cm square pots prior to spray application (track sprayer at 187 L/ha applications rate). $T_1$ families ($T_2$ plants) that segregate in the anticipated 3 Resistant:1 Sensitive model for a dominantly-inherited single locus with Mendelian inheritance as determined by Chi square analysis (P>0.05) were determined.

Seed was collected from 5 to 15 $T_2$ individuals ($T_3$ seed). Twenty-five $T_3$ siblings from each of 3 randomly-selected $T_2$ families were progeny tested. Data showing no segregation demonstrate that dgt-32 and dgt-33 v1 were each stably integrated and inherited in a Mendelian fashion to at least three generations.

Additional Herbicide Tolerance Characterization of $T_3$ DGT Lines.

$T_3$ generation *Arabidopsis* seed is stratified, and sown into selection trays. A transformed control line containing dgt-1 and the non-transformed control are planted in a similar manner. Seedlings are transferred to individual 3-inch pots in the greenhouse. All plants are sprayed with the use of a track sprayer set at 187 L/ha. The plants are sprayed with a range of glyphosate from 420-3360 g ae/ha (DURANGO™ DMA, Dow AgroSciences). All applications are formulated in water. Each treatment is replicated 4 times, and plants are evaluated at 7 and 14 days after treatment.

Example 9

Transformation of Additional Crop Species

Soybean is transformed with dgt-28, dgt-31, dgt-32, and/or dgt-33 (with or without a chloroplast transit peptide) to provide high levels of resistance to the herbicide glyphosate, utilizing a method known to those of skill in the art, for example, substantially the same techniques previously described in Example 11 or Example 13 of PCT International Patent Publication No. WO 2007/053482, which reference is incorporated herein by this reference in its entirety.

Cotton is transformed with dgt-28, dgt-31, dgt-32, and/or dgt-33 (with or without a chloroplast transit peptide) to provide high levels of resistance to the herbicide glyphosate by utilizing a method known to those of skill in the art, for example, substantially the same techniques previously described in Examples 14 of U.S. Pat. No. 7,838,733, or Example 12 of PCT International Patent Publication No. WO 2007/053482, each of which references are incorporated herein by this reference in its entirety.

Canola is transformed with dgt-28, dgt-31, dgt-32, and/or dgt-33 (with or without a chloroplast transit peptide) to provide high levels of resistance to the herbicide glyphosate by utilizing a method known to those of skill in the art, for example, substantially the same techniques previously described in Example 26 of U.S. Pat. No. 7,838,733, or Example 22 of PCT International Patent Publication No. WO 2007/053482.

Example 10

Maize Transformation

DNA Constructs for Maize Transformation.

Standard cloning methods, as described above, were used in the construction of binary vectors for use in *Agrobacterium tumefaciens*-mediated transformation of maize. Table 16 lists the vectors which were constructed for maize transformation. The following gene elements were used in the vectors which contained dgt-28; the *Zea mays* Ubiquitin 1 promoter (ZmUbi1; U.S. Pat. No. 5,510,474) was used to drive the dgt-28 coding sequence which is flanked by a *Zea mays* Lipase 3' untranslated region (ZmLip 3'UTR; U.S. Pat. No. 7,179,902), the selectable marker cassette consists of the *Zea mays* Ubiquitin 1 promoter which was used to drive the aad-1 coding sequence (U.S. Pat. No. 7,838,733) which is flanked by a *Zea mays* Lipase 3' untranslated region. The aad-1 coding sequence confers tolerance to the phenoxy auxin herbicides, such as, 2,4-dichlorophenoxyacetic acid (2,4-D) and to aryloxyphenoxypropionate (AOPP) herbicides.

The dgt-28 constructs were built as standard binary vectors and *Agrobacterium* superbinary system vectors (Japan Tobacco, Tokyo, JP). The standard binary vectors include; pDAB 107663, pDAB 107664, pDAB 107665, and pDAB 107665. The *Agrobacterium* superbinary system vectors include pDAB108384, pDAB108385, pDAB108386, and pDAB108387.

Additional constructs were completed which contain a yellow fluorescent protein (yfp; US Patent Application 2007/0298412) reporter gene. pDAB109812 contains a yfp reporter gene cassette which is driven by the *Zea mays* Ubiquitin 1 promoter and flanked by the *Zea mays* per 5 3' untranslated region (Zm per5 3'UTR; U.S. Pat. No. 7,179,902), the selectable marker cassette consists of the sugar cane bacilliform virus promoter (SCBV; U.S. Pat. No. 5,994,123) which is used to drive the expression of aad-1 and is flanked by the *Zea mays* Lipase 3' untranslated region. pDAB101556 contains a yfp cassette which is driven by the *Zea mays* Ubiquitin 1 promoter and flanked by the *Zea mays* per 5 3' untranslated region, the selectable marker cassette consists of the *Zea mays* Ubiquitin 1 promoter which is used to drive the expression of aad-1 and is flanked by the *Zea mays* Lipase 3' untranslated region. pDAB107698 contains a dgt-28 cassette which is driven by the *Zea mays* Ubiquitin 1 promoter and is flanked by a *Zea mays* Lipase 3' untranslated region, an yfp cassette which is driven by the *Zea mays* Ubiquitin 1 promoter and flanked by the *Zea mays* per 5 3' untranslated region, the selectable marker cassette consists of the sugar cane bacilliform virus promoter which is used to drive the expression of aad-1 and is flanked by the *Zea mays* Lipase 3' untranslated region. All three of these constructs are standard binary vectors.

TABLE 16

Maize Transformation Vectors

| Plasmid No. | FIG. No: | Description of Gene Elements |
| --- | --- | --- |
| pDAB107663 | 34 | ZmUbi1/TraP4 dgt-28/ZmLip 3'UTR :: ZmUbi1/aad-1/ZmLip 3'UTR binary vector |
| pDAB107664 | 35 | ZmUbi1/TraP8 dgt-28/ZmLip 3'UTR :: ZmUbi1/aad-1/ZmLip 3'UTR binary vector |
| pDAB107665 | 36 | ZmUbi1/TraP23 dgt-28/ZmLip 3'UTR :: ZmUbi1/aad-1/ZmLip 3'UTR binary vector |

TABLE 16-continued

Maize Transformation Vectors

| Plasmid No. | FIG. No: | Description of Gene Elements |
|---|---|---|
| pDAB107666 | 37 | ZmUbi1/TraP5 dgt-28/ZmLip 3'UTR :: ZmUbi1/aad-1/ZmLip 3'UTR binary vector |
| pDAB109812 | 38 | ZmUbi1/yfp/ZmPer5 3'UTR :: SCBV/aad-1/ZmLip 3'UTR binary vector |
| pDAB101556 | 39 | ZmUbi1/yfp/ZmPer5 3'UTR :: ZmUbi1/aad-1/ZmLip 3'UTR binary vector |
| pDAB107698 | 40 | ZmUbi1/TraP8 dgt-28/ZmLip 3'UTR :: ZmUbi1/yffi/ZmLip 3'UTR::SCBV/aad-1/ZmLip 3'UTR |
| pDAB 108384 | 41 | ZmUbi1/TraP4 dgt-28/ZmLip 3'UTR :: ZmUbi1/aad-1/ZmLip 3'UTR superbinary vector |
| pDAB108385 | 42 | ZmUbi1/TraP8 dgt-28/ZmLip 3'UTR :: ZmUbi1/aad-1/ZmLip 3'UTR superbinary precursor |
| pDAB108386 | 43 | ZmUbi1/TraP23 dgt-28/ZmLip 3'UTR :: ZmUbi1/aad-1/ZmLip 3'UTR superbinary precursor |
| pDAB108387 | 44 | ZmUbi1/TraP5 dgt-28/ZmLip 3'UTR :: ZmUbi1/aad-1/ZmLip 3'UTR superbinary precursor |

Ear Sterilization and Embryo Isolation.

To obtain maize immature embryos, plants of the *Zea mays* inbred line B104 were grown in the greenhouse and were self or sib-pollinated to produce ears. The ears were harvested approximately 9-12 days post-pollination. On the experimental day, ears were surface-sterilized by immersion in a 20% solution of sodium hypochlorite (5%) and shaken for 20-30 minutes, followed by three rinses in sterile water. After sterilization, immature zygotic embryos (1.5-2.4 mm) were aseptically dissected from each ear and randomly distributed into micro-centrifuge tubes containing liquid infection media (LS Basal Medium, 4.43 gm/L; N6 Vitamin Solution [1000×], 1.00 mL/L; L-proline, 700.0 mg/L; Sucrose, 68.5 gm/L; D(+) Glucose, 36.0 gm/L; 10 mg/ml of 2,4-D, 150 µL/L). For a given set of experiments, pooled embryos from three ears were used for each transformation.

*Agrobacterium* Culture Initiation:

Glycerol stocks of *Agrobacterium* containing the binary transformation vectors described above were streaked on AB minimal medium plates containing appropriate antibiotics and were grown at 20° C. for 3-4 days. A single colony was picked and streaked onto YEP plates containing the same antibiotics and was incubated at 28° C. for 1-2 days.

*Agrobacterium* Culture and Co-Cultivation.

*Agrobacterium* colonies were taken from the YEP plate, suspended in 10 mL of infection medium in a 50 mL disposable tube, and the cell density was adjusted to $OD_{600}$ nm of 0.2-0.4 using a spectrophotometer. The *Agrobacterium* cultures were placed on a rotary shaker at 125 rpm, room temperature, while embryo dissection was performed. Immature zygotic embryos between 1.5-2.4 mm in size were isolated from the sterilized maize kernels and placed in 1 mL of the infection medium) and washed once in the same medium. The *Agrobacterium* suspension (2 mL) was added to each tube and the tubes were placed on a shaker platform for 10-15 minutes. The embryos were transferred onto co-cultivation media (MS Salts, 4.33 gm/L; L-proline, 700.0 mg/L; Myo-inositol, 100.0 mg/L; Casein enzymatic hydrolysate 100.0 mg/L; 30 mM Dicamba-KOH, 3.3 mg/L; Sucrose, 30.0 gm/L; Gelzan™, 3.00 gm/L; Modified MS-Vitamin [1000×], 1.00 ml/L; 8.5 mg/ml $AgNo_3$, 15.0 mg/L; DMSO, 100 µM), oriented with the scutellum facing up and incubated at 25° C., under 24-hour light at 50 µmole $m^{-2}$ $sec^{-1}$ light intensity for 3 days.

Callus Selection and Regeneration of Putative Events.

Following the co-cultivation period, embryos were transferred to resting media (MS Salts, 4.33 gm/L; L-proline, 700.0 mg/L; 1,2,3,5/4,6-Hexahydroxycyclohexane, 100 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan 2.30 gm/L; Modified MS-Vitamin [1000×], 1.00 ml/L; 8.5 mg/ml AgNo3, 15.0 mg/L; Carbenicillin, 250.0 mg/L) without selective agent and incubated under 24-hour light at 50 µmole $m^{-2}$ $sec^{-1}$ light intensity and at 25° C. for 3 days.

Growth inhibition dosage response experiments suggested that glyphosate concentrations of 0.25 mM and higher were sufficient to inhibit cell growth in the untransformed B104 maize line. Embryos were transferred onto Selection 1 media containing 0.5 mM glyphosate (MS Salts, 4.33 gm/L; L-proline, 700.0 mg/L; Myo-inositol, 100.0 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan™ 2.30 gm/L; Modified MS-Vitamin [1000×], 1.00 ml/L; 8.5 mg/ml AgNo3, 15.0 mg/L; Carbenicillin, 250.0 mg/L) and incubated in either dark and/or under 24-hour light at 50 µmole $m^{-2}$ $sec^{-1}$ light intensity for 7-14 days at 28° C.

Proliferating embryogenic calli were transferred onto Selection 2 media containing 1.0 mM glyphosate (MS Salts, 4.33 gm/L; 1,2,3,5/4,6-Hexahydroxycyclohexane, 100 mg/L; L-proline, 700.0 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan™ 2.30 gm/L; Modified MS-Vitamin [1000×], 1.00 ml/L; 8.5 mg/mL AgNo3, 15.0 mg/L; Carbenicillin, 250.0 mg/L; R-Haloxyfop acid 0.1810 mg/L), and were incubated in either dark and/or under 24-hour light at 50 µmole $m^{-2}$ $sec^{-1}$ light intensity for 14 days at 28° C. This selection step allowed transgenic callus to further proliferate and differentiate. The callus selection period lasted for three to four weeks.

Proliferating, embryogenic calli were transferred onto PreReg media containing 0.5 mM glyphosate (MS Salts, 4.33 gm/L; 1,2,3,5/4,6-Hexahydroxycyclohexane, 100 mg/L; L-proline, 350.0 mg/L; MES [(2-(n-morpholino)-ethanesulfonic acid), free acid] 0.250 gm/L; Casein enzymatic hydrolysate 50.0 mg/L; NAA-NaOH 0.500 mg/L; ABA-EtOH 2.50 mg/L; BA 1.00 mg/L; Sucrose, 45.0 gm/L; Gelzan™ 2.50 gm/L; Modified MS-Vitamin [1000×], 1.00 ml/L; 8.5 mg/ml AgNo3, 1.00 mg/L; Carbenicillin, 250.0 mg/L) and cultured under 24-hour light at 50 µmole $m^{-2}$ $sec^{-1}$ light intensity for 7 days at 28° C.

Embryogenic calli with shoot-like buds were transferred onto Regeneration media containing 0.5 mM glyphosate (MS Salts, 4.33 gm/L; 1,2,3,5/4,6-Hexahydroxycyclohexane, 100.0 mg/L; Sucrose, 60.0 gm/L; Gellan Gum G434™ 3.00 gm/L; Modified MS-Vitamin [1000×], 1.00 ml/L; Carbenicillin, 125.0 mg/L) and cultured under 24-hour light at 50 µmole $m^{-2}$ $sec^{-1}$ light intensity for 7 days.

Small shoots with primary roots were transferred to rooting media (MS Salts, 4.33 gm/L; Modified MS-Vitamin [1000×], 1.00 ml/L; 1,2,3,5/4,6-Hexahydroxycyclohexane, 100 mg/L; Sucrose, 60.0 gm/L; Gellan Gum G434™ 3.00 gm/L; Carbenicillin, 250.0 mg/L) in phytotrays and were incubated under 16/8 hr. light/dark at 140-190 µmole $m^{-2}$ $sec^{-1}$ light intensity for 7 days at 27° C. Putative transgenic plantlets were analyzed for transgene copy number using the protocols described above and transferred to soil.

Molecular Confirmation of the Presence of the Dgt-28 and Aad-1 Transgenes within Maize Plants.

The presence of the dgt-28 and aad-1 polynucleotide sequences were confirmed via hydrolysis probe assays. Isolated To Maize plants were initially screened via a hydrolysis probe assay, analogous to TAQMAN™, to confirm the presence of a aad-1 and dgt-28 transgenes. The data generated from these studies were used to determine the transgene copy number and used to select transgenic maize events for back crossing and advancement to the $T_1$ generation.

A two-step amplification reaction was performed with an extension at 60° C. for 40 seconds with fluorescence acquisition. All samples were run and the averaged Cycle threshold (Ct) values were used for analysis of each sample. Analysis of real time PCR data was performed using Light-Cycler® software release 1.5 using the relative quant module and is based on the ΔΔCt method. Controls included a sample of genomic DNA from a single copy calibrator and known two copy check that were included in each run. Table 18 lists the results of the hydrolysis probe assays.

TABLE 17

Primer and probe sequences used for hydrolysis probe assay of aad-1, dgt-28 and internal reference (Invertase).

| Oligonucleotide Name | Gene Detected | SEQ ID NO: | Oligo Sequence |
|---|---|---|---|
| GAAD1F | aad-1 forward primer | 58 | TGTTCGGTTCCCTCTACCAA |
| GAAD1P | aad-1 probe | 59 | CACAGAACCGTCGCTTCAGCAACA |
| GAAD1R | aad-1 reverse primer | 60 | CAACATCCATCACCTTGACTGA |
| IV-Probe | Invertase probe | 61 | CGAGCAGACCGCCGTGTACTTCTACC |
| IVF-Taq | Invertase forward primer | 62 | TGGCGGACGACGACTTGT |
| IVR-Taq | Invertase reverse primer | 63 | AAAGTTTGGAGGCTGCCGT |
| zmDGT28 F | dgt-28 forward primer | 64 | TTCAGCACCCGTCAGAAT |
| zmDGT28 FAM | dgt-28 probe | 65 | TGCCGAGAACTTGAGGAGGT |
| zmDGT28 R | dgt-28 reverse primer | 66 | TGGTCGCCATAGCTTGT |

Tissue samples were collected in 96-well plates, tissue maceration was performed with a KLECO™ tissue pulverizer and stainless steel beads (Hoover Precision Products, Cumming, Ga.), in Qiagen™ RLT buffer. Following tissue maceration, the genomic DNA was isolated in high-throughput format using the Biosprint 96™ Plant kit (Qiagen, Germantown, Md.) according to the manufacturer's suggested protocol. Genomic DNA was quantified by Quant-IT™ Pico Green DNA assay kit (Molecular Probes, Invitrogen, Carlsbad, Calif.). Quantified genomic DNA was adjusted to around 2 ng/µL for the hydrolysis probe assay using a BIOROBOT3000™ automated liquid handler (Qiagen, Germantown, Md.). Transgene copy number determination by hydrolysis probe assay, analogous to TAQMAN® assay, was performed by real-time PCR using the LIGHTCYCLER®480 system (Roche Applied Science, Indianapolis, Ind.). Assays were designed for aad-1, dgt-28 and an internal reference gene Invertase (Genbank Accession No: U16123.1) using the LIGHTCYCLER® Probe Design Software 2.0. For amplification, LIGHTCYCLER®480 Probes Master mix (Roche Applied Science, Indianapolis, Ind.) was prepared at 1×final concentration in a 10 µL volume multiplex reaction containing 0.4 µM of each primer for aad-1 and dgt-28 and 0.2 µM of each probe (Table 17).

TABLE 18

$T_0$ copy amount results for dgt-28 events. Low copy events consisted of 1-2 transgene copies, single copy numbers are listed in parenthesis. High copy events contained 3 or more transgene copies.

| Plasmid used for Transformation | # of Low Copy Events (single copy) | # of High Copy Events |
|---|---|---|
| pDAB107663 | 43 (31) | 10 |
| pDAB107664 | 30 (24) | 5 |
| pDAB107665 | 40 (27) | 10 |
| pDAB107666 | 24 (12) | 12 |
| pDAB109812 | 2 (1) | 0 |
| pDAB101556 | 25 (15) | 10 |
| pDAB107698 | 3 (1) | 2 |

Example 11

Herbicide Tolerance in Dgt-28 Transformed Corn

*Zea mays* dgt-28 transformation events ($T_0$) were allowed to acclimate in the greenhouse and were grown until plants had transitioned from tissue culture to greenhouse growing conditions (i.e., 2-4 new, normal looking leaves had emerged from the whorl). Plants were grown at 27° C. under 16 hour light:8 hour dark conditions in the greenhouse. The plants were then treated with commercial formulations of DURANGO DMA™ (containing the herbicide glyphosate) with the addition of 2% w/v ammonium-sulfate. Herbicide applications were made with a track sprayer at a spray volume of 187 L/ha, 50-cm spray height. $T_0$ plants were sprayed with a range of glyphosate from 280-4480 g ae/ha glyphosate, which is capable of significant injury to untransformed corn lines. A lethal dose is defined as the rate that causes >95% injury to the B104 inbred.

The results of the To dgt-28 corn plants demonstrated that tolerance to glyphosate was achieved at rates up to 4480 g ae/ha. A specific media type was used in the To generation. Minimal stunting and overall plant growth of transformed plants compared to the non-transformed controls demonstrated that dgt-28 provides robust tolerance to glyphosate when linked to the TraP5, TraP8, and TraP23 chloroplast transit peptides.

Selected $T_0$ plants are selfed or backcrossed for further characterization in the next generation. 100 chosen dgt-28 lines containing the $T_1$ plants are sprayed with 140-1120 g ae/ha glufosinate or 105-1680 g ae/ha glyphosate. Both the selectable marker and glyphosate resistant gene are constructed on the same plasmid. Therefore, if one herbicide tolerant gene is selected for by spraying with an herbicide, both genes are believed to be present. At 14 DAT, resistant and sensitive plants are counted to determine the percentage of lines that segregated as a single locus, dominant Mendelian trait (3R:1S) as determined by Chi square analysis. These data demonstrate that dgt-28 is inheritable as a robust glyphosate resistance gene in a monocot species. Increased rates of glyphosate are applied to the $T_1$ or $F_1$ survivors to further characterize the tolerance and protection that is provided by the dgt-28 gene.

Post-Emergence Herbicide Tolerance in dgt-28 Transformed to Corn.

To events of dgt-28 linked with TraP4, TraP5, TraP8 and TraP23 were generated by *Agrobacterium* transformation and were allowed to acclimate under controlled growth chamber conditions until 2-4 new, normal looking leaves had emerged from the whorl. Plants were assigned individual identification numbers and sampled for copy number analyses of both dgt-28 and aad-1. Based on copy number analyses, plants were selected for protein expression analyses. Plants were transplanted into larger pots with new growing media and grown at 27° C. under 16 hour light:8 hour dark conditions in the greenhouse. Remaining plants that were not sampled for protein expression were then treated with commercial formulations of DURANGO DMA™ (glyphosate) with the addition of 2% w/v ammonium-sulfate. Treatments were distributed so that each grouping of plants contained $T_0$ events of varying copy number. Herbicide applications were made with a track sprayer at a spray volume of 187 L/ha, 50-cm spray height. $T_0$ plants were sprayed with a range of glyphosate from 280-4480 g ae/ha glyphosate capable of significant injury to untransformed corn lines. A lethal dose is defined as the rate that causes >95% injury to the B104 inbred. B104 was the genetic background of the transformants.

Results of To dgt-28 corn plants demonstrate that tolerance to glyphosate was achieved up to 4480 g ae/ha. Table 19. Minimal stunting and overall plant growth of transformed plants compared to the non-transformed controls demonstrated that dgt-28 provides robust protection to glyphosate when linked to TraP5, TraP8, and TraP23.

TABLE 19

Response of $T_0$ dgt-28 events of varying copy numbers to rates of glyphosate ranging from 280-4480 g ae/ha + 2.0% w/v ammonium sulfate 14 days after treatment.

| Application Rate | % Injury <20% | % Injury 20-40% | % Injury >40% | Ave | Std. Dev. | Range (%) |
|---|---|---|---|---|---|---|
| TraP4 dgt-28 | | | | | | |
| 0 g ae/ha glyphosate | 4 | 0 | 0 | 0.0 | 0.0 | 0 |
| 280 g ae/ha | 5 | 0 | 0 | 1.0 | 2.2 | 0-5 |
| 560 g ae/ha | 6 | 0 | 0 | 2.0 | 4.0 | 0-10 |
| 1120 g ae/ha | 12 | 0 | 0 | 1.3 | 3.1 | 0-10 |
| 2240 g ae/ha | 7 | 0 | 0 | 1.7 | 4.5 | 0-12 |
| 4480 g ae/ha | 7 | 0 | 0 | 1.1 | 3.0 | 0-8 |
| TraP8 dgt-28 | | | | | | |
| 0 g ae/ha glyphosate | 6 | 0 | 0 | 0.0 | 0.0 | 0 |
| 280 g ae/ha | 5 | 1 | 0 | 6.7 | 8.8 | 0-20 |
| 560 g ae/ha | 0 | 2 | 0 | 20.0 | 0.0 | 20 |
| 1120 g ae/ha | 7 | 0 | 0 | 1.4 | 2.4 | 0-5 |
| 2240 g ae/ha | 3 | 1 | 0 | 7.5 | 15.0 | 0-30 |
| 4480 g ae/ha | 6 | 0 | 0 | 1.7 | 4.1 | 0-10 |
| TraP23 dgt-28 | | | | | | |
| 0 g ae/ha glyphosate | 6 | 0 | 0 | 0.8 | 2.0 | 0-5 |
| 280 g ae/ha | 7 | 0 | 0 | 0.0 | 0.0 | 0 |
| 560 g ae/ha | 4 | 0 | 0 | 1.3 | 2.5 | 0-5 |
| 1120 g ae/ha | 10 | 2 | 0 | 3.3 | 7.8 | 0-20 |
| 2240 g ae/ha | 6 | 0 | 0 | 1.3 | 3.3 | 0-8 |
| 4480 g ae/ha | 6 | 1 | 0 | 4.3 | 7.9 | 0-20 |
| TraP5 dgt-28 | | | | | | |
| 0 g ae/ha glyphosate | 4 | 0 | 0 | 0.0 | 0.0 | 0 |
| 280 g ae/ha | 7 | 1 | 0 | 5.0 | 14.1 | 0-40 |
| 560 g ae/ha | 8 | 0 | 0 | 0.6 | 1.8 | 0-5 |
| 1120 g ae/ha | 7 | 1 | 0 | 5.0 | 14.1 | 0-40 |
| 2240 g ae/ha | 8 | 0 | 0 | 0.0 | 0.0 | 0 |
| 4480 g ae/ha | 8 | 0 | 0 | 0.0 | 0.0 | 0 |

Protein expression analyses by standard ELISA demonstrated a mean range of DGT-28 protein from 12.6-22.5 ng/cm$^2$ across the constructs tested.

Confirmation of Glyphosate Tolerance in the $F_1$ Generation Under Greenhouse Conditions.

Single copy $T_0$ plants that were not sprayed were backcrossed to the non-transformed background B104 for further characterization in the next generation. In the $T_1$ generation, glyphosate tolerance was assessed to confirm the inheritance of the dgt-28 gene. For $T_1$ plants, the herbicide ASSURE II™ (35 g ae/ha quizalofop-methyl) was applied at the V1 growth stage to select for the AAD-1 protein. Both the selectable marker and glyphosate resistant gene are constructed on the same plasmid. Therefore if one gene is selected, both genes are believed to be present. After 7 DAT, resistant and sensitive plants were counted and null plants were removed from the population. These data demonstrate that dgt-28 (v1) is heritable as a robust glyphosate resistance gene in a monocot species. Plants were sampled for characterization of DGT-28 protein by standard ELISA and RNA transcript level. Resistant plants were sprayed with 560-4480 g ae/ha glyphosate as previously described. The data demonstrate robust tolerance of dgt-28 linked with the chloroplast transit peptides TraP4, TraP5, TraP8 and TraP23 up to 4480 g ae/ha glyphosate. Table 20.

TABLE 20

Response of $F_1$ single copy dgt-28 events to rates of glyphosate ranging from 560-4480 g ae/ha + 2.0% w/v ammonium sulfate 14 days after treatment.

| | % Injury | | | % Injury | | Range |
|---|---|---|---|---|---|---|
| Application Rate | <20% | 20-40% | >40% | Ave | Std. Dev. | (%) |
| B104/TraP4::dgt-28 | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 9.0 | 1.2 | 8-10 |
| 2240 g ae/ha | 4 | 0 | 0 | 2.5 | 2.9 | 0-5 |
| 4480 g ae/ha | 4 | 0 | 0 | 0.0 | 0.0 | 0 |
| B104/TraP8::dgt-28 | | | | | | |
| 0 g ae/ha glyphosate | 4 | 0 | 0 | 0.0 | 0.0 | 0 |
| 560 g ae/ha | 4 | 0 | 0 | 1.3 | 2.5 | 0-5 |
| 1120 g ae/ha | 4 | 0 | 0 | 0.0 | 0.0 | 0 |
| 2240 g ae/ha | 4 | 0 | 0 | 5.0 | 4.1 | 0-10 |
| 4480 g ae/ha | 4 | 0 | 0 | 6.3 | 2.5 | 5-10 |
| B104/TraP23::dgt-28 | | | | | | |
| 0 g ae/ha glyphosate | 4 | 0 | 0 | 0.0 | 0.0 | 0 |
| 560 g ae/ha | 3 | 1 | 0 | 10.0 | 10.0 | 5-25 |
| 1120 g ae/ha | 2 | 2 | 0 | 18.8 | 11.8 | 10-35 |
| 2240 g ae/ha | 4 | 0 | 0 | 12.5 | 2.9 | 10-15 |
| 4480 g ae/ha | 3 | 1 | 0 | 10.0 | 7.1 | 5-20 |
| B104/TraP5::dgt-28 | | | | | | |
| 0 g ae/ha glyphosate | 4 | 0 | 0 | 0.0 | 0.0 | 0 |
| 560 g ae/ha | 4 | 0 | 0 | 8.0 | 0.0 | 8 |
| 1120 g ae/ha | 4 | 0 | 0 | 11.3 | 3.0 | 8-15 |
| 2240 g ae/ha | 4 | 0 | 0 | 12.5 | 2.9 | 10-15 |
| 4480 g ae/ha | 4 | 0 | 0 | 10.0 | 2.5 | 10-15 |
| Non-transformed B104 | | | | | | |
| 0 g ae/ha glyphosate | 4 | 0 | 0 | 0.0 | 0.0 | 0 |
| 560 g ae/ha | 0 | 0 | 4 | 100.0 | 0.0 | 100 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

Protein expression data demonstrate a range of mean DGT-28 protein from 42.2-88.2 ng/cm$^2$ across $T_1$ events and constructs tested, establishing protein expression in the $T_1$ generation.

Characterization of Dgt-28 Corn Under Field Conditions.

Single copy $T_1$ events were sent to a field location to create both hybrid hemizygous and inbred homozygous seed for additional characterization. Hybrid seeds were created by crossing $T_1$ events in the maize transformation line B104 to the inbred line 4XP811 generating hybrid populations segregating 1:1 (hemizygous:null) for the event. The resulting seeds were shipped to 2 separate locations. A total of five single copy events per construct were planted at each location in a randomized complete block design in triplicate. The fields were designed for glyphosate applications to occur at the V4 growth stage and a separate grouping of plants to be applied at the V8 growth stage. The 4XP811/B104 conventional hybrid was used as a negative control.

Experimental rows were treated with 184 g ae/ha ASSURE II™ (106 g ai/L quizalofop-methyl) to eliminate null segregants. All experimental entries segregated 1:1 (sensitive:resistant) (p=0.05) with respect to the ASSURE II™ application. Selected resistant plants were sampled from each event for quantification of the DGT-28 protein by standard ELISA.

Quizalofop-methyl resistant plants were treated with the commercial herbicide DURANGO DMA™ (480 g ae/L glyphosate) with the addition of 2.5% w/v ammonium-sulfate at either the V4 or V8 growth stages. Herbicide applications were made with a boom sprayer calibrated to deliver a volume of 187 L/ha, 50-cm spray height. Plants were sprayed with a range of glyphosate from 1120-4480 g ae/ha glyphosate, capable of significant injury to untransformed corn lines. A lethal dose is defined as the rate that causes >95% injury to the 4XP811 inbred. Visual injury assessments were taken for the percentage of visual chlorosis, percentage of necrosis, percentage of growth inhibition and total visual injury at 7, 14 and 21 DAT (days after treatment). Assessments were compared to the untreated checks for each line and the negative controls.

Visual injury data for all assessement timings demonstrated robust tolerance up to 4480 g ae/ha DURANGO DMA™ at both locations and application timings. Representative events for the V4 application are presented from one location and are consistent with other events, application timings and locations. Table 21. One event from the construct containing dgt-28 linked with TraP23 (pDAB 107665) was tolerant to the ASSURE II™ selection for the AAD-1 protein, but was sensitive to all rates of glyphosate applied.

TABLE 21

Response of dgt-28 events applied with a range of glyphosate from 1120-4480 g ae/ha + 2.5% w/v ammonium sulfate at the V4 growth stage.

| | % Injury | | | % Injury | | Range |
|---|---|---|---|---|---|---|
| Application Rate | <20% | 20-40% | >40% | Ave | Std. Dev. | (%) |
| 4XPB11//B104/TraP4::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 0.0 | 0.0 | 0 |
| 4XPB11//B104/TraP8::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 0.0 | 0.0 | 0 |
| 4XPB11//B104/TraP23::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 0.0 | 0.0 | 0 |
| 4XPB11//B104/TraP5::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 0.0 | 0.0 | 0 |
| Non-transformed 4XPB11//B104 | | | | | | |
| 0 g ae/ha glyphosate | 4 | 0 | 0 | 0.0 | 0.0 | 0 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

Additional assessments were made during the reproductive growth stage for the 4480 g ae/ha glyphosate rate. Visual assessments of tassels, pollination timing and ear fill were similar to the untreated checks of each line for all constructs, application timings and locations. Quantification results for the DGT-28 protein demonstrated a range of mean protein expression from 186.4-303.0 ng/cm². Data demonstrates robust tolerance of dgt-28 transformed corn under field conditions through the reproductive growth stages up to 4480 g ae/ha glyphosate. Data also demonstrated DGT-28 protein detection and function based on spray tolerance results.

Confirmation of Heritability and Tolerance of Dgt-28 Corn in the Homozygous State.

Seed from the $T_1S2$ were planted under greenhouse conditions as previously described. The same five single copy lines that were characterized under field conditions were characterized in the homogeneous state. Plants were grown until the V3 growth stage and separated into three rates of glyphosate ranging from 1120-4480 g ae/ha glyphosate (DURANGO DMA™) and four replicates per treatment. Applications were made in a track sprayer as previously described and were formulated in 2.0% w/v ammonium sulfate. An application of ammonium sulfate served as an untreated check for each line. Visual assessments were taken 7 and 14 days after treatment as previously described. Data demonstrated robust tolerance up to 4480 g ae/ha glyphosate for all events tested. Table 22.

TABLE 22

Response of homozygous dgt-28 events applied with a range of glyphosate from 1120-4480 g ae/ha + 2.0% w/v ammonium sulfate.

| Application Rate | % Injury <20% | % Injury 20-40% | % Injury >40% | Ave | Std. Dev. | Range (%) |
|---|---|---|---|---|---|---|
| TraP4::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 3.8 | 2.5 | 0-5 |
| 4480 g ae/ha | 4 | 0 | 0 | 14.3 | 1.5 | 12-15 |
| TraP8::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 9.0 | 1.2 | 8-10 |
| 4480 g ae/ha | 4 | 0 | 0 | 11.3 | 2.5 | 10-15 |
| TraP23::dgt-28 | | | | | | |
| 0 g ae/ha glyphosate | 4 | 0 | 0 | 0.0 | 0.0 | 0 |
| 1120 g ae/ha | 4 | 0 | 0 | 4.5 | 3.3 | 0-8 |
| 2240 g ae/ha | 4 | 0 | 0 | 7.5 | 2.9 | 5-10 |
| 4480 g ae/ha | 4 | 0 | 0 | 15.0 | 0.0 | 15 |
| TraP5::dgt-28 | | | | | | |
| 0 g ae/ha glyphosate | 4 | 0 | 0 | 0.0 | 0.0 | 0 |
| 1120 g ae/ha | 4 | 0 | 0 | 1.3 | 2.5 | 0-5 |
| 2240 g ae/ha | 4 | 0 | 0 | 9.0 | 2.0 | 8-12 |
| 4480 g ae/ha | 4 | 0 | 0 | 15.0 | 2.4 | 12-18 |
| Non-transformed B104 | | | | | | |
| 0 g ae/ha glyphosate | 4 | 0 | 0 | 0.0 | 0.0 | 0 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

The line from pDAB 107665 that was not tolerant under field conditions demonstrated no tolerance to glyphosate and therefore consistent with field observations (data not shown). With the exception of the one line previously mentioned, all replicates that were treated with glyphosate from the lines were not sensitive to glyphosate. Therefore data demonstrates heritability to a homogeneous population of dgt-28 corn in a Mendelian fashion. Expression of the DGT-28 protein by standard ELISA demonstrated a range of mean protein expression from 27.5-65.8 ng/cm² across single copy events that were tolerant to glyphosate. Data demonstrates functional protein and stability of the DGT-28 protein across generations.

Example 12

Postemergence Herbicide Tolerance Use of Glyphosate as a Selectable Marker

As previously described, T0 transformed plants were moved from tissue culture and acclimated in the greenhouse. The events tested contained dgt-28 linked to TraP5, TraP8, and TraP23 chloroplast transit peptides. It was demonstrated that these $T_0$ plants provided robust tolerance up to 4480 g ae/ha glyphosate, and non-transformed plants were controlled with glyphosate at concentrations as low as 280 g ae/ha. These data demonstrate that dgt-28 can be utilized as a selectable marker using a concentration of glyphosate ranging from 280-4480 g ae/ha.

A number of seed from fixed lines of corn which contain the dgt-28 transgene are spiked into a number of non-transformed corn seed. The seed are planted and allowed to grow to the V1-V3 developmental stage, at which time the plantlets are sprayed with a selecting dose of glyphosate in the range of 280-4480 g ae/ha. Following 7-10 days, sensitive and resistant plants are counted, and the amount of glyphosate tolerant plants correlates with the original number of transgenic seed containing the dgt-28 transgene which are planted.

Example 13

Stacking of Dgt-28 Corn

The AAD-1 protein is used as the selectable marker in dgt-28 transformed corn for research purposes. The aad-1 gene can also be utilized as a herbicide tolerant trait in corn to provide robust 2,4-D tolerance up to a V8 application in a crop. Four events from the constructs pDAB 107663 (TraP4::dgt-28), pDAB 107664 (TraP8::dgt-28) and pDAB 107666 (TraP5::dgt-28) were characterized for the tolerance of a tank mix application of glyphosate and 2,4-D. The characterization study was completed with $F_1$ seed under greenhouse conditions. Applications were made in a track sprayer as previously described at the following rates: 1120-2240 g ae/ha glyphosate (selective for the dgt-28 gene), 1120-2240 g ae/ha 2,4-D (selective for the aad-1 gene), or a tank mixture of the two herbicides at the rates described. Plants were graded at 7 and 14 DAT. Spray results for applications of the herbicides at 2240 g ae/ha are shown in Table 23.

TABLE 23

Response of F₁ aad-1 and dgt-28 corn sprayed with 2240 g ae/ha of
2,4-D, glyphosate and a tank mix combination of the two herbicides 14 days after treatment.

| F₁ Event | 2240 g ae/ha 2,4-D | | 2240 g ae/ha glyphosate | | 2240 g ae/ha 2,4-D + 2240 g ae/ha glyphosate | |
|---|---|---|---|---|---|---|
| | Mean % injury | Std. Dev. | Mean % injury | Std. Dev. | Mean % injury | Std. Dev. |
| 107663[3]-012.AJ001 | 5.0 | 4.1 | 3.8 | 4.8 | 8.8 | 3.0 |
| 107663[3]-029.AJ001 | 2.5 | 5.0 | 1.3 | 2.5 | 5.0 | 5.8 |
| 107663[3]-027.AJ001 | 2.5 | 2.9 | 11.8 | 2.9 | 13.8 | 2.5 |
| 107663[3]-011.AJ001 | 3.8 | 2.5 | 11.5 | 1.0 | 12.8 | 1.5 |
| B104 | 27.5 | 17.7 | 100.0 | 0.0 | 100.0 | 0.0 |

The results confirm that dgt-28 can be successfully stacked with aad-1, thus increasing the spectrum herbicides that may be applied to the crop of interest (glyphosate+ phenoxyactetic acids for dgt-28 and aad-1, respectively). In crop production where hard to control broadleaf weeds or resistant weed biotypes exist the stack can be used as a means of weed control and protection of the crop of interest. Additional input or output traits can also be stacked with the dgt-28 gene in corn and other plants.

Example 14

Transformation of Other Crops

Additional crops are transformed using known techniques. For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5):587-96.). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," Plant Physiol. 1997 November; 115(3):971-980. For *Agrobacterium*-mediated transformation of rice, see, e.g., Hiei et al., "Transformation of rice mediated by *Agrobacterium tumefaciens*," Plant Mol. Biol. 1997 September; 35(1-2):205-18. Each of the foregoing references are incorporated herein by this reference in its entirety.

Other (non *Agrobacterium*)transformation techniques are used to transform dgt-28, dgt-32, or dgt-33, for example, into Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa*, *Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense*, and *frutescens*), Lettuce (*Lactuca sativa, perennis*, and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna*, and *Tetragonolobus* spp.), Sunflower (*Helianthus annuus*), Squash (*Cucurbita* spp.), Cucumber (*Cucumis sativa*). Tobacco (*Nicotiana* spp.), Arabidopsis (*Arabidopsis thaliana*), Turfgrass (*Lolium, Agrostis, Poa, Cynodon*, and other genera), Clover (*Trifolium*), Vetch (*Vicia*).

Glyphosate resistance conferred by dgt-28, dgt-32, and dgt-33 increases the applicability of glyphosate herbicides for in-season use in many deciduous and evergreen timber cropping systems. Glyphosate herbicide resistant timber species increase the flexibility of over-the-top use of these herbicides without injury concerns. Thus, dgt-28, dgt-32, and/or dgt-33 are transformed into the timber species: alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp.), and pine (*Pinus* spp.).

Glyphosate herbicide resistance increases the applicability of glyphosate herbicides for the selective weed control in ornamental and fruit-bearing species. Thus, dgt-28, dgt-32, and/or dgt-33 are transformed into the ornamental and fruit-bearing species: rose (*Rosa* spp.), burning bush (*Euonymus* spp.), petunia (*Petunia* spp.), begonia (*Begonia* spp.), rhododendron (*Rhododendron* spp.), crabapple or apple (*Malus* spp.), pear (*Pyrus* spp.), peach (*Prunus* spp.), and marigolds (*Tagetes* spp.).

Example 15

Stacking with Other Traits

Transgenic crops containing insect resistance (IR) traits are prevalent in corn, soybean, and cotton plants throughout North America, and usage of these traits is expanding worldwide. Commercial transgenic crops combining insect resistant and herbicide tolerant (HT) traits have been developed by multiple seed companies. These include *Bacillus thuringiensis* traits (e.g., Bt toxins listed at the website lifesci.sussex.ac.uk, 2006), non-Bt insect resistance traits, and any or all of the HT traits mentioned above. The ability to control multiple pest problems through IR traits is a valuable commercial product concept. However, the convenience of this product concept will be restricted if weed control and insect control are independent of one another.

Dgt-28, dgt-31, dgt-32, or dgt-33, alone or stacked with one or more additional HT traits, are stacked with one or more additional input traits (e.g., insect resistance, fungal resistance, or stress tolerance, et al.) (see www.isb.vt.edu), either through conventional breeding or jointly as a novel transformation event. IR trait(s) is/are stacked with dgt-28, dgt-31, dgt-32, or dgt-33. Upon obtaining a coding sequence of an IR trait, expression elements (e.g., promoter, intron, 3'UTR, etc.) are added and the IR trait is molecularly stacked with dgt-28, dgt-31, dgt-32, or dgt-33 via recombinant DNA methodologies.

The IR traits include: Cry1F (U.S. Pat. Nos. 5,126,133; 5,188,960; 5,691,308; 6,096,708; 6,573,240; and 6,737, 273), Cry1A(c) (U.S. Pat. Nos. 6,114,138; 5,710,020; 6,251, 656; and 6,229,004), Cry1F and Cry1A(c) as a triple stack with either dgt-28, dgt-31, dgt-32, or dgt-33, Cry34Ab(1) (U.S. Pat. Nos. 7,323,556; 7,897,342; 7,888,495; 7,875,430; 7,932,033; 7,956,246; 6,340,593), Cry35 Ab(1) (U.S. Pat. Nos. 6,340,593; 7,323,556; 7,897,342; 7,888,495; 7,875, 430; 7,932,033; 7,956,246), and/or Cry35Ab(1) and Cry 34Ab(1) as a triple stack with dgt-28, dgt-31, dgt-32, and/or dgt-33.

Benefits include the improved weed control offered by dgt-28, dgt-31, dgt-32, or dgt-33, and described in previous examples, linked with the ability to manage insect pests and/or other agronomic stresses. Plants comprising such traits stacked with dgt-28, dgt-31, dgt-32, and/or dgt-33 provide a complete agronomic package of improved crop quality with the ability to flexibly and cost effectively control any number of agronomic issues. Combined IR and HT traits have application in most agronomic and horticultural/ornamental crops and forestry.

The combination of dgt-28, dgt-31, dgt-32, or dgt-33, and the commensurate herbicide tolerance and insect resistance afforded by any of the number of Bt or non-Bt IR genes can be applied to the crop species listed herein. Use of any of various commercial herbicides listed herein in such crops is made possible by dgt-28, dgt-31, dgt-32, or dgt-33 transformation and stacking with the corresponding HT trait or IR trait, either by conventional breeding or genetic engineering. Specific application rates of herbicides representative of these chemistries are determined by the herbicide labels compiled in the CPR (Crop Protection Reference) book or similar compilation, labels compiled online (e.g., cdms.net/ manuf/manufasp), or any commercial or academic crop protection guides such as the Crop Protection Guide from Agriliance (2005).

Example 16

DGT Trait Stacked with an AAD Trait in any Crop

By stacking a dgt trait with an aad trait (e.g., aad-1 described in U.S. Pat. No. 7,838,733; or aad-12 described in PCT International Patent Publication No. WO 2007/053482 A2), either through conventional breeding or jointly as a novel transformation event, weed control efficacy, flexibility, and the ability to manage weed shifts and herbicide resistance development are improved.

Transforming crops with aad-1 allows a grower to selectively apply aryloxyalkanoate herbicides in monocot crops. Such monocot crops will have a higher margin of phenoxy auxin safety. In addition, phenoxy auxins can be selectively applied in dicot crops transformed with aad-1. Transforming crops with aad-12 allows a grower to selectively apply pyridyloxy auxin and aryloxyalkanoate herbicides in dicot crops to control weed species. By stacking dgt-28, dgt-31, dgt-32, or dgt-33 with the aad-1 or aad-12 traits, growers are provided a broader spectrum of herbicides for the management of weeds. Moreover, the use of herbicide combinations results in more flexibility for managing herbicide resistance within weed species.

The following weed control options are provided for a plant wherein a dgt trait and an aad trait are stacked in any monocot or dicot crop species:

A. Glyphosate is applied at a standard postemergent application rate (420 to 2160 g ae/ha, for example, 560 to 1120 g ae/ha) for the control of most grass and broadleaf weed species. The dgt traits can provide tolerance at these application rates of glyphosate. For the control of glyphosate resistant broadleaf weeds like *Conyza canadensis* or weeds inherently difficult to control with glyphosate (e.g., *Commelina* spp), 280-2240 g ae/ha (for example, 560-1120 g ae/ha) of 2,4-D is applied sequentially, tank mixed, or as a premix with glyphosate to provide additional control. Both aad-1 and aad-12 provide tolerance to 2,4-D. In addition, aad-12 provides tolerance to pyridyloxy auxin herbicides such as triclopyr and fluroxypyr. The pyridyloxy auxin herbicides are applied to control glyphosate resistant broadleaf weeds like *Conyza canadensis* and *Commelina* spp. For triclopyr, application rates typically range from 70-1120 g ae/ha, for example, 140-420 g ae/ha. For fluroxypyr, application rates typically range from 35-560 g ae/ha, for example, 70-280 ae/ha.

B. Glyphosate is applied at a standard postemergent application rate (420 to 2160 g ae/ha, for example, 560 to 1120 g ae/ha) for the control of most grass and broadleaf weed species. For the control of glyphosate resistant grass species like *Lolium rigidum* or *Eleusine indica*, 10-200 g ae/ha (for example, 20-100 g ae/ha) quizalofop is applied sequentially, tank mixed, or as a premix with glyphosate to provide effective control. Aad-1 provides tolerance to quizalofop. Stacking aad-1 in combination with dgt-28, dgt-31, dgt-32, or dgt-33 in crop species results in crops that are tolerant to the herbicides described above.

C. Glyphosate is efficacious in controlling grass species other than broadleaf weed species. Aad-1 and dgt-28, dgt-31, dgt-32, or dgt-33 stacked traits allow for the application of grass-effective rates of glyphosate (105-840 g ae/ha, for example, 210-420 g ae/ha). 2,4-D (at 280-2240 g ae/ha, for example, 560-1120 g ae/ha) is then applied sequentially, tank mixed, or as a premix with grass-effective rates of glyphosate to provide necessary broadleaf weed control. An AOPP herbicide like quizalofop at 10-200 g ae/ha (for example, 20-100 g ae/ha and 20-35 g ae/ha), is used for more robust grass weed control and/or for delaying the development of glyphosate resistant grasses. The low rate of glyphosate also provides some benefit to the broadleaf weed control; however, primary control is from the 2,4-D.

D. Likewise, aad-12 and dgt-28, dgt-31, dgt-32, or dgt-33 stacked traits allow for the application of grass-effective rates of glyphosate (105-840 g ae/ha, for example, 210-420 g ae/ha). 2,4-D (at 280-2240 g ae/ha, for example, 560-1120 g ae/ha) is then applied sequentially, tank mixed, or as a premix with grass-effective rates of glyphosate to provide necessary broadleaf weed control. Triclopyr and fluroxypyr used at rates mentioned above also are acceptable components in the treatment regimen. The low rate of glyphosate also provides some benefit to the broadleaf weed control; however, primary control is from the 2,4-D, triclopyr, or fluroxypyr.

Use of one or more commercial aryloxy auxin herbicides alone or in combination (sequentially or independently) is facilitated by aad-12 transformation into crops. Likewise the use of one or more commercial phenoxy auxin herbicides alone or in combination (sequentially or independently) with one or more commercial AOPP herbicides is facilitated by aad-1. Stacking either of these traits with dgt-28, dgt-31, dgt-32, or dgt-33 allows for more robust management of weed species. The specific rates of other herbicides representative of these chemistries are determined by the herbicide labels compiled in the CPR (Crop Protection Reference) book or similar compilation, labels compiled online (e.g., cdms.net/manuf/manufasp), or any commercial or academic crop protection guides such as the Crop Protection Guide from Agriliance (2005).

Example 17

DGT Trait Stacked with AHAS Trait in any Crop

Traits encoding imidazolinone herbicide tolerance (AHAS) are currently present in a number of crops planted in North America including, but not limited to, corn, rice, sunflower, and wheat. Additional imidazolinone tolerant crops (e.g., cotton and sugar beet) have been under development. Many imidazolinone herbicides (e.g., imazamox, imazethapyr, imazaquin, and imazapic) are currently used selectively in various conventional crops. The use of imazethapyr, imazamox, and the non-selective imazapyr has been facilitated through imidazolinone tolerance traits like AHAS. Imidazolinone tolerant HTCs to date have the advantage of being non-transgenic. This chemistry class also has significant soil residual activity, thus being able to provide weed control that extends beyond the application timing, unlike glyphosate or glufosinate-based systems. However, the spectrum of weeds controlled by imidazolinone herbicides is not as broad as glyphosate (Agriliance, 2003). Additionally, imidazolinone herbicides have a mode of action (inhibition of acetolactate synthase, ALS) to which many weeds have developed resistance (Heap I (2004). The international survey of herbicide resistant weeds, available at www.weedscience.com).

Dgt-28, dgt-31, dgt-32, or dgt-33 is stacked with an imidazolinone tolerance trait, either through conventional breeding or jointly as a novel transformation event, and weed control efficacy, flexibility, and ability to manage weed shifts and herbicide resistance development are improved.

The following weed control options are provided for a plant wherein a dgt trait and an imidazolinone tolerance trait are stacked in any monocot or dicot crop species:
A. Imazethapyr is applied at a standard postemergent application rate (35 to 280 g ae/ha, for example, 70-140 g ae/ha) for the control of many grass and broadleaf weed species.
  i) ALS-inhibitor resistant broadleaf weeds like *Amaranthus rudis, Ambrosia trifida, Chenopodium album* (among others, Heap, 2004) are controlled by tank mixing glyphosate at 420 to 2160 g ae/ha, for example, 560 to 1120 g ae/ha.
  ii) Inherently more tolerant broadleaf species to imidazolinone herbicides like *Ipomoea* spp. are controlled by tank mixing glyphosate at 420 to 2160 g ae/ha, for example, 560 to 1120 g ae/ha.
  iii) ALS-inhibitor resistant grass weeds like *Sorghum halepense* and *Lolium* spp. are controlled by tank mixing glyphosate at 420 to 2160 g ae/ha, for example, 560 to 1120 g ae/ha.
  iv) Inherently tolerant grass weed species (e.g., *Agropyron repens*) are controlled by tank mixing glyphosate at 420 to 2160 g ae/ha, for example, 560 to 1120 g ae/ha.

Use of any of various commercial imidazolinone herbicides, alone or in multiple combinations, is facilitated by dgt-28 transformation with dgt-28, dgt-31, dgt-32, or dgt-33, and stacking with any imidazolinone tolerance trait, either by conventional breeding or genetic engineering. Specific rates of other herbicides representative of these chemistries are determined by the herbicide labels compiled in the CPR (Crop Protection Reference) book or similar compilation, labels compiled online (e.g., cdms.net/manuf/manufasp), or any commercial or academic crop protection guides such as the Crop Protection Guide from Agriliance (2005).

Example 18

Soybean Transformation

Transgenic soybean (*Glycine max*) containing a stably integrated dgt-28 transgene was generated through *Agrobacterium*-mediated transformation of soybean cotyledonary node explants. A disarmed *Agrobacterium* strain carrying a binary vector containing a functional dgt-28 was used to initiate transformation.

*Agrobacterium*-mediated transformation was carried out using a modified half-cotyledonary node procedure of Zeng et al. (Zeng P., Vadnais D. A., Zhang Z., Polacco J. C., (2004), Plant Cell Rep., 22(7): 478-482). Briefly, soybean seeds (cv. Maverick) were germinated on basal media and cotyledonary nodes are isolated and infected with *Agrobacterium*. Shoot initiation, shoot elongation, and rooting media are supplemented with cefotaxime, timentin and vancomycin for removal of *Agrobacterium*. Selection via a herbicide was employed to inhibit the growth of non-transformed shoots. Selected shoots were transferred to rooting medium for root development and then transferred to soil mix for acclimatization of plantlets.

Terminal leaflets of selected plantlets were treated topically (leaf paint technique) with a herbicide to screen for putative transformants. The screened plantlets were transferred to the greenhouse, allowed to acclimate and then leaf-painted with a herbicide to reconfirm tolerance. These putative transformed $T_0$ plants were sampled and molecular analyses were used to confirm the presence of the herbicidal selectable marker, and the dgt-28 transgene. $T_0$ plants were allowed to self fertilize in the greenhouse to produce $T_1$ seed.

A second soybean transformation method can be used to produce additional transgenic soybean plants. A disarmed *Agrobacterium* strain carrying a binary vector containing a functional dgt-28 is used to initiate transformation.

*Agrobacterium*-mediated transformation was carried out using a modified half-seed procedure of Paz et al., (Paz M., Martinez J., Kalvig A., Fonger T., and Wang K., (2005) *Plant Cell Rep.*, 25: 206-213). Briefly, mature soybean seeds were sterilized overnight with chlorine gas and imbibed with sterile $H_2O$ twenty hours before *Agrobacterium*-mediated plant transformation. Seeds were cut in half by a longitudinal cut along the hilum to separate the seed and remove the seed coat. The embryonic axis was excised and any axial shoots/buds were removed from the cotyledonary node. The resulting half seed explants were infected with *Agrobacterium*. Shoot initiation, shoot elongation, and rooting media were supplemented with cefotaxime, timentin and vancomycin for removal of *Agrobacterium*. Herbicidal selection was employed to inhibit the growth of non-transformed shoots. Selected shoots were transferred to rooting medium for root development and then transferred to soil mix for acclimatization of plantlets.

Putative transformed $T_0$ plants were sampled and molecular analyses was used to confirm the presence of the selectable marker and the dgt-28 transgene. Several events were identified as containing the transgenes. These $T_0$ plants were advanced for further analysis and allowed to self fertilize in the greenhouse to give rise to $T_1$ seed.

Confirmation of Heritability of Dgt-28 to the $T_1$ Generation.

Heritability of the DGT-28 protein into $T_1$ generation was assessed in one of two ways. The first method included planting $T_1$ seed into Metro-mix media and applying 411 g ae/ha IGNITE™ 280 SL on germinated plants at the $1^{st}$ trifoliate growth stage. The second method consisted of homogenizing seed for a total of 8 replicates using a ball bearing and a genogrinder. ELISA strip tests to detect for the PAT protein were then used to detect heritable events as the selectable marker was on the same plasmid as dgt-28. For either method if a single plant was tolerant to glufosinate or was detected with the PAT ELISA strip test, the event demonstrated heritability to the $T_1$ generation.

A total of five constructs were screened for heritability as previously described. The plasmids contained dgt-28 linked with TraP4, TraP8 and TraP23. The events across constructs demonstrated 68% heritability of the PAT::DGT-28 protein to the $T_1$ generation.

Postemergence Herbicide Tolerance in Dgt-28 Transformed $T_1$ Soybean.

Seeds from $T_1$ events that were determined to be heritable by the previously described screening methods were planted in Metro-mix media under greenhouse conditions. Plants were grown until the $1^{st}$ trifoliate was fully expanded and treated with 411 g ae/ha IGNITE™ 280 SL for selection of the pat gene as previously described. Resistant plants from each event were given unique identifiers and sampled for zygosity analyses of the dgt-28 gene. Zygosity data were used to assign 2 hemizygous and 2 homozygous replicates to each rate of glyphosate applied allowing for a total of 4 replicates per treatment when enough plants existed. These plants were compared against wildtype Petite havana tobacco. All plants were sprayed with a track sprayer set at 187 L/ha. The plants were sprayed from a range of 560-4480 g ae/ha DURANGO™ dimethylamine salt (DMA). All applications were formulated in water with the addition of 2% w/v ammonium sulfate (AMS). Plants were evaluated at 7 and 14 days after treatment. Plants were assigned an injury rating with respect to overall visual stunting, chlorosis, and necrosis. The $T_1$ generation is segregating, so some variable response is expected due to difference in zygosity.

TABLE 24

Spray results demonstrate at 14 DAT (days after treatment) robust tolerance up to 4480 g ae/ha glyphosate of at least one dgt-28 event per construct characterized. Representative single copy events of the constructs all provided tolerance up to 4480 g ae/ha compared to the Maverick negative control.

| Application Rate | % Injury <20% | % Injury 20-40% | % Injury >40% | Ave | Std. Dev. | Range (%) |
|---|---|---|---|---|---|---|
| pDAB107543 (TraP4::dgt-28) | | | | | | |
| 0 g ae/ha glyphosate | 4 | 0 | 0 | 0.0 | 0.0 | 0 |
| 560 g ae/ha | 0 | 4 | 0 | 33.8 | 7.5 | 25-40 |
| 1120 g ae/ha | 2 | 2 | 0 | 25.0 | 11.5 | 15-35 |
| 2240 g ae/ha | 2 | 2 | 0 | 17.5 | 2.9 | 15-20 |
| 4480 g ae/ha | 0 | 2 | 2 | 33.8 | 13.1 | 20-45 |
| pDAB107545 (TraP8::dgt-28) | | | | | | |
| 0 g ae/ha glyphosate | 4 | 0 | 0 | 0.0 | 0.0 | 0 |
| 560 g ae/ha | 4 | 0 | 0 | 1.5 | 1.0 | 0-2 |
| 1120 g ae/ha | 4 | 0 | 0 | 2.8 | 1.5 | 2-5 |
| 2240 g ae/ha | 4 | 0 | 0 | 5.0 | 2.4 | 2-8 |
| 4480 g ae/ha | 4 | 0 | 0 | 9.5 | 1.9 | 8-12 |
| pDAB107548 (TraP4::dgt-28) | | | | | | |
| 0 g ae/ha glyphosate | 4 | 0 | 0 | 0.0 | 0.0 | 0 |
| 560 g ae/ha | 4 | 0 | 0 | 1.8 | 2.4 | 0-5 |
| 1120 g ae/ha | 4 | 0 | 0 | 2.8 | 1.5 | 2-5 |
| 2240 g ae/ha | 4 | 0 | 0 | 3.5 | 1.7 | 2-5 |
| 4480 g ae/ha | 4 | 0 | 0 | 8.8 | 3.0 | 5-12 |
| pDAB107553 (TraP23::dgt-28) | | | | | | |
| 0 g ae/ha glyphosate | 4 | 0 | 0 | 0.0 | 0.0 | 0 |
| 560 g ae/ha | 4 | 0 | 0 | 5.0 | 0.0 | 5 |
| 1120 g ae/ha | 4 | 0 | 0 | 9.0 | 1.2 | 8-10 |
| 2240 g ae/ha | 4 | 0 | 0 | 10.5 | 1.0 | 10-12 |
| 4480 g ae/ha | 4 | 0 | 0 | 16.5 | 1.7 | 15-18 |
| Maverick (neg. control) | | | | | | |
| 0 g ae/ha glyphosate | 4 | 0 | 0 | 0.0 | 0.0 | 0 |
| 560 g ae/ha | 0 | 0 | 4 | 82.5 | 12.6 | 70-100 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

Dgt-28 Protection Against Elevated Glyphosate Rates in the $T_2$ Generation.

A 45 plant progeny test was conducted on two to five $T_2$ lines of dgt-28 per construct. Homozygous lines were chosen based on zygosity analyses completed in the previous generation. The seeds were planted as previously described. Plants were then sprayed with 411 g ae/ha IGNITE 280 SL for the selection of the pat selectable marker as previously described. After 3 DAT, resistant and sensitive plants were counted.

For constructs containing TraP4 linked with dgt-28 (pDAB107543 and pDAB 107548), nine out of twelve lines tested did not segregate, thereby confirming homogeneous lines in the $T_2$ generation. Lines containing TraP8 linked with dgt-28 (pDAB 107545) demonstrated two out of the four lines with no segregants and demonstrating Mendelian inheritance through at least two generation of dgt-28 in soybean. Tissue samples were taken from resistant plants and the DGT-28 protein was quantified by standard ELISA methods. Data demonstrated a range of mean DGT-28 protein from 32.8-107.5 ng/cm$^2$ for non-segregating $T_2$ lines tested. Lines from the construct pDAB 107553 (TraP23::dgt-28) were not previously selected with glufosinate, and the dose response of glyphosate was utilized as both to test homogenosity and tolerance to elevated rates of glyphosate. Replicates from the lines from construct pDAB107553 were tolerant to rates ranging from 560-4480 g ae/ha glyphosate, and were therefore confirmed to be a homogeneous population and heritable to at least two generations.

Rates of DURANGO DMA ranging from 560-4480 g ae/ha glyphosate were applied to 2-3 trifoliate soybean as previously described. Visual injury data 14 DAT confirmed the tolerance results that were demonstrated in the $T_1$ generation.

TABLE 25

The data demonstrate robust tolerance of the dgt-28 tobacco up to 3360 g ae/ha glyphosate through two generations, compared to the non-transformed control.

|  | % Injury | | | % Injury | | |
|---|---|---|---|---|---|---|
| Application Rate | <20% | 20-40% | >40% | Ave | Std. Dev. | Range (%) |
| pDAB107543 (TraP4::dgt-28) | | | | | | |
| 0 g ae/ha glyphosate | 4 | 0 | 0 | 0.0 | 0.0 | 0 |
| 560 g ae/ha | 4 | 0 | 0 | 8.0 | 0.0 | 8 |
| 1120 g ae/ha | 4 | 0 | 0 | 14.3 | 1.5 | 12-15 |
| 2240 g ae/ha | 4 | 0 | 0 | 18.0 | 0.0 | 18 |
| 4480 g ae/ha | 0 | 4 | 0 | 24.5 | 3.3 | 20-28 |
| pDAB107545 (TraP8::dgt-28) | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 2.8 | 1.5 | 2-5 |
| 2240 g ae/ha | 4 | 0 | 0 | 5.0 | 0.0 | 5 |
| 4480 g ae/ha | 4 | 0 | 0 | 10.0 | 0.0 | 10 |
| pDAB107548 (TraP4::dgt-28) | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 10.0 | 0.0 | 10 |
| pDAB107553 (TraP23::dgt-28) | | | | | | |
| 0 g ae/ha glyphosate | 4 | 0 | 0 | — | 0.0 | 0.0 |
| 560 g ae/ha | 4 | 0 | 0 | — | 10.0 | 0.0 |
| 1120 g ae/ha | 4 | 0 | 0 | — | 10.0 | 4.4 |
| 2240 g ae/ha | 4 | 0 | 0 | — | 13.0 | 2.4 |
| 4480 g ae/ha | 3 | 1 | 0 | — | 15.5 | 4.1 |
| Maverick (neg. control) | | | | | | |
| 0 g ae/ha glyphosate | 4 | 0 | 0 | 0.0 | 0.0 | 0 |
| 560 g ae/ha | 0 | 0 | 4 | 77.5 | 15.0 | 70-100 |
| 1120 g ae/ha | 0 | 0 | 4 | 97.5 | 2.9 | 95-100 |
| 2240 g ae/ha | 0 | 0 | 4 | 100.0 | 0.0 | 100 |
| 4480 g ae/ha | 0 | 0 | 4 | 100.0 | 0.0 | 100 |

Example 19

Transformation of Rice with Dgt-28

In an exemplary method, transgenic rice (*Oryza sativa*) containing a stably integrated dgt-28 transgene is generated through *Agrobacterium*-mediated transformation of sterilized rice seed. A disarmed *Agrobacterium* strain carrying a binary vector containing a functional dgt-28 is used to initiate transformation.

Culture media are adjusted to pH 5.8 with 1 M KOH and solidified with 2.5 g/l Phytagel (Sigma-Aldrich, St. Louis, Mo.). Embryogenic calli are cultured in 100×20 mm petri dishes containing 30 ml semi-solid medium. Rice plantlets are grown on 50 ml medium in MAGENTA boxes. Cell suspensions are maintained in 125 ml conical flasks containing 35 mL liquid medium and rotated at 125 rpm. Induction and maintenance of embryogenic cultures occur in the dark at 25-26° C., and plant regeneration and whole-plant culture occur in illuminated room with a 16-h photoperiod (Zhang et al. 1996).

Induction and maintenance of embryogenic callus is performed on a modified NB basal medium as described previously (Li et al. 1993), wherein the media is adapted to contain 500 mg/L glutamine. Suspension cultures are initiated and maintained in SZ liquid medium (Zhang et al. 1998) with the inclusion of 30 g/L sucrose in place of maltose. Osmotic medium (NBO) consisting of NB medium with the addition of 0.256 M each of mannitol and sorbitol. Herbicide resistant callus is selected on NB medium supplemented with the appropriate herbicide selective agent for 3-4 weeks. Pre-regeneration is performed on medium (PRH50) consisting of NB medium with 2,4-dichlorophenoxyacetic acid (2,4-D), 1 mg/l α-naphthaleneacetic acid (NAA), 5 mg/l abscisic acid (ABA) and selective herbicide for 1 week. Regeneration of plantlets follow the culturing on regeneration medium (RNH50) comprising NB medium containing 2,4-D, 0.5 mg/l NAA, and selective herbicide until putatively transgenic shoots are regenerated. Shoots are transferred to rooting medium with half-strength Murashige and Skoog basal salts and Gamborg's B5 vitamins, supplemented with 1% sucrose and selective herbicide.

Mature desiccated seeds of *Oryza sativa* L. *japonica* cv. Taipei 309 are sterilized as described in Zhang et al. 1996. Embryogenic tissues are induced by culturing sterile mature rice seeds on NB medium in the dark. The primary callus approximately 1 mm in diameter, is removed from the scutellum and used to initiate cell suspension in SZ liquid medium. Suspensions are then maintained as described in Zhang 1996. Suspension-derived embryogenic tissues are removed from liquid culture 3-5 days after the previous subculture and placed on NBO osmotic medium to form a circle about 2.5 cm across in a petri dish and cultured for 4 h prior to bombardment. Sixteen to twenty hours after bombardment, tissues are transferred from NBO medium onto NBH50 selection medium, ensuring that the bombarded surface is facing upward, and incubated in the dark for 14-17 days. Newly formed callus is then separated from the original bombarded explants and placed nearby on the same medium. Following an additional 8-12 days, relatively compact, opaque callus is visually identified, and transferred to PRH50 pre-regeneration medium for 7 days in the dark. Growing callus, which become more compact and opaque is then subcultured onto RNH50 regeneration medium for a period of 14-21 days under a 16-h photoperiod. Regenerating shoots are transferred to MAGENTA boxes containing ½ MSH50 medium. Multiple plants regenerated from a single explant are considered siblings and are treated as one independent plant line. A plant is scored as positive for the dgt-28 gene if it produces thick, white roots and grows vigorously on ½ MSH50 medium. Once plantlets reach the top of the MAGENTA boxes, they are transferred to soil in a 6-cm pot under 100% humidity for a week, and then are moved to a growth chamber with a 14-h light period at 30° C. and in the dark at 21° C. for 2-3 weeks before transplanting into 13-cm pots in the greenhouse. Seeds are collected and dried at 37° C. for one week prior to storage at 4° C.

$T_0$ Analysis of Dgt-28 Rice.

Transplanted rice transformants obtained via *Agrobacterium* transformation were transplanted into media and acclimated to greenhouse conditions. All plants were sampled for PCR detection of dgt-28 and results demonstrate twenty-two PCR positive events for pDAB 110827 (TraP8::dgt-28) and a minimum of sixteen PCR positive events for pDAB 110828 (TraP23::dgt-28). Southern analysis for dgt-28 of the PCR positive events demonstrated simple (1-2 copy) events for both constructs. Protein expression of selected To events demonstrated DGT-28 protein expression ranges from below levels of detection to 130 ng/cm$^2$. Selected To events from construct pDAB 110828 were treated with 2240 g ae/ha DURANGO DMA™ as previously described and assessed 7 and 14 days after treatment. Data demonstrated robust tolerance to the rate of glyphosate applied. All PCR positive plants were allowed to produced T$_1$ seed for further characterization.

Dgt-28 Heritability in Rice.

A 100 plant progeny test was conducted on four T$_1$ lines of dgt-28 from construct pDAB 110827 containing the chloroplast transit peptide TraP8. The seeds were planted into pots filled with media. All plants were then sprayed with 560 g ae/ha DURANGO DMA™ for the selection of the dgt-28 gene as previously described. After 7 DAT, resistant and sensitive plants were counted. Two out of the four lines tested for each construct segregated as a single locus, dominant Mendelian trait (3R:1 S) as determined by Chi square analysis. Dgt-28 is a heritable glyphosate resistance gene in multiple species.

Postemergence Herbicide Tolerance in Dgt-28 Transformed T$_1$ Rice.

T$_1$ resistant plants from each event used in the progeny testing were given unique identifiers and sampled for zygosity analyses of the dgt-28 gene. Zygosity data were used to assign 2 hemizygous and 2 homozygous replicates to each rate of glyphosate applied allowing for a total of 4 replicates per treatment. These plants were compared against wildtype kitaake rice. All plants were sprayed with a track sprayer set at 187 L/ha. The plants were sprayed from a range of 560-2240 g ae/ha DURANGO DMA™. All applications were formulated in water with the addition of 2% w/v ammonium sulfate (AMS). Plants were evaluated at 7 and 14 days after treatment. Plants were assigned an injury rating with respect to overall visual stunting, chlorosis, and necrosis. The T$_1$ generation is segregating, so some variable response is expected due to difference in zygosity.

Spray results demonstrate at 7 DAT (days after treatment) minimal vegetative injury to elevated rates of glyphosate were detected (data not shown).

TABLE 26

Visual injury data at 14 DAT demonstrates less than 15% mean visual injury up to 2240 g ae/ha glyphosate.

| | % Injury | | | % Injury | | |
|---|---|---|---|---|---|---|
| Application Rate | <20% | 20-40% | >40% | Ave | Std. Dev. | Range (%) |
| TraP8::dgt-28 Event 1 | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| TraP8::dgt-28 Event 2 | | | | | | |
| 0 g ae/ha glyphosate | 4 | 0 | 0 | 0.0 | 0.0 | 0 |
| 560 g ae/ha | 4 | 0 | 0 | 3.8 | 4.8 | 0-10 |
| 1120 g ae/ha | 4 | 0 | 0 | 12.0 | 3.6 | 8-15 |
| 2240 g ae/ha | 4 | 0 | 0 | 15.0 | 6.0 | 8-20 |
| Non-transformed control | | | | | | |
| 0 g ae/ha glyphosate | 4 | 0 | 0 | 0.0 | 0.0 | 0 |
| 560 g ae/ha | 0 | 0 | 4 | 81.3 | 2.5 | 80-85 |
| 1120 g ae/ha | 0 | 0 | 4 | 95.0 | 5.8 | 90-100 |
| 2240 g ae/ha | 0 | 0 | 4 | 96.3 | 4.8 | 90-100 |

Protein detection of DGT-28 was assessed for replicates from all four T$_1$ lines tested from pDAB 110827. Data demonstrated DGT-28 mean protein ranges from 20-82 ng/cm$^2$ and 21-209 ng/cm$^2$ for hemizgyous and homozygous replicates respectively. These results demonstrated stable protein expression to the T$_1$ generation and tolerance of dgt-28 rice up to 2240 g ae/ha glyphosate following an application of 560 g ae/ha glyphosate used for selection.

Example 20

Transformation of Turf Grass with Dgt-28

*Agrobacterium tumefaciens*-mediated genetic transformation of the dgt-28 transgene in creeping bentgrass is achieved through embryogenic callus initiated from seeds (cv. Penn-A-4). See "Efficiency of *Agrobacterium tumefaciens*-mediated turfgrass (*Agrostis stolonifera* L) transformation" (Luo et. al., 2004).

Callus cells are infected with an *A. tumefaciens* strain harboring a super-binary vector that contains an herbicide-resistant transgene (e.g., dgt-28, dgt-31, dgt-32, or dgt-33) driven by a monocot specific promoter. The overall stable transformation efficiency ranges from 18% to 45%. Southern blot and genetic analysis confirm transgene integration within the creeping bentgrass genome and normal transmission and stable expression of the transgene in the T$_1$ generation. All independent transformation events carry one to three copies of the transgene, and a majority (60-65%) contain only a single copy of the transgene with no apparent rearrangements.

Mature seeds are dehusked with sand paper and surface sterilized in 10% (v/v) Clorox™ bleach (6% sodium hypochlorite) plus 0.2% (v/v) Tween 20 (Polysorbate 20) with vigorous shaking for 90 min. Following rinsing five times in sterile distilled water, the seeds are placed onto callus-induction medium (MS basal salts and vitamins, 30 g/l sucrose, 500 mg/l casein hydrolysate, 6.6 mg/l 3,6-dichloro-o-anisic acid (dicamba), 0.5 mg/l 6-benzylaminopurine (BAP) and 2 g/l Phytagel. The pH of the medium is adjusted to 5.7 before autoclaving at 120° C. for 20 min).

The culture plates containing prepared seed explants are kept in the dark at room temperature for 6 weeks. Embryogenic calli are visually selected and subcultured on fresh callus-induction medium in the dark at room temperature for 1 week before co-cultivation.

One day before *Agrobacterium* mediated-infection, the embryogenic callus is divided into 1- to 2-mm pieces and placed on callus-induction medium containing 100 acetosyringone. A 10-μl aliquot of *Agrobacterium* suspension (OD=1.0 at 660 nm) which harbors the dgt-28, dgt-31, dgt-32, or dgt-33 transgene is then applied to each piece of callus, followed by 3 days of co-cultivation in the dark at 25° C. The callus is then transferred and cultured for 2 weeks on callus-induction medium plus 125 mg/l cefotaxime and 250 mg/l carbenicillin to suppress bacterial growth.

Selection of transgenic plants occurs when the callus is moved to callus-induction medium containing 250 mg/l cefotaxime and a herbicide. The callus material is maintained on this medium for 8 weeks with a selection subculture interval of 3 weeks. The selection process is performed at room temperature in the dark.

For plant regeneration, the herbicide-resistant proliferating callus events are first moved to regeneration medium (MS basal medium, 30 g/l sucrose, 100 mg/l myo-inositol, 1 mg/l BAP and 2 g/l Phytagel) supplemented with cefotaxime, and a herbicide for selection. These calli are kept in the dark at room temperature for 1 week and then moved into the light for 2-3 weeks to develop shoots.

Developed shoots are separated and transferred to hormone-free regeneration medium containing a herbicide and cefotaxime to promote root growth while maintaining selection pressure and suppressing any remaining Agrobacterium cells. Plantlets with well-developed roots (3-5 weeks) are then transferred to soil and grown either in the greenhouse or in the field.

Transgenic plants are maintained out of doors in a containment nursery β-6 months) until the winter solstice in December. The vernalized plants are then transferred to the greenhouse and kept at 25° C. under a 16/8 h photoperiod and surrounded by non-transgenic control plants that physically isolate the transgenic plants from other pollen sources. The transgenic plants begin flowering 3-4 weeks after being moved back into the greenhouse. These plants are out-crossed with the pollen from the surrounding control plants. The seeds collected from each individual transgenic plant are germinated in soil at 25° C., and $T_1$ plants are grown in the greenhouse for further analysis.

Other grasses are transformed with dgt-28 according to the described protocol, including Annual meadowgrass (*Poa annua*), Bahiagrass, Bentgrass, Bermudagrass, Bluegrass, Bluestems, Brachiaria, Bromegrass, Browntop bent (*Agrostis capillaries*), Buffalograss, Canary Grass, Carpetgrass, Centipedegrass, Chewings fescue (*Festuca rubra commutate*), Crabgrass, Creeping bent (*Agrostis stolonifera*), Crested hairgrass (*Koeleria macrantha*), Dallisgrass, Fescue, Festolium, Hard/sheeps fescue (*Festuca ovina*), Gramagrass, Indiangrass, Johnsongrass, Lovegrass, mixes (Equine, Pasture, etc.), Native Grasses, Orchardgrass, Perennial ryegrass (*Lolium perenne*), Redtop, Rescuegrass, annual and perennial Ryegrass, Slender creeping red fescue (*Festuca rubra trichophylla*), Smooth-stalked meadowgrass (*Poa pratensis*), St. Augustine, Strong creeping red fescue (*Festuca rubra rubra*), Sudangrass, Switchgrass, Tall fescue (*Festuca arundinacea*), Tufted hairgrass (*Deschampsia caespitosa*), Turfgrasses, Wheatgrass, and Zoysiagrass.

Example 21

Transformation of Brassica Spp. with DGT Trait

A dgt-28, dgt-31, dgt-32, or dgt-33 gene conferring resistance to glyphosate is used to transform *Brassica napus* var. Nexera™ 710 with *Agrobacterium*-mediated transformation.

*Brassica napus* seeds are surface-sterilized with 10% commercial bleach for 10 minutes and rinsed 3 times with sterile distilled water. The seeds are then placed on one half concentration of MS basal medium (Murashige and Skoog, 1962) and maintained under growth regime set at 25° C., and a photoperiod of 16 hrs light/8 hrs dark.

Hypocotyl segments (3-5 mm) are excised from 5-7 day old seedlings and placed on callus induction medium K1D1 (MS medium with 1 mg/l kinetin and 1 mg/l 2,4-D) for 3 days as pre-treatment. The segments are then transferred into a petri plate and treated with an *Agrobacterium tumefaciens* strain containing a construct comprising dgt-28. The *Agrobacterium tumefaciens* is grown overnight at 28° C. in the dark on a shaker at 150 rpm and subsequently re-suspended in the culture medium.

After a 30 min treatment of the hypocotyl segments with *Agrobacterium*, these segments are placed back on the callus induction medium for 3 days. Following co-cultivation, the segments are placed in K1D1TC (callus induction medium containing 250 mg/l Carbenicillin and 300 mg/l Timentin) for one week of recovery. Alternately, the segments are placed directly on selection medium K1D1H1 (above medium with a herbicide). Carbenicillin and Timentin are the antibiotics used to kill the *Agrobacterium*. The selection agent allows for the growth of the transformed cells.

Callus samples from isolated independent events are tested by PCR. Samples that test positive for the presence of dgt-28, dgt-31, dgt-32, or dgt-33 are confirmed and advanced to media for regeneration. The callused hypocotyl segments are then placed on B3Z1H1 (MS medium, 3 mg/l benzylamino purine, 1 mg/l Zeatin, 0.5 gm/1 MES [2-(N-morpholino) ethane sulfonic acid], 5 mg/l silver nitrate, selective herbicide, Carbenicillin and Timentin) shoot regeneration medium. After 3 weeks shoots begin regeneration. Hypocotyl segments along with the shoots are transferred to B3Z1H3 medium (MS medium, 3 mg/l benzylamino purine, 1 mg/l Zeatin, 0.5 gm/1 MES [2-(N-morpholino) ethane sulfonic acid], 5 mg/l silver nitrate, selective herbicide, Carbenicillin and Timentin) for another 3 weeks.

Shoots are excised from the hypocotyl segments and transferred to shoot elongation medium MESH10 (MS, 0.5 gm/1 MES, selective herbicide, Carbenicillin, Timentin) for 2-4 weeks. The elongated shoots are cultured for root induction on MSI.1 (MS with 0.1 mg/l Indolebutyric acid). Once the plants establish a root system, the plants are transplanted into soil. The plants are acclimated under controlled environmental conditions in a Conviron™ for 1-2 weeks before transfer to the greenhouse.

The transformed $T_0$ plants are self-pollinated in the greenhouse to obtain $T_1$ seed. The $T_0$ plants and $T_1$ progeny are sprayed with a range of glyphosate herbicide concentrations to establish the level of protection by the dgt-28, dgt-31, dgt-32, or dgt-33 gene.

Example 22

Transformation of Tobacco with Dgt-28

Tobacco (cv. Petit Havana) leaf pieces were transformed using *Agrobacterium tumefaciens* containing the dgt-28 transgene. Single colonies containing the plasmid which contains the dgt-28 transgene were inoculated into 4 mL of YEP medium containing spectinomycin (50 µg/mL) and streptomycin (125 µg/mL) and incubated overnight at 28° C. on a shaker at 190 rpm. The 4 mL seed culture was subsequently used to inoculate a 25 mL culture of the same medium in a 125 mL baffled Erlenmeyer flask. This culture was incubated at 28° C. shaking at 190 rpm until it reached an $OD_{600}$ of ~1.2. Ten mL of *Agrobacterium* suspension were then placed into sterile 60×20 mm Petri™ dishes.

Freshly cut leaf pieces (0.5 cm²) from plants aseptically grown on MS medium (Phytotechnology Labs, Shawnee Mission, Kans.,) with 30 g/L sucrose in PhytaTrays™

(Sigma, St. Louis, Mo.) were soaked in 10 mL of overnight culture of *Agrobacterium* for a few minutes, blotted dry on sterile filter paper and then placed onto the same medium with the addition of 1 mg/L indoleacetic acid and 1 mg/L 6-benzylamino purine. Three days later, leaf pieces co-cultivated with *Agrobacterium* harboring the dgt-28 transgene were transferred to the same medium with 5 mg/L Basta™ and 250 mg/L cephotaxime.

After 3 weeks, individual T₀ plantlets were transferred to MS medium with 10 mg/L Basta™ and 250 mg/L cephotaxime an additional 3 weeks prior to transplanting to soil and transfer to the greenhouse. Selected $T_0$ plants (as identified using molecular analysis protocols described above) were allowed to self-pollinate and seed was collected from capsules when they were completely dried down. $T_1$ seedlings were screened for zygosity and reporter gene expression (as described below) and selected plants containing the dgt-28 transgene were identified.

Plants were moved into the greenhouse by washing the agar from the roots, transplanting into soil in 13.75 cm square pots, placing the pot into a Ziploc® bag (SC Johnson & Son, Inc.), placing tap water into the bottom of the bag, and placing in indirect light in a 30° C. greenhouse for one week. After 3-7 days, the bag was opened; the plants were fertilized and allowed to grow in the open bag until the plants were greenhouse-acclimated, at which time the bag was removed. Plants were grown under ordinary warm greenhouse conditions (27° C. day, 24° C. night, 16 hour day, minimum natural+supplemental light=1200 $\mu E/m^2 s^1$).

Prior to propagation, $T_0$ plants were sampled for DNA analysis to determine the insert dgt-28 copy number by real-time PCR. Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy™ DNA isolation procedure was then followed (Qiagen, DNeasy 69109). An aliquot of the extracted DNA was then stained with Pico Green (Molecular Probes P7589) and read in the fluorometer (BioTek™) with known standards to obtain the concentration in ng/µl. A total of 100 ng of total DNA was used as template. The PCR reaction was carried out in the 9700 Geneamp™ thermocycler (Applied Biosystems), by subjecting the samples to 94° C. for 3 minutes and 35 cycles of 94° C. for 30 seconds, 64° C. for 30 seconds, and 72° C. for 1 minute and 45 seconds followed by 72° C. for 10 minutes. PCR products were analyzed by electrophoresis on a 1% agarose gel stained with EtBr and confirmed by Southern blots.

Five to nine PCR positive events with 1-3 copies of dgt-28 gene from 3 constructs containing a different chloroplast transit peptide sequence (TraP4, TraP8 and TraP23) were regenerated and moved to the greenhouse.

All PCR positive plants were sampled for quantification of the DGT-28 protein by standard ELISA. DGT-28 protein was detected in all PCR positive plants and a trend for an increase in protein concentration was noted with increasing copy number of dgt-28.

Aad-12 (v1) Heritability in Tobacco.

A 100 plant progeny test was conducted on five $T_1$ lines of dgt-28 per construct. Constructs contained one of the following chloroplast transit peptide sequences: TraP4, TraP8 or TraP23. The seeds were stratified, sown, and transplanted with respect much like that of the *Arabidopsis* procedure exemplified above, with the exception that null plants were not removed by in initial selection prior to transplanting. All plants were then sprayed with 280 g ae/ha IGNITE 280 SL for the selection of the pat selectable marker as previously described. After 3 DAT, resistant and sensitive plants were counted.

Four out of the five lines tested for each construct segregated as a single locus, dominant Mendelian trait (3R:1 S) as determined by Chi square analysis. Dgt-28 is a heritable glyphosate resistance gene in multiple species.

Postemergence Herbicide Tolerance in Dgt-28 Transformed $T_1$ Tobacco.

$T_1$ resistant plants from each event used in the progeny testing were given unique identifiers and sampled for zygosity analyses of the dgt-28 gene. Zygosity data were used to assign 2 hemizygous and 2 homozygous replicates to each rate of glyphosate applied allowing for a total of 4 replicates per treatment. These plants were compared against wildtype Petite havana tobacco. All plants were sprayed with a track sprayer set at 187 L/ha. The plants were sprayed from a range of 560-4480 g ae/ha DURANGO DMA™. All applications were formulated in water with the addition of 2% w/v ammonium sulfate (AMS). Plants were evaluated at 7 and 14 days after treatment. Plants were assigned an injury rating with respect to overall visual stunting, chlorosis, and necrosis. The $T_1$ generation is segregating, so some variable response is expected due to difference in zygosity.

Spray results demonstrate at 7 DAT (days after treatment) minimal vegetative injury to elevated rates of glyphosate were detected (data not shown). Following 14 DAT, visual injury data demonstrates increased injury with single copy events of the construct containing TraP4 compared to single copy events from the constructs TraP8 and TraP23. Table 27.

TABLE 27

At a rate of 2240 g ae/ha glyphosate, an average injury of 37.5% was demonstrated with the event containing TraP4, where events containing TraP8 and TraP23 demonstrated an average injury of 9.3% and 9.5% respectively.

| | % Injury | | | % Injury | | Range |
|---|---|---|---|---|---|---|
| Application Rate | <20% | 20-40% | >40% | Ave | Std. Dev. | (%) |
| TraP4::dgt-28 (pDAB107543) | | | | | | |
| 0 g ae/ha glyphosate | 4 | 0 | 0 | 0.0 | 0.0 | 0 |
| 560 g ae/ha | 2 | 2 | 0 | 18.0 | 8.1 | 10-25 |
| 1120 g ae/ha | 1 | 3 | 0 | 24.5 | 4.9 | 18-30 |
| 2240 g ae/ha | 0 | 3 | 1 | 37.5 | 6.5 | 30-45 |
| 4480 g ae/ha | 0 | 2 | 2 | 42.5 | 2.9 | 40-45 |
| TraP8::dgt-28 (pDAB107545) | | | | | | |
| 0 g ae/ha glyphosate | 4 | 0 | 0 | 0.0 | 0.0 | 0 |
| 560 g ae/ha | 4 | 0 | 0 | 3.3 | 3.9 | 0-8 |
| 1120 g ae/ha | 4 | 0 | 0 | 6.5 | 1.7 | 5-8 |
| 2240 g ae/ha | 4 | 0 | 0 | 9.3 | 3.0 | 5-12 |
| 4480 g ae/ha | 2 | 2 | 0 | 17.5 | 6.5 | 10-25 |
| TraP23::dgt-28 (pDAB107553) | | | | | | |
| 0 g ae/ha glyphosate | 4 | 0 | 0 | 0.0 | 0.0 | 0 |
| 560 g ae/ha | 4 | 0 | 0 | 10.0 | 1.6 | 8-12 |
| 1120 g ae/ha | 4 | 0 | 0 | 8.8 | 3.0 | 5-12 |
| 2240 g ae/ha | 4 | 0 | 0 | 9.5 | 4.2 | 5-15 |
| 4480 g ae/ha | 4 | 0 | 0 | 15.8 | 1.5 | 15-18 |

TABLE 27-continued

At a rate of 2240 g ae/ha glyphosate, an average injury of 37.5% was demonstrated with the event containing TraP4, where events containing TraP8 and TraP23 demonstrated an average injury of 9.3% and 9.5% respectively.

| | % Injury | | | % Injury | | Range |
|---|---|---|---|---|---|---|
| Application Rate | <20% | 20-40% | >40% | Ave | Std. Dev. | (%) |
| Petite havana | | | | | | |
| 0 g ae/ha glyphosate | 4 | 0 | 0 | 0.0 | 0.0 | 0 |
| 560 g ae/ha | 0 | 0 | 4 | 85.0 | 4.1 | 80-90 |
| 1120 g ae/ha | 0 | 0 | 4 | 91.3 | 2.5 | 90-95 |
| 2240 g ae/ha | 0 | 0 | 4 | 94.5 | 3.3 | 90-98 |
| 4480 g ae/ha | 0 | 0 | 4 | 98.3 | 2.4 | 95-100 |

These results demonstrated tolerance of dgt-28 up to 4480 g ae/ha glyphosate, as well as differences in tolerance provided by chloroplast transit peptide sequences linked to the dgt-28 gene.

Dgt-28 Protection Against Elevated Glyphosate Rates in the $T_2$ Generation.

A 25 plant progeny test was conducted on two to three $T_2$ lines of dgt-28 per construct. Homozygous lines were chosen based on zygosity analyses completed in the previous generation. The seeds were stratified, sown, and transplanted as previously described. All plants were then sprayed with 280 g ae/ha Ignite 280 SL for the selection of the pat selectable marker as previously described. After 3 DAT, resistant and sensitive plants were counted. All lines tested for each construct did not segregate thereby confirming homogeneous lines in the $T_2$ generation and demonstrating Mendelian inheritance through at least two generation of dgt-28 in tobacco.

Rates of DURANGO DMA™ ranging from 420-3360 g ae/ha glyphosate were applied to 2-3 leaf tobacco as previously described. Visual injury data 14 DAT confirmed the tolerance results that were demonstrated in the T1 generation. Foliar results from a two copy lines from the construct containing TraP4 demonstrated similar tolerance to that of single copy TraP8 and TraP23 lines (data not shown).

TABLE 28

Single copy lines from the construct containing TraP4 with dgt-28 demonstrated increased injury compared to lines from constructs containing TraP8 and TraP23 with dgt-28.

| | % Injury | | | % Injury | | Range |
|---|---|---|---|---|---|---|
| Application Rate | <20% | 20-40% | >40% | Ave | Std. Dev. | (%) |
| TraP4::dgt-28 (pDAB107543) | | | | | | |
| 0 g ae/ha glyphosate | 4 | 0 | 0 | 0.0 | 0.0 | 0 |
| 420 g ae/ha | 0 | 4 | 0 | 23.8 | 4.8 | 20-30 |
| 840 g ae/ha | 0 | 4 | 0 | 30.0 | 4.1 | 25-35 |
| 1680 g ae/ha | 0 | 4 | 0 | 35.0 | 5.8 | 30-40 |
| 3360 g ae/ha | 0 | 4 | 0 | 31.3 | 2.5 | 30-35 |
| TraP8::dgt-28 (pDAB107545) | | | | | | |
| 0 g ae/ha glyphosate | 4 | 0 | 0 | 0.0 | 0.0 | 0 |
| 420 g ae/ha | 4 | 0 | 0 | 0.0 | 0.0 | 0 |
| 840 g ae/ha | 4 | 0 | 0 | 2.5 | 2.9 | 0-5 |
| 1680 g ae/ha | 4 | 0 | 0 | 9.3 | 3.4 | 5-12 |
| 3360 g ae/ha | 4 | 0 | 0 | 10.5 | 1.0 | 10-12 |
| TraP23::dgt-28 (pDAB107553) | | | | | | |
| 0 g ae/ha glyphosate | 4 | 0 | 0 | 0.0 | 0.0 | 0 |
| 420 g ae/ha | 4 | 0 | 0 | 0.0 | 0.0 | 0 |
| 840 g ae/ha | 4 | 0 | 0 | 6.3 | 2.5 | 5-10 |
| 1680 g ae/ha | 4 | 0 | 0 | 10.0 | 0.0 | 10 |
| 3360 g ae/ha | 3 | 1 | 0 | 13.8 | 4.8 | 10-20 |
| Petite havana | | | | | | |
| 0 g ae/ha glyphosate | 4 | 0 | 0 | 0.0 | 0.0 | 0 |
| 420 g ae/ha | 0 | 0 | 4 | 95.0 | 0.0 | 95 |
| 840 g ae/ha | 0 | 0 | 4 | 98.8 | 1.0 | 98-100 |
| 1680 g ae/ha | 0 | 0 | 4 | 99.5 | 1.0 | 98-100 |
| 3360 g ae/ha | 0 | 0 | 4 | 100 | 0.0 | 100 |

The data demonstrate robust tolerance of dgt-28 tobacco up to 3360 g ae/ha glyphosate through two generations compared to the non-transformed control.

Selected plants from each event were sampled prior to glyphosate applications for analyses of the DGT-28 protein by standard DGT-28 ELISA. Data demonstrated DGT-28 mean protein expression of the simple (1-2 copy) lines across constructs ranging from 72.8-114.5 ng/cm$^2$. Data demonstrates dgt-28 is expressing protein in the $T_2$ generation of transformed tobacco and tolerance data confirms functional DGT-28 protein.

Stacking of Dgt-28 to Increase Herbicide Spectrum in Tobacco (Cv. Petit Havana).

Homozygous dgt-28 (pDAB107543 and pDAB107545) and aad-12 v1 (pDAB3278) plants (see PCT/US2006/042133 for the latter, which is incorporated herein by this reference in its entirety) were both reciprocally crossed and $F_1$ seed was collected. The $F_1$ seed from two reciprocal crosses of each gene were stratified and treated 6 reps of each cross were treated with 1120 g ae/ha glyphosate (selective for the dgt-28 gene), 1120 g ae/ha 2,4-D (selective for the aad-12 gene), or a tank mixture of the two herbicides at the rates described. Plants were graded at 14 DAT. Spray results are shown in Table 29.

TABLE 29

Response of $F_1$ aad-12 and dgt-28

| Application Rate | aad-12 × TraP4::dgt-28 | aad-12 × TraP8::dgt-28 Tolerance | Petite havana |
|---|---|---|---|
| 1120 g ae/ha 2,4-D | ++++ | ++++ | — |
| 1120 g ae/ha glyphosate | ++ | ++ | — |
| 1120 g ae/ha 2,4-D + 1120 g ae/ha glyphosate | ++ | ++ | — |

The results confirm that dgt-28 can be successfully stacked with aad-12 (v1), thus increasing the spectrum herbicides that may be applied to the crop of interest (glyphosate+phenoxyacetic acids for dgt-28 and aad-12, respectively). In crop production where hard to control broadleaf weeds or resistant weed biotypes exist the stack can be used as a means of weed control and protection of the crop of interest. Additional input or output traits could also be stacked with the dgt-28 gene.

Example 23

Resistance to Glyphosate in Wheat

Production of Binary Vectors Encoding DGT-28.

Binary vectors containing DGT-28 expression and PAT selection cassettes were designed and assembled using skills and techniques commonly known in the art. Each DGT-28 expression cassette contained the promoter, 5' untranslated region and intron from the Ubiquitin (UN) gene from *Zea mays* (Toki et al. Plant Physiology 1992, 100 1503-07), followed by a coding sequence consisting of one of four transit peptides (TraP4, TraP8, TraP23 or TraP5) fused to the 5' end of a synthetic version of the 5-enolpyruvylshikimate-3-phosphate synthase gene (DGT-28), which had been codon optimized for expression in plants. The DGT-28 expression cassette terminated with a 3' untranslated region (UTR) comprising the transcriptional terminator and polyadenylation site of a lipase gene (Vpl) from *Z. mays* (Paek et al. Mol Cells 1998 30; 8(3) 336-42). The PAT selection cassette comprised of the promoter, 5' untranslated region and intron from the Actin (Act1) gene from *Oryza sativa* (McElroy et al. *The Plant Cell* 1990 2(2) 163-171), followed by a synthetic version of the phosphinothricin acetyl transferase (PAT) gene isolated from *Streptomyces viridochromogenes*, which had been codon optimized for expression in plants. The PAT gene encodes a protein that confers resistance to inhibitors of glutamine synthetase comprising phophinothricin, glufosinate, and bialaphos (Wohlleben et al. Gene 1988, 70(1), 25-37). The selection cassette was terminated with the 3' UTR comprising the transcriptional terminator and polyadenylation sites from the 35s gene of cauliflower mosaic virus (CaMV) (Chenault et al. Plant Physiology 1993 101 (4), 1395-1396).

The selection cassette was synthesized by a commercial gene synthesis vendor (GeneArt, Life Technologies) and cloned into a Gateway-enabled binary vector. The DGT-28 expression cassettes were sub-cloned into pDONR221. The resulting ENTRY clone was used in a LR Clonase II (Invitrogen, Life Technologies) reaction with the Gateway-enabled binary vector encoding the phosphinothricin acetyl transferase (PAT) expression cassette. Colonies of all assembled plasmids were initially screened by restriction digestion of purified DNA using restriction endonucleases obtained from New England BioLabs (NEB; Ipswich, Mass.) and Promega (Promega Corporation, WI). Plasmid DNA preparations were performed using the QIAprep Spin Miniprep Kit (Qiagen, Hilden) or the Pure Yield Plasmid Maxiprep System (Promega Corporation, WI), following the instructions of the suppliers. Plasmid DNA of selected clones was sequenced using ABI Sanger Sequencing and Big Dye Terminator v3.1 cycle sequencing protocol (Applied Biosystems, Life Technologies). Sequence data were assembled and analyzed using the SEQUENCHER™ software (Gene Codes Corporation, Ann Arbor, Mich.).

The resulting four binary expression clones: pDAS000122 (TraP4-DGT28), pDAS000123 (TraP8-DGT28), pDAS000124 (TraP23-DGT28) and pDAS000125 (TraP5-DGT28) were each transformed into *Agrobacterium tumefaciens* strain EHA105.

Production of Transgenic Wheat Events with Dgt-28 Expression Construct.

Transgenic wheat plants expressing one of the four DGT-28 expression constructs were generated by *Agrobacterium*-mediated transformation using the donor wheat line Bobwhite MPB26RH, following a protocol similar to Wu et al. Transgenic Research 2008, 17:425-436. Putative TO transgenic events were selected for phosphinothricin (PPT) tolerance, the phenotype conferred by the PAT selectable marker, and transferred to soil. The T0 plants were grown under glasshouse containment conditions and T1 seed was produced. Overall, about 45 independent T0 events were generated for each DGT-28 expression construct.

Glyphosate Resistance in to Wheat Dgt-28 Wheat Events.

To events were allowed to acclimate in the greenhouse and were grown until 2-4 new, normal looking leaves had emerged from the whorl (i.e., plants had transitioned from tissue culture to greenhouse growing conditions). Plants were grown at 25° C. under 12 hour of supplemental lighting in the greenhouse until maturity. An initial screen of glyphosate tolerance and Taqman analyses was completed on $T_1$ plants grown under the same conditions as previously described. Data allowed for determination of heritable $T_1$ events to be further characterized. Six low copy (1-2 copy) and two multi-copy $T_1$ events were replanted under greenhouse conditions and grown until the 3 leaf stage. $T_1$ plants were sprayed with a commercial formulation of glyphosate (Durango DMA™) from a range of 420-3360 g ae/ha, which are capable of significant injury to untransformed wheat lines. The addition of 2% w/v ammonium sulfate was included in the application. A lethal dose is defined as the rate that causes >75% injury to the Bob White MPB26RH non-transformed control. Herbicide was applied.

In this example, the glyphosate applications were utilized for both determining the segregation of the dgt-28 gene in the $T_1$ generation as well as demonstrating tolerance to increasing levels of glyphosate. The response of the plants is presented in terms of a scale of visual injury 21 days after treatment (DAT). Data are presented as a histogram of individuals exhibiting less than 25% visual injury (4), 25%-50% visual injury (3), 50%-75% visual injury (2) and greater than 75% injury (1). An arithmetic mean and standard deviation is presented for each construct used for wheat transformation. The scoring range of individual response is also indicated in the last column for each rate and transformation. Wild-type, non-transformed wheat (c.v. Bob White MPB26RH) served as a glyphosate sensitive control. In the $T_1$ generation hemizygous and homozygous plants were available for testing for each event and therefore were included for each rate of glyphosate tested. Hemizgyous plants will contain half of the dose of the gene as homozygous plants, therefore variability of response to glyphosate may be expected in the $T_1$ generation.

The results of the $T_1$ dgt-28 wheat plants demonstrated that tolerance to glyphosate was achieved at rates up to 3360 g ae/ha with the chloroplast transit peptides TraP4, TraP5, TraP8 and TraP23. Table 30. Data are of a low copy $T_1$ event but are representative of the population for each construct.

TABLE 30

Response of low copy $T_1$ dgt-28 wheat events to glyphosate 21 days after treatment.

| Application Rate | % Injury <25% | 25-50% | 50-75% | >75% | Ave | Std. Dev. | % Injury Range (%) |
|---|---|---|---|---|---|---|---|
| TraP4::dgt-28 | | | | | | | |
| 420 g ae/ha | 5 | 0 | 0 | 0 | 4.00 | 0.00 | 4 |
| 840 g ae/ha | 6 | 2 | 0 | 0 | 3.75 | 0.46 | 3-4 |
| 1680 g ae/ha | 4 | 2 | 0 | 0 | 3.67 | 0.52 | 3-4 |
| 3360 g ae/ha | 4 | 2 | 0 | 0 | 3.67 | 0.52 | 3-4 |
| TraP8::dgt-28 | | | | | | | |
| 420 g ae/ha | 5 | 3 | 0 | 0 | 3.63 | 0.52 | 3-4 |
| 840 g ae/ha | 3 | 5 | 0 | 0 | 3.38 | 0.52 | 3-4 |
| 1680 g ae/ha | 4 | 3 | 0 | 0 | 3.57 | 0.53 | 3-4 |
| 3360 g ae/ha | 5 | 5 | 0 | 0 | 3.50 | 0.53 | 3-4 |
| TraP23::dgt-28 | | | | | | | |
| 420 g ae/ha | 9 | 2 | 0 | 0 | 3.82 | 0.40 | 3-4 |
| 840 g ae/ha | 8 | 1 | 0 | 0 | 3.89 | 0.33 | 3-4 |
| 1680 g ae/ha | 7 | 5 | 0 | 0 | 3.58 | 0.0 | 3-4 |
| 3360 g ae/ha | 8 | 2 | 0 | 0 | 3.80 | 4.8 | 3-4 |
| TraP5::dgt-28 | | | | | | | |
| 420 g ae/ha | 5 | 2 | 0 | 0 | 3.71 | 0.49 | 3-4 |
| 840 g ae/ha | 4 | 2 | 0 | 0 | 3.67 | 0.52 | 3-4 |
| 1680 g ae/ha | 7 | 3 | 0 | 0 | 3.70 | 0.48 | 3-4 |
| 3360 g ae/ha | 6 | 0 | 0 | 0 | 4.00 | 0.00 | 3-4 |
| Bobwhite MPB26RH | | | | | | | |
| 420 g ae/ha | 0 | 1 | 1 | 10 | 1.25 | 0.62 | 1-3 |
| 840 g ae/ha | 0 | 0 | 0 | 10 | 1.00 | 0.00 | 1 |
| 1680 g ae/ha | 0 | 0 | 0 | 12 | 1.17 | 0.58 | 1-3 |
| 3360 g ae/ha | 0 | 0 | 0 | 10 | 1.00 | 0.00 | 1 |

At 21 DAT, resistant and sensitive plants are counted to determine the percentage of lines that segregated as a single locus, dominant Mendelian trait (3R:1 S) as determined by Chi square analysis. Table 31. These data demonstrate that dgt-28 is inheritable as a robust glyphosate resistance gene in a monocot species.

TABLE 31

Percentage of $T_1$ dgt-28 events by construct that demonstrated heritablity in a mendelian fashion based off of a glyphosate selection at rates ranging from 420-3360 g ae/ha.

| Construct ID | CTP:GOI | % $T_1$ events tested that segregated at a single locus | % $T_1$ events tested that segregated as 2 loci | No. $T_1$ events tested |
|---|---|---|---|---|
| pDAS000122 | TraP4::dgt-28 | 62.5% | 37.5% | 8 |
| pDAS000123 | TraP8::dgt-28 | 87.5% | 12.5% | 8 |
| pDAS000124 | TraP23::dgt-28 | 12.5% | 87.5% | 8 |
| pDAS000125 | TraP5::dgt-28 | 62.5% | 0.0% | 8 |

Molecular Confirmation of to Transgenic Plants for Integration of T-DNAs Encoding DGT-28.

Genomic DNA was extracted from freeze-dried leaf material of all putative T0 wheat plants. Freshly harvested leaf tissue was snap frozen in liquid nitrogen and freeze-dried for 24 h in a Labconco Freezone 4.5® (Labconco, Kansas City, Mo.) at −40° C. and 133×10$^{-3}$ mBar pressure. The lyophilized material was subjected to DNA extraction using the DNeasy® Plant DNA Extraction Mini kit (Qiagen) following the manufacturer's instructions.

DNA from each To plant was tested for the presence-absence of carryover *Agrobacterium tumefaciens* strain and for the number of integrated copies of the T-DNA encoding DGT-28. The presence-absence of *A. tumefaciens* strain was performed using a duplex Taqman® qPCR assay to amplify the endogenous ubiquitin gene (forward and reverse primers and probe:

```
5' GCGAAGATCCAGGACAAGGA 3'
(SEQ ID NO: 85; Forward primer)

5' CTGCTTACCGGCAAAGATGAG 3'
(SEQ ID NO: 86; Reverse primer)

5' TTCCCCCGGACCAGCAGCGT 3'
(SEQ ID NO: 87; Probe)
``` from the wheat genome, and virC from pTiBo542:

```
5' CCGACGAGAAAGACCAGCAA 3'
(SEQ ID NO: 88; Forward primer)

5' CTTAAGTTGTCGATCGGGACTGT 3'
(SEQ ID NO: 89; Reverse primer)

5' TGAGCCTCTCGTCGCCGATCACAT 3'
(SEQ ID NO: 90; Probe).
```

The number of integrated T-DNA copies was estimated using a duplex Taqman® qPCR assay following the procedure of Livak and Schmittgen (Methods 2001 25:402-8). The assay amplified the endogenous single-copy puroindoline-b (Pinb) gene in the D-genome of hexaploid wheat (Gautier et al. Plant Science 2000 153, 81-91):

```
5' ATTTTCCATTCACTTGGCCC 3'
(SEQ ID NO: 91; Forward primer)

5' TGCTATCTGGCTCAGCTGC 3'
(SEQ ID NO: 92; Reverse primer)

5' ATGGTGGAAGGGCGGTTGTGA 3'
(SEQ ID NO: 93; Probe)
``` and a region of the Actin (Act1) promoter present on the T-DNA:

```
5' CTCCCGCGCACCGATCTG 3'
(SEQ ID NO: 94; Forward primer)

5' CCCGCCCCTCTCCTCTTTC 3'
(SEQ ID NO: 95; Reverse primer)

5' AAGCCGCCTCTCGCCCACCCA 3'
(SEQ ID NO: 96; Probe).
```

Plants that did not amplify a product from virC and from which correct products were amplified with primers to the endogenous ubiquitin and rice actin promoter were classified as transgenic. The number of integrated T-DNA was estimated from 2ΔΔc(T), according to Livak and Schmittgen (Methods 2001 25:402-8). Overall, about 95% of all T0 plants had at least one integrated copy of the T-DNA. Table 32.

TABLE 32

Number of independent $T_0$ plants generated and estimated number of integrated T-DNA encoding DGT-28.

| Vector | # Independent T0 plants tested | # Independent T0 events positive for transgene | # Multi-copy (≥4) T-DNA events | # Low-copy (≥3) T-DNA events |
|---|---|---|---|---|
| pDAS000122 | 45 | 43 | 15 | 28 |
| pDAS000123 | 44 | 42 | 11 | 31 |
| pDAS000124 | 45 | 44 | 21 | 23 |
| pDAS000125 | 46 | 39 | 15 | 24 |

Development of PCR Zygosity Assays for Tracking Transgene Inheritance.

The sequences flanking the T-DNA integration sites were identified by digestion of purified genomic DNA with eight restriction endonucleases, followed by ligation of double-stranded adapters specific to the overhangs created by the restriction endonucleases. Following adapter ligation, PCR was performed with a biotinylated primer to either the 3' or 5' end of the T-DNA encoding DGT-28 and a primer to each adapter. The PCR products were captured and purified on Ampure Solid Phase Reversible Immobilization (SPRI) beads (Agencourt Bioscience Corporation, Beckman Coulter Company). A nested PCR was then performed and the amplification products were Sanger sequenced using BigDye® v3.1 chemistry (Applied Biosystems) on an ABI3730xl® automated capillary electrophoresis platform. Sequence analysis performed using Sequencher software (GeneCodes, Ann Arbor, Mich.) was used to generate (where possible) a consensus sequence. The resulting consensus sequence and singletons were used as BlastN queries against assembled genome survey sequence contigs for flow-sorted chromosome arms of wheat variety Chinese Spring (www.wheatgenome.org) to determine the chromosomes in which T-DNA integration had occurred and to enable the design of sub-genome-specific primers for the development of PCR zygosity assays.

Two PCR assays were developed for each transgenic event to enable transgene inheritance to be tracked in subsequent generations. The first assay (hereafter referred to as out-out PCR) was designed to amplify across the T-DNA integration site. Sub-genome-specific amplification in this assay was achieved using on-off PCR with primers designed to position the penultimate base (which contained a phosphorthioate linkage) over nucleotide sequence variation that distinguished the targeted locus from duplicated (both homoeologous and paralogous) copies of the locus elsewhere in the wheat genome. The second assay (hereafter referred to as in-out PCR) was designed to amplify from the T-DNA into the endogenous sequence. This assay utilised one of the primers from the out-out PCR assay and a primer designed to the 3' or 5' end of the T-DNAs encoding DGT-28. The PCR primers were designed to be between 18 and 27 nucleotides in length and to have a melting temperature of 60 to 65° C., optimal 63° C. Both out-out and in-out PCR assays were performed in a 25 µl reaction volume with 0.2 mM dNTP, 1x Phusion PCR buffer (New England BioLabs), 1.5 mM MgCl$_2$, 0.5U Hotstart Phusion DNA polymerase (New England BioLabs), 25 ng purified genomic DNA and 0.4 µM of each primer. PCR cycling conditions were 98° C. for 30s then (98° C. for 10s, 65° C. for 20s, 72° C. for 60s) for 40 cycles. The zygosity of transgenic plants was assigned as shown in Table 33.

TABLE 33

Transgenic events for which PCR zygosity assays were developed and primer sequences used for out-out and in-out PCR.

| Construct | Event code | Primer 1 (5'->3')* | Primer 2 (5'->3')* | Size (bp) |
|---|---|---|---|---|
| *Out-out PCR* | | | | |
| pDAS000122 | hh08-6678-2-1 | GGTTTGTTGAATCCCT CTGTTGG*T (SEQ ID NO: 97) | GTGGTCATGACAGTAT GATAACAG*G (SEQ ID NO: 98) | 303 |
| pDAS000122 | hh08-6678-8-1 | GGGTCTGCCCAATGAA GCG*A (SEQ ID NO: 99) | TCTCGCTTCTCTCATA ACACATCGT*G (SEQ ID NO: 100) | 217 |
| pDAS000123 | hh08-6729-5-1 | GACCTCTCTCACCCTC CTCCT*C (SEQ ID NO: 101) | CCAAATAATAAGTGAG AGAGGGCA*T (SEQ ID NO: 102) | 286 |
| pDAS000123 | mp45-6739-14-1 | TAGTTCCCCTGTCGTG TGCAA*A (SEQ ID NO: 103) | CAACAGCAGCCTCACC AATCA*C (SEQ ID NO: 104) | 555 |
| pDAS000123 | mp45-6739-5-1 | CAAGAACGGTGCTCCT TTTTTAA*G (SEQ ID NO: 105) | AGCCCTTCCTCTGCAT CCTT*A (SEQ ID NO: 106) | 440 |
| pDAS000124 | y102-6762-8-1 | GGCTGTGTTGCACACA AATAGAG*A (SEQ ID NO: 107) | CAGCAGCACGGTAGGT AGATTG*T (SEQ ID NO: 108) | 473 |
| pDAS000124 | gt19-6752-4-1 | CCGATAAGACGGCAAC TGATTAA*A (SEQ ID NO: 109) | AGGCTGGCTTCTAGTG GAAGGA*G (SEQ ID NO: 110) | 215 |
| pDAS000124 | hh08-6761-1-1 | GGGTTTCCGGCTGGAG AC*G (SEQ ID NO: 111) | CCAAAAGCAATTTTCG TTATAAGATGC*C (SEQ ID NO: 112) | 302 |

TABLE 33-continued

Transgenic events for which PCR zygosity assays were developed
and primer sequences used for out-out and in-out PCR.

| Construct | Event code | Primer 1 (5'->3')* | Primer 2 (5'->3')* | Size (bp) |
|---|---|---|---|---|
| OlipDAS000124 | y102-6762-6-1 | CCAGATAATCTGTGGG CTCCT*G (SEQ ID NO: 113) | GCAGCAGCTTGCCTTA AGC*A (SEQ ID NO: 114) | 161 |
| pDAS000125 | hh08-6780-10-1 | TGCTTGTTTCTGTTGT CATCATAGGT*T (SEQ ID NO: 115) | CATTTGTTGGGTTTCC ACGTAC*G (SEQ ID NO: 116) | 145 |
| pDAS000125 | hh08-6780-8-1 | GAGCGCGGCTAAAGGT CAAAA*C (SEQ ID NO: 117) | CCGATTTACATGGACT TGATGGAG*T (SEQ ID NO: 118) | 241 |
| | | In-out PCR | | |
| pDAS000122 | hh08-6678-2-1 | GGTTTGTTGAATCCCT CTGTTGG*T (SEQ ID NO: 119) | GCCGCCTCCAGTGAGT GTTGCTGCTTGTGTA*G (SEQ ID NO: 120) | 732 |
| pDAS000122 | hh08-6678-8-1 | GGGTCTGCCCAATGAA GCG*A (SEQ ID NO: 121) | GCCGCCTCCATAATGT GTGAGTAGTTCCCAGA TAAG*G (SEQ ID NO: 122) | 297 |
| pDAS000123 | hh08-6729-5-1 | GCCGCCTCCAGTGAGT GTTGCTGCTTGTGTA*G (SEQ ID NO: 123) | CCAAATAATAAGTGAG AGAGGGGCA*T (SEQ ID NO: 124) | 510 |
| pDAS000123 | mp45-6739-14-1 | GCCGCCTCCAGTGAGT GTGAGTAGTTCCCAGA TAAG*G (SEQ ID NO: 125) | CAACAGCAGCCTCACC AATCA*C (SEQID NO: 126) | 510 |
| pDAS000123 | mp45-6739-5-1 | GCCGCCTCCATAATGT GTGAGTAGTTCCCAGA CCTT*A (SEQ ID NO: 127) | AGCCCTTCCTCTGCAT TAAG*G (SEQ ID NO: 128) | 580 |
| pDAS000124 | y102-6762-8-1 | GCCGCCTCCAGTGAGT GTGAGTAGTTCCCAGA TAAG*G (SEQ ID NO: 129) | CAGCAGCACGGTAGGT AGATTG*T (SEQ ID NO: 130) | 672 |
| pDAS000124 | gt19-6752-4-1 | GCCGCCTCCAGTGAGT GTTGCTGCTTGTGTA*G (SEQ ID NO: 131) | AGGCTGGCTTCTAGTG GAAGGA*G (SEQ ID NO: 132) | 594 |
| pDAS000124 | hh08-6761-1-1 | GCCGCCTCCATAATGT GTGAGTAGTTCCCAGA TAAG*G (SEQ ID NO: 133) | CCAAAAGCAATTTTCG TTATAAGATGC*C (SEQ ID NO: 134) | 528 |
| pDAS000124 | y102-6762-6-1 | GCCGCCTCCAGTGAGT GTTGCTGCTTGTGTA*G (SEQ ID NO: 135) | GCAGCAGCTTGCCTTA AGC*A (SEQ ID NO: 136) | 633 |
| pDAS000125 | hh08-6780-10-1 | GCCGCCTCCAGTGAGT GTGAGTAGTTCCCAGA TAAG*G (SEQ ID NO: 137) | CATTTGTTGGGTTTCC ACGTAC*G (SEQ ID NO: 138) | 280 |
| pDAS000125 | hh08-6780-8-1 | GCCGCCTCCAGTGAGT GTTGCTGCTTGTGTA*G (SEQ ID NO: 139) | CCGATTTACATGGACT TGATGGAG*T (SEQ ID NO: 140) | 680 |

*indicates phosphorthioate linkage

Phenotypic Assessment of T₁ Transgenic Plants for Glyphosate Tolerance.

To determine if transgenic events with DGT-28 expression constructs exhibited glyphosate tolerance, T1 plants derived from individual events were phenotypically assessed under glasshouse containment conditions. Two phenotypic screens were performed. In the first (preliminary) screen, transgenic events (with sufficient $T_1$ seed for both phenotypic screens) were assessed for glufosinate and glyphosate tolerance to confirm DGT-28 expression and to establish the rank order for herbicide tolerance among events. In the second (detailed) screen, selected transgenic events were assessed for glyphosate tolerance at different spray dose rates to establish the level of herbicide tolerance conferred within events and between DGT-28 expression constructs.

Twelve T1 seed per selected event and three replicates (12 seeds each) of the untransformed donor wheat line Bobwhite MPB26RH were sown in 85 mm pots and grown to the 2-leaf stage under well-watered conditions at 25° C. with supplementary lighting providing a 12 hour photoperiod. The pots were placed in a randomised design to allow environmental effects to be removed during data analysis. The transgenic events screened are listed in Table 34. At the 2-leaf stage, all T1 plants and the first replicate of 12 untransformed donor wheat plants were sprayed with glufosinate at a dose rate of 420 g ai/ha. The plants were visually inspected after four days and representative plants capturing the range of phenotypic responses were used to develop a scoring scale from 0 to 6. Table 35.

TABLE 34

Transgenic events tested in preliminary screen.

| Entry | Vector | Event Code | Estimated number of integrated T-DNA encoding DGT-28* |
|---|---|---|---|
| 1 | pDAS000122 | hh08-6678-6-1 | Low-copy event |
| 2 | pDAS000122 | mp45-6696-2-1 | Low-copy event |
| 3 | pDAS000122 | hh08-6718-2-1 | Low-copy event |
| 4 | pDAS000122 | km51-6686-1-1 | Low-copy event |
| 5 | pDAS000122 | mp45-6677-5-1 | Low-copy event |
| 6 | pDAS000122 | mp45-6696-4-1 | Low-copy event |
| 7 | pDAS000122 | mp45-6711-2-1 | Low-copy event |
| 8 | pDAS000122 | mp45-6711-4-1 | Low-copy event |
| 9 | pDAS000122 | hh08-6678-7-1 | Low-copy event |
| 10 | pDAS000122 | mp45-6711-7-1 | Low-copy event |
| 11 | pDAS000122 | mp45-6711-3-1 | Low-copy event |
| 12 | pDAS000122 | hh08-6678-2-1 | Low-copy event |
| 13 | pDAS000122 | mp45-6711-5-1 | Low-copy event |
| 14 | pDAS000122 | mp45-6711-6-1 | Low-copy event |
| 15 | pDAS000122 | mp45-6696-1-1 | Low-copy event |
| 16 | pDAS000122 | hh08-6678-8-1 | Low-copy event |
| 17 | pDAS000122 | gt19-6680-3-1 | Multi-copy event |
| 18 | pDAS000122 | mp45-6711-10-1 | Multi-copy event |
| 19 | pDAS000122 | mp45-6711-31-1 | Multi-copy event |
| 20 | pDAS000122 | yl02-6709-1-1 | Multi-copy event |
| 21 | pDAS000122 | mp45-6711-11-1 | Multi-copy event |
| 22 | pDAS000123 | hh08-6729-6-1 | Low-copy event |
| 23 | pDAS000123 | mp45-6739-4-1 | Low-copy event |
| 24 | pDAS000123 | gt19-6733-7-1 | Low-copy event |
| 25 | pDAS000123 | mp45-6739-7-1 | Low-copy event |
| 26 | pDAS000123 | gt19-6733-9-1 | Low-copy event |
| 27 | pDAS000123 | gt19-6733-2-1 | Low-copy event |
| 28 | pDAS000123 | yl02-6735-5-1 | Low-copy event |
| 29 | pDAS000123 | yl02-6735-1-1 | Low-copy event |
| 30 | pDAS000123 | hh08-6729-8-1 | Low-copy event |
| 31 | pDAS000123 | gt19-6733-5-1 | Low-copy event |
| 32 | pDAS000123 | mp45-6739-14-1 | Low-copy event |
| 33 | pDAS000123 | mp45-6739-2-1 | Low-copy event |
| 34 | pDAS000123 | hh08-6729-5-1 | Low-copy event |
| 35 | pDAS000123 | mp45-6739-5-1 | Low-copy event |
| 36 | pDAS000123 | hh08-6729-7-1 | Low-copy event |
| 37 | pDAS000123 | hh08-6729-9-1 | Low-copy event |
| 38 | pDAS000123 | gt19-6733-10-1 | Low-copy event |
| 39 | pDAS000123 | gt19-6733-8-1 | Low-copy event |
| 40 | pDAS000123 | hh08-6729-3-1 | Multi-copy event |
| 41 | pDAS000123 | mp45-6739-16-1 | Multi-copy event |
| 42 | pDAS000123 | gt19-6733-6-1 | Multi-copy event |
| 43 | pDAS000123 | di01-6745-1-1 | Multi-copy event |
| 44 | pDAS000123 | gt19-6733-1-1 | Multi-copy event |
| 45 | pDAS000123 | mp45-6739-1-1 | Multi-copy event |
| 46 | pDAS000124 | mp45-6756-4-1 | Low-copy event |
| 47 | pDAS000124 | yl02-6762-3-1 | Low-copy event |
| 48 | pDAS000124 | yl02-6762-11-1 | Low-copy event |
| 49 | pDAS000124 | gt19-6752-10-1 | Low-copy event |
| 50 | pDAS000124 | gt19-6752-14-1 | Low-copy event |
| 51 | pDAS000124 | yl02-6762-4-1 | Low-copy event |
| 52 | pDAS000124 | mp45-6756-2-1 | Low-copy event |
| 53 | pDAS000124 | mp45-6756-1-1 | Low-copy event |
| 54 | pDAS000124 | yl02-6762-8-1 | Low-copy event |
| 55 | pDAS000124 | yl02-6762-6-1 | Low-copy event |
| 56 | pDAS000124 | gt19-6752-4-1 | Low-copy event |
| 57 | pDAS000124 | gt19-6752-23-1 | Low-copy event |
| 58 | pDAS000124 | hh08-6761-1-1 | Low-copy event |
| 59 | pDAS000124 | hh08-6761-3-1 | Low-copy event |
| 60 | pDAS000124 | yl02-6762-1-1 | Low-copy event |
| 61 | pDAS000124 | yl02-6762-7-1 | Low-copy event |
| 62 | pDAS000124 | gt19-6752-7-1 | Low-copy event |
| 63 | pDAS000124 | yl02-6762-12-1 | Multi-copy event |
| 64 | pDAS000124 | gt19-6752-6-1 | Multi-copy event |
| 65 | pDAS000124 | gt19-6752-22-1 | Multi-copy event |
| 66 | pDAS000124 | gt19-6752-24-1 | Multi-copy event |
| 67 | pDAS000124 | gt19-6752-18-1 | Multi-copy event |
| 68 | pDAS000124 | yl02-6762-5-1 | Multi-copy event |
| 69 | pDAS000125 | hh08-6780-9-1 | Low-copy event |
| 70 | pDAS000125 | yl02-6781-8-1 | Low-copy event |
| 71 | pDAS000125 | hh08-6780-1-1 | Low-copy event |
| 72 | pDAS000125 | hh08-6785-3-1 | Low-copy event |
| 73 | pDAS000125 | hh08-6780-7-1 | Low-copy event |
| 74 | pDAS000125 | hh08-6780-4-1 | Low-copy event |
| 75 | pDAS000125 | gt19-6777-2-1 | Low-copy event |
| 76 | pDAS000125 | hh08-6785-4-1 | Low-copy event |
| 77 | pDAS000125 | yl02-6781-4-1 | Low-copy event |
| 78 | pDAS000125 | hh08-6780-16-1 | Low-copy event |
| 79 | pDAS000125 | hh08-6780-8-1 | Low-copy event |
| 80 | pDAS000125 | hh08-6780-10-1 | Low-copy event |
| 81 | pDAS000125 | hh08-6780-11-1 | Low-copy event |
| 82 | pDAS000125 | hh08-6780-12-1 | Low-copy event |
| 83 | pDAS000125 | hh08-6780-6-1 | Low-copy event |
| 84 | pDAS000125 | gt19-6777-5-1 | Low-copy event |
| 85 | pDAS000125 | hh08-6785-7-1 | Low-copy event |
| 86 | pDAS000125 | hh08-6780-13-1 | Low-copy event |
| 87 | pDAS000125 | hh08-6785-1-1 | Low-copy event |
| 88 | pDAS000125 | hh08-6785-8-1 | Multi-copy event |
| 89 | pDAS000125 | yl02-6781-1-1 | Multi-copy event |
| 90 | pDAS000125 | hh08-6780-3-1 | Multi-copy event |
| 91 | pDAS000125 | yl02-6781-7-1 | Multi-copy event |
| 92 | pDAS000125 | hh08-6780-15-1 | Multi-copy event |

*Based on duplex Taqman® qPCR assay. Low- and multi-copy indicates ≤3 and ≥4 integrated T-DNA, respectively.

TABLE 35

Scoring scale used to record phenotypic response to glufosinate at 4 days after spraying.

| Score | Description |
|---|---|
| 0 | Delayed germination or poor plant establishment; exclude from subsequent analyses |
| 1 | >75% leaves necrotic; chlorotic/wilted/dead shoot |
| 2 | 25-75% leaves necrotic; shoot/leaves mostly chlorotic |
| 3 | 10-25% leaves necrotic; <50% leaves chlorotic; moderate wilting; minor chlorotic shoot |
| 4 | <10% leaves necrotic; minor wilting; minor chlorosis |
| 5 | Necrotic leaf tips; remaining plant healthy |
| 6 | Healthy plant |

Each plant in the trial was then scored relative to the scoring scale, with the scorer "blinded" with regard to plant genotype to eliminate scoring bias. Five days after glufosinate scoring, all T1 plants and the first and second replicates of untransformed donor wheat plants were sprayed with glyphosate at a dose rate of 420 g ai/ha. The remaining third replicate of untransformed donor wheat line (total 12 plants) was not sprayed. The plants were visually inspected at 7, 14 and 21 days after spraying. A scoring scale capturing the range of phenotypic responses was developed for each time point and used to score the entire trial. At each time point, the scorer "blinded" with regard to the plant genotype. The scoring scale at 7 days after spraying ranged from 0 to 7 (Table 36), and from 1 to 4 at 14 and 21 days after spraying (Table 37). Plant length, tiller number and morphological abnormalities were also recorded for each plant at 14 days after glyphosate spraying. Plants with delayed germination or poor establishment were excluded from subsequent analyses.

TABLE 36

Scoring scale used to record phenotypic response to glyphosate at 7 days after spraying.

| Score | Description |
|---|---|
| 0 | Plant dead |
| 1 | >75% leaves necrotic; chlorotic/wilted/dead shoot |
| 2 | 50-75% leaves necrotic; severe chlorosis and wilting |
| 3 | 25-50% leaves necrotic; <50% chlorotic leaves; moderate wilting |
| 4 | 10-25% leaves necrotic; <25% leaves chlorotic; minor wilting |
| 5 | <10% leaves necrotic; minor chlorosis |
| 6 | Necrotic leaf tips; remaining plant healthy |
| 7 | Healthy plant |

TABLE 37

Scoring scale used to record phenotypic response to glyphosate at 14 and 21 days after spraying.

| Score | Description |
|---|---|
| 1 | Plant dead |
| 2 | 50-75% leaves necrotic; severe chlorosis and wilting; plant dying |
| 3 | <25% leaves necrotic; <25% leaves chlorotic; minor wilting; signs of growth |
| 4 | Healthy plant |

Analysis of glufosinate response failed to reveal a clear phenotypic difference between untransformed donor wheat plants that were sprayed and untransformed donor plants that were not sprayed (data not shown). As a consequence, the tolerance of the transgenic events to glufosinate could not be reliably assessed. In contrast, analysis of glyphosate response at 21 days after spraying revealed a clear phenotypic difference between the sprayed and unsprayed untransformed donor plants. Table 38. Hence, analyses for glyphosate tolerance among the transgenic events was based on response scores collected at 21 days after spraying. A transgenic event was considered to exhibit glyphosate tolerance when 4 or more of the 12 $T_1$ plants for that event had a response score greater than or equal to 3. This criteria was based on the expectation that each event would segregate 1:2:1 (homozygous present: hemizygous:homozygous absent) for the transgene in the T1 generation and to enable events with weak DGT28 expression to be identified. The transgenic events were rank ordered for observed glyphosate tolerance using an arbitrary aggregate score calculated from individual tolerant plants. The aggregate score was calculated from the response scores at 14 and 21 days and plant length, tiller number and morphological abnormalities recorded at 14 days after spraying.

TABLE 38

Phenotypic response of untransformed donor wheat plants to herbicide treatment at 21 days after spraying.

| | Glufosinate sprayed | Glyphosate sprayed | Survival rate |
|---|---|---|---|
| Replicate 1 | Yes | Yes | 10 of 12 dead/dying |
| Replicate 2 | No | Yes | 10 of 12 dead/dying |
| Replicate 3 | No | No | 12 of 12 healthy |

Overall, 67 of the 92 transgenic events screened showed evidence for glyphosate tolerance. Table 39. Six transgenic events estimated to have <3 integrated copies of the transgene and two transgenic events estimated to have 4 or more integrated transgene were selected for each DGT-28 expression vectors for inclusion in the second (detailed) phenotypic screen.

TABLE 39

Rank ordered phenotypic response of transgenic events to glyphosate treatment.

| Construct | Event code | Estimated T-DNA copy number | % glyphosate tolerant plants | Event phenotype | Standardised aggregate score* | Selected for detailed screen |
|---|---|---|---|---|---|---|
| pDAS000122 | mp45-6711-7-1 | Low-copy | 66.7% | Tolerant | 8.0 | Yes |
| pDAS000124 | gt19-6752-4-1 | Low-copy | 91.7% | Tolerant | 7.3 | Yes |
| pDAS000122 | gt19-6680-3-1 | Multi-copy | 100.0% | Tolerant | 7.2 | Yes |
| pDAS000123 | gt19-6733-1-1 | Multi-copy | 50.0% | Tolerant | 7.2 | No |
| pDAS000122 | mp45-6711-4-1 | Low-copy | 66.7% | Tolerant | 6.2 | Yes |
| pDAS000125 | hh08-6780-8-1 | Low-copy | 58.3% | Tolerant | 6.1 | Yes |
| pDAS000123 | mp45-6739-16-1 | Multi-copy | 75.0% | Tolerant | 6.1 | Yes |
| pDAS000125 | hh08-6780-10-1 | Low-copy | 75.0% | Tolerant | 6.1 | Yes |
| pDAS000125 | hh08-6785-8-1 | Multi-copy | 50.0% | Tolerant | 5.9 | Yes |
| pDAS000125 | hh08-6785-7-1 | Low-copy | 50.0% | Tolerant | 5.8 | Yes |
| pDAS000124 | gt19-6752-22-1 | Multi-copy | 91.7% | Tolerant | 5.8 | Yes |
| pDAS000123 | di01-6745-1-1 | Multi-copy | 100.0% | Tolerant | 5.7 | Yes |
| pDAS000122 | hh08-6678-2-1 | Low-copy | 75.0% | Tolerant | 5.5 | Yes |
| pDAS000122 | hh08-6678-7-1 | Low-copy | 58.3% | Tolerant | 5.3 | Yes |
| pDAS000125 | hh08-6780-6-1 | Low-copy | 66.7% | Tolerant | 5.2 | Yes |
| pDAS000123 | gt19-6733-6-1 | Multi-copy | 83.3% | Tolerant | 5.0 | No |
| pDAS000125 | hh08-6780-11-1 | Low-copy | 66.7% | Tolerant | 5.0 | Yes |
| pDAS000125 | hh08-6780-7-1 | Low-copy | 66.7% | Tolerant | 3.7 | Yes |
| pDAS000124 | yl02-6762-8-1 | Low-copy | 83.3% | Tolerant | 3.5 | Yes |
| pDAS000124 | yl02-6762-6-1 | Low-copy | 83.3% | Tolerant | 3.3 | Yes |
| pDAS000122 | mp45-6711-2-1 | Low-copy | 66.7% | Tolerant | 3.2 | Yes |
| pDAS000122 | mp45-6711-11-1 | Multi-copy | 100.0% | Tolerant | 3.0 | Yes |
| pDAS000122 | mp45-6677-5-1 | Low-copy | 33.3% | Tolerant | 2.7 | No |
| pDAS000125 | hh08-6785-4-1 | Low-copy | 58.3% | Tolerant | 2.5 | No |

TABLE 39-continued

Rank ordered phenotypic response of transgenic events to glyphosate treatment.

| Construct | Event code | Estimated T-DNA copy number | % glyphosate tolerant plants | Event phenotype | Standardised aggregate score* | Selected for detailed screen |
|---|---|---|---|---|---|---|
| pDAS000123 | yl02-6735-1-1 | Low-copy | 83.3% | Tolerant | 2.1 | Yes |
| pDAS000122 | mp45-6711-3-1 | Low-copy | 66.7% | Tolerant | 1.7 | No |
| pDAS000125 | yl02-6781-1-1 | Multi-copy | 41.7% | Tolerant | 1.7 | No |
| pDAS000124 | hh08-6761-1-1 | Low-copy | 100.0% | Tolerant | 1.6 | Yes |
| pDAS000125 | hh08-6780-16-1 | Low-copy | 91.7% | Tolerant | 1.4 | No |
| pDAS000123 | hh08-6729-8-1 | Low-copy | 83.3% | Tolerant | 1.1 | Yes |
| pDAS000125 | hh08-6780-1-1 | Low-copy | 91.7% | Tolerant | 0.9 | No |
| pDAS000123 | hh08-6729-5-1 | Low-copy | 83.3% | Tolerant | 0.7 | Yes |
| pDAS000124 | mp45-6756-1-1 | Low-copy | 66.7% | Tolerant | 0.7 | Yes |
| pDAS000123 | mp45-6739-14-1 | Low-copy | 91.7% | Tolerant | 0.5 | Yes |
| pDAS000125 | gt19-6777-2-1 | Low-copy | 75.0% | Tolerant | 0.3 | No |
| pDAS000124 | yl02-6762-5-1 | Multi-copy | 91.7% | Tolerant | 0.2 | No |
| pDAS000125 | hh08-6780-3-1 | Multi-copy | 66.7% | Tolerant | 0.0 | Yes |
| pDAS000122 | mp45-6696-1-1 | Low-copy | 83.3% | Tolerant | −0.1 | No |
| pDAS000122 | hh08-6678-8-1 | Low-copy | 58.3% | Tolerant | −0.1 | Yes |
| pDAS000125 | hh08-6780-12-1 | Low-copy | 75.0% | Tolerant | −0.3 | No |
| pDAS000125 | yl02-6781-4-1 | Low-copy | 66.7% | Tolerant | −0.4 | No |
| pDAS000124 | gt19-6752-6-1 | Multi-copy | 50.0% | Tolerant | −0.9 | No |
| pDAS000122 | mp45-6696-4-1 | Low-copy | 66.7% | Tolerant | −0.9 | No |
| pDAS000125 | hh08-6780-9-1 | Low-copy | 66.7% | Tolerant | −1.1 | No |
| pDAS000123 | mp45-6739-5-1 | Low-copy | 83.3% | Tolerant | −1.1 | Yes |
| pDAS000124 | yl02-6762-1-1 | Low-copy | 66.7% | Tolerant | −1.1 | No |
| pDAS000123 | yl02-6735-5-1 | Low-copy | 83.3% | Tolerant | −1.3 | No |
| pDAS000124 | yl02-6762-7-1 | Low-copy | 91.7% | Tolerant | −1.6 | Yes |
| pDAS000124 | gt19-6752-24-1 | Multi-copy | 50.0% | Tolerant | −1.6 | No |
| pDAS000123 | mp45-6739-7-1 | Low-copy | 41.7% | Tolerant | −1.7 | No |
| pDAS000124 | gt19-6752-18-1 | Multi-copy | 100.0% | Tolerant | −1.7 | Yes |
| pDAS000123 | gt19-6733-2-1 | Low-copy | 66.7% | Tolerant | −1.8 | No |
| pDAS000124 | gt19-6752-10-1 | Low-copy | 33.3% | Tolerant | −2.0 | No |
| pDAS000123 | mp45-6739-4-1 | Low-copy | 66.7% | Tolerant | −2.0 | Yes |
| pDAS000125 | gt19-6777-5-1 | Low-copy | 50.0% | Tolerant | −2.4 | No |
| pDAS000124 | gt19-6752-14-1 | Low-copy | 58.3% | Tolerant | −2.5 | No |
| pDAS000122 | yl02-6709-1-1 | Multi-copy | 50.0% | Tolerant | −2.5 | No |
| pDAS000125 | yl02-6781-8-1 | Low-copy | 58.3% | Tolerant | −2.7 | No |
| pDAS000124 | gt19-6752-23-1 | Low-copy | 83.3% | Tolerant | −2.7 | No |
| pDAS000124 | mp45-6756-2-1 | Low-copy | 75.0% | Tolerant | −2.7 | No |
| pDAS000124 | yl02-6762-3-1 | Low-copy | 66.7% | Tolerant | −3.4 | No |
| pDAS000123 | gt19-6733-8-1 | Low-copy | 41.7% | Tolerant | −3.4 | No |
| pDAS000123 | hh08-6729-7-1 | Low-copy | 50.0% | Tolerant | −3.6 | No |
| pDAS000125 | hh08-6785-3-1 | Low-copy | 66.7% | Tolerant | −4.2 | No |
| pDAS000123 | mp45-6739-1-1 | Multi-copy | 33.3% | Tolerant | −4.4 | No |
| pDAS000122 | mp45-6711-31-1 | Multi-copy | 41.7% | Tolerant | −4.5 | No |
| pDAS000125 | hh08-6780-15-1 | Multi-copy | 66.7% | Tolerant | −4.8 | No |
| pDAS000123 | gt19-6733-10-1 | Low-copy | 33.3% | Tolerant | −5.1 | No |
| pDAS000125 | hh08-6780-13-1 | Low-copy | 100.0% | Tolerant | −5.5 | No |
| pDAS000122 | mp45-6711-5-1 | Low-copy | 75.0% | Tolerant | −5.7 | No |
| pDAS000122 | mp45-6711-10-1 | Multi-copy | 58.3% | Tolerant | −10.4 | No |
| pDAS000123 | gt19-6733-5-1 | Low-copy | 0.0% | Susceptible | n/a | No |
| pDAS000124 | gt19-6752-7-1 | Low-copy | 0.0% | Susceptible | n/a | No |
| pDAS000122 | hh08-6718-2-1 | Low-copy | 0.0% | Susceptible | n/a | No |
| pDAS000123 | hh08-6729-9-1 | Low-copy | 0.0% | Susceptible | n/a | No |
| pDAS000124 | hh08-6761-3-1 | Low-copy | 0.0% | Susceptible | n/a | No |
| pDAS000125 | hh08-6785-1-1 | Low-copy | 0.0% | Susceptible | n/a | No |
| pDAS000122 | mp45-6696-2-1 | Low-copy | 0.0% | Susceptible | n/a | No |
| pDAS000123 | mp45-6739-2-1 | Low-copy | 0.0% | Susceptible | n/a | No |
| pDAS000122 | km51-6686-1-1 | Low-copy | 8.3% | Susceptible | n/a | No |
| pDAS000122 | mp45-6711-6-1 | Low-copy | 8.3% | Susceptible | n/a | No |
| pDAS000124 | yl02-6762-12-1 | Multi-copy | 8.3% | Susceptible | n/a | No |
| pDAS000123 | gt19-6733-7-1 | Low-copy | 16.7% | Susceptible | n/a | No |
| pDAS000123 | hh08-6729-3-1 | Multi-copy | 16.7% | Susceptible | n/a | No |
| pDAS000124 | mp45-6756-4-1 | Low-copy | 16.7% | Susceptible | n/a | No |
| pDAS000125 | hh08-6780-4-1 | Low-copy | 16.7% | Susceptible | n/a | No |
| pDAS000122 | hh08-6678-6-1 | Low-copy | 25.0% | Susceptible | n/a | No |
| pDAS000123 | gt19-6733-9-1 | Low-copy | 25.0% | Susceptible | n/a | No |
| pDAS000123 | hh08-6729-6-1 | Low-copy | 25.0% | Susceptible | n/a | No |
| pDAS000124 | yl02-6762-11-1 | Low-copy | 25.0% | Susceptible | n/a | No |
| pDAS000124 | yl02-6762-4-1 | Low-copy | 25.0% | Susceptible | n/a | No |
| pDAS000125 | yl02-6781-7-1 | Multi-copy | 25.0% | Susceptible | n/a | No |

*A positive score indicates higher glyphosate tolerance. The standardised aggregate score for the untreated untransformed donor wheat plants was 12.2.

Detailed Phenotypic Screen.

Four replicates of 12 T1 seeds per selected event and eight replicates (12 seeds each) of the untransformed donor wheat line Bobwhite MPB26RH were sown in 85 mm pots and grown to the 2-leaf stage under well-watered conditions at 25° C. with supplementary lighting providing a 12 hour photoperiod. The pots were placed in a randomised design to allow environmental effects to be removed during data analysis. The transgenic events screened are listed in Table 40. At the 2-leaf stage, plant length and number of leaves was recorded for each plant before spraying with glyphosate. The first, second, third and fourth replicate of T1 plants for each selected event and the untransformed donor wheat line were sprayed at a dose rate of 420, 840, 1680 and 3360 g ai/ha, respectively. The fifth, sixth, seventh and eighth replicate of untransformed donor wheat line (total 48 plants) were not sprayed. At 7, 14 and 21 days after spraying, the plants were scored for plant length, number of leaves and phenotypic response to glyphosate using the scoring scale in Table 37. Any morphological abnormalities were also recorded. For scoring, the scorer was "blinded" with regard to plant genotype and spray dose rate to prevent scoring bias. Plants with delayed germination and poor establishment (criteria: plant length <6 cm) at the pre-spray scoring were excluded from subsequent analyses.

TABLE 40

Transgenic events tested in detailed phenotypic screen.

| Entry | Vector | Event Code | Estimated number of integrated T-DNA encoding DGT-28* |
|---|---|---|---|
| 1 | pDAS000122 | mp45-6677-5-1 | Low-copy event |
| 2 | pDAS000122 | mp45-6711-7-1 | Low-copy event |
| 3 | pDAS000122 | mp45-6711-4-1 | Low-copy event |
| 4 | pDAS000122 | hh08-6678-2-1 | Low-copy event |
| 5 | pDAS000122 | hh08-6678-7-1 | Low-copy event |
| 6 | pDAS000122 | hh08-6678-8-1 | Low-copy event |
| 7 | pDAS000122 | mp45-6711-2-1 | Low-copy event |
| 8 | pDAS000122 | gt19-6680-3-1 | Multi-copy event |
| 9 | pDAS000122 | mp45-6711-11-1 | Multi-copy event |
| 10 | pDAS000123 | yl02-6735-1-1 | Low-copy event |
| 11 | pDAS000123 | hh08-6729-8-1 | Low-copy event |
| 12 | pDAS000123 | hh08-6729-5-1 | Low-copy event |
| 13 | pDAS000123 | mp45-6739-14-1 | Low-copy event |
| 14 | pDAS000123 | mp45-6739-5-1 | Low-copy event |
| 15 | pDAS000123 | mp45-6739-7-1 | Low-copy event |
| 16 | pDAS000123 | mp45-6739-4-1 | Low-copy event |
| 17 | pDAS000123 | mp45-6739-16-1 | Multi-copy event |
| 18 | pDAS000123 | di01-6745-1-1 | Multi-copy event |
| 19 | pDAS000124 | gt19-6752-4-1 | Low-copy event |
| 20 | pDAS000124 | yl02-6762-8-1 | Low-copy event |
| 21 | pDAS000124 | yl02-6762-6-1 | Low-copy event |
| 22 | pDAS000124 | hh08-6761-1-1 | Low-copy event |
| 23 | pDAS000124 | mp45-6756-1-1 | Low-copy event |
| 24 | pDAS000124 | yl02-6762-7-1 | Low-copy event |
| 25 | pDAS000124 | gt19-6752-22-1 | Multi-copy event |
| 26 | pDAS000124 | gt19-6752-18-1 | Multi-copy event |
| 27 | pDAS000125 | hh08-6780-8-1 | Low-copy event |
| 28 | pDAS000125 | hh08-6780-10-1 | Low-copy event |
| 29 | pDAS000125 | hh08-6785-7-1 | Low-copy event |
| 30 | pDAS000125 | hh08-6780-6-1 | Low-copy event |
| 31 | pDAS000125 | hh08-6780-11-1 | Low-copy event |
| 32 | pDAS000125 | hh08-6780-7-1 | Low-copy event |

*Based on duplex Taqman ® qPCR assay. Low- and multi-copy indicates ≤3 and ≥4 integrated T-DNA, respectively.

Analysis of glyphosate response at 7, 14 and 21 days after spraying revealed a clear-cut phenotypic difference between the sprayed and unsprayed untransformed donor wheat plants. This differentiation was maximal at 21 days and was observed across all glyphosate dose rates. Table 41. To assess the tolerance of the transgenic events to glyphosate at each spray dose rate, null T1 plants (i.e., plants not carrying the transgene) were excluded from subsequent analyses. T1 plants with a response score of less than three at 21 days after spraying were considered to have the null genotype. Analysis of variance (ANOVA) based on tolerant phenotypes revealed a significant effect for DGT-28 expression construct, transgenic event and glyphosate spray dose. Table 41. However, multiple comparison tests failed to unveil meaningful biological interpretation for the origin of these differences due to the limited range of response scores (i.e., 1 to 4; Table 40) used to record the phenotype of individual plants. In general, the eight independent transgenic events tested for each DGT-28 expression construct showed similar tolerance to glyphosate at each spray dose rate, indicating that all four DGT-28 transgenes conferred a dominant phenotype and that a single copy was sufficient to confer glyphosate tolerance. Each of the DGT-28 expression constructs revealed effective tolerance to at least 3360 g ai/ha glyphosate.

TABLE 41

Phenotypic response of untransformed donor wheat plants to different glyphosate treatments at 21 days after spraying.

| | Dose Rate (g ai/ha) | No. plants at pre-spray scoring | No. surviving plants at 14 days after spraying | No. surviving plants at 21 days after spraying |
|---|---|---|---|---|
| Replicate 1 | 420 | 10 | 0 | 0 |
| Replicate 2 | 840 | 10 | 3 | 0 |
| Replicate 3 | 1680 | 11 | 0 | 0 |
| Replicate 4 | 3360 | 10 | 1 | 0 |
| Replicate 5 | 0 | 9 | 8 | 8 |
| Replicate 6 | 0 | 8 | 8 | 8 |
| Replicate 7 | 0 | 12 | 12 | 12 |
| Replicate 8 | 0 | 12 | 12 | 12 |

TABLE 42

Analysis of variance (ANOVA) based on glyphosate tolerant plants.

| | Df[1] | Sum of Squares | Mean Square | F-value | Pr(>F)[2] |
|---|---|---|---|---|---|
| Replicate | 11 | 1.29 | 0.12 | 0.728 | 0.71181 |
| Vector | 4 | 139.54 | 34.88 | 216.025 | 2.00E−16*** |
| Event_Code | 29 | 178.52 | 6.16 | 38.122 | 2.00E−16*** |
| Spray_Dose | 3 | 2.14 | 0.71 | 4.417 | 0.00427** |

[1]Degrees of freedom;
[2]Statistically significant at 0.001(*) and 0.01 (), respectively.

Molecular Confirmation of T-DNA Presence in Glyphosate Tolerant T1 Plants.

The PCR zygosity assays developed in Example 2 were used to confirm the presence of T-DNA encoding DGT-28 in the glyphosate tolerant T1 plants saved for T2 seed production (see Example 6). Overall, PCR zygosity tests were performed for 104 T1 plants, of which 89% were confirmed to contain at least one copy of the transgene. Table 43. These results confirmed that the observed glyphosate tolerance was conferred by the presence of T-DNA encoding DGT-28.

TABLE 43

Observed transgene segregation among T1 plants.

| Construct | Event Code | Homozygous for presence of transgene | Hemizygous for presence of transgene | Homozygous for absence of transgene | Escapes plants observed |
|---|---|---|---|---|---|
| pDAS000122 | hh08-6678-2-1 | 0 | 7 | 2 | Yes |
| pDAS000122 | hh08-6678-8-1 | 2 | 7 | 0 | No |
| pDAS000123 | hh08-6729-5-1 | 7 | 4 | 0 | No |
| pDAS000123 | mp45-6739-14-1 | 1 | 8 | 0 | No |
| pDAS000123 | mp45-6739-5-1 | 0 | 9 | 0 | No |
| pDAS000124 | gt19-6752-4-1 | 5 (homo or hemi) | | 3 | Yes |
| pDAS000124 | hh08-6761-1-1 | 3 | 2 | 3 | Yes |
| pDAS000124 | yl02-6762-6-1 | 7 (homo or hemi) | | 2 | Yes |
| pDAS000124 | yl02-6762-8-1 | 3 | 6 | 0 | No |
| pDAS000125 | hh08-6780-10-1 | 6 | 4 | 0 | No |
| pDAS000125 | hh08-6780-8-1 | 2 | 7 | 1 | Yes |

Generation of T2 Seed for Glyphosate Tolerant Transgenic Events.

About eight glyphosate tolerant T1 plants were saved from the phenotypic screens for the 32 transgenic events that were selected for inclusion in the detailed phenotypic screen (Table 40). The plants were transferred to 200 mm pots and grown under well-watered conditions at 25° C. with supplementary lighting providing a 12 hour photoperiod. The spikes on each plant were individually bagged prior to anthesis to prevent out-crossing.

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertain and which fall within the limits of the appended claims.

What is claimed is:

1. An isolate nucleic acid molecule comprising:
a polynucleotide operably linked to a heterologous promoter, wherein the polynucleotide encodes a 5-enolpyruvylshikimate-3-phosphate synthase (EPSPS) linked to a chloroplast transit peptide (CTP), wherein the EPSPS is at least 90% identical to SEQ ID NO 1, and wherein the EPSPS comprises an alanine at the position corresponding to position 84 of SEQ ID NO 1.

2. The nucleic acid molecule of claim 1, wherein the first methionine residue of the 5-enolpyruvylshikimate 3-phosphate synthase is replaced by the CTP.

3. A vector comprising the nucleic acid molecule of claim 1.

4. The vector of claim 3, comprising a further polynucleotide encoding a heterologous polypeptide.

5. The vector of claim 3, wherein the vector is a plant transformation vector.

6. A host cell that contains the nucleic acid molecule of claim 1, wherein the host cell is a bacterial cell or a plant cell.

7. The vector of claim 5, wherein the promoter is an AtUbi10 promoter.

8. The host cell of claim 6, wherein the host cell is a plant cell.

9. A transgenic plant material comprising the plant cell of claim 8, wherein the plant material is a plant part, plant organ, or plant seed.

10. The transgenic plant material of claim 9, wherein the plant material is tolerant to glyphosate, when compared to a wild-type plant of the same species that does not comprise the polynucleotide operably linked to the heterologous promoter.

11. The transgenic plant material of claim 9, wherein the transgenic plant material is resistant to an herbicide selected from the group consisting of glufosinate; 2,4-dichlorophenoxyacetic acid (2,4-D); and an herbicide that inhibits acetolactate synthase (ALS).

12. A transgenic tissue culture of regenerable cells produced from the transgenic plant material of claim 9.

13. A transgenic protoplast produced from the transgenic plant material of claim 9.

14. The transgenic tissue culture of claim 12, wherein the regenerable cells are produced from a tissue type selected from the group consisting of leaves, pollen, embryos, cotyledons, hypocotyls, meristematic cells, roots, root tips, anthers, flowers, stems and pods.

15. A plant regenerated from the tissue culture of claim 12, wherein the plant is resistant to glyphosate.

16. A method of generating a plant, plant part, plant organ, plant seed, or plant cell resistant to glyphosate, the method comprising:
transforming the plant, plant part, plant organ, plant seed, or plant cell with the nucleic acid molecule of claim 1; and
expressing the polypeptide encoded by the polynucleotide, thereby generating the plant, plant part, plant organ, or plant cell resistant to glyphosate.

17. A method for controlling weeds in an area under cultivation containing herbicide-resistant plants, the method comprising:
planting a plant or a plant seed comprising the nucleic acid molecule of claim 1 in the area under cultivation; and
applying to the area under cultivation a sufficient amount of herbicide to give at least 85% control of a weed species in the area under cultivation.

18. The method according to claim 17, wherein the herbicide is glyphosate.

19. The method according to claim 17, wherein the nucleic acid molecule comprises a second polynucleotide encoding a heterologous polypeptide.

20. The method according to claim 19, wherein the second polynucleotide is α-ketoglutarate-dependent dioxygenase 1 (aad-1) or α-ketoglutarate-dependent dioxygenase 12 (aad-12).

21. A plant having stably integrated into its genome the nucleic acid molecule of claim 1.

22. The plant of claim 21, wherein the plant is selected from the group consisting of wheat, corn, soybean, tobacco, brachiaria, rice, millet, barley, tomato, apple, pear, strawberry, orange, alfalfa, cotton, carrot, potato, sugar beets, yam, lettuce, spinach, petunia, rose, chrysanthemum, turf grass, pine, fir, spruce, heavy metal accumulating plants, sunflower, safflower, rapeseed, and *Arabidopsis*.

23. The plant of claim 21, wherein the plant is a species selected from the group consisting of genera *Asparagus, Avena, Brachiaria, Brassica, Citrus, Citrullus, Capsicum, Cucurbita, Daucus, Erigeron, Glycine, Gossypium, Hordeum, Helianthus, Lactuca, Lolium, Lycopersicon, Malts, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea*.

* * * * *

```
                       SEQUENCE LISTING

<160> NUMBER OF SEQ ID NOS: 145

<210> SEQ ID NO 1
<211> LENGTH: 415
<212> TYPE: PRT
<213> ORGANISM: Streptomyces sviceus

<400> SEQUENCE: 1

Met Arg Gly Met Pro Ala Leu Ser Leu Pro Gly Ser Lys Ser Ile Thr
1               5                   10                  15

Ala Arg Ala Leu Phe Leu Ala Ala Ala Asp Gly Val Thr Thr Leu
            20                  25                  30

Val Arg Pro Leu Arg Ser Asp Asp Thr Glu Gly Phe Ala Glu Gly Leu
        35                  40                  45

Val Arg Leu Gly Tyr Arg Val Gly Arg Thr Pro Asp Thr Trp Gln Val
    50                  55                  60

Asp Gly Arg Pro Gln Gly Pro Ala Val Ala Glu Ala Asp Val Tyr Cys
65                  70                  75                  80

Arg Asp Gly Ala Thr Thr Ala Arg Phe Leu Pro Thr Leu Ala Ala Ala
                85                  90                  95

Gly His Gly Thr Tyr Arg Phe Asp Ala Ser Pro Gln Met Arg Arg Arg
            100                 105                 110

Pro Leu Leu Pro Leu Ser Arg Ala Leu Arg Asp Leu Gly Val Asp Leu
        115                 120                 125

Arg His Glu Glu Ala Glu Gly His His Pro Leu Thr Val Arg Ala Ala
    130                 135                 140

Gly Val Glu Gly Gly Glu Val Thr Leu Asp Ala Gly Gln Ser Ser Gln
145                 150                 155                 160

Tyr Leu Thr Ala Leu Leu Leu Leu Gly Pro Leu Thr Arg Gln Gly Leu
                165                 170                 175
```

```
Arg Ile Arg Val Thr Asp Leu Val Ser Ala Pro Tyr Val Glu Ile Thr
            180                 185                 190

Leu Ala Met Met Arg Ala Phe Gly Val Glu Val Ala Arg Glu Gly Asp
        195                 200                 205

Val Phe Val Pro Pro Gly Gly Tyr Arg Ala Thr Thr Tyr Ala Ile
    210                 215                 220

Glu Pro Asp Ala Ser Thr Ala Ser Tyr Phe Phe Ala Ala Ala Ala Leu
225                 230                 235                 240

Thr Pro Gly Ala Glu Val Thr Val Pro Gly Leu Gly Thr Gly Ala Leu
                245                 250                 255

Gln Gly Asp Leu Gly Phe Val Asp Val Leu Arg Arg Met Gly Ala Glu
            260                 265                 270

Val Ser Val Gly Ala Asp Ala Thr Thr Val Arg Gly Thr Gly Glu Leu
        275                 280                 285

Arg Gly Leu Thr Ala Asn Met Arg Asp Ile Ser Asp Thr Met Pro Thr
    290                 295                 300

Leu Ala Ala Ile Ala Pro Phe Ser Ala Pro Val Arg Ile Glu Asp
305                 310                 315                 320

Val Ala Asn Thr Arg Val Lys Glu Cys Asp Arg Leu Glu Ala Cys Ala
                325                 330                 335

Glu Asn Leu Arg Arg Leu Gly Val Arg Val Ala Thr Gly Pro Asp Trp
            340                 345                 350

Ile Glu Ile His Pro Gly Pro Ala Thr Gly Ala Gln Val Thr Ser Tyr
        355                 360                 365

Gly Asp His Arg Ile Val Met Ser Phe Ala Val Thr Gly Leu Arg Val
    370                 375                 380

Pro Gly Ile Ser Phe Asp Asp Pro Gly Cys Val Arg Lys Thr Phe Pro
385                 390                 395                 400

Gly Phe His Glu Ala Phe Ala Glu Leu Arg Arg Gly Ile Gly Ser
                405                 410                 415

<210> SEQ ID NO 2
<211> LENGTH: 1248
<212> TYPE: DNA
<213> ORGANISM: Streptomyces sviceus

<400> SEQUENCE: 2
atgagaggga tgccagcctt gtctttacct ggatcaaaga gtatcacagc tagggcactc      60
tttcttgctg ctgctgctga tggggttact actttggtga ggccattgag aagtgacgac     120
acagaaggat tcgctgaggg gttagttcgt ttaggctatc gtgtagggag acacccgat      180 acttggcaag tcgatggcag accacaagga ccagcagtgg ctgaggctga cgtctactgt     240
agagacggag caaccaccgc tagattcttg ccaaccttag cagctgctgg tcacggaaca     300
tacagatttg atgcttcacc acagatgagg agacgtcctc ttttgcccct aagcagagcc     360
ttgagggatt tgggtgtcga tcttagacac gaagaagctg aaggtcatca ccctctgact     420
gtccgtgctg ctggggttga aggaggagag gttactttgg atgctggtca gtcaagtcag     480
tatctcactg ccttgttgct ccttggtccc cttacaagac aaggactgag gataagggtt     540
actgatttgg tgtcagcacc atacgtggag attacgcttg caatgatgag ggctttcgga     600
gttgaagtgg caagggaggg agatgtgttc gttgttccac tggtggata tcgtgcaact     660 acgtatgcta tagaacccga cgcaagtact gcttcttact tcttcgcagc tgctgctttg     720
actcctggag ctgaagtgac tgtacctggg ttaggcacgg gagcacttca aggagatttg     780
```

| | |
|---|---|
| ggatttgtag atgtcttaag gagaatggga gccgaggtgt ccgtaggagc tgatgcaacc | 840 |
| actgttagag gaactggtga attgcgtggc cttacagcca acatgagaga cataagtgat | 900 |
| acgatgccga ccctcgctgc aatagcaccc tttgctagtg ctccagttag aatcgaggat | 960 |
| gttgccaaca ctcgtgtcaa agaatgtgac agacttgagg cttgtgcaga gaaccttagg | 1020 |
| aggttgggag taagggttgc aacgggtccg gactggattg agatacaccc tggtccagct | 1080 |
| actggtgctc aagtcacaag ctatggtgat cacagaattg tgatgtcatt tgcagtgact | 1140 |
| ggacttcgtg tgcctgggat cagcttcgac gaccctggct gtgttcgtaa gacttttcct | 1200 |
| gggtttcacg aggctttcgc agaattgagg cgtggcattg ggagctga | 1248 |

<210> SEQ ID NO 3
<211> LENGTH: 1251
<212> TYPE: DNA
<213> ORGANISM: Streptomyces sviceus

<400> SEQUENCE: 3

| | |
|---|---|
| atggcaagag ggatgccagc cttgtcgctg cctggctcaa agtcgatcac ggctagagca | 60 |
| ctctttctcg cagcagcagc cgacggagtc accacgcttg tgagaccgct gcggtcagac | 120 |
| gacaccgagg gttttgcgga aggcctcgtc agactgggct atcgggttgg gaggactccc | 180 |
| gacacgtggc aagtggacgg aaggccacaa ggtccagcag ttgccgaggc tgatgtgtat | 240 |
| tgtagagacg gtgcaacaac ggctaggttc ctccccacac tcgcagctgc tggacacggg | 300 |
| acctacagat ttgatgcctc tccccagatg aggagaaggc cactgctgcc tctttctagg | 360 |
| gctttgaggg accttggcgt tgatcttcgc cacgaggaag cggaagggca ccaccccttg | 420 |
| accgtgagag ctgctggagt cgagggaggt gaggttacac tcgatgctgg acagtcctct | 480 |
| cagtacttga cggcactgct gctgctcggt ccgctcacac gccaagggct gcggattcgc | 540 |
| gtcactgatc tggttagcgc tccgtacgtg gagattacac ttgcgatgat gagagctttt | 600 |
| ggggtcgagg ttgcacgcga aggcgacgtt tccgtggtgc ctcctggtgg ctacagagcg | 660 |
| actacgtacg cgattgagcc agatgccagc accgcaagct acttctttgc agctgctgcg | 720 |
| ttgacacctg gagccgaggt cacagtgcct ggactcggga ccggagcgct tcaagggat | 780 |
| ctcggcttcg tggacgtgct gcggaggatg ggtgccgagg tcagcgtggg agcagacgct | 840 |
| acgactgtta gaggcacggg tgagcttaga ggccttacag caaacatgag ggacatatcc | 900 |
| gacacgatgc cgacgcttgc tgccatcgct ccgttcgctt cagcacccgt cagaattgaa | 960 |
| gatgtggcga acactcgcgt caaagagtgc gacagacttg aagcgtgtgc cgagaacttg | 1020 |
| aggaggttgg gagtgagagt cgcaactggt ccagactgga tcgagatcca ccctggtcca | 1080 |
| gctactggag cgcaagtcac aagctatggc gaccatagga ttgttatgtc attcgcagtg | 1140 |
| accggactca gagttcctgg gatctctttc gacgaccctg gttgcgtgcg gaaaacgttc | 1200 |
| cctggcttcc acgaggcatt tgcggagctg cggagaggaa ttggttcctg a | 1251 |

<210> SEQ ID NO 4
<211> LENGTH: 1248
<212> TYPE: DNA
<213> ORGANISM: Streptomyces sviceus

<400> SEQUENCE: 4

| | |
|---|---|
| atgcgtggta tgcctgcact gagcctgcct ggtagcaaaa gcattaccgc acgtgcactg | 60 |
| tttctggctg cagcagcaga tggtgttacc accctggttc gtcctctgcg ttctgatgat | 120 |
| accgaaggtt ttgcagaagg tctggttcgt ctgggttatc gtgttggtcg tacaccggat | 180 |

```
acctggcaag ttgatggtcg tccgcagggt ccggcagttg ccgaagcaga tgtttattgc      240
cgtgatggtg caaccaccgc acgttttctg ccgaccctgg cagcagccgg tcatggcacc      300
tatcgttttg atgcatctcc gcagatgcgt cgtcgtccgc tgctgccgct gtctcgtgca      360
ctgcgtgatc tgggtgttga tctgcgtcat gaagaagcag aaggtcatca tccgctgacc      420
gttcgtgcag ccggtgttga aggtggtgaa gtgaccctgg atgccggtca gagcagccag      480
tatctgaccg cactgctgct gctgggtccg ctgacacgtc agggtctgcg tattcgtgtt      540
accgatctgg ttagcgcacc gtatgtggaa attaccctgg caatgatgcg tgcatttggt      600
gttgaagttg cacgtgaagg tgatgttttt gttgttccgc tggtggttta tcgcgcaacc      660
acctatgcaa ttgaaccgga tgcaagcacc gcaagctatt tttttgcagc agcagccctg      720
acaccgggtg cagaagttac cgttcctggt ctgggcacag gtgcactgca gggtgatctg      780
ggatttgttg atgttctgcg tcgtatgggt gccgaagtta gcgttggtgc agatgccacc      840
accgttcgtg gtacaggtga actgcgtggt ctgaccgcaa atatgcgtga tattagcgat      900
accatgccga cactggctgc aattgcaccg tttgcaagcg caccggttcg tattgaagat      960
gttgccaaca cccgtgttaa agaatgtgat cgtctggaag catgtgcaga aaatctgcgt     1020
cgtctgggcg ttcgtgttgc aaccggtccg gattggattg aaattcatcc gggtccggca     1080
accggtgcac aggttaccag ctatggtgat catcgtatcg ttatgagctt tgcagttacc     1140
ggtctgcgtg ttccgggtat tagctttgat gatccgggtt gtgttcgtaa aacctttccg     1200
ggttttcatg aagctttgc agaactgcgt cgtggtattg gtagctaa                    1248

<210> SEQ ID NO 5
<211> LENGTH: 1599
<212> TYPE: DNA
<213> ORGANISM: Glycine max

<400> SEQUENCE: 5
atggctcaag tctcccgtgt tcacaatctt gctcagtcaa cccaaatctt tggacattca       60
agcaactcaa acaaactgaa gtctgtgaat tctgtctcac ttcgcccacg cctttgggga      120
gcatccaaga gtcgcatacc aatgcacaag aatgggagtt tcatgggcaa cttcaatgtt      180
gggaaaggca attctggtgt cttcaaagtt tcagcttctg ttgcagccgc agagaaaccc      240
agcacttccc ctgagattgt tcttgaaccc attaaggact tcagtggaac aatcactctg      300
cctggatcaa agagtctttc aaacagaata cttctcttgg cagctctgag tgaaggaacc      360
actgtagttg acaacctttt gtactctgaa gatattcatt acatgttggg tgctctcaga      420
actcttgggt tgagagttga agatgacaag accacaaaac aagccatagt gaaggatgt      480 ggtgggttgt ttccaacaag caagaatcc aaagatgaga tcaacttgtt tcttggcaat      540
gctggaattg caatgagaag cctcactgct gcagtagttg cagctggtgg aatgcaagt      600 tatgtccttg atggtgtccc cagaatgagg gaaaggccca tcggtgacct tgtggctggc      660
ctgaaacagc ttggagcaga tgttgattgc ttccttgggca caaactgccc tccagtgaga      720
gtgaatggga agggaggttt gcctggtgga aaggtcaaac tgagtggatc agtctcttcc      780
cagtatctga ctgccttgct catggctgcc cctctggctt gggtgatgt ggagattgaa      840 atagtggaca gttgattc tgttccatat gtggaaatga ccctcaaact catggagagg      900
tttggagttt ctgttgaaca ttctggcaac tgggatcgtt tccttgtaca tggaggtcag      960
aagtacaaaa gccctggcaa tgcctttgtt gaaggggatg caagctctgc ttcctatctc     1020
```

| | |
|---|---|
| ttggctgggg ctgccatcac tggtgggacc atcactgtga atggctgtgg caccctcatcc | 1080 |
| cttcaaggtg atgtaaagtt tgcagaggtc ttggagaaaa tgggtgccaa ggtcacctgg | 1140 |
| tctgagaaca gtgtaactgt gtctggacct cccagagact tcagtggcag aaaggttctc | 1200 |
| cgtggaattg atgtgaacat gaacaagatg ccagatgtgg ccatgaccct cgctgttgta | 1260 |
| gccctgtttg caaatggacc aactgcaatc cgtgatgttg cttcatggag ggtgaaggag | 1320 |
| acagagagga tgattgccat ttgcacagaa ctccgcaaac ttggtgcaac agttgaagag | 1380 |
| ggaccagatt actgtgtgat aaccccacct gagaagctca atgtgacagc cattgacacc | 1440 |
| tatgatgacc acagaatggc aatggctttc tcccttgctg cctgtggtga tgtgcctgtg | 1500 |
| actatcaaag accctgggtg cacaaggaag acatttccag actactttga agttttggag | 1560 |
| aggttgacaa agcactgagt agttagctta atcacctag | 1599 |

<210> SEQ ID NO 6
<211> LENGTH: 1551
<212> TYPE: DNA
<213> ORGANISM: Brassica napus

<400> SEQUENCE: 6

| | |
|---|---|
| atggctcaat cttcaaggat tgccacggt gttcagaacc cttgtgtgat catatccaat | 60 |
| ctcagtaaga gcaatcagaa caaatcaccc ttctctgtct ccctcaaaac tcatcaacca | 120 |
| cgtgcatcta gttggggatt gaagaaaagt gggacaatgc tgaacggatc agtcattagg | 180 |
| cctgtaaagg ttacagcctc tgtgtccacg agtgaaaagg caagcgagat cgtcttacaa | 240 |
| ccgattagag aaatctctgg gcttatcaag ttgcctggct ccaaatcact ctccaatagg | 300 |
| atacttcttt tggctgcact gagtgaaggc acaactgttg tggacaactt gctcaactcc | 360 |
| gatgatatca actacatgct tgacgccttg aagaagttag gactcaatgt ggagagagat | 420 |
| agcgttaaca atcgtgctgt cgtagaagga tgtggtggca tctttcctgc atctctggat | 480 |
| tctaagagcg acatcgagct ttacttgggc aatgctgcaa cagccatgag accgttaact | 540 |
| gctgctgtta ccgcagctgg aggaaatgct agttatgtgc ttgatggtgt tccaagaatg | 600 |
| agggaaaggc caatagggga tttggtcgtc ggactgaaac agctcggtgc tgacgttgaa | 660 |
| tgtactttag gcacaaactg tcctcccgtg cgtgttaacg caaatggtgg actgcctggt | 720 |
| ggaaaggtca gttgtctgg ctccatttcc agtcaatacc ttacggcttt gctcatggct | 780 |
| gcaccacttg ccttaggtga tgtggagatt gagatcattg acaagctcat atctgttccg | 840 |
| tacgtggaaa tgacacttaa gctgatggaa agattcggag tttcagccga acattccgat | 900 |
| agctgggatc gtttctttgt aaagggtggg cagaagtaca agtctcctgg caatgcttat | 960 |
| gtggaaggtg acgcttcttc agctagttac ttcttggctg gtgcagccat aactggcgag | 1020 |
| acagttaccg tggaaggatg cggaactacc agcctccaag gtgatgtcaa gttcgcagag | 1080 |
| gtgttggaaa gatggggtg caaagtttcc tggacagaga actcagttac tgtaacggga | 1140 |
| cctagtaggg atgcttttgg gatgcgtcac cttagggcag ttgacgtgaa catgaacaag | 1200 |
| atgccagatg tcgctatgac tttagcagtt gtggcactgt tgccgatgg tcctacaacg | 1260 |
| attagggacg tagcttcttg gagagtcaaa gaaactgaga ggatgatcgc catttgtact | 1320 |
| gagcttcgta agttgggtgc cacagttgaa gaagggtccg attactgcgt gattactcct | 1380 |
| ccagctaaag ttaagcctgc tgagattgat acctatgatg accacagaat ggctatggcc | 1440 |
| tttagcctcg ctgcatgtgc cgatgttcca gtcacgatca aggaccctgg ctgtactaga | 1500 |
| aagacatttc ccgactactt tcaagtgctt gagtcaatca cgaaacactg a | 1551 |

<210> SEQ ID NO 7
<211> LENGTH: 1551
<212> TYPE: DNA
<213> ORGANISM: Brassica napus

<400> SEQUENCE: 7

```
atggctcaat cttcaaggat tgccacggt gttcagaacc cttgtgtgat catatccaat      60
ctcagtaaga gcaatcagaa caaatcaccc ttctctgtct ccctcaaaac tcatcaacca    120
cgtgcatcta gttggggatt gaagaaaagc ggaacaatgc tgaacggatc agtcattagg    180
cctgtaaagg ttactgcatc tgtgtccacg agtgaaaagg caagcgagat cgtcttacaa    240
ccgattagag aaatctctgg gcttatcaag ttgcctggct ccaaatcact ctccaatagg    300
atacttcttt tggctgcact gagtgaaggc acaactgttg tggacaactt gctcaactcc    360
gatgatatca actacatgct tgacgccttg aagaagttag gactcaatgt ggagagagat    420
agcgttaaca atcgtgctgt cgtagaagga tgtggtggaa tctttcctgc atctctggat    480
tctaagagcg acatcgagct ttacttgggc aatgctgcaa cagccatgag atccttaact    540
gctgctgtta ccgcagctgg tggaaatgct agttatgtgc ttgatggtgt tccaagaatg    600
agggaaaggc aatagggga tttggtcgtc ggactcaaac agctcggtgc tgacgttgaa    660
tgtactttag gcacaaactg tcctcccgtc cgtgttaacg caaatggtgg actgcctggt    720
ggaaaagtca agttgtctgg ctccatttcc agtcaatacc ttacggcttt gctcatggct    780
gcaccacttg cctaggtga tgtggagatt gagatcattg acaagctcat atctgttccg    840
tacgtggaaa tgacacttaa gctgatggaa agattcggag tttcagccga acattccgat    900
agctgggatc gtttctttgt aaagggaggg cagaagtaca agtctcctgg aaacgcatac    960
gtggaaggtg acgcttcttc agctagttac ttcttggctg gtgcagccat aactggcgag   1020
acagttaccg tggaaggatg cggaactacc agcctccaag gtgatgtcaa gttcgcagag   1080
gtgttggaaa agatggggtg caaagtttcc tggacagaga actcagttac tgtaacggga   1140
cctagtaggg atgcttttgg gatgcgtcac cttagagccg ttgacgtgaa catgaacaag   1200
atgccagatg tcgctatgac cttagctgtg ttgcactgt ttgccgatgg tcctacaacg   1260
attagggacg tagcctcttg gagagtcaaa gaaaccgaga ggatgatcgc catttgtact   1320
gagcttcgta agttgggtgc cacagttgaa gaagggtccg attactgcgt gattactcct   1380
ccagctaaag ttaagccagc agagattgat acctatgatg accacagaat ggctatggct   1440
ttcagcctcg ctgcatgtgc cgatgttcca gtcacgatca aggaccctgg ctgtactaga   1500
aagacatttc ccgactactt tcaagtgctt gagtcaatca cgaaacactg a             1551
```

<210> SEQ ID NO 8
<211> LENGTH: 1551
<212> TYPE: DNA
<213> ORGANISM: Brassica napus

<400> SEQUENCE: 8

```
atggctcaat cttcaaggat tgccacggt gttcagaacc cttgtgtgat catatccaat      60
ctcagtaaga gcaatcagaa caaatcaccc ttctctgtct ccctgaaaac tcatcaacca    120
cgtgcatcta gttggggatt gaagaaaagt ggcacaatgc tgaacggatc agtcattagg    180
cctgtaaagg ttacagcctc tgtgtccacg agtgaaaagg caagcgagat cgtcttacaa    240
ccgattagag aaatctctgg gcttatcaag ttgcctggct ccaaatcact ctccaatagg    300
```

```
atacttcttt tggctgcact gagtgaaggg acaactgttg tggacaactt gctcaactcc      360
gatgatatca actacatgct tgacgccttg aagaagttag gactcaatgt ggagagagat      420
agcgttaaca atcgtgctgt cgtagaagga tgtggtggaa tctttcctgc atctctggat      480
tctaagagcg acatcgagct ttacttgggc aatgctggca tcgccatgag atccttaact      540
gctgctgtta ccgcagctgg tggaaatgct agttatgtgc ttgatggtgt tccaagaatg      600
agggaaaggc caataggga tttggttgtc ggactcaaac agctcggtgc tgacgttgaa        660
tgtactttag gcacaaactg tcctcccgtg cgtgttaacg caaatggtgg actgcctggt      720
ggaaaggtca agttgtctgg ctccatttcc agtcaatacc ttacggcttt gctcatggct      780
gcaccacttg ccttaggtga tgtggagatt gagatcattg acaagctcat atctgttccg      840
tacgtggaaa tgacacttaa gctgatggaa agattcggag tttcagccga acattccgat      900
agctgggatc gtttcttcgt aaagggaggg cagaagtaca agtctcctgg gaacgcatac      960
gtggaaggtg acgcttcttc agctagttac ttcttggctg gtgcagccat aactggcgag    1020
acagttaccg tggaaggatg cggaactacc agccttcaag tgatgtcaa gttcgcagag     1080
gtgttggaaa agatggggtg caaagttttcc tggacagaga actcagttac tgtaacggga    1140
cctagtaggg atgcttttgg aatgagacac cttaggcag ttgacgtgaa catgaacaag      1200
atgccagatg tcgctatgac tttagctgta gtggcactgt tcgcagatgg tcctacaacg    1260
ataagggacg tagcctcttg gagagtcaaa gaaaccgaga ggatgatcgc catttgtact    1320
gagcttcgta agttgggtgc cacagttgaa gaagggtccg attactgcgt gattactcct    1380
ccagctaaag ttaagccagc agagattgat acctatgatg accacagaat ggctatggcc    1440
tttagcctcg ctgcatgtgc cgatgttcca gtcacgatca aggaccctgg ctgtactaga    1500
aagacatttc ccgactactt tcaagtgctt gagtcaatca cgaaacactg a              1551

<210> SEQ ID NO 9
<211> LENGTH: 1533
<212> TYPE: DNA
<213> ORGANISM: Triticum aestivum

<400> SEQUENCE: 9
atggcaatgg ctgctgctgc tactatggct gcaagcgctt cctcttccgc tgtgagctta      60
gacagagcag ctccagcacc atctaggcgt ctgccaatgc cagcagctag accagctagg    120
agaggtgcag tccgtttgtg gggaccaagg ggagcagctg cacgtgctac aagtgtcgca    180
gcaccagcag caccgagtgg agctgaggaa gtcgtgcttc aacctatcag agagatcagc    240
ggtgccgtcc agctccctgg gtcaaagtca cttagcaaca gaatacttct tttgagcgca    300
ttgtcagagg gcacgacagt ggtggataac cttctgaact ctgaagatgt tcactacatg    360
cttgaggctt tggaggcatt aggtctttct gttgaagccg ataaggttgc taagcgtgct    420
gtggtggttg gttgcggagg gagattccca gttgagaaag atgctcaaga ggaagttaag    480
ctgtttctgg gaaatgctgg gattgcaatg aggagcttga ctgctgctgt ggttgctgct    540
ggtggaaatg ccacatacgt ccttgatgga gtgcctagaa tgagagagag accgattggg    600
gatctggtgg ttggccttca gcaacttgga gcagacgctg actgctttct tggaacaaac    660
tgtccacccg ttaggatcaa cgggaaagga ggtctccctg gtgggaaggt taagttgtct    720
ggatcaatct ctagtcagta tctgtcatca cttctcatgg ctgcacctct tgcacttgaa    780
gatgttgaga ttgaaatcat agacaaactc atatcagttc catacgtgga aatgacgctg    840
aagctgatgg agaggttcgg agtgacagca gagcactcag attcttggga taggttctac    900
```

```
atcaaggag gtcagaagta caaatcacct gggaacgctt acgtggaagg tgatgcctct    960
tctgcttcct acttcctcgc tggagcagca atcaccggag gaactgttac tgtcgaaggt   1020
tgcggaacta cttccttgca aggggacgtc aagttcgcag aagtcttaga atgatggga    1080 gctaaagtta cttggaccga tacaagtgtt acagtgactg gtcctccacg tcaaccctt    1140 ggaaggaagc acctcaaagc cgttgatgtt aacatgaaca agatgccaga tgtcgccatg   1200
acgcttgccg ttgtggctct gttcgcagat ggtcccacag ccattagaga cgtggccagc   1260
tggagggtga agaaactga aggatggtc gccattagaa cagagttaac caaacttgga    1320
gctactgtgg aagagggacc cgactattgc atcattacac ctcccgagaa gctgaacata   1380
accgctattg acacttatga tgatcatcgt atggctatgg ccttttcatt agcagcttgc   1440
gctgaggtgc cagtaaccat tagagatcct gggtgtacta ggaaaacttt ccctaactac   1500
ttcgatgtcc tttcaacatt cgtgaagaat tga                                1533
```

<210> SEQ ID NO 10
<211> LENGTH: 1281
<212> TYPE: DNA
<213> ORGANISM: Streptomyces roseosporus

<400> SEQUENCE: 10

```
atgacggtga tagagatacc tgggtctaag tctgttacag ccagagcact gttcttggca     60
gctgctgccg atgggacgac tactcttctt agaccattgc gtagcgatga cactgagggc    120
ttcgcagaag gactgaggaa tctgggctat gctgtggaac aagaggctga taggtggcgt    180
gtccaaggca gaccagctgg accagcagcc acggaagcag atgtctattg cagagatggt    240
gccaccaccg ctaggttcct tccgacactg cagcagcag ctgcttccgg aacctacaga     300
ttcgacgctt cagcacagat gcgtcgtcgt ccccttgctc cattgacaag ggcacttaca    360
gccttgggtg tggatcttag acacgaagga gcagacggac atcatccgct caccgttcgt    420
gcagctggca tcgaaggagg agaattgacg ctcgacgctg gcgagtccag ccaatacttg    480
acagcactgc tcatgctcgg acctcttaca caaagggac ttcgcatcga agttacagaa      540
ctcgtctctg caccctacgt ggaaatcacc ctcgctatga tgagagactt tggtgtggag    600
gttgagaggg agggaatac cttcaccgtt ccaagcccat cttcaagact taggtccaat     660
agaggtggac ccataggagg ctatagagct actacgtatg ctgtcgagcc agatgcctca    720
actgcctctt acttctttgc agctgctgcc ctcactggtc gcgaggtcac agtgcctgga    780
ttggggactg gagctttgca aggtgatttg cgtttcgtgg atgtgctgag agaaatgggt    840
gccgaggtgt ctgttggtcc ggacgccaca actgtgcgct caactggcag attgagggga    900
atcactgtga acatgagaga tatctcagac acgatgccta cactcgcagc tattgcacct    960
tatgccgatg gtccagtggt gattgaagat gttgccaaca cccgtgtgaa ggagtgtgac   1020
cgtctggagg cttgtgctga gaatctgagg gcaatgggaa tcaccgtcca tacgggtccg   1080
gataggatag aaatccatcc tggaacacct aaaccgactg ggatcgccac ccacggagat   1140
caccgcatag tcatgtcatt tgccgtcgct ggccttcgca ctcctggcct cacttacgac   1200
gaccctggct gcgtgcgtaa gaccttccct agatttcacg aggtgtttgc cgacttcgct   1260
cacgaccttg agggaaggtg a                                             1281
```

<210> SEQ ID NO 11
<211> LENGTH: 1248
<212> TYPE: DNA

<213> ORGANISM: Streptomyces griseus

<400> SEQUENCE: 11

| | |
|---|---|
| atgggtgcag tgacagtcat cgacattcct ggaagcaaga gcgtgacagc aagggcactc | 60 |
| ttcttggcag cagcagccga tggaacgaca acactgcttc gtcctctgag gtcagacgac | 120 |
| acggaggggt ttgccgaggg tcttaagaat ctcggttatg ccgttgagca agaggctgac | 180 |
| cgttggaggg tcgaaggcag accggatggt ccagctgctc cggatgcaga tgtctactgc | 240 |
| cgtgatggtg caacgactgc acgctttctt ccaaccctcg tcgcagcagc agcttctgga | 300 |
| acgtatcgtt tcgacgcctc agcacagatg aggagacgtc ccttggctcc actcactagg | 360 |
| gcactgacag ctcttggcgt ggatttgaga catggtggag aggagggtca tcatccactg | 420 |
| actgtcagag ctgctggcat agaaggtggc gatgttgtcc ttgacgctgg tgaatcttct | 480 |
| cagtatctca cagcccttct tatgttgggt ccgttgactg ccaaaggtct tagaatcgaa | 540 |
| gtcactgatc tcgtgagcgc tccttacgtt gaaatcactc tggccatgat gagagatttc | 600 |
| ggagttgatg ttagcagaga aggaaacact ttcaccgtgc cgtccggagg ctatagagct | 660 |
| acagcctacg ctgtggagcc agacgcaagc acggcttctt acttctttgc agcagctgcc | 720 |
| ctcactggac gcgaggtgac ggtccctggg ctgggaattg tgctcttca aggagacctt | 780 |
| cgttttgtgg acgtgctgcg tgatatggga gcagaggtgt ctgttggacc agatgccacg | 840 |
| acagtgcgct caactggcag actccgtggc attacagtta ctatgagaga catttcagac | 900 |
| acgatgccaa cactcgctgc tattgcacct cacgctgatg acccgtccg tattgaggac | 960 |
| gtggcaaaca ctcgtgtcaa ggaatgtgat aggcttgagg catgtgctca aaaccttaga | 1020 |
| gctatgggaa tcacggtgca tactgggcac gattggattg agattctccc tgggactcca | 1080 |
| aagccaacgg gaatagctac gcacggagat cacagaatcg ttatgtcctt cgcagtggct | 1140 |
| ggtttgttga cccctgggct gacatacgat gatcctggct gcgtccgcaa gacttttcca | 1200 |
| aggttccacg aagttttcgc tgactttgct gcatcacccc aagcctga | 1248 |

<210> SEQ ID NO 12
<211> LENGTH: 1368
<212> TYPE: DNA
<213> ORGANISM: Glycine max

<400> SEQUENCE: 12

| | |
|---|---|
| atggcaagcg ttgcagcagc agaaaaaccg agcacctctc cggaaattgt tctggaaccg | 60 |
| attaaagatt ttagcggcac cattaccctg cctggtagca aaagcctgag caatcgtatt | 120 |
| ctgctgctgg cagcactgag cgaaggcacc accgttgttg ataatctgct gtatagcgaa | 180 |
| gatattcatt atatgctggg tgcactgcgt accctgggtc tgcgtgttga agatgataaa | 240 |
| accaccaaac aggccattgt tgaaggttgt ggtggtctgt ttccgaccag caaagaaagc | 300 |
| aaagatgaaa ttaacctgtt tctgggtaat gcaggcaccg caatgcgtcc gctgaccgca | 360 |
| gcagttgttg cagccggtgg taatgcaagc tatgttctgg atggtgttcc gcgtatgcgt | 420 |
| gaacgtccga ttggtgatct ggttgccggt ctgaacagc tgggtgcaga tgttgattgt | 480 |
| tttctgggca ccaattgtcc tccggttcgt gttaatggta aaggtggtct gccgggtggt | 540 |
| aaagttaaac tgagcggtag cgttagcagc cagtatctga ccgcactgct gatggcagct | 600 |
| ccgctggcac tggtgatgt tgaaattgaa attgtggata aactgattc tgtgccgtat | 660 |
| gttgaaatga ccctgaaact gatggaacgt tttggtgtta gcgttgaaca tagcggtaat | 720 |
| tgggatcgtt ttctggttca tggtggccag aaatataaat ctccgggtaa tgcctttgtt | 780 |

```
gaaggtgatg caagcagcgc aagctatctg ctggcaggcg cagcaattac cggtggtaca    840
attaccgtta atggttgtgg caccagcagc ctgcagggcg atgttaaatt tgccgaagtg    900
ctggaaaaaa tgggtgcaaa agtgacctgg tctgaaaata gcgttaccgt tagcggtccg    960
ccgcgtgatt ttagcggtcg taaagttctg cgtggcattg atgtgaatat gaacaaaatg   1020
ccggatgttg ccatgaccct ggcagttgtt gccctgtttg caaatggtcc gaccgcaatt   1080
cgtgatgttg caagctggcg tgttaaagaa accgaacgca tgattgcaat ttgtaccgaa   1140
ctgcgtaaac tgggtgcaac cgttgaagaa ggtccggatt attgcgttat tacaccgccg   1200
gaaaaactga atgttaccgc cattgatacc tatgatgatc atcgtatggc aatggcattt   1260
agcctggcag catgtggtga tgttccggtg accattaaag atccgggttg tacacgtaaa   1320
acctttccag attattttga agttctggaa cgcctgacca acattaa                 1368
```

<210> SEQ ID NO 13
<211> LENGTH: 1368
<212> TYPE: DNA
<213> ORGANISM: Glycine max

<400> SEQUENCE: 13

```
atggcaagcg ttgcagcagc agaaaaaccg agcacctctc cggaaattgt tctggaaccg     60
attaaagatt ttagcggcac cattaccctg cctggtagca aaagcctgag caatcgtatt    120
ctgctgctgg cagcactgag cgaaggcacc accgttgttg ataatctgct gtatagcgaa    180
gatattcatt atatgctggg tgcactgcgt accctgggtc tgcgtgttga agatgataaa    240
accaccaaac aggccattgt tgaaggttgt ggtggtctgt ttccgaccag caaagaaagc    300
aaagatgaaa ttaacctgtt tctgggtaat gcagcaaccg caatgcgtcc gctgaccgca    360
gcagttgttg cagccggtgg taatgcaagc tatgttctgg atggtgttcc gcgtatgcgt    420
gaacgtccga ttggtgatct ggttgccggt ctgaaacagc tgggtgcaga tgttgattgt    480
tttctgggca ccaattgtcc tccggttcgt gttaatggta aggtggtctt gccgggtggt    540
aaagttaaac tgagcggtag cgttagcagc cagtatctga ccgcactgct gatggcagct    600
ccgctggcac tgggtgatgt tgaaattgaa attgtggata aactgatttc tgtgccgtat    660
gttgaaatga ccctgaaact gatggaacgt tttggtgtta gcgttgaaca tagcggtaat    720
tgggatcgtt ttctggttca tggtggccag aaatataaat ctccgggtaa tgcctttgtt    780
gaaggtgatg caagcagcgc aagctatctg ctggcaggcg cagcaattac cggtggtaca    840
attaccgtta atggttgtgg caccagcagc ctgcagggcg atgttaaatt tgccgaagtg    900
ctggaaaaaa tgggtgcaaa agtgacctgg tctgaaaata gcgttaccgt tagcggtccg    960
ccgcgtgatt ttagcggtcg taaagttctg cgtggcattg atgtgaatat gaacaaaatg   1020
ccggatgttg ccatgaccct ggcagttgtt gccctgtttg caaatggtcc gaccgcaatt   1080
cgtgatgttg caagctggcg tgttaaagaa accgaacgca tgattgcaat ttgtaccgaa   1140
ctgcgtaaac tgggtgcaac cgttgaagaa ggtccggatt attgcgttat tacaccgccg   1200
gaaaaactga atgttaccgc cattgatacc tatgatgatc atcgtatggc aatggcattt   1260
agcctggcag catgtggtga tgttccggtg accattaaag atccgggttg tacacgtaaa   1320
acctttccag attattttga agttctggaa cgcctgacca acattaa                 1368
```

<210> SEQ ID NO 14
<211> LENGTH: 1368
<212> TYPE: DNA

<213> ORGANISM: Glycine max

<400> SEQUENCE: 14

| | | | | | |
|---|---|---|---|---|---|
| atggcaagcg | ttgcagcagc | agaaaaaccg | agcacctctc | cggaaattgt | tctggaaccg | 60 |
| attaaagatt | ttagcggcac | cattaccctg | cctggtagca | aaagcctgag | caatcgtatt | 120 |
| ctgctgctgg | cagcactgag | cgaaggcacc | accgttgttg | ataatctgct | gtatagcgaa | 180 |
| gatattcatt | atatgctggg | tgcactgcgt | accctgggtc | tgcgtgttga | agatgataaa | 240 |
| accaccaaac | aggccattgt | tgaaggttgt | ggtggtctgt | ttccgaccag | caaagaaagc | 300 |
| aaagatgaaa | ttaacctgtt | tctgggtaat | gcagcaaccg | caatgcgtag | cctgaccgca | 360 |
| gcagttgttg | cagccggtgg | taatgcaagc | tatgttctgg | atggtgttcc | gcgtatgcgt | 420 |
| gaacgtccga | ttggtgatct | ggttgccggt | ctgaaacagc | tgggtgcaga | tgttgattgt | 480 |
| tttctgggca | ccaattgtcc | tccggttcgt | gttaatggta | aggtggtct | gccgggtggt | 540 |
| aaagttaaac | tgagcggtag | cgttagcagc | cagtatctga | ccgcactgct | gatggcagct | 600 |
| ccgctggcac | tgggtgatgt | tgaaattgaa | attgtggata | aactgatttc | tgtgccgtat | 660 |
| gttgaaatga | ccctgaaact | gatggaacgt | tttggtgtta | gcgttgaaca | tagcggtaat | 720 |
| tgggatcgtt | ttctggttca | tggtggccag | aaatataaat | ctccgggtaa | tgcctttgtt | 780 |
| gaaggtgatg | caagcagcgc | aagctatctg | ctggcaggcg | cagcaattac | cggtggtaca | 840 |
| attaccgtta | tggttgtgg | caccagcagc | ctgcagggcg | atgttaaatt | tgccgaagtg | 900 |
| ctggaaaaaa | tgggtgcaaa | agtgacctgg | tctgaaaata | gcgttaccgt | tagcggtccg | 960 |
| ccgcgtgatt | ttagcggtcg | taaagttctg | cgtggcattg | atgtgaatat | gaacaaaatg | 1020 |
| ccggatgttg | ccatgaccct | ggcagttgtt | gccctgtttg | caaatggtcc | gaccgcaatt | 1080 |
| cgtgatgttg | caagctggcg | tgttaaagaa | accgaacgca | tgattgcaat | ttgtaccgaa | 1140 |
| ctgcgtaaac | tgggtgcaac | cgttgaagaa | ggtccggatt | attgcgttat | tacaccgccg | 1200 |
| gaaaaactga | atgttaccgc | cattgatacc | tatgatgatc | atcgtatggc | aatggcattt | 1260 |
| agcctggcag | catgtggtga | tgttccggtg | accattaaag | atccggggttg | tacacgtaaa | 1320 |
| acctttccag | attattttga | agttctggaa | cgcctgacca | aacattaa | | 1368 |

<210> SEQ ID NO 15
<211> LENGTH: 1368
<212> TYPE: DNA
<213> ORGANISM: Glycine max

<400> SEQUENCE: 15

| | | | | | |
|---|---|---|---|---|---|
| atggcaagcg | ttgcagcagc | agaaaaaccg | agcacctctc | cggaaattgt | tctggaaccg | 60 |
| attaaagatt | ttagcggcac | cattaccctg | cctggtagca | aaagcctgag | caatcgtatt | 120 |
| ctgctgctgg | cagcactgag | cgaaggcacc | accgttgttg | ataatctgct | gtatagcgaa | 180 |
| gatattcatt | atatgctggg | tgcactgcgt | accctgggtc | tgcgtgttga | agatgataaa | 240 |
| accaccaaac | aggccattgt | tgaaggttgt | ggtggtctgt | ttccgaccag | caaagaaagc | 300 |
| aaagatgaaa | ttaacctgtt | tctgggtaat | gcaggcatcg | caatgcgtag | cctgaccgca | 360 |
| gcagttgttg | cagccggtgg | taatgcaagc | tatgttctgg | atggtgttcc | gcgtatgcgt | 420 |
| gaacgtccga | ttggtgatct | ggttgccggt | ctgaaacagc | tgggtgcaga | tgttgattgt | 480 |
| tttctgggca | ccaattgtcc | tccggttcgt | gttaatggta | aggtggtct | gccgggtggt | 540 |
| aaagttaaac | tgagcggtag | cgttagcagc | cagtatctga | ccgcactgct | gatggcagct | 600 |
| ccgctggcac | tgggtgatgt | tgaaattgaa | attgtggata | aactgatttc | tgtgccgtat | 660 |

```
gttgaaatga ccctgaaact gatggaacgt tttggtgtta gcgttgaaca tagcggtaat    720
tgggatcgtt ttctggttca tggtggccag aaatataaat ctccgggtaa tgcctttgtt    780
gaaggtgatg caagcagcgc aagctatctg ctggcaggcg cagcaattac cggtggtaca    840
attaccgtta atggttgtgg caccagcagc ctgcagggcg atgttaaatt tgccgaagtg    900
ctggaaaaaa tgggtgcaaa agtgacctgg tctgaaaata gcgttaccgt tagcggtccg    960
ccgcgtgatt ttagcggtcg taaagttctg cgtggcattg atgtgaatat gaacaaaatg   1020
ccggatgttg ccatgaccct ggcagttgtt gccctgtttg caaatggtcc gaccgcaatt   1080
cgtgatgttg caagctggcg tgttaaagaa accgaacgca tgattgcaat ttgtaccgaa   1140
ctgcgtaaac tgggtgcaac cgttgaagaa ggtccggatt attgcgttat tacaccgccg   1200
gaaaaactga atgttaccgc cattgatacc tatgatgatc atcgtatggc aatggcattt   1260
agcctggcag catgtggtga tgttccggtg accattaaag atccgggttg tacacgtaaa   1320
acctttccag attattttga agttctggaa cgcctgacca aacattaa                1368
```

<210> SEQ ID NO 16
<211> LENGTH: 1350
<212> TYPE: DNA
<213> ORGANISM: Brassica napus

<400> SEQUENCE: 16

```
atgaccagcg aaaaagccag cgaaattgtt ctgcagccga ttcgtgaaat tagcggtctg     60
attaaactgc ctggtagcaa aagcctgagc aatcgtattc tgctgctggc agcactgagc    120
gaaggcacca ccgttgttga taatctgctg aacagcgacg atattaacta tatgctggat    180
gccctgaaaa aactgggtct gaatgttgaa cgtgatagcg ttaataatcg tgccgttgtt    240
gaaggttgtg gtggcatttt tccggcaagc ctggatagca aatccgatat cgaactgtat    300
ctgggtaatg cagccaccgc aatgcgtccg ctgaccgcag cagttaccgc agccggtggt    360
aatgcaagct atgttctgga tggtgttccg cgtatgcgtg aacgtccgat tggtgatctg    420
gttgttggtc tgaaacagct gggtgcagat gttgaatgta ccctgggcac caattgtccg    480
cctgttcgtg ttaatgcaaa tggtggtctg cctggtggta aagttaaact gagcggtagc    540
attagcagcc agtatctgac cgcactgctg atggcagctc cgctggcact gggtgatgtt    600
gaaatcgaga ttattgataa actgatcagc gttccgtatg ttgaaatgac cctgaaactg    660
atggaacgtt tggtgttag cgcagaacat agcgatagct gggatcgctt ttttgttaaa    720
ggtggccaga aatataaatc tccgggtaac gcctatgttg aaggtgatgc aagcagcgca    780
tcttattttc tggcaggcgc agcaattacc ggtgaaaccg ttaccgttga aggttgcggt    840
acaaccagcc tgcagggtga tgttaaattt gccgaagtgc tggaaaaaat gggttgtaaa    900
gtgagctgga ccgaaaatag cgttaccgtt accggtccga gccgtgatgc atttggtatg    960
cgtcatctgc gtcagttga tgtgaacatg aacaaaatgc cggatgttgc catgaccctg   1020
gcagttgttg cactgtttgc agatggtccg accaccattc gtgatgttgc aagctggcgt   1080
gttaaagaaa ccgaacgcat gattgcaatt tgtaccgaac tgcgtaaact gggtgcaacc   1140
gttgaagaag gtagcgatta ttgcgttatt accccctccg gcaaagttaa ccggcagaa   1200 atcgatacct atgatgatca tcgtatggca atggcattta gcctggcagc atgtgcagat   1260
gttccggtga ccattaaaga tccgggttgt acacgtaaaa cctttccgga ttattttcag   1320
gtgctggaaa gcatcaccaa acactaataa                                    1350
```

<210> SEQ ID NO 17
<211> LENGTH: 1347
<212> TYPE: DNA
<213> ORGANISM: Brassica napus

<400> SEQUENCE: 17

| | | | | | | |
|---|---|---|---|---|---|---|
| atgaccagcg | aaaaagccag | cgaaattgtt | ctgcagccga | ttcgtgaaat | tagcggtctg | 60 |
| attaaactgc | ctggtagcaa | aagcctgagc | aatcgtattc | tgctgctggc | agcactgagc | 120 |
| gaaggcacca | ccgttgttga | taatctgctg | aacagcgacg | atattaacta | tatgctggat | 180 |
| gccctgaaaa | aactgggtct | gaatgttgaa | cgtgatagcg | ttaataatcg | tgccgttgtt | 240 |
| gaaggttgtg | gtggcatttt | tccggcaagc | ctggatagca | aatccgatat | cgaactgtat | 300 |
| ctgggtaatg | cagccaccgc | aatgcgtagc | ctgaccgcag | cagttaccgc | agccggtggt | 360 |
| aatgcaagct | atgttctgga | tggtgttccg | cgtatgcgtg | aacgtccgat | tggtgatctg | 420 |
| gttgttggtc | tgaaacagct | gggtgcagat | gttgaatgta | ccctgggcac | caattgtccg | 480 |
| cctgttcgtg | ttaatgcaaa | tggtggtctg | cctggtggta | aagttaaaact | gagcggtagc | 540 |
| attagcagcc | agtatctgac | cgcactgctg | atggcagctc | cgctggcact | gggtgatgtt | 600 |
| gaaatcgaga | ttattgataa | actgatcagc | gttccgtatg | ttgaaatgac | cctgaaactg | 660 |
| atggaacgtt | ttggtgttag | cgcagaacat | agcgatagct | gggatcgctt | ttttgttaaa | 720 |
| ggtggccaga | atataaaatc | tccgggtaac | gcctatgttg | aaggtgatgc | aagcagcgca | 780 |
| tcttattttc | tggcaggcgc | agcaattacc | ggtgaaaccg | ttaccgttga | aggttgcggt | 840 |
| acaaccagcc | tgcagggtga | tgttaaattt | gccgaagtgc | tggaaaaaat | gggttgtaaa | 900 |
| gtgagctgga | ccgaaaatag | cgttaccgtt | accggtccga | gccgtgatgc | atttggtatg | 960 |
| cgtcatctgc | gtgcagttga | tgtgaacatg | aacaaaatgc | cggatgttgc | catgaccctg | 1020 |
| gcagttgttg | cactgttttgc | agatggtccg | accaccattc | gtgatgttgc | aagctggcgt | 1080 |
| gttaaagaaa | ccgaacgcat | gattgcaatt | tgtaccgaac | tgcgtaaact | gggtgcaacc | 1140 |
| gttgaagaag | gtagcgatta | ttgcgttatt | acccctccgg | caaaagttaa | accggcagaa | 1200 |
| atcgatacct | atgatgatca | tcgtatggca | atggcatttta | gcctggcagc | atgtgcagat | 1260 |
| gttccggtga | ccattaaaga | tccgggttgt | acacgtaaaa | cctttccgga | ttattttcag | 1320 |
| gtgctggaaa | gcatcaccaa | acactaa | | | | 1347 |

<210> SEQ ID NO 18
<211> LENGTH: 1350
<212> TYPE: DNA
<213> ORGANISM: Brassica napus

<400> SEQUENCE: 18

| | | | | | | |
|---|---|---|---|---|---|---|
| atgaccagcg | aaaaagccag | cgaaattgtt | ctgcagccga | ttcgtgaaat | tagcggtctg | 60 |
| attaaactgc | ctggtagcaa | aagcctgagc | aatcgtattc | tgctgctggc | agcactgagc | 120 |
| gaaggcacca | ccgttgttga | taatctgctg | aacagcgacg | atattaacta | tatgctggat | 180 |
| gccctgaaaa | aactgggtct | gaatgttgaa | cgtgatagcg | ttaataatcg | tgccgttgtt | 240 |
| gaaggttgtg | gtggcatttt | tccggcaagc | ctggatagca | aatccgatat | cgaactgtat | 300 |
| ctgggtaatg | caggtattgc | aatgcgtagc | ctgaccgcag | cagttaccgc | agccggtggt | 360 |
| aatgcaagct | atgttctgga | tggtgttccg | cgtatgcgtg | aacgtccgat | tggtgatctg | 420 |
| gttgttggtc | tgaaacagct | gggtgcagat | gttgaatgta | ccctgggcac | caattgtccg | 480 |
| cctgttcgtg | ttaatgcaaa | tggtggtctg | cctggtggta | aagttaaaact | gagcggtagc | 540 |

| | |
|---|---|
| attagcagcc agtatctgac cgcactgctg atggcagctc cgctggcact gggtgatgtt | 600 |
| gaaatcgaga ttattgataa actgatcagc gttccgtatg ttgaaatgac cctgaaactg | 660 |
| atggaacgtt ttggtgttag cgcagaacat agcgatagct gggatcgctt ttttgttaaa | 720 |
| ggtggccaga aatataaatc tccgggtaac gcctatgttg aaggtgatgc aagcagcgca | 780 |
| tcttattttc tggcaggcgc agcaattacc ggtgaaaccg ttaccgttga aggttgcggt | 840 |
| acaaccagcc tgcagggtga tgttaaattt gccgaagtgc tggaaaaaat gggttgtaaa | 900 |
| gtgagctgga ccgaaaatag cgttaccgtt accggtccga gccgtgatgc atttggtatg | 960 |
| cgtcatctgc gtgcagttga tgtgaacatg aacaaaatgc cggatgttgc catgaccctg | 1020 |
| gcagttgttg cactgtttgc agatggtccg accaccattc gtgatgttgc aagctggcgt | 1080 |
| gttaaagaaa ccgaacgcat gattgcaatt tgtaccgaac tgcgtaaact gggtgcaacc | 1140 |
| gttgaagaag gtagcgatta ttgcgttatt accccctccgg caaaagttaa accggcagaa | 1200 |
| atcgatacct atgatgatca tcgtatggca atggcattta gcctggcagc atgtgcagat | 1260 |
| gttccggtga ccattaaaga tccgggttgt acacgtaaaa cctttccgga ttattttcag | 1320 |
| gtgctggaaa gcatcaccaa acactaataa | 1350 |

<210> SEQ ID NO 19
<211> LENGTH: 1371
<212> TYPE: DNA
<213> ORGANISM: Triticum aestivum

<400> SEQUENCE: 19

| | |
|---|---|
| atggcaacca gcgttgcagc accggcagct ccgtctggtg ccgaagaagt tgttctgcag | 60 |
| ccgattcgtg aaattagcgg tgcagttcag ctgcctggta gcaaaagcct gagcaatcgt | 120 |
| attctgctgc tgtctgcact gagcgaaggc accaccgttg ttgataatct gctgaatagc | 180 |
| gaagatgtgc attatatgct ggaagcactg gaagccctgg gtctgagcgt tgaagcagat | 240 |
| aaagttgcaa acgtgccgt tgttgttggt tgtggtggtc gttttccggt tgaaaaagat | 300 |
| gcacaggaag aagttaaaact gtttctgggt aatgccggta ccgcaatgcg tccgctgacc | 360 |
| gcagcagttg ttgcagccgg tggtaatgca acctatgttc tggatggtgt tccgcgtatg | 420 |
| cgtgaacgtc cgattggtga tctggttgtt ggtctgcagc agctgggtgc agatgcagat | 480 |
| tgttttctgg gcaccaattg tcctccggtt cgtattaatg gtaaaggtgg tctgccgggt | 540 |
| ggtaaagtta aactgagcgg tagcattagc agccagtatc tgagcagcct gctgatggca | 600 |
| gcaccgctgg cactggaaga tgtggaaatt gaaattattg ataaactgat tagcgtgccg | 660 |
| tatgttgaaa tgaccctgaa actgatggaa cgttttggtg ttaccgcaga acatagcgat | 720 |
| agctgggatc gcttttatat taaaggtggc agaaatatata atctccgggt aatgcctat | 780 |
| gttgaaggtg atgcaagcag cgcaagctat tttctggcag gcgcagcaat taccggtggc | 840 |
| accgttaccg ttgaaggttg tggtacaacc agcctgcagg gtgatgttaa atttgccgaa | 900 |
| gtgctggaaa tgatgggtgc aaaagttacc tggaccgata ccagcgttac cgttaccggt | 960 |
| ccgccgcgtc agccgtttgg tcgtaaacat ctgaaagccg tggatgtgaa tatgaataaa | 1020 |
| atgccggatg ttgccatgac cctggcagtt gttgccctgt ttgcagatgg tccgaccgca | 1080 |
| attcgtgatg ttgcaagctg gcgtgttaaa gaaaccgaac gtatggttgc aattcgtacc | 1140 |
| gaactgacca aactgggtgc aaccgttgaa gaaggtccgg attattgcat tattacaccg | 1200 |
| ccggaaaaac tgaatattac cgccattgat acctatgatg atcatcgtat ggcaatggca | 1260 |

```
tttagcctgg cagcatgtgc agaagttccg gttaccattc gtgatccggg ttgtacacgt    1320
aaaacctttc cgaattattt tgatgttctg agcacctttg tgaaaaatta a             1371

<210> SEQ ID NO 20
<211> LENGTH: 1371
<212> TYPE: DNA
<213> ORGANISM: Triticum aestivum

<400> SEQUENCE: 20
atggcaacca gcgttgcagc accggcagct ccgtctggtg ccgaagaagt tgttctgcag     60
ccgattcgtg aaattagcgg tgcagttcag ctgcctggta gcaaaagcct gagcaatcgt    120
attctgctgc tgtctgcact gagcgaaggc accaccgttg ttgataatct gctgaatagc    180
gaagatgtgc attatatgct ggaagcactg gaagccctgg gtctgagcgt tgaagcagat    240
aaagttgcaa acgtgccgt  tgttgttggt tgtggtggtc gttttccggt tgaaaaagat    300
gcacaggaag aagttaaact gtttctgggt aatgccgcaa ccgcaatgcg tccgctgacc    360
gcagcagttg ttgcagccgg tggtaatgca acctatgttc tggatggtgt tccgcgtatg    420
cgtgaacgtc cgattggtga tctggttgtt ggtctgcagc agctgggtgc agatgcagat    480
tgttttctgg gcaccaattg tcctccggtt cgtattaatg gtaaaggtgg tctgccgggt    540
ggtaaagtta aactgagcgg tagcattagc agccagtatc tgagcagcct gctgatggca    600
gcaccgctgg cactggaaga tgtggaaatt gaaattattg taaaactgat tagcgtgccg    660
tatgttgaaa tgaccctgaa actgatggaa cgttttggtg ttaccgcaga acatagcgat    720
agctgggatc gcttttatat taaaggtggc cagaaatata atctcccggg taatgcctat    780
gttgaaggtg atgcaagcag cgcaagctat tttctggcag gcgcagcaat taccggtggc    840
accgttaccg ttgaaggttg tggtacaacc agcctgcagg gtgatgttaa atttgccgaa    900
gtgctggaaa tgatgggtgc aaaagttacc tggaccgata ccagcgttac cgttaccggt    960
ccgccgcgtc agccgtttgg tcgtaaacat ctgaaagccg tggatgtgaa tatgaataaa   1020
atgccggatg ttgccatgac cctggcagtt gttgccctgt ttgcagatgg tccgaccgca   1080
attcgtgatg ttgcaagctg gcgtgttaaa gaaaccgaac gtatggttgc aattcgtacc   1140
gaactgacca aactgggtgc aaccgttgaa gaaggtccgg attattgcat tattacaccg   1200
ccggaaaaac tgaatattac cgccattgat acctatgatg atcatcgtat ggcaatggca   1260
tttagcctgg cagcatgtgc agaagttccg gttaccattc gtgatccggg ttgtacacgt   1320
aaaacctttc cgaattattt tgatgttctg agcacctttg tgaaaaatta a            1371

<210> SEQ ID NO 21
<211> LENGTH: 1371
<212> TYPE: DNA
<213> ORGANISM: Triticum aestivum

<400> SEQUENCE: 21
atggcaacca gcgttgcagc accggcagct ccgtctggtg ccgaagaagt tgttctgcag     60
ccgattcgtg aaattagcgg tgcagttcag ctgcctggta gcaaaagcct gagcaatcgt    120
attctgctgc tgtctgcact gagcgaaggc accaccgttg ttgataatct gctgaatagc    180
gaagatgtgc attatatgct ggaagcactg gaagccctgg gtctgagcgt tgaagcagat    240
aaagttgcaa acgtgccgt  tgttgttggt tgtggtggtc gttttccggt tgaaaaagat    300
gcacaggaag aagttaaact gtttctgggt aatgccgcaa ccgcaatgcg tagcctgacc    360
gcagcagttg ttgcagccgg tggtaatgca acctatgttc tggatggtgt tccgcgtatg    420
```

-continued

```
cgtgaacgtc cgattggtga tctggttgtt ggtctgcagc agctgggtgc agatgcagat    480
tgttttctgg gcaccaattg tcctccggtt cgtattaatg gtaaaggtgg tctgccgggt    540
ggtaaagtta aactgagcgg tagcattagc agccagtatc tgagcagcct gctgatggca    600
gcaccgctgg cactggaaga tgtggaaatt gaaattattg ataaactgat tagcgtgccg    660
tatgttgaaa tgaccctgaa actgatggaa cgttttggtg ttaccgcaga acatagcgat    720
agctgggatc gcttttatat taaaggtggc cagaaatata aatctccggg taatgcctat    780
gttgaaggtg atgcaagcag cgcaagctat tttctggcag gcgcagcaat taccggtggc    840
accgttaccg ttgaaggttg tggtacaacc agcctgcagg gtgatgttaa atttgccgaa    900
gtgctggaaa tgatgggtgc aaaagttacc tggaccgata ccagcgttac cgttaccggt    960
ccgccgcgtc agccgtttgg tcgtaaacat ctgaaagccg tggatgtgaa tatgaataaa   1020
atgccggatg ttgccatgac cctggcagtt gttgccctgt ttgcagatgg tccgaccgca   1080
attcgtgatg ttgcaagctg gcgtgttaaa gaaaccgaac gtatggttgc aattcgtacc   1140
gaactgacca aactgggtgc aaccgttgaa gaaggtccgg attattgcat tattacaccg   1200
ccggaaaaac tgaatattac cgccattgat acctatgatg atcatcgtat ggcaatggca   1260
tttagcctgg cagcatgtgc agaagttccg gttaccattc gtgatccggg ttgtacacgt   1320
aaaacctttc cgaattattt tgatgttctg agcacctttg tgaaaaatta a            1371
```

<210> SEQ ID NO 22
<211> LENGTH: 1371
<212> TYPE: DNA
<213> ORGANISM: Triticum aestivum

<400> SEQUENCE: 22

```
atggcaacca gcgttgcagc accggcagct ccgtctggtg ccgaagaagt tgttctgcag     60
ccgattcgtg aaattagcgg tgcagttcag ctgcctggta gcaaaagcct gagcaatcgt    120
attctgctgc tgtctgcact gagcgaaggc accaccgttg ttgataatct gctgaatagc    180
gaagatgtgc attatatgct ggaagcactg gaagccctgg gtctgagcgt tgaagcagat    240
aaagttgcaa acgtgccgt tgttgttggt tgtggtggtc gttttccggt tgaaaaagat    300
gcacaggaag aagttaaact gtttctgggt aatgccggta ttgcaatgcg tagcctgacc    360
gcagcagttg ttgcagccgg tggtaatgca acctatgttc tggatggtgt tccgcgtatg    420
cgtgaacgtc cgattggtga tctggttgtt ggtctgcagc agctgggtgc agatgcagat    480
tgttttctgg gcaccaattg tcctccggtt cgtattaatg gtaaaggtgg tctgccgggt    540
ggtaaagtta aactgagcgg tagcattagc agccagtatc tgagcagcct gctgatggca    600
gcaccgctgg cactggaaga tgtggaaatt gaaattattg ataaactgat tagcgtgccg    660
tatgttgaaa tgaccctgaa actgatggaa cgttttggtg ttaccgcaga acatagcgat    720
agctgggatc gcttttatat taaaggtggc cagaaatata aatctccggg taatgcctat    780
gttgaaggtg atgcaagcag cgcaagctat tttctggcag gcgcagcaat taccggtggc    840
accgttaccg ttgaaggttg tggtacaacc agcctgcagg gtgatgttaa atttgccgaa    900
gtgctggaaa tgatgggtgc aaaagttacc tggaccgata ccagcgttac cgttaccggt    960
ccgccgcgtc agccgtttgg tcgtaaacat ctgaaagccg tggatgtgaa tatgaataaa   1020
atgccggatg ttgccatgac cctggcagtt gttgccctgt ttgcagatgg tccgaccgca   1080
attcgtgatg ttgcaagctg gcgtgttaaa gaaaccgaac gtatggttgc aattcgtacc   1140
```

```
gaactgacca aactgggtgc aaccgttgaa gaaggtccgg attattgcat tattacaccg    1200
ccggaaaaac tgaatattac cgccattgat acctatgatg atcatcgtat ggcaatggca    1260
tttagcctgg cagcatgtgc agaagttccg gttaccattc gtgatccggg ttgtacacgt    1320
aaaacctttc cgaattattt tgatgttctg agcacctttg tgaaaaatta a             1371
```

<210> SEQ ID NO 23
<211> LENGTH: 1281
<212> TYPE: DNA
<213> ORGANISM: Streptomyces roseosporus

<400> SEQUENCE: 23

```
atgaccgtta ttgaaattcc gggtagcaaa agcgttaccg cacgtgcact gtttctggca    60
gcagcagcag atggcaccac caccctgctg cgtccgctgc gtagtgatga taccgaaggt    120
tttgcagaag gtctgcgtaa tctgggttat gcagttgaac aggaagcaga tcgttggcgc    180
gttcagggtc gtccggcagg tccggctgca accgaagcag atgtttattg tcgtgatggt    240
gcaaccaccg cacgttttct gcctaccctg gcagccgcag ccgcaagcgg cacctatcgt    300
tttgatgcaa gcgcacagat gcgtcgtcgt cgctggcac cgctgacccg tgcactgacc    360
gcactgggtg ttgatctgcg tcatgaaggt gcagatggtc atcatccgct gaccgttcgt    420
gcagcaggta ttgaaggtgg tgaactgacc ctggatgccg gtgaaagcag ccagtatctg    480
accgctctgc tgatgctggg tcctctgacc accaaaggtc tgcgcattga agttaccgaa    540
ctggttagcg caccgtatgt ggaaattacc ctggcaatga tgcgcgattt ggtgttgaa    600 gttgaacgtg aaggcaatac ctttaccgtt ccgagcccga gcagccgtct gcgtagcaat    660
cgtggtggtc cgattggtgg ttatcgtgca accacctatg ccgttgaacc ggatgcaagc    720
accgcaagct atttttttgc agcagcagcc ctgaccggtc gtgaagttac cgttccgggt    780
ctgggcacag gtgcactgca gggtgatctg cgttttgttg atgttctgcg tgaaatgggt    840
gcagaagtta gcgttggtcc ggatgccacc accgttcgta gcaccggtcg tctgcgtggt    900
attaccgtta atatgcgtga tattagcgat accatgccga cactggctgc aattgcaccg    960
tatgcagatg gtccggttgt tattgaagat gttgcaaata cccgtgtgaa agaatgtgat    1020
cgtctggaag catgtgcaga aaatctgcgt gccatgggta ttaccgtgca taccggtccg    1080
gatcgtattg aaattcatcc gggtacaccg aaaccgaccg gtattgcaac ccatggtgat    1140
catcgtattg ttatgagctt tgcagttgca ggtctgcgta caccgggtct gacctatgat    1200
gatccgggtt gtgttcgtaa aacctttccg cgttttcatg aagtgtttgc agattttgcc    1260
catgatctgg aaggtcgtta a                                              1281
```

<210> SEQ ID NO 24
<211> LENGTH: 1248
<212> TYPE: DNA
<213> ORGANISM: Streptomyces griseus

<400> SEQUENCE: 24

```
atgggtgcag ttaccgttat tgatattccg ggtagcaaaa gcgttaccgc acgtgcactg    60
tttctggcag cagcagcaga tggcaccacc accctgctgc gtccgctgcg tagtgatgat    120
accgaaggtt ttgcagaagg tctgaaaaat ctgggttatg cagttgaaca ggaagcagat    180
cgttggcgcg ttgaaggtcg tccggatggt ccggcagcac cggatgcaga tgtttattgt    240
cgtgatggtg caaccaccgc acgttttctg ccgaccctgg ttgcagcagc agccagcggc    300
acctatcgtt ttgatgcaag cgcacagatg cgtcgtcgtc gctggcacc gctgacccgt    360
```

```
gcactgaccg cactgggtgt tgatctgcgt catggtggtg aagaaggtca tcatccgctg      420
accgttcgtg cagcaggtat tgaaggtggt gatgttgttc tggatgccgg tgaaagcagc      480
cagtatctga ccgctctgct gatgctgggt cctctgaccg caaaaggtct gcgtattgaa      540
gttaccgatc tggttagcgc accgtatgtg gaaattaccc tggcaatgat gcgcgatttt      600
ggtgttgatg ttagccgtga aggtaatacc tttaccgttc cgagcggtgg ttatcgtgca      660
accgcctatg ccgttgaacc ggatgcaagc accgcaagct attttttgc agcagccgca       720 ctgaccggtc gtgaagttac cgttccgggt ctgggtattg gtgcactgca gggtgatctg      780
cgttttgttg atgttctgcg tgatatgggt gccgaagtta gcgttggtcc ggatgccacc      840
accgttcgta gcaccggtcg tctgcgtggt attaccgtta ccatgcgtga tattagtgat      900
accatgccga cactggcagc aattgcaccg catgccgatg gtccggttcg tattgaagat      960
gttgcaaata cccgtgtgaa agaatgtgat cgtctggaag catgtgcaca gaatctgcgt     1020
gcaatgggta ttaccgtgca taccggtcat gattggattg aaattctgcc tggtacaccg     1080
aaaccgaccg gtattgcaac ccatggtgat catcgtattg ttatgagctt gcagttgca      1140 ggtctgctga caccgggtct gacctatgat gatcccgggtt gtgttcgtaa aaccttttccg    1200 cgttttcatg aagtgtttgc agattttgca gcaagtccgc aggcataa                  1248
```

<210> SEQ ID NO 25
<211> LENGTH: 40
<212> TYPE: DNA
<213> ORGANISM: Artificial Sequence
<220> FEATURE:
<223> OTHER INFORMATION: DGT28 MutF primer

<400> SEQUENCE: 25
gatgtttatt gccgtgatgg tggaaccacc gcacgttttc                            40

<210> SEQ ID NO 26
<211> LENGTH: 40
<212> TYPE: DNA
<213> ORGANISM: Artificial Sequence
<220> FEATURE:
<223> OTHER INFORMATION: DGT28 MutR primer

<400> SEQUENCE: 26
gaaaacgtgc ggtggttcca ccatcacggc aataaacatc                            40

<210> SEQ ID NO 27
<211> LENGTH: 33
<212> TYPE: DNA
<213> ORGANISM: Artificial Sequence
<220> FEATURE:
<223> OTHER INFORMATION: DGT28 Mut2F primer

<400> SEQUENCE: 27
gggtccgctg gcacgtcagg gtctgcgtat tcg                                   33

<210> SEQ ID NO 28
<211> LENGTH: 39
<212> TYPE: DNA
<213> ORGANISM: Artificial Sequence
<220> FEATURE:
<223> OTHER INFORMATION: DGT28 Mut2R primer

<400> SEQUENCE: 28
cgaatacgca gaccctgacg tgccagcgga cccagcagc                             39

<210> SEQ ID NO 29
<211> LENGTH: 26
<212> TYPE: DNA
<213> ORGANISM: Artificial Sequence
<220> FEATURE:
<223> OTHER INFORMATION: pMALDGT32F primer

<400> SEQUENCE: 29
catatgaccg ttattgaaat tccggg                                         26

<210> SEQ ID NO 30
<211> LENGTH: 27
<212> TYPE: DNA
<213> ORGANISM: Artificial Sequence
<220> FEATURE:
<223> OTHER INFORMATION: pMALDGT32R primer

<400> SEQUENCE: 30
gatatcctat tattaacgac cttccag                                        27

<210> SEQ ID NO 31
<211> LENGTH: 26
<212> TYPE: DNA
<213> ORGANISM: Artificial Sequence
<220> FEATURE:
<223> OTHER INFORMATION: pMALDGT33F primer

<400> SEQUENCE: 31
catatgggtg cagttaccgt tattga                                         26

<210> SEQ ID NO 32
<211> LENGTH: 26
<212> TYPE: DNA
<213> ORGANISM: Artificial Sequence
<220> FEATURE:
<223> OTHER INFORMATION: pMALDGT33R primer

<400> SEQUENCE: 32
gatatcctat tattatgcct gcggac                                         26

<210> SEQ ID NO 33
<211> LENGTH: 213
<212> TYPE: DNA
<213> ORGANISM: Artificial Sequence
<220> FEATURE:
<223> OTHER INFORMATION: TraP4 v2 Chloroplast Transit Peptide

<400> SEQUENCE: 33
atgcttgcta gacaaggtgg aagtctgaga gcttctcaat gcaacgctgg acttgctaga    60
agagttgaag ttggtgctct tgttgttcct agacctatct ctgttaacga cgttgttcct   120
cacgtttact ctgctccact ttctgttgct agaaggtctt gctctaagtc ctccattagg   180
tccactagaa ggcttcaaac tactgtgtgc tct                                213

<210> SEQ ID NO 34
<211> LENGTH: 186
<212> TYPE: DNA
<213> ORGANISM: Artificial Sequence
<220> FEATURE:
<223> OTHER INFORMATION: TraP5 v2 Chloroplast Transit Peptide

<400> SEQUENCE: 34
atgcaactcc tgaatcagag gcaagccctg cgtcttggtc gttcatctgc ttcaaagaac    60
cagcaagttg ctccactggc ctctaggcct gcttcttcct tgagcgtcag cgcatccagc   120

```
gtcgcacctg cacctgcttg ctcagctcct gctggagctg gaaggcgtgc tgttgtcgtg    180
agagca                                                              186

<210> SEQ ID NO 35
<211> LENGTH: 198
<212> TYPE: DNA
<213> ORGANISM: Artificial Sequence
<220> FEATURE:
<223> OTHER INFORMATION: TraP8 v2 Chloroplast Transit Peptide

<400> SEQUENCE: 35
atggctcaat ctagcagaat ctgccacggt gtgcagaacc catgtgtgat catttccaat    60
ctctccaaat ccaaccagaa caaatctcct ttctcagtca gcctcaagac tcaccagcag    120
cagcgtcgtg cttaccagat atctagctgg ggattgaaga agtcaaacaa cgggtccgtg    180
attcgtccgg ttaaggca                                                 198

<210> SEQ ID NO 36
<211> LENGTH: 198
<212> TYPE: DNA
<213> ORGANISM: Artificial Sequence
<220> FEATURE:
<223> OTHER INFORMATION: TraP9 v2 Chloroplast Transit Peptide

<400> SEQUENCE: 36
atggcacaag ccagccgtat ctgccagaat ccatgtgtga tatccaatct ccccaaaagc    60
aaccaccgta gtccccttt ctctgtctca ctcaagacgc atcagcctag agcctcttca    120
tggggactta agaagtctgg caccatgctg aacggttcag tgattagacc cgtcaaggtg    180
acagcttctg tttccgca                                                 198

<210> SEQ ID NO 37
<211> LENGTH: 225
<212> TYPE: DNA
<213> ORGANISM: Artificial Sequence
<220> FEATURE:
<223> OTHER INFORMATION: TraP12 v2 Chloroplast Transit Peptide

<400> SEQUENCE: 37
atggcacaat ctagcagaat ctgccacggt gtgcagaacc catgtgtgat catttcaaat    60
ctctcaaagt ccaatcagaa caaatcacct ttctccgtct ccctcaagac acaccagcat    120
ccaagggcat acccgataag cagctcatgg ggactcaaga agagcggaat gactctgatt    180
ggctctgagc ttcgtcctct taaggttatg tcctctgttt ccgca                   225

<210> SEQ ID NO 38
<211> LENGTH: 207
<212> TYPE: DNA
<213> ORGANISM: Artificial Sequence
<220> FEATURE:
<223> OTHER INFORMATION: TraP13 v2 Chloroplast Transit Peptide

<400> SEQUENCE: 38
atggcacaag ttagcagaat ctgtaatggt gtgcagaacc catctcttat ctccaatctc    60
tcaaagtcca gccaacgtaa gtctcccctc agcgtgtctc tgaaaactca gcagcccaga    120
gcttcttcat ggggtttgaa gaaatctgga acgatgctta acggctcagt cattcgtccg    180
gttaaggtga cagcctccgt ctccgct                                       207

<210> SEQ ID NO 39
```

```
<211> LENGTH: 186
<212> TYPE: DNA
<213> ORGANISM: Artificial Sequence
<220> FEATURE:
<223> OTHER INFORMATION: TraP14 v2 Chloroplast Transit Peptide

<400> SEQUENCE: 39
atgatacttg gatctagccc aactctgcca cacgcatcac atccagccag acctggtcct      60
gccagaccga tttcagtgaa cgacgtcgtt ccccatgtct actccgctcc tctctccgtg     120
gctaggcgtt cttgtagcaa gtccagcatt aggtctacgc gtagattgca gaccacagtc     180
tgctca                                                                186

<210> SEQ ID NO 40
<211> LENGTH: 186
<212> TYPE: DNA
<213> ORGANISM: Artificial Sequence
<220> FEATURE:
<223> OTHER INFORMATION: TraP23 v2 Chloroplast Transit Peptide

<400> SEQUENCE: 40
atggcacaga tcaacaagtc tgctaatggg gttaggaacg cttcactgat aagcaacttc      60
tccaataccc gtcaagccaa atccccttc tccctctcat gcggaacaag actgaagaac      120
agcagcagag gtttgaagaa ggtggcagtt aggctcattg ctcccgtgt caaagtgtct      180
gcctca                                                                186

<210> SEQ ID NO 41
<211> LENGTH: 207
<212> TYPE: DNA
<213> ORGANISM: Artificial Sequence
<220> FEATURE:
<223> OTHER INFORMATION: TraP24 v2 Chloroplast Transit Peptide

<400> SEQUENCE: 41
atgcaactgc tcaaccagag acaagccttg aggctcggga ggtcctctgc ctctaagaat      60
cagcaagtgg caccgcttgc cagccgtccc atttctgtga cgacgtcgt gccacacgtc      120
tacagcgcac ctctgtccgt tgctagacgc tcctgctcta agtcatcaat ccgcagcact     180
agaaggcttc agacgaccgt ttgttca                                         207

<210> SEQ ID NO 42
<211> LENGTH: 1467
<212> TYPE: DNA
<213> ORGANISM: Artificial Sequence
<220> FEATURE:
<223> OTHER INFORMATION: In-frame fusion of dgt-32 v3 and TraP14 v2

<400> SEQUENCE: 42
atgatacttg gatctagccc aactctgcca cacgcatcac atccagccag acctggtcct      60
gccagaccga tttcagtgaa cgacgtcgtt ccccatgtct actccgctcc tctctccgtg     120
gctaggcgtt cttgtagcaa gtccagcatt aggtctacgc gtagattgca gaccacagtc     180
tgctcaatga cggtgataga gatacctggg tctaagtctg ttacagccag agcactgttc     240
ttggcagctg ctgccgatgg gacgactact cttcttagac cattgcgtag cgatgacact     300
gagggcttcg cagaaggact gaggaatctg gctatgctg tggaacaaga ggctgatagg     360
tggcgtgtcc aaggcagacc agctggacca gcagccacgg aagcagatgt ctattgcaga     420
gatggtgcca ccaccgctag gttccttccg acactggcag cagcagctgc ttccggaacc     480
tacagattcg acgcttcagc acagatgcgt cgtcgtcccc ttgctccatt gacaagggca     540
```

```
cttacagcct tgggtgtgga tcttagacac gaaggagcag acggacatca tccgctcacc      600
gttcgtgcag ctggcatcga aggaggagaa ttgacgctcg acgctggcga gtccagccaa      660
tacttgacag cactgctcat gctcggacct cttacaacaa agggacttcg catcgaagtt      720
acagaactcg tctctgcacc ctacgtggaa atcaccctcg ctatgatgag agactttggt      780
gtggaggttg agagggaggg gaataccttc accgttccaa gcccatcttc aagacttagg      840
tccaatagag gtggacccat aggaggctat agagctacta cgtatgctgt cgagccagat      900
gcctcaactg cctcttactt ctttgcagct gctgccctca ctggtcgcga ggtcacagtg      960
cctggattgg ggactggagc tttgcaaggt gatttgcgtt tcgtggatgt gctgagagaa     1020
atgggtgccg aggtgtctgt tggtccggac gccacaactg tgcgctcaac tggcagattg     1080 agggaatca ctgtgaacat gagagatatc tcagacacga tgcctacact cgcagctatt     1140
gcaccttatg ccgatggtcc agtggtgatt gaagatgttg ccaacacccg tgtgaaggag     1200
tgtgaccgtc tggaggcttg tgctgagaat ctgagggcaa tgggaatcac cgtccatacg     1260
ggtccggata ggatagaaat ccatcctgga acacctaaac cgactgggat cgccacccac     1320
ggagatcacc gcatagtcat gtcatttgcc gtcgctggcc ttcgcactcc tggcctcact     1380
tacgacgacc ctggctgcgt gcgtaagacc ttccctagat tcacgaggt gtttgccgac     1440 ttcgctcacg accttgaggg aaggtga                                         1467

<210> SEQ ID NO 43
<211> LENGTH: 1455
<212> TYPE: DNA
<213> ORGANISM: Artificial Sequence
<220> FEATURE:
<223> OTHER INFORMATION: In-frame fusion of dgt-33 v3 and TraP24 v2

<400> SEQUENCE: 43
atgcaactgc tcaaccagag acaagccttg aggctcggga ggtcctctgc ctctaagaat       60
cagcaagtgg caccgcttgc cagccgtccc atttctgtga cgacgtcgt gccacacgtc       120 tacagcgcac ctctgtccgt tgctagacgc tcctgtctca agtcatcaat ccgcagcact      180
agaaggcttc agacgaccgt tgttcaatg ggtgcagtga cagtcatcga cattcctgga      240
agcaagagcg tgacagcaag ggcactcttc ttggcagcag cagccgatgg aacgacaaca      300
ctgcttcgtc ctctgaggtc agacgacacg gaggggtttg ccgagggtct taagaatctc      360
ggttatgccg ttgagcaaga ggctgaccgt tggagggtcg aaggcagacc ggatggtcca      420
gctgctccga tgcagatgt ctactgccgt gatggtgcaa cgactgcacg ctttcttcca      480
accctcgtcg cagcagcagc ttctggaacg tatcgtttcg acgcctcagc acagatgagg      540
agacgtccct ggctccact cactagggca ctgcagctc ttggcgtgga tttgagacat      600
ggtggagagg agggtcatca tccactgact gtcagagctg ctggcataga aggtggcgat      660
gttgtccttg acgctggtga atcttctcag tatctcacag cccttcttat gttgggtccg      720
ttgactgcca aaggtcttag aatcgaagtc actgatctcg tgagcgctcc ttacgttgaa      780
atcactctgg ccatgatgag agatttcgga gttgatgtta gcagagaagg aaacactttc      840
accgtgccgt ccggaggcta tagagctaca gcctacgctg tggagccaga cgcaagcacg      900
gcttcttact ctttgcagc agctgccctc actggacgcg aggtgacggt ccctgggctg      960
ggaattggtg ctcttcaagg agaccttcgt tttgtggacg tgctgcgtga tatgggagca     1020
gaggtgtctg ttgaccaga tgccacgaca gtgcgctcaa ctggcagact ccgtggcatt     1080
```

```
acagttacta tgagagacat ttcagacacg atgccaacac tcgctgctat tgcacctcac    1140
gctgatggac ccgtccgtat tgaggacgtg gcaaacactc gtgtcaagga atgtgatagg    1200
cttgaggcat gtgctcaaaa ccttagagct atgggaatca cggtgcatac tgggcacgat    1260
tggattgaga ttctccctgg gactccaaag ccaacgggaa tagctacgca cggagatcac    1320
agaatcgtta tgtccttcgc agtggctggt ttgttgaccc ctgggctgac atacgatgat    1380
cctggctgcg tccgcaagac ttttccaagg ttccacgaag ttttcgctga ctttgctgca    1440
tcaccccaag cctga                                                    1455
```

```
<210> SEQ ID NO 44
<211> LENGTH: 19
<212> TYPE: DNA
<213> ORGANISM: Artificial Sequence
<220> FEATURE:
<223> OTHER INFORMATION: DSM2A primer

<400> SEQUENCE: 44
agccacatcc cagtaacga                                                19

<210> SEQ ID NO 45
<211> LENGTH: 17
<212> TYPE: DNA
<213> ORGANISM: Artificial Sequence
<220> FEATURE:
<223> OTHER INFORMATION: DSM2S primer

<400> SEQUENCE: 45
cctccctctt tgacgcc                                                  17

<210> SEQ ID NO 46
<211> LENGTH: 20
<212> TYPE: DNA
<213> ORGANISM: Artificial Sequence
<220> FEATURE:
<223> OTHER INFORMATION: DSM2 Cy5 probe

<400> SEQUENCE: 46
cagcccaatg aggcatcagc                                               20

<210> SEQ ID NO 47
<211> LENGTH: 23
<212> TYPE: DNA
<213> ORGANISM: Artificial Sequence
<220> FEATURE:
<223> OTHER INFORMATION: DGT28F primer

<400> SEQUENCE: 47
cttcaaggag atttgggatt tgt                                           23

<210> SEQ ID NO 48
<211> LENGTH: 17
<212> TYPE: DNA
<213> ORGANISM: Artificial Sequence
<220> FEATURE:
<223> OTHER INFORMATION: DGT28R primer

<400> SEQUENCE: 48
gagggtcggc atcgtat                                                  17

<210> SEQ ID NO 49
<211> LENGTH: 25
<212> TYPE: DNA
<213> ORGANISM: Artificial Sequence
```

```
<220> FEATURE:
<223> OTHER INFORMATION: TAFFY-HEX probe

<400> SEQUENCE: 49
agagaagttt cgacggattt cgggc                                          25

<210> SEQ ID NO 50
<211> LENGTH: 22
<212> TYPE: DNA
<213> ORGANISM: Artificial Sequence
<220> FEATURE:
<223> OTHER INFORMATION: TAFII15-F primer

<400> SEQUENCE: 50
gaggattagg gtttcaacgg ag                                             22

<210> SEQ ID NO 51
<211> LENGTH: 21
<212> TYPE: DNA
<213> ORGANISM: Artificial Sequence
<220> FEATURE:
<223> OTHER INFORMATION: TAFII15-R primer

<400> SEQUENCE: 51
gagaattgag ctgagacgag g                                              21

<210> SEQ ID NO 52
<211> LENGTH: 24
<212> TYPE: DNA
<213> ORGANISM: Artificial Sequence
<220> FEATURE:
<223> OTHER INFORMATION: Forward oligo primer

<400> SEQUENCE: 52
ctgcaggtca acggatcagg atat                                           24

<210> SEQ ID NO 53
<211> LENGTH: 24
<212> TYPE: DNA
<213> ORGANISM: Artificial Sequence
<220> FEATURE:
<223> OTHER INFORMATION: Reverse oligo primer

<400> SEQUENCE: 53
tgggctgaat tgaagacatg ctcc                                           24

<210> SEQ ID NO 54
<211> LENGTH: 20
<212> TYPE: DNA
<213> ORGANISM: Artificial Sequence
<220> FEATURE:
<223> OTHER INFORMATION: AT26410LP primer

<400> SEQUENCE: 54
cgtccacaaa gctgaatgtg                                                20

<210> SEQ ID NO 55
<211> LENGTH: 20
<212> TYPE: DNA
<213> ORGANISM: Artificial Sequence
<220> FEATURE:
<223> OTHER INFORMATION: AT26410RP primer

<400> SEQUENCE: 55
cgaagtcatg gaagccactt                                                20
```

```
<210> SEQ ID NO 56
<211> LENGTH: 23
<212> TYPE: DNA
<213> ORGANISM: Artificial Sequence
<220> FEATURE:
<223> OTHER INFORMATION: DGT28F primer

<400> SEQUENCE: 56
cttcaaggag atttgggatt tgt                                              23

<210> SEQ ID NO 57
<211> LENGTH: 17
<212> TYPE: DNA
<213> ORGANISM: Artificial Sequence
<220> FEATURE:
<223> OTHER INFORMATION: DGT28R primer

<400> SEQUENCE: 57
gagggtcggc atcgtat                                                     17

<210> SEQ ID NO 58
<211> LENGTH: 20
<212> TYPE: DNA
<213> ORGANISM: Artificial Sequence
<220> FEATURE:
<223> OTHER INFORMATION: aad 1 forward primer

<400> SEQUENCE: 58
tgttcggttc cctctaccaa                                                  20

<210> SEQ ID NO 59
<211> LENGTH: 24
<212> TYPE: DNA
<213> ORGANISM: Artificial Sequence
<220> FEATURE:
<223> OTHER INFORMATION: aad 1 probe

<400> SEQUENCE: 59
cacagaaccg tcgcttcagc aaca                                             24

<210> SEQ ID NO 60
<211> LENGTH: 22
<212> TYPE: DNA
<213> ORGANISM: Artificial Sequence
<220> FEATURE:
<223> OTHER INFORMATION: aad 1 reverse primer

<400> SEQUENCE: 60
caacatccat caccttgact ga                                               22

<210> SEQ ID NO 61
<211> LENGTH: 26
<212> TYPE: DNA
<213> ORGANISM: Artificial Sequence
<220> FEATURE:
<223> OTHER INFORMATION: Invertase probe

<400> SEQUENCE: 61
cgagcagacc gccgtgtact tctacc                                           26

<210> SEQ ID NO 62
<211> LENGTH: 18
<212> TYPE: DNA
<213> ORGANISM: Artificial Sequence
<220> FEATURE:
<223> OTHER INFORMATION: Invertase forward primer
```

```
<400> SEQUENCE: 62
tggcggacga cgacttgt                                                  18

<210> SEQ ID NO 63
<211> LENGTH: 19
<212> TYPE: DNA
<213> ORGANISM: Artificial Sequence
<220> FEATURE:
<223> OTHER INFORMATION: Invertase reverse primer

<400> SEQUENCE: 63
aaagtttgga ggctgccgt                                                 19

<210> SEQ ID NO 64
<211> LENGTH: 18
<212> TYPE: DNA
<213> ORGANISM: Artificial Sequence
<220> FEATURE:
<223> OTHER INFORMATION: dgt 28 forward primer

<400> SEQUENCE: 64
ttcagcaccc gtcagaat                                                  18

<210> SEQ ID NO 65
<211> LENGTH: 20
<212> TYPE: DNA
<213> ORGANISM: Artificial Sequence
<220> FEATURE:
<223> OTHER INFORMATION: dgt 28 probe

<400> SEQUENCE: 65
tgccgagaac ttgaggaggt                                                20

<210> SEQ ID NO 66
<211> LENGTH: 17
<212> TYPE: DNA
<213> ORGANISM: Artificial Sequence
<220> FEATURE:
<223> OTHER INFORMATION: dgt 28 reverse primer

<400> SEQUENCE: 66
tggtcgccat agcttgt                                                   17

<210> SEQ ID NO 67
<211> LENGTH: 72
<212> TYPE: PRT
<213> ORGANISM: Streptomyces griseus

<400> SEQUENCE: 67

Asp Arg Trp Arg Val Glu Gly Arg Pro Asp Gly Pro Ala Ala Pro Asp
1               5                   10                  15

Ala Asp Val Tyr Cys Arg Asp Gly Ala Thr Thr Ala Arg Phe Leu Pro
            20                  25                  30

Thr Leu Val Ala Ala Ala Ala Ser Gly Thr Tyr Arg Phe Asp Ala Ser
        35                  40                  45

Ala Gln Met Arg Arg Arg Pro Leu Ala Pro Leu Thr Arg Ala Leu Thr
    50                  55                  60

Ala Leu Gly Val Asp Leu Arg His
65                  70

<210> SEQ ID NO 68
<211> LENGTH: 72
```

```
<212> TYPE: PRT
<213> ORGANISM: Streptomyces roseosporus

<400> SEQUENCE: 68

Asp Arg Trp Arg Val Gln Gly Arg Pro Ala Gly Pro Ala Ala Thr Glu
1               5                   10                  15

Ala Asp Val Tyr Cys Arg Asp Gly Ala Thr Thr Ala Arg Phe Leu Pro
            20                  25                  30

Thr Leu Ala Ala Ala Ala Ser Gly Thr Tyr Arg Phe Asp Ala Ser
        35                  40                  45

Ala Gln Met Arg Arg Arg Pro Leu Ala Pro Leu Thr Arg Ala Leu Thr
    50                  55                  60

Ala Leu Gly Val Asp Leu Arg His
65                  70

<210> SEQ ID NO 69
<211> LENGTH: 71
<212> TYPE: PRT
<213> ORGANISM: Streptomyces sviceus

<400> SEQUENCE: 69

Asp Thr Trp Gln Val Asp Gly Arg Pro Gln Gly Pro Ala Val Ala Glu
1               5                   10                  15

Ala Asp Val Tyr Cys Arg Asp Gly Ala Thr Thr Ala Arg Phe Leu Pro
            20                  25                  30

Thr Leu Ala Ala Ala Gly His Gly Thr Tyr Arg Phe Asp Ala Ser Pro
        35                  40                  45

Gln Met Arg Arg Arg Pro Leu Leu Pro Leu Ser Arg Ala Leu Arg Asp
    50                  55                  60

Leu Gly Val Asp Leu Arg His
65                  70

<210> SEQ ID NO 70
<211> LENGTH: 70
<212> TYPE: PRT
<213> ORGANISM: Unknown
<220> FEATURE:
<223> OTHER INFORMATION: unknown origination, described as SEQ ID NO:29
      in US PAT NO 7834249

<400> SEQUENCE: 70

Asp Asp Trp Val Val Glu Gly Leu Gly Gln Ala Pro Asn Leu Asp Ala
1               5                   10                  15

Asp Ile Trp Cys Glu Asp Ala Gly Thr Val Ala Arg Phe Leu Pro Pro
            20                  25                  30

Phe Val Ala Ala Gly Gln Gly Lys Phe Thr Phe Asp Gly Ser Glu Gln
        35                  40                  45

Leu Arg Arg Arg Pro Leu Arg Pro Val Val Asp Gly Ile Arg His Leu
    50                  55                  60

Gly Ala Arg Val Ser Ser
65                  70

<210> SEQ ID NO 71
<211> LENGTH: 72
<212> TYPE: PRT
<213> ORGANISM: Agrobacterium tumefaciens

<400> SEQUENCE: 71

Asp Thr Trp Ile Ile Asp Gly Val Gly Asn Gly Gly Leu Leu Ala Pro
1               5                   10                  15
```

Glu Ala Pro Leu Asp Phe Gly Asn Ala Ala Thr Gly Cys Arg Leu Thr
            20                  25                  30

Met Gly Leu Val Gly Val Tyr Asp Phe Asp Ser Thr Phe Ile Gly Asp
        35                  40                  45

Ala Ser Leu Thr Lys Arg Pro Met Gly Arg Val Leu Asn Pro Leu Arg
 50                  55                  60

Glu Met Gly Val Gln Val Lys Ser
 65                  70

<210> SEQ ID NO 72
<211> LENGTH: 80
<212> TYPE: PRT
<213> ORGANISM: Brassica napus

<400> SEQUENCE: 72

Val Asn Asn Arg Ala Val Val Glu Gly Cys Gly Gly Ile Phe Pro Ala
 1               5                  10                  15

Ser Leu Asp Ser Lys Ser Asp Ile Glu Leu Tyr Leu Gly Asn Ala Gly
            20                  25                  30

Thr Ala Met Arg Pro Leu Thr Ala Ala Val Thr Ala Ala Gly Gly Asn
        35                  40                  45

Ala Ser Tyr Val Leu Asp Gly Val Pro Arg Met Arg Glu Arg Pro Ile
 50                  55                  60

Gly Asp Leu Val Val Gly Leu Lys Gln Leu Gly Ala Asp Val Glu Cys
 65                  70                  75                  80

<210> SEQ ID NO 73
<211> LENGTH: 80
<212> TYPE: PRT
<213> ORGANISM: Glycine max

<400> SEQUENCE: 73

Thr Thr Lys Gln Ala Ile Val Glu Gly Cys Gly Gly Leu Phe Pro Thr
 1               5                  10                  15

Ser Lys Glu Ser Lys Asp Glu Ile Asn Leu Phe Leu Gly Asn Ala Gly
            20                  25                  30

Thr Ala Met Arg Pro Leu Thr Ala Ala Val Val Ala Ala Gly Gly Asn
        35                  40                  45

Ala Ser Tyr Val Leu Asp Gly Val Pro Arg Met Arg Glu Arg Pro Ile
 50                  55                  60

Gly Asp Leu Val Ala Gly Leu Lys Gln Leu Gly Ala Asp Val Asp Cys
 65                  70                  75                  80

<210> SEQ ID NO 74
<211> LENGTH: 80
<212> TYPE: PRT
<213> ORGANISM: Triticum aestivum

<400> SEQUENCE: 74

Val Ala Lys Arg Ala Val Val Gly Cys Gly Gly Arg Phe Pro Val
 1               5                  10                  15

Glu Lys Asp Ala Gln Glu Glu Val Lys Leu Phe Leu Gly Asn Ala Gly
            20                  25                  30

Thr Ala Met Arg Pro Leu Thr Ala Ala Val Val Ala Ala Gly Gly Asn
        35                  40                  45

Ala Thr Tyr Val Leu Asp Gly Val Pro Arg Met Arg Glu Arg Pro Ile
 50                  55                  60

Gly Asp Leu Val Val Gly Leu Gln Gln Leu Ala Asp Ala Asp Cys
65                  70                  75                  80

<210> SEQ ID NO 75
<211> LENGTH: 74
<212> TYPE: PRT
<213> ORGANISM: Escherichia coli

<400> SEQUENCE: 75

Asp Arg Thr Arg Cys Glu Ile Ile Gly Asn Gly Gly Pro Leu His Ala
1               5                   10                  15

Asp Gly Ala Leu Glu Leu Phe Leu Gly Asn Ala Gly Thr Ala Met Arg
            20                  25                  30

Pro Leu Ala Ala Ala Leu Cys Leu Gly Ser Asn Asp Ile Val Leu Thr
        35                  40                  45

Gly Glu Pro Arg Met Lys Glu Arg Pro Ile Gly His Leu Val Asp Ala
50                  55                  60

Leu Arg Leu Gly Gly Ala Lys Ile Thr Tyr
65                  70

<210> SEQ ID NO 76
<211> LENGTH: 516
<212> TYPE: PRT
<213> ORGANISM: Brassica napus

<400> SEQUENCE: 76

Met Ala Gln Ser Ser Arg Ile Cys His Gly Val Gln Asn Pro Cys Val
1               5                   10                  15

Ile Ile Ser Asn Leu Ser Lys Ser Gln Asn Lys Ser Pro Phe Ser
            20                  25                  30

Val Ser Leu Lys Thr His Gln Pro Arg Ala Ser Ser Trp Gly Leu Lys
        35                  40                  45

Lys Ser Gly Thr Met Leu Asn Gly Ser Val Ile Arg Pro Val Lys Val
50                  55                  60

Thr Ala Ser Val Ser Thr Ser Glu Lys Ala Ser Glu Ile Val Leu Gln
65                  70                  75                  80

Pro Ile Arg Glu Ile Ser Gly Leu Ile Lys Leu Pro Gly Ser Lys Ser
            85                  90                  95

Leu Ser Asn Arg Ile Leu Leu Leu Ala Ala Leu Ser Glu Gly Thr Thr
        100                 105                 110

Val Val Asp Asn Leu Leu Asn Ser Asp Asp Ile Asn Tyr Met Leu Asp
    115                 120                 125

Ala Leu Lys Lys Leu Gly Leu Asn Val Glu Arg Asp Ser Val Asn Asn
    130                 135                 140

Arg Ala Val Val Glu Gly Cys Gly Gly Ile Phe Pro Ala Ser Leu Asp
145                 150                 155                 160

Ser Lys Ser Asp Ile Glu Leu Tyr Leu Gly Asn Ala Gly Thr Ala Met
                165                 170                 175

Arg Pro Leu Thr Ala Ala Val Thr Ala Ala Gly Gly Asn Ala Ser Tyr
            180                 185                 190

Val Leu Asp Gly Val Pro Arg Met Arg Glu Arg Pro Ile Gly Asp Leu
        195                 200                 205

Val Val Gly Leu Lys Gln Leu Gly Ala Asp Val Glu Cys Thr Leu Gly
    210                 215                 220

Thr Asn Cys Pro Pro Val Arg Val Asn Ala Asn Gly Gly Leu Pro Gly
225                 230                 235                 240

```
Gly Lys Val Lys Leu Ser Gly Ser Ile Ser Ser Gln Tyr Leu Thr Ala
            245                 250                 255

Leu Leu Met Ala Ala Pro Leu Ala Leu Gly Asp Val Glu Ile Glu Ile
        260                 265                 270

Ile Asp Lys Leu Ile Ser Val Pro Tyr Val Glu Met Thr Leu Lys Leu
            275                 280                 285

Met Glu Arg Phe Gly Val Ser Ala Glu His Ser Asp Ser Trp Asp Arg
        290                 295                 300

Phe Phe Val Lys Gly Gln Lys Tyr Lys Ser Pro Gly Asn Ala Tyr
305                 310                 315                 320

Val Glu Gly Asp Ala Ser Ser Ala Ser Tyr Phe Leu Ala Gly Ala Ala
            325                 330                 335

Ile Thr Gly Glu Thr Val Thr Val Glu Gly Cys Gly Thr Thr Ser Leu
        340                 345                 350

Gln Gly Asp Val Lys Phe Ala Glu Val Leu Glu Lys Met Gly Cys Lys
            355                 360                 365

Val Ser Trp Thr Glu Asn Ser Val Thr Val Thr Gly Pro Ser Arg Asp
    370                 375                 380

Ala Phe Gly Met Arg His Leu Arg Ala Val Asp Val Asn Met Asn Lys
385                 390                 395                 400

Met Pro Asp Val Ala Met Thr Leu Ala Val Val Ala Leu Phe Ala Asp
            405                 410                 415

Gly Pro Thr Thr Ile Arg Asp Val Ala Ser Trp Arg Val Lys Glu Thr
        420                 425                 430

Glu Arg Met Ile Ala Ile Cys Thr Glu Leu Arg Lys Leu Gly Ala Thr
            435                 440                 445

Val Glu Glu Gly Ser Asp Tyr Cys Val Ile Thr Pro Pro Ala Lys Val
    450                 455                 460

Lys Pro Ala Glu Ile Asp Thr Tyr Asp Asp His Arg Met Ala Met Ala
465                 470                 475                 480

Phe Ser Leu Ala Ala Cys Ala Asp Val Pro Val Thr Ile Lys Asp Pro
            485                 490                 495

Gly Cys Thr Arg Lys Thr Phe Pro Asp Tyr Phe Gln Val Leu Glu Ser
        500                 505                 510

Ile Thr Lys His
        515

<210> SEQ ID NO 77
<211> LENGTH: 455
<212> TYPE: PRT
<213> ORGANISM: Glycine max

<400> SEQUENCE: 77

Met Ala Ser Val Ala Ala Ala Glu Lys Pro Ser Thr Ser Pro Glu Ile
1               5                   10                  15

Val Leu Glu Pro Ile Lys Asp Phe Ser Gly Thr Ile Thr Leu Pro Gly
            20                  25                  30

Ser Lys Ser Leu Ser Asn Arg Ile Leu Leu Leu Ala Ala Leu Ser Glu
        35                  40                  45

Gly Thr Thr Val Val Asp Asn Leu Leu Tyr Ser Glu Asp Ile His Tyr
    50                  55                  60

Met Leu Gly Ala Leu Arg Thr Leu Gly Leu Arg Val Glu Asp Asp Lys
65                  70                  75                  80

Thr Thr Lys Gln Ala Ile Val Glu Gly Cys Gly Gly Leu Phe Pro Thr
            85                  90                  95
```

Ser Lys Glu Ser Lys Asp Glu Ile Asn Leu Phe Leu Gly Asn Ala Gly
            100                 105                 110

Thr Ala Met Arg Pro Leu Thr Ala Ala Val Val Ala Ala Gly Gly Asn
        115                 120                 125

Ala Ser Tyr Val Leu Asp Gly Val Pro Arg Met Arg Glu Arg Pro Ile
    130                 135                 140

Gly Asp Leu Val Ala Gly Leu Lys Gln Leu Gly Ala Asp Val Asp Cys
145                 150                 155                 160

Phe Leu Gly Thr Asn Cys Pro Pro Val Arg Val Asn Gly Lys Gly Gly
                165                 170                 175

Leu Pro Gly Gly Lys Val Lys Leu Ser Gly Ser Val Ser Ser Gln Tyr
            180                 185                 190

Leu Thr Ala Leu Leu Met Ala Ala Pro Leu Ala Leu Gly Asp Val Glu
        195                 200                 205

Ile Glu Ile Val Asp Lys Leu Ile Ser Val Pro Tyr Val Glu Met Thr
    210                 215                 220

Leu Lys Leu Met Glu Arg Phe Gly Val Ser Val Glu His Ser Gly Asn
225                 230                 235                 240

Trp Asp Arg Phe Leu Val His Gly Gly Gln Lys Tyr Lys Ser Pro Gly
                245                 250                 255

Asn Ala Phe Val Glu Gly Asp Ala Ser Ser Ala Ser Tyr Leu Leu Ala
            260                 265                 270

Gly Ala Ala Ile Thr Gly Gly Thr Ile Thr Val Asn Gly Cys Gly Thr
        275                 280                 285

Ser Ser Leu Gln Gly Asp Val Lys Phe Ala Glu Val Leu Glu Lys Met
    290                 295                 300

Gly Ala Lys Val Thr Trp Ser Glu Asn Ser Val Thr Val Ser Gly Pro
305                 310                 315                 320

Pro Arg Asp Phe Ser Gly Arg Lys Val Leu Arg Gly Ile Asp Val Asn
                325                 330                 335

Met Asn Lys Met Pro Asp Val Ala Met Thr Leu Ala Val Val Ala Leu
            340                 345                 350

Phe Ala Asn Gly Pro Thr Ala Ile Arg Asp Val Ala Ser Trp Arg Val
        355                 360                 365

Lys Glu Thr Glu Arg Met Ile Ala Ile Cys Thr Glu Leu Arg Lys Leu
    370                 375                 380

Gly Ala Thr Val Glu Glu Gly Pro Asp Tyr Cys Val Ile Thr Pro Pro
385                 390                 395                 400

Glu Lys Leu Asn Val Thr Ala Ile Asp Thr Tyr Asp Asp His Arg Met
                405                 410                 415

Ala Met Ala Phe Ser Leu Ala Ala Cys Gly Asp Val Pro Val Thr Ile
            420                 425                 430

Lys Asp Pro Gly Cys Thr Arg Lys Thr Phe Pro Asp Tyr Phe Glu Val
        435                 440                 445

Leu Glu Arg Leu Thr Lys His
    450                 455

<210> SEQ ID NO 78
<211> LENGTH: 456
<212> TYPE: PRT
<213> ORGANISM: Triticum aestivum

<400> SEQUENCE: 78

Met Ala Thr Ser Val Ala Ala Pro Ala Ala Pro Ser Gly Ala Glu Glu

-continued

```
1               5                   10                  15
Val Val Leu Gln Pro Ile Arg Glu Ile Ser Gly Ala Val Gln Leu Pro
                20                  25                  30

Gly Ser Lys Ser Leu Ser Asn Arg Ile Leu Leu Ser Ala Leu Ser
                35                  40                  45

Glu Gly Thr Thr Val Val Asp Asn Leu Leu Asn Ser Glu Asp Val His
                50                  55                  60

Tyr Met Leu Glu Ala Leu Glu Ala Leu Gly Leu Ser Val Glu Ala Asp
65                  70                  75                  80

Lys Val Ala Lys Arg Ala Val Val Gly Cys Gly Gly Arg Phe Pro
                85                  90                  95

Val Glu Lys Asp Ala Gln Glu Val Lys Leu Phe Leu Gly Asn Ala
                100                 105                 110

Gly Thr Ala Met Arg Pro Leu Thr Ala Ala Val Ala Ala Gly Gly
                115                 120                 125

Asn Ala Thr Tyr Val Leu Asp Gly Val Pro Arg Met Arg Glu Arg Pro
                130                 135                 140

Ile Gly Asp Leu Val Val Gly Leu Gln Gln Leu Gly Ala Asp Ala Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
                180                 185                 190

Tyr Leu Ser Ser Leu Leu Met Ala Ala Pro Leu Ala Leu Glu Asp Val
                195                 200                 205

Glu Ile Glu Ile Ile Asp Lys Leu Ile Ser Val Pro Tyr Val Glu Met
                210                 215                 220

Thr Leu Lys Leu Met Glu Arg Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Ser Tyr Phe Leu
                260                 265                 270

Ala Gly Ala Ala Ile Thr Gly Gly Thr Val Thr Val Glu Gly Cys Gly
                275                 280                 285

Thr Thr Ser Leu Gln Gly Asp Val Lys Phe Ala Glu Val Leu Glu Met
                290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
                340                 345                 350

Leu Phe Ala Asp Gly Pro Thr Ala Ile Arg Asp Val Ala Ser Trp Arg
                355                 360                 365

Val Lys Glu Thr Glu Arg Met Val Ala Ile Arg Thr Glu Leu Thr Lys
                370                 375                 380

Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
                420                 425                 430
```

Ile Arg Asp Pro Gly Cys Thr Arg Lys Thr Phe Pro Asn Tyr Phe Asp
    435                 440                 445

Val Leu Ser Thr Phe Val Lys Asn
    450                 455

<210> SEQ ID NO 79
<211> LENGTH: 1464
<212> TYPE: DNA
<213> ORGANISM: Artificial Sequence
<220> FEATURE:
<223> OTHER INFORMATION: In-frame fusion of dgt-28 v5 and TraP4 v2

<400> SEQUENCE: 79

| | | | | | |
|---|---|---|---|---|---|
| atgcttgcta | gacaaggtgg | aagtctgaga | gcttctcaat | gcaacgctgg | acttgctaga | 60 |
| agagttgaag | ttggtgctct | tgttgttcct | agacctatct | ctgttaacga | cgttgttcct | 120 |
| cacgtttact | ctgctccact | ttctgttgct | agaaggtctt | gctctaagtc | ctccattagg | 180 |
| tccactagaa | ggcttcaaac | tactgtgtgc | tctgctgcaa | gagggatgcc | agccttgtct | 240 |
| ttacctggat | caaagagtat | cacagctagg | gcactctttc | ttgctgctgc | tgctgatggg | 300 |
| gttactactt | tggtgaggcc | attgagaagt | gacgacacag | aaggattcgc | tgagggtta | 360 |
| gttcgtttag | ctatcgtgt | agggaggaca | cccgatactt | ggcaagtcga | tggcagacca | 420 |
| caaggaccag | cagtggctga | ggctgacgtc | tactgtagag | acggagcaac | caccgctaga | 480 |
| ttcttgccaa | ccttagcagc | tgctggtcac | ggaacataca | gatttgatgc | ttcaccacag | 540 |
| atgaggagac | gtcctctttt | gcccttaagc | agagccttga | gggatttggg | tgtcgatctt | 600 |
| agacacgaag | aagctgaagg | tcatcaccct | ctgactgtcc | gtgctgctgg | ggttaagga | 660 |
| ggagaggtta | ctttggatgc | tggtcagtca | agtcagtatc | tcactgcctt | gttgctcctt | 720 |
| ggtccccta | caagacaagg | actgaggata | agggttactg | atttggtgtc | agcaccatac | 780 |
| gtggagatta | cgcttgcaat | gatgagggct | tcggagttg | aagtggcaag | ggagggagat | 840 |
| gtgttcgttg | ttccacctgg | tggatatcgt | gcaactacgt | atgctataga | acccgacgca | 900 |
| agtactgctt | cttacttctt | cgcagctgct | gctttgactc | ctggagctga | agtgactgta | 960 |
| cctgggttag | gcacgggagc | acttcaagga | gatttgggat | ttgtagatgt | cttaaggaga | 1020 |
| atgggagccg | aggtgtccgt | aggagctgat | gcaaccactg | ttagaggaac | tggtgaattg | 1080 |
| cgtggcctta | cagccaacat | gagagacata | agtgatacga | tgccgaccct | cgctgcaata | 1140 |
| gcacccttg | ctagtgctcc | agttagaatc | gaggatgttg | ccaacactcg | tgtcaaagaa | 1200 |
| tgtgacagac | ttgaggcttg | tgcagagaac | cttaggaggt | tgggagtaag | ggttgcaacg | 1260 |
| ggtccggact | ggattgagat | acaccctggt | ccagctactg | gtgctcaagt | cacaagctat | 1320 |
| ggtgatcaca | gaattgtgat | gtcatttgca | gtgactggac | ttcgtgtgcc | tgggatcagc | 1380 |
| ttcgacgacc | ctggctgtgt | tcgtaagact | tttcctgggt | tcacgaggc | tttcgcagaa | 1440 |
| ttgaggcgtg | gcattgggag | ctga | | | | 1464 |

<210> SEQ ID NO 80
<211> LENGTH: 1434
<212> TYPE: DNA
<213> ORGANISM: Artificial Sequence
<220> FEATURE:
<223> OTHER INFORMATION: In-frame fusion of dgt-28 v5 and TraP5 v2

<400> SEQUENCE: 80
atgcaactcc tgaatcagag gcaagccctg cgtcttggtc gttcatctgc ttcaaagaac    60

```
cagcaagttg ctccactggc tctaggcct gcttcttcct tgagcgtcag cgcatccagc     120
gtcgcacctg cacctgcttg ctcagctcct gctggagctg aaggcgtgc tgttgtcgtg     180 agagcagcaa gagggatgcc agccttgtct ttacctggat caaagagtat cacagctagg    240
gcactctttc ttgctgctgc tgctgatggg gttactactt tggtgaggcc attgagaagt    300
gacgacacag aaggattcgc tgaggggtta gttcgtttag ctatcgtgt agggaggaca    360 cccgatactt ggcaagtcga tggcagacca caaggaccag cagtggctga ggctgacgtc    420
tactgtagag acggagcaac caccgctaga ttcttgccaa ccttagcagc tgctggtcac    480
ggaacataca gatttgatgc ttcaccacag atgaggagac gtcctctttt gcccttaagc    540
agagccttga gggatttggg tgtcgatctt agacacgaag aagctgaagg tcatcaccct    600
ctgactgtcc gtgctgctgg ggttaagga ggagaggtta cttggatgc tggtcagtca    660 agtcagtatc tcactgcctt gttgctcctt ggtcccctta caagacaagg actgaggata    720
agggttactg atttggtgtc agcaccatac gtggagatta cgcttgcaat gatgagggct    780
ttcggagttg aagtggcaag ggaggagat gtgttcgttt ttccacctgg tggatatcgt    840
gcaactacgt atgctataga acccgacgca agtactgctt cttacttctt cgcagctgct    900
gctttgactc ctggagctga agtgactgta cctgggttag gcacgggagc acttcaagga    960
gatttgggat ttgtagatgt cttaaggaga atgggagccg aggtgtccgt aggagctgat    1020
gcaaccactg ttagaggaac tggtgaattg cgtggcctta cagccaacat gagagacata    1080
agtgatacga tgccgaccct cgctgcaata gcaccctttg ctagtgctcc agttagaatc    1140
gaggatgttg ccaacactcg tgtcaaagaa tgtgacagac ttgaggcttg tgcagagaac    1200
cttaggaggt tgggagtaag ggttgcaacg ggtccggact ggattgagat acaccctggt    1260
ccagctactg gtgctcaagt cacaagctat ggtgatcaca gaattgtgat gtcatttgca    1320
gtgactggac ttcgtgtgcc tgggatcagc ttcgacgacc ctggctgtgt tcgtaagact    1380
tttcctgggt ttcacgaggc tttcgcagaa ttgaggcgtg gcattgggag ctga         1434
```

<210> SEQ ID NO 81
<211> LENGTH: 1446
<212> TYPE: DNA
<213> ORGANISM: Artificial Sequence
<220> FEATURE:
<223> OTHER INFORMATION: In-frame fusion of dgt-28 v5 and TraP8 v2

<400> SEQUENCE: 81

```
atggctcaat ctagcagaat ctgccacggt gtgcagaacc catgtgtgat catttccaat     60
ctctccaaat ccaaccagaa caaatctcct ttctcagtca gcctcaagac tcaccagcag    120
cagcgtcgtg cttaccagat atctagctgg ggattgaaga agtcaaacaa cgggtccgtg    180
attcgtccgg ttaaggcagc aagagggatg ccagccttgt ctttacctgg atcaaagagt    240
atcacagcta gggcactctt tcttgctgct gctgctgatg gggttactac tttggtgagg    300
ccattgagaa gtgacgacac agaaggattc gctgaggggt tagttcgttt aggctatcgt    360
gtagggagga caccgatac ttggcaagtc gatggcagac cacaaggacc agcagtggct    420
gaggctgacg tctactgtag agacggagca accaccgcta gattcttgcc aaccttagca    480
gctgctggtc acggaacata cagatttgat gcttcaccac agatgaggag cgtcctcttt    540 tgcccttaa gcagagcctt gagggatttg gtgtcgatc ttagacacga agaagctgaa     600
ggtcatcacc ctctgactgt ccgtgctgct ggggttgaag gaggagaggt tactttggat    660
gctggtcagt caagtcagta tctcactgcc ttgttgctcc ttggtcccct tacaagacaa    720
```

```
ggactgagga taagggttac tgatttggtg tcagcaccat acgtggagat tacgcttgca    780
atgatgaggg ctttcggagt tgaagtggca agggagggag atgtgttcgt tgttccacct    840
ggtggatatc gtgcaactac gtatgctata gaacccgacg caagtactgc ttcttacttc    900
ttcgcagctg ctgctttgac tcctggagct gaagtgactg tacctggggtt aggcacggga   960 gcacttcaag gagatttggg atttgtagat gtcttaagga gaatgggagc cgaggtgtcc   1020
gtaggagctg atgcaaccac tgttagagga actggtgaat tgcgtggcct tacagccaac   1080
atgagagaca taagtgatac gatgccgacc ctcgctgcaa tagcacccct tgctagtgct   1140
ccagttagaa tcgaggatgt tgccaacact cgtgtcaaag aatgtgacag acttgaggct   1200
tgtgcagaga accttaggag gttgggagta agggttgcaa cgggtccgga ctggattgag   1260
atacaccctg gtccagctac tggtgctcaa gtcacaagct atggtgatca cagaattgtg   1320
atgtcatttg cagtgactgg acttcgtgtg cctgggatca gcttcgacga ccctggctgt   1380
gttcgtaaga cttttcctgg gtttcacgag gctttcgcag aattgaggcg tggcattggg   1440
agctga                                                              1446

<210> SEQ ID NO 82
<211> LENGTH: 1446
<212> TYPE: DNA
<213> ORGANISM: Artificial Sequence
<220> FEATURE:
<223> OTHER INFORMATION: In-frame fusion of dgt-28 v5 and TraP9 v2

<400> SEQUENCE: 82
atggcacaag ccagccgtat ctgccagaat ccatgtgtga tatccaatct ccccaaaagc     60
aaccaccgta gtccccttt ctctgtctca ctcaagacgc atcagcctag agcctcttca    120
tggggactta agaagtctgg caccatgctg aacggttcag tgattagacc cgtcaaggtg    180
acagcttctg tttccgcagc aagagggatg ccagccttgt ctttacctgg atcaaagagt    240
atcacagcta gggcactctt tcttgctgct gctgctgatg gggttactac tttggtgagg    300
ccattgagaa gtgacgacac agaaggattc gctgagggggt tagttcgttt aggctatcgt    360
gtagggagga caccccgatac ttggcaagtc gatggcagac acaaggacc agcagtggct    420 gaggctgacg tctactgtag agacggagca accaccgcta gattcttgcc aaccttagca    480
gctgctggtc acggaacata cagatttgat gcttcaccac agatgaggag acgtcctctt    540
ttgcccttaa gcagagcctt gagggatttg gtgtcgatc ttagacacga agaagctgaa    600
ggtcatcacc ctctgactgt ccgtgctgct gggggttgaag gagggaggggt tactttggat    660 gctggtcagt caagtcagta tctcactgcc ttgttgctcc ttggtcccct tacaagacaa    720
ggactgagga taagggttac tgatttggtg tcagcaccat acgtggagat tacgcttgca    780
atgatgaggg ctttcggagt tgaagtggca agggagggag atgtgttcgt tgttccacct    840
ggtggatatc gtgcaactac gtatgctata gaacccgacg caagtactgc ttcttacttc    900
ttcgcagctg ctgctttgac tcctggagct gaagtgactg tacctggggtt aggcacggga   960 gcacttcaag gagatttggg atttgtagat gtcttaagga gaatgggagc cgaggtgtcc   1020
gtaggagctg atgcaaccac tgttagagga actggtgaat tgcgtggcct tacagccaac   1080
atgagagaca taagtgatac gatgccgacc ctcgctgcaa tagcacccct tgctagtgct   1140
ccagttagaa tcgaggatgt tgccaacact cgtgtcaaag aatgtgacag acttgaggct   1200
tgtgcagaga accttaggag gttgggagta agggttgcaa cgggtccgga ctggattgag   1260
```

```
atacaccctg gtccagctac tggtgctcaa gtcacaagct atggtgatca cagaattgtg    1320
atgtcatttg cagtgactgg acttcgtgtg cctgggatca gcttcgacga ccctggctgt    1380
gttcgtaaga cttttcctgg gtttcacgag gctttcgcag aattgaggcg tggcattggg    1440
agctga                                                                1446
```

<210> SEQ ID NO 83
<211> LENGTH: 1473
<212> TYPE: DNA
<213> ORGANISM: Artificial Sequence
<220> FEATURE:
<223> OTHER INFORMATION: In-frame fusion of dgt-28 v5 and TraP12 v2

<400> SEQUENCE: 83

```
atggcacaat ctagcagaat ctgccacggt gtgcagaacc catgtgtgat catttcaaat      60
ctctcaaagt ccaatcagaa caaatcacct ttctccgtct ccctcaagac acaccagcat     120
ccaagggcat acccgataag cagctcatgg ggactcaaga gagcggaat gactctgatt      180 ggctctgagc ttcgtcctct taaggttatg tcctctgttt ccgcagcaag agggatgcca    240
gccttgtctt tacctggatc aaagagtatc acagctaggg cactcttcct gctgctgct    300 gctgatgggg ttactacttt ggtgaggcca ttgagaagtg acgacacaga aggattcgct    360
gaggggttag ttcgtttagg ctatcgtgta gggaggacac ccgatacttg gcaagtcgat    420
ggcagaccac aaggaccagc agtggctgag gctgacgtct actgtagaga cggagcaacc    480
accgctagat tcttgccaac cttagcagct gctggtcacg gaacatacag atttgatgct    540
tcaccacaga tgaggagacg tcctcttttg cccttaagca gagccttgag ggatttgggt    600
gtcgatctta gacacgaaga agctgaaggt catcaccctc tgactgtccg tgctgctggg    660
gttgaaggag gagaggttac tttggatgct ggtcagtcaa gtcagtatct cactgccttg    720
ttgctccttg gtcccttac aagacaagga ctgaggataa gggttactga tttggtgtca    780
gcaccatacg tggagattac gcttgcaatg atgggggctt cggagttga agtggcaagg    840 gagggagatg tgttcgttgt tccacctggt ggatatcgtg caactacgta tgctatagaa    900
cccgacgcaa gtactgcttc ttacttcttc gcagctgctg cttttgactcc tggagctgaa    960 gtgactgtac ctgggttagg cacgggagca cttcaaggag atttgggatt tgtagatgtc    1020
ttaaggagaa tgggagccga ggtgtccgta ggagctgatg caaccactgt tagaggaact    1080
ggtgaattgc gtggccttac agccaacatg agagacataa gtgatacgat gccgacccct    1140
gctgcaatag cacccttttgc tagtgctcca gttagaatcg aggatgttgc caacactcgt    1200
gtcaaagaat gtgacagact tgaggcttgt gcagagaacc ttaggaggtt gggagtaagg    1260
gttgcaacgg gtccggactg gattgagata caccctggtc cagctactgg tgctcaagtc    1320
acaagctatg gtgatcacag aattgtgatg tcatttgcag tgactggact tcgtgtgcct    1380
gggatcagct tcgacgaccc tggctgtgtt cgtaagactt ttcctgggtt tcacgaggct    1440
ttcgcagaat gaggcgtgg cattgggagc tga                                 1473
```

<210> SEQ ID NO 84
<211> LENGTH: 1455
<212> TYPE: DNA
<213> ORGANISM: Artificial Sequence
<220> FEATURE:
<223> OTHER INFORMATION: In-frame fusion of dgt-28 v5 and TraP13 v2

<400> SEQUENCE: 84

```
atggcacaag ttagcagaat ctgtaatggt gtgcagaacc catctcttat ctccaatctc     60
```

```
tcaaagtcca gccaacgtaa gtctcccctc agcgtgtctc tgaaaactca gcagcccaga    120
gcttcttcat ggggtttgaa gaaatctgga acgatgctta acggctcagt cattcgtccg    180
gttaaggtga cagcctccgt ctccgctgct agagggatgc cagccttgtc tttacctgga    240
tcaaagagta tcacagctag ggcactcttt cttgctgctg ctgctgatgg ggttactact    300
ttggtgaggc cattgagaag tgacgacaca gaaggattcg ctgaggggtt agttcgttta    360
ggctatcgtg tagggaggac acccgatact tggcaagtcg atggcagacc acaaggacca    420
gcagtggctg aggctgacgt ctactgtaga gacggagcaa ccaccgctag attcttgcca    480
accttagcag ctgctggtca cggaacatac agatttgatg cttcaccaca gatgaggaga    540
cgtcctcttt tgcccttaag cagagccttg agggatttgg gtgtcgatct tagacacgaa    600
gaagctgaag gtcatcaccc tctgactgtc cgtgctgctg gggttgaagg aggagaggtt    660
actttggatg ctggtcagtc aagtcagtat ctcactgcct tgttgctcct tggtcccctt    720
acaagacaag gactgaggat aagggttact gatttggtgt cagcaccata cgtggagatt    780
acgcttgcaa tgatgagggc tttcggagtt gaagtggcaa gggagggaga tgtgttcgtt    840
gttccacctg gtggatatcg tgcaactacg tatgctatag aacccgacgc aagtactgct    900
tcttacttct tcgcagctgc tgctttgact cctggagctg aagtgactgt acctgggtta    960
ggcacgggag cacttcaagg agatttggga tttgtagatg tcttaaggag aatgggagcc    1020
gaggtgtccg taggagctga tgcaaccact gttagaggaa ctggtgaatt gcgtggcctt    1080
acagccaaca tgagagacat aagtgatacg atgccgaccc tcgctgcaat agcacccttt    1140
gctagtgctc cagttagaat cgaggatgtt gccaacactc gtgtcaaaga atgtgacaga    1200
cttgaggctt gtgcagagaa ccttaggagg ttgggagtaa gggttgcaac gggtccggac    1260
tggattgaga tacaccctgg tccagctact ggtgctcaag tcacaagcta tggtgatcac    1320
agaattgtga tgtcatttgc agtgactgga cttcgtgtgc ctgggatcag cttcgacgac    1380
cctggctgtg ttcgtaagac ttttcctggg tttcacgagg ctttcgcaga attgaggcgt    1440
ggcattggga gctga                                                    1455
```

<210> SEQ ID NO 85
<211> LENGTH: 20
<212> TYPE: DNA
<213> ORGANISM: Artificial sequence
<220> FEATURE:
<223> OTHER INFORMATION: ubiquitin gene forward primer

<400> SEQUENCE: 85
gcgaagatcc aggacaagga    20

<210> SEQ ID NO 86
<211> LENGTH: 21
<212> TYPE: DNA
<213> ORGANISM: Artificial sequence
<220> FEATURE:
<223> OTHER INFORMATION: ubiquitin gene reverse primer

<400> SEQUENCE: 86
ctgcttaccg gcaaagatga g    21

<210> SEQ ID NO 87
<211> LENGTH: 20
<212> TYPE: DNA
<213> ORGANISM: Artificial sequence
<220> FEATURE:

```
<223> OTHER INFORMATION: ubiquitin gene probe

<400> SEQUENCE: 87
ttcccccgga ccagcagcgt                                              20

<210> SEQ ID NO 88
<211> LENGTH: 20
<212> TYPE: DNA
<213> ORGANISM: Artificial sequence
<220> FEATURE:
<223> OTHER INFORMATION: virC gene forward primer

<400> SEQUENCE: 88
ccgacgagaa agaccagcaa                                              20

<210> SEQ ID NO 89
<211> LENGTH: 22
<212> TYPE: DNA
<213> ORGANISM: Artificial sequence
<220> FEATURE:
<223> OTHER INFORMATION: virC gene reverse primer

<400> SEQUENCE: 89
ttaagttgtc gatcgggact gt                                           22

<210> SEQ ID NO 90
<211> LENGTH: 24
<212> TYPE: DNA
<213> ORGANISM: Artificial sequence
<220> FEATURE:
<223> OTHER INFORMATION: virC gene probe

<400> SEQUENCE: 90
tgagcctctc gtcgccgatc acat                                         24

<210> SEQ ID NO 91
<211> LENGTH: 20
<212> TYPE: DNA
<213> ORGANISM: Artificial sequence
<220> FEATURE:
<223> OTHER INFORMATION: puroindoline b (Pinb) gene forward primer

<400> SEQUENCE: 91
attttccatt cacttggccc                                              20

<210> SEQ ID NO 92
<211> LENGTH: 19
<212> TYPE: DNA
<213> ORGANISM: Artificial sequence
<220> FEATURE:
<223> OTHER INFORMATION: puroindoline b (Pinb) gene reverse primer

<400> SEQUENCE: 92
tgctatctgg ctcagctgc                                               19

<210> SEQ ID NO 93
<211> LENGTH: 21
<212> TYPE: DNA
<213> ORGANISM: Artificial sequence
<220> FEATURE:
<223> OTHER INFORMATION: puroindoline b (Pinb) gene probe

<400> SEQUENCE: 93
atggtggaag ggcggttgtg a                                            21
```

```
<210> SEQ ID NO 94
<211> LENGTH: 18
<212> TYPE: DNA
<213> ORGANISM: Artificial sequence
<220> FEATURE:
<223> OTHER INFORMATION: Actin (Act1) promoter forward primer

<400> SEQUENCE: 94
ctcccgcgca ccgatctg                                                 18

<210> SEQ ID NO 95
<211> LENGTH: 19
<212> TYPE: DNA
<213> ORGANISM: Artificial sequence
<220> FEATURE:
<223> OTHER INFORMATION: Actin (Act1) promoter reverse primer

<400> SEQUENCE: 95
cccgcccctc tcctctttc                                                19

<210> SEQ ID NO 96
<211> LENGTH: 21
<212> TYPE: DNA
<213> ORGANISM: Artificial sequence
<220> FEATURE:
<223> OTHER INFORMATION: Actin (Act1) promoter probe

<400> SEQUENCE: 96
aagccgcctc tcgcccaccc a                                             21

<210> SEQ ID NO 97
<211> LENGTH: 24
<212> TYPE: DNA
<213> ORGANISM: Artificial sequence
<220> FEATURE:
<223> OTHER INFORMATION: pDAS000122 primer 1

<400> SEQUENCE: 97
ggtttgttga atccctctgt tggt                                          24

<210> SEQ ID NO 98
<211> LENGTH: 25
<212> TYPE: DNA
<213> ORGANISM: Artificial sequence
<220> FEATURE:
<223> OTHER INFORMATION: pDAS000122 primer 2

<400> SEQUENCE: 98
gtggtcatga cagtatgata acagg                                         25

<210> SEQ ID NO 99
<211> LENGTH: 20
<212> TYPE: DNA
<213> ORGANISM: Artificial sequence
<220> FEATURE:
<223> OTHER INFORMATION: pDAS000122 primer 1

<400> SEQUENCE: 99
gggtctgccc aatgaagcga                                               20

<210> SEQ ID NO 100
<211> LENGTH: 26
<212> TYPE: DNA
<213> ORGANISM: Artificial sequence
<220> FEATURE:
<223> OTHER INFORMATION: pDAS000122 primer 2
```

<400> SEQUENCE: 100
tctcgcttct ctcataacac atcgtg　　　　　　　　　　　　　　　　　26

<210> SEQ ID NO 101
<211> LENGTH: 22
<212> TYPE: DNA
<213> ORGANISM: Artificial sequence
<220> FEATURE:
<223> OTHER INFORMATION: pDAS000123 primer 1

<400> SEQUENCE: 101
gacctctctc accctcctcc tc　　　　　　　　　　　　　　　　　　22

<210> SEQ ID NO 102
<211> LENGTH: 26
<212> TYPE: DNA
<213> ORGANISM: Artificial sequence
<220> FEATURE:
<223> OTHER INFORMATION: pDAS000123 primer 2

<400> SEQUENCE: 102
ccaaataata agtgagagag gggcat　　　　　　　　　　　　　　　　26

<210> SEQ ID NO 103
<211> LENGTH: 22
<212> TYPE: DNA
<213> ORGANISM: Artificial sequence
<220> FEATURE:
<223> OTHER INFORMATION: pDAS000123 primer 1

<400> SEQUENCE: 103
tagttcccct gtcgtgtgca aa　　　　　　　　　　　　　　　　　　22

<210> SEQ ID NO 104
<211> LENGTH: 22
<212> TYPE: DNA
<213> ORGANISM: Artificial sequence
<220> FEATURE:
<223> OTHER INFORMATION: pDAS000123 primer 2

<400> SEQUENCE: 104
caacagcagc ctcaccaatc ac　　　　　　　　　　　　　　　　　　22

<210> SEQ ID NO 105
<211> LENGTH: 24
<212> TYPE: DNA
<213> ORGANISM: Artificial sequence
<220> FEATURE:
<223> OTHER INFORMATION: pDAS000123 primer 1

<400> SEQUENCE: 105
caagaacggt gctccttttt taag　　　　　　　　　　　　　　　　　24

<210> SEQ ID NO 106
<211> LENGTH: 21
<212> TYPE: DNA
<213> ORGANISM: Artificial sequence
<220> FEATURE:
<223> OTHER INFORMATION: pDAS000123 primer 2

<400> SEQUENCE: 106
agcccttcct ctgcatcctt a　　　　　　　　　　　　　　　　　　　21

<210> SEQ ID NO 107
<211> LENGTH: 24

```
<212> TYPE: DNA
<213> ORGANISM: Artificial sequence
<220> FEATURE:
<223> OTHER INFORMATION: pDAS000124 primer 1

<400> SEQUENCE: 107
ggctgtgttg cacacaaata gaga                                              24

<210> SEQ ID NO 108
<211> LENGTH: 23
<212> TYPE: DNA
<213> ORGANISM: Artificial sequence
<220> FEATURE:
<223> OTHER INFORMATION: pDAS000124 primer 2

<400> SEQUENCE: 108
cagcagcacg gtaggtagat tgt                                               23

<210> SEQ ID NO 109
<211> LENGTH: 24
<212> TYPE: DNA
<213> ORGANISM: Artificial sequence
<220> FEATURE:
<223> OTHER INFORMATION: pDAS000124 primer 1

<400> SEQUENCE: 109
ccgataagac ggcaactgat taaa                                              24

<210> SEQ ID NO 110
<211> LENGTH: 23
<212> TYPE: DNA
<213> ORGANISM: Artificial sequence
<220> FEATURE:
<223> OTHER INFORMATION: pDAS000124 primer 2

<400> SEQUENCE: 110
aggctggctt ctagtggaag gag                                               23

<210> SEQ ID NO 111
<211> LENGTH: 19
<212> TYPE: DNA
<213> ORGANISM: Artificial sequence
<220> FEATURE:
<223> OTHER INFORMATION: pDAS000124 primer 1

<400> SEQUENCE: 111
gggtttccgg ctggagacg                                                    19

<210> SEQ ID NO 112
<211> LENGTH: 28
<212> TYPE: DNA
<213> ORGANISM: Artificial sequence
<220> FEATURE:
<223> OTHER INFORMATION: pDAS000124 primer 2

<400> SEQUENCE: 112
ccaaaagcaa ttttcgttat aagatgcc                                          28

<210> SEQ ID NO 113
<211> LENGTH: 22
<212> TYPE: DNA
<213> ORGANISM: Artificial sequence
<220> FEATURE:
<223> OTHER INFORMATION: OlipDAS000124 primer 1

<400> SEQUENCE: 113
```
ccagataatc tgtgggctcc tg                                    22

<210> SEQ ID NO 114
<211> LENGTH: 20
<212> TYPE: DNA
<213> ORGANISM: Artificial sequence
<220> FEATURE:
<223> OTHER INFORMATION: OlipDAS000124 primer 2

<400> SEQUENCE: 114
gcagcagctt gccttaagca                                       20

<210> SEQ ID NO 115
<211> LENGTH: 27
<212> TYPE: DNA
<213> ORGANISM: Artificial sequence
<220> FEATURE:
<223> OTHER INFORMATION: pDAS000125 primer 1

<400> SEQUENCE: 115
tgcttgtttc tgttgtcatc ataggtt                               27

<210> SEQ ID NO 116
<211> LENGTH: 23
<212> TYPE: DNA
<213> ORGANISM: Artificial sequence
<220> FEATURE:
<223> OTHER INFORMATION: pDAS000125 primer 2

<400> SEQUENCE: 116
catttgttgg gtttccacgt acg                                   23

<210> SEQ ID NO 117
<211> LENGTH: 22
<212> TYPE: DNA
<213> ORGANISM: Artificial sequence
<220> FEATURE:
<223> OTHER INFORMATION: pDAS000125 primer 1

<400> SEQUENCE: 117
gagcgcggct aaaggtcaaa ac                                    22

<210> SEQ ID NO 118
<211> LENGTH: 25
<212> TYPE: DNA
<213> ORGANISM: Artificial sequence
<220> FEATURE:
<223> OTHER INFORMATION: pDAS000125 primer 2

<400> SEQUENCE: 118
ccgatttaca tggacttgat ggagt                                 25

<210> SEQ ID NO 119
<211> LENGTH: 24
<212> TYPE: DNA
<213> ORGANISM: Artificial sequence
<220> FEATURE:
<223> OTHER INFORMATION: pDAS000122 primer 1

<400> SEQUENCE: 119
ggtttgttga atccctctgt tggt                                  24

<210> SEQ ID NO 120
<211> LENGTH: 32
<212> TYPE: DNA
<213> ORGANISM: Artificial sequence

```
<220> FEATURE:
<223> OTHER INFORMATION: pDAS000122 primer 2

<400> SEQUENCE: 120
gccgcctcca gtgagtgttg ctgcttgtgt ag                           32

<210> SEQ ID NO 121
<211> LENGTH: 20
<212> TYPE: DNA
<213> ORGANISM: Artificial sequence
<220> FEATURE:
<223> OTHER INFORMATION: pDAS000122 primer 1

<400> SEQUENCE: 121
gggtctgccc aatgaagcga                                         20

<210> SEQ ID NO 122
<211> LENGTH: 37
<212> TYPE: DNA
<213> ORGANISM: Artificial sequence
<220> FEATURE:
<223> OTHER INFORMATION: pDAS000122 primer 2

<400> SEQUENCE: 122
gccgcctcca taatgtgtga gtagttccca gataagg                      37

<210> SEQ ID NO 123
<211> LENGTH: 32
<212> TYPE: DNA
<213> ORGANISM: Artificial sequence
<220> FEATURE:
<223> OTHER INFORMATION: pDAS000123 primer 1

<400> SEQUENCE: 123
gccgcctcca gtgagtgttg ctgcttgtgt ag                           32

<210> SEQ ID NO 124
<211> LENGTH: 26
<212> TYPE: DNA
<213> ORGANISM: Artificial sequence
<220> FEATURE:
<223> OTHER INFORMATION: pDAS000123 primer 2

<400> SEQUENCE: 124
ccaaataata agtgagagag gggcat                                  26

<210> SEQ ID NO 125
<211> LENGTH: 37
<212> TYPE: DNA
<213> ORGANISM: Artificial sequence
<220> FEATURE:
<223> OTHER INFORMATION: pDAS000123 primer 1

<400> SEQUENCE: 125
gccgcctcca taatgtgtga gtagttccca gataagg                      37

<210> SEQ ID NO 126
<211> LENGTH: 22
<212> TYPE: DNA
<213> ORGANISM: Artificial sequence
<220> FEATURE:
<223> OTHER INFORMATION: pDAS000123 primer 2

<400> SEQUENCE: 126
caacagcagc ctcaccaatc ac                                      22
```

```
<210> SEQ ID NO 127
<211> LENGTH: 37
<212> TYPE: DNA
<213> ORGANISM: Artificial sequence
<220> FEATURE:
<223> OTHER INFORMATION: pDAS000123 primer 1

<400> SEQUENCE: 127
gccgcctcca taatgtgtga gtagttccca gataagg                                  37

<210> SEQ ID NO 128
<211> LENGTH: 21
<212> TYPE: DNA
<213> ORGANISM: Artificial sequence
<220> FEATURE:
<223> OTHER INFORMATION: pDAS000123 primer 2

<400> SEQUENCE: 128
agcccttcct ctgcatcctt a                                                   21

<210> SEQ ID NO 129
<211> LENGTH: 37
<212> TYPE: DNA
<213> ORGANISM: Artificial sequence
<220> FEATURE:
<223> OTHER INFORMATION: pDAS000124 primer 1

<400> SEQUENCE: 129
gccgcctcca taatgtgtga gtagttccca gataagg                                  37

<210> SEQ ID NO 130
<211> LENGTH: 23
<212> TYPE: DNA
<213> ORGANISM: Artificial sequence
<220> FEATURE:
<223> OTHER INFORMATION: pDAS000124 primer 2

<400> SEQUENCE: 130
cagcagcacg gtaggtagat tgt                                                 23

<210> SEQ ID NO 131
<211> LENGTH: 32
<212> TYPE: DNA
<213> ORGANISM: Artificial sequence
<220> FEATURE:
<223> OTHER INFORMATION: pDAS000124 primer 1

<400> SEQUENCE: 131
gccgcctcca gtgagtgttg ctgcttgtgt ag                                       32

<210> SEQ ID NO 132
<211> LENGTH: 23
<212> TYPE: DNA
<213> ORGANISM: Artificial sequence
<220> FEATURE:
<223> OTHER INFORMATION: pDAS000124 primer 2

<400> SEQUENCE: 132
aggctggctt ctagtggaag gag                                                 23

<210> SEQ ID NO 133
<211> LENGTH: 37
<212> TYPE: DNA
<213> ORGANISM: Artificial sequence
<220> FEATURE:
<223> OTHER INFORMATION: pDAS000124 primer 1
```

```
<400> SEQUENCE: 133
gccgcctcca taatgtgtga gtagttccca gataagg                              37

<210> SEQ ID NO 134
<211> LENGTH: 28
<212> TYPE: DNA
<213> ORGANISM: Artificial sequence
<220> FEATURE:
<223> OTHER INFORMATION: pDAS000124 primer 2

<400> SEQUENCE: 134
ccaaaagcaa ttttcgttat aagatgcc                                       28

<210> SEQ ID NO 135
<211> LENGTH: 32
<212> TYPE: DNA
<213> ORGANISM: Artificial sequence
<220> FEATURE:
<223> OTHER INFORMATION: pDAS000124 primer 1

<400> SEQUENCE: 135
gccgcctcca gtgagtgttg ctgcttgtgt ag                                  32

<210> SEQ ID NO 136
<211> LENGTH: 20
<212> TYPE: DNA
<213> ORGANISM: Artificial sequence
<220> FEATURE:
<223> OTHER INFORMATION: pDAS000124 primer 2

<400> SEQUENCE: 136
gcagcagctt gccttaagca                                                20

<210> SEQ ID NO 137
<211> LENGTH: 37
<212> TYPE: DNA
<213> ORGANISM: Artificial sequence
<220> FEATURE:
<223> OTHER INFORMATION: pDAS000125 primer 1

<400> SEQUENCE: 137
gccgcctcca taatgtgtga gtagttccca gataagg                             37

<210> SEQ ID NO 138
<211> LENGTH: 23
<212> TYPE: DNA
<213> ORGANISM: Artificial sequence
<220> FEATURE:
<223> OTHER INFORMATION: pDAS000125 primer 2

<400> SEQUENCE: 138
catttgttgg gtttccacgt acg                                            23

<210> SEQ ID NO 139
<211> LENGTH: 32
<212> TYPE: DNA
<213> ORGANISM: Artificial sequence
<220> FEATURE:
<223> OTHER INFORMATION: pDAS000125 primer 1

<400> SEQUENCE: 139
gccgcctcca gtgagtgttg ctgcttgtgt ag                                  32

<210> SEQ ID NO 140
```

```
<211> LENGTH: 25
<212> TYPE: DNA
<213> ORGANISM: Artificial sequence
<220> FEATURE:
<223> OTHER INFORMATION: pDAS000125 primer 2

<400> SEQUENCE: 140
ccgatttaca tggacttgat ggagt                                    25

<210> SEQ ID NO 141
<211> LENGTH: 6
<212> TYPE: PRT
<213> ORGANISM: Artificial sequence
<220> FEATURE:
<223> OTHER INFORMATION: Synthetic peptide

<400> SEQUENCE: 141

Leu Gly Asn Ala Ala Thr
1               5

<210> SEQ ID NO 142
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa can be Ala, Ser, or Thr

<400> SEQUENCE: 142

Ala Leu Leu Met Xaa Ala Pro Leu Thr
1               5

<210> SEQ ID NO 143
<211> LENGTH: 1431
<212> TYPE: DNA
<213> ORGANISM: Artificial sequence
<220> FEATURE:
<223> OTHER INFORMATION: DGT-31 and TRAP23 construct

<400> SEQUENCE: 143
atggcacaga tcaacaagtc tgctaatggg gttaggaacg cttcactgat aagcaacttc        60
tccaataccc gtcaagccaa atccccttc tccctctcat gcggaacaag actgaagaac       120
agcagcagag gtttgaagaa ggtggcagtt aggctcattg gctcccgtgt caaagtgtct       180
gcctcaatga ctgtgattga catccctggc tcaaagtcag ttactgccag agcattgttc       240
ctcgcagcag ctgctgatgg cactacaact cttttgagac ctcttcacag cgatgacacg       300
gaaggcttca ctgagggtct cactcgtttg ggatacgcag tggttagaga acccgatagg       360
tggcacatag aaggacgtcc ctccggtcca gcagcagcag atgcagaagt tcactgtagg       420
gacggtgcta caactgctcg ctttcttcca acccttgcag ctgctgctgc ctccggaacg       480
tatcgtttcg acgcatcagc tcagatgagg cgtagacccc tcgctcccct cacgaaagct       540
cttagaacac ttggagtgga ccttaggcat gatggagctg aaggccacca ccccttgaca       600
attcaagcct ctggtgttaa gggtggagga cttacgctcg acgctggtga gtcatctcag       660
tacttgacag ctctgctcat gcttggtcct ctgaccgcag agggactgag aatagaagtt       720
acggagcttg tctctgctcc ttatgtggag atcaccttg caatgatgag aggctttggt       780
gtggaggtta ttagggaggg gaatactttc actgtgcctc ctggaggtta cagagctaca       840
acttatgcca tagaaccgga cgcaagcaca gcttcctact ctttgcagc agcagccctc       900
```

```
actgggaggg aagtgacggt gcctggcttg ggcactggag cacttcaagg tgatcttagg    960
ttcacggagg tcctcagaag gatggacgct gatgttcgca caacgtccga ctctacaaca   1020
gtgcgctcag atggtcgcct tgctgggttg actgtcaaca tgagggacat aagcgacaca   1080
atgccaacac tggcagctat agctccgtac gcaagctcac cagttaggat cgaggatgtc   1140
gcaaacaccc gtgtgaagga atgtgatagg ctggaggctt gcgctcagaa tctccgctca   1200
atgggcatca ccgttcgcac tggaccagat tggattgaga tccatcctgg gactcctaga   1260
ccgaccgaga tagccacaca cggtgatcat agaatcgtca tgtcatttgc cgtggctgga   1320
cttagaaccc ctgggatgtc ttacgatgac cctggctgcg ttcgcaagac ttttcctcgt   1380
tttcatgaag agtttgcagc cttcgtggag cgctcatccg ctggagagtg a            1431
```

<210> SEQ ID NO 144
<211> LENGTH: 1245
<212> TYPE: DNA
<213> ORGANISM: Artificial sequence
<220> FEATURE:
<223> OTHER INFORMATION: DGT-31 v3 nucleotide

<400> SEQUENCE: 144

```
atgactgtga ttgacatccc tggctcaaag tcagttactg ccagagcatt gttcctcgca     60
gcagctgctg atggcactac aactcttttg agacctcttc acagcgatga cacggaaggc    120
ttcactgagg gtctcactcg tttgggatac gcagtggtta gagaacccga taggtggcac    180
atagaaggac gtccctccgg tccagcagca gcagatgcag aagttcactg tagggacggt    240
gctacaactg ctcgctttct tccaacccct tgcagctgctg ctgcctccgg aacgtatcgt    300
ttcgacgcat cagctcagat gaggcgtaga ccctcgctc ccctcacgga agctcttaga    360
acacttggag tggaccttag gcatgatgga gctgaaggcc accccctt gacaattcaa      420 gcctctggtg ttaagggtgg aggacttacg ctcgacgctg gtgagtcatc tcagtacttg    480
acagctctgc tcatgcttgg tcctctgacc gcagagggac tgagaataga agttacggag    540
cttgtctctg ctccttatgt ggagatcacc cttgcaatga tgagaggctt tggtgtggag    600
gttgttaggg aggggaatac tttcactgtg cctcctggag gttacagagc tacaacttat    660
gccatagaac cggacgcaag cacagcttcc tacttctttg cagcagcagc cctcactggg    720
agggaagtga cggtgcctgg cttgggcact ggagcacttc aaggtgatct taggttcacg    780
gaggtcctca gaaggatgga cgctgatgtt cgcacaacgt ccgactctac aacagtgcgc    840
tcagatggtc gccttgctgg gttgactgtc aacatgaggg acataagcga cacaatgcca    900
acactggcag ctatagctcc gtacgcaagc tcaccagtta ggatcgagga tgtcgcaaac    960
acccgtgtga aggaatgtga taggctggag gcttgcgctc agaatctccg ctcaatgggc   1020
atcaccgttc gcactggacc agattggatt gagatccatc ctgggactcc tagaccgacc   1080
gagatagcca cacacggtga tcatagaatc gtcatgtcat ttgccgtggc tggacttaga   1140
acccctggga tgtcttacga tgaccctggc tgcgttcgca agactttcc tcgttttcat   1200 gaagagtttg cagccttcgt ggagcgctca tccgctggag agtga                    1245
```

<210> SEQ ID NO 145
<211> LENGTH: 414
<212> TYPE: PRT
<213> ORGANISM: Artificial sequence
<220> FEATURE:
<223> OTHER INFORMATION: DGT-31 protein

```
<400> SEQUENCE: 145

Met Thr Val Ile Asp Ile Pro Gly Ser Lys Ser Val Thr Ala Arg Ala
1               5                   10                  15

Leu Phe Leu Ala Ala Ala Asp Gly Thr Thr Thr Leu Leu Arg Pro
            20                  25                  30

Leu His Ser Asp Asp Thr Glu Gly Phe Thr Glu Gly Leu Thr Arg Leu
            35                  40                  45

Gly Tyr Ala Val Val Arg Glu Pro Asp Arg Trp His Ile Glu Gly Arg
        50                  55                  60

Pro Ser Gly Pro Ala Ala Ala Asp Ala Glu Val His Cys Arg Asp Gly
65                  70                  75                  80

Ala Thr Thr Ala Arg Phe Leu Pro Thr Leu Ala Ala Ala Ala Ser
                85                  90                  95

Gly Thr Tyr Arg Phe Asp Ala Ser Ala Gln Met Arg Arg Arg Pro Leu
            100                 105                 110

Ala Pro Leu Thr Glu Ala Leu Arg Thr Leu Gly Val Asp Leu Arg His
            115                 120                 125

Asp Gly Ala Glu Gly His His Pro Leu Thr Ile Gln Ala Ser Gly Val
130                 135                 140

Lys Gly Gly Leu Thr Leu Asp Ala Gly Glu Ser Ser Gln Tyr Leu
145                 150                 155                 160

Thr Ala Leu Leu Met Leu Gly Pro Leu Thr Ala Glu Gly Leu Arg Ile
                165                 170                 175

Glu Val Thr Glu Leu Val Ser Ala Pro Tyr Val Glu Ile Thr Leu Ala
            180                 185                 190

Met Met Arg Gly Phe Gly Val Glu Val Val Arg Glu Gly Asn Thr Phe
            195                 200                 205

Thr Val Pro Pro Gly Gly Tyr Arg Ala Thr Thr Tyr Ala Ile Glu Pro
        210                 215                 220

Asp Ala Ser Thr Ala Ser Tyr Phe Phe Ala Ala Ala Leu Thr Gly
225                 230                 235                 240

Arg Glu Val Thr Val Pro Gly Leu Gly Thr Gly Ala Leu Gln Gly Asp
                245                 250                 255

Leu Arg Phe Thr Glu Val Leu Arg Arg Met Asp Ala Asp Val Arg Thr
            260                 265                 270

Thr Ser Asp Ser Thr Thr Val Arg Ser Asp Gly Arg Leu Ala Gly Leu
        275                 280                 285

Thr Val Asn Met Arg Asp Ile Ser Asp Thr Met Pro Thr Leu Ala Ala
        290                 295                 300

Ile Ala Pro Tyr Ala Ser Ser Pro Val Arg Ile Glu Asp Val Ala Asn
305                 310                 315                 320

Thr Arg Val Lys Glu Cys Asp Arg Leu Glu Ala Cys Ala Gln Asn Leu
                325                 330                 335

Arg Ser Met Gly Ile Thr Val Arg Thr Gly Pro Asp Trp Ile Glu Ile
            340                 345                 350

His Pro Gly Thr Pro Arg Pro Thr Glu Ile Ala Thr His Gly Asp His
        355                 360                 365

Arg Ile Val Met Ser Phe Ala Val Ala Gly Leu Arg Thr Pro Gly Met
        370                 375                 380
```

```
Ser Tyr Asp Asp Pro Gly Cys Val Arg Lys Thr Phe Pro Arg Phe His
385                 390                 395                 400

Glu Glu Phe Ala Ala Phe Val Glu Arg Ser Ser Ala Gly Glu
                405                 410
```